United States Patent
Plasterk

(10) Patent No.: US 12,005,104 B2
(45) Date of Patent: Jun. 11, 2024

(54) CANCER VACCINES FOR COLORECTAL CANCER

(71) Applicant: CureVac Netherlands B.V., Amsterdam (NL)

(72) Inventor: Ronald Hans Anton Plasterk, Amsterdam (NL)

(73) Assignee: CureVac Netherlands B.V., Amsterdam (NL)

(*) Notice: Subject to any disclaimer, the term of this patent is extended or adjusted under 35 U.S.C. 154(b) by 594 days.

(21) Appl. No.: 17/263,290

(22) PCT Filed: Jul. 25, 2019

(86) PCT No.: PCT/NL2019/050495
§ 371 (c)(1),
(2) Date: Jan. 26, 2021

(87) PCT Pub. No.: WO2020/022902
PCT Pub. Date: Jan. 30, 2020

(65) Prior Publication Data
US 2021/0213117 A1    Jul. 15, 2021

(30) Foreign Application Priority Data

Jul. 26, 2018 (NL) .................... 2021400
Jan. 24, 2019 (NL) .................... 2022447
Apr. 5, 2019 (EP) .................... 19167600

(51) Int. Cl.
*A61K 39/00* (2006.01)
*C12Q 1/6886* (2018.01)

(52) U.S. Cl.
CPC ........ *A61K 39/0011* (2013.01); *C12Q 1/6886* (2013.01); *A61K 2039/82* (2018.08)

(58) Field of Classification Search
CPC .. Y02A 50/30; C12Q 1/6886; A61K 2039/82; A61K 39/0011
See application file for complete search history.

(56) References Cited

FOREIGN PATENT DOCUMENTS

| | | |
|---|---|---|
| EP | 1130094 A2 | 9/2001 |
| WO | 2000055174 A1 | 9/2000 |
| WO | 2000073801 A2 | 12/2000 |
| WO | 2017173321 A1 | 10/2017 |
| WO | 2018213803 A1 | 11/2018 |
| WO | 2019126186 A1 | 6/2019 |

OTHER PUBLICATIONS

Orfanelli, T. et al., "Shared tumor antigens in uterine cancers with microsatellite instability: Putative targets for immunotherapeutic approaches", Gynecologic Oncology, Jun. 2019, 154(1):91, DOI: 10.1016/j.ygyno.2019.04.214.

Roudko, V. et al., "Widespread immunogenic poly-epitope frameshift mutations in microsatellite unstable tumors", bioRxiv 2019; doi: https://doi.org/10.1101/662262; pp. 1-53.

Hartmaier, R. et al., "Genomic analysis of 63,220 tumors reveals insights into tumor uniqueness and targeted cancer immunotherapy strategies", Genome Medicine, BioMed Central, vol. 9, Article No. 16 (2017), pp. 1-9.

Batista, M.T. et al., "Abstract 1463: FAST vaccines based on frameshift neoantigens may have advantages over personal vaccines", Proceedings of American Association for Cancer Research Annual Meeting 2019, Mar. 29, 2019, vol. 79, Nr.: 13, p. 1463.

Zhang, J. et al., "Using Frameshift Peptide Arrays for Cancer Neo-Antigens Screening", Scientific Reports, vol. 8, No. 1, (2018), pp. 1-10.

Koster, J. et al., "A library of Neo Open Reading Frame peptides (NOPs) as a sustainable resource of common neoantigens in up to 50% of cancer patients", Scientific Reports, 2019, vol. 9, Nr: 1.

Schwitalle, Y. et al., "Immunogenic peptides generated by frameshift mutations in DNA mismatch repair-deficient cancer cells", Cancer Immun. 2004 Academy of Cancer Immunology, CH-ISSN 1424-9734, vol. 4, Nr:1, pp. 1-10.

Luhui, S. et al., "Abstract 469: Progress towards developing a universal, prophylactic cancer vaccine.", American Association for Cancer Research; vol. 73, No. 8, Suppl. 1, Apr. 2013 (Apr. 1, 2013).

Primary Examiner — Bao Q Li
(74) Attorney, Agent, or Firm — Verrill Dana, LLP

(57) ABSTRACT

The invention relates to the field of cancer, in particular colorectal cancer. In particular, it relates to the field of immune system directed approaches for tumor reduction and control. Some aspects of the invention relate to vaccines, vaccinations and other means of stimulating an antigen specific immune response against a tumor in individuals. Such vaccines comprise neoantigens resulting from frameshift mutations that bring out-of-frame sequences of the APC, ARID1A, KMT2D, RNF43, SOX9, TCF7L2, TP53, and ZFP36L2 genes in-frame. Such vaccines are also useful for 'off the shelf' use.

9 Claims, 45 Drawing Sheets

Specification includes a Sequence Listing.

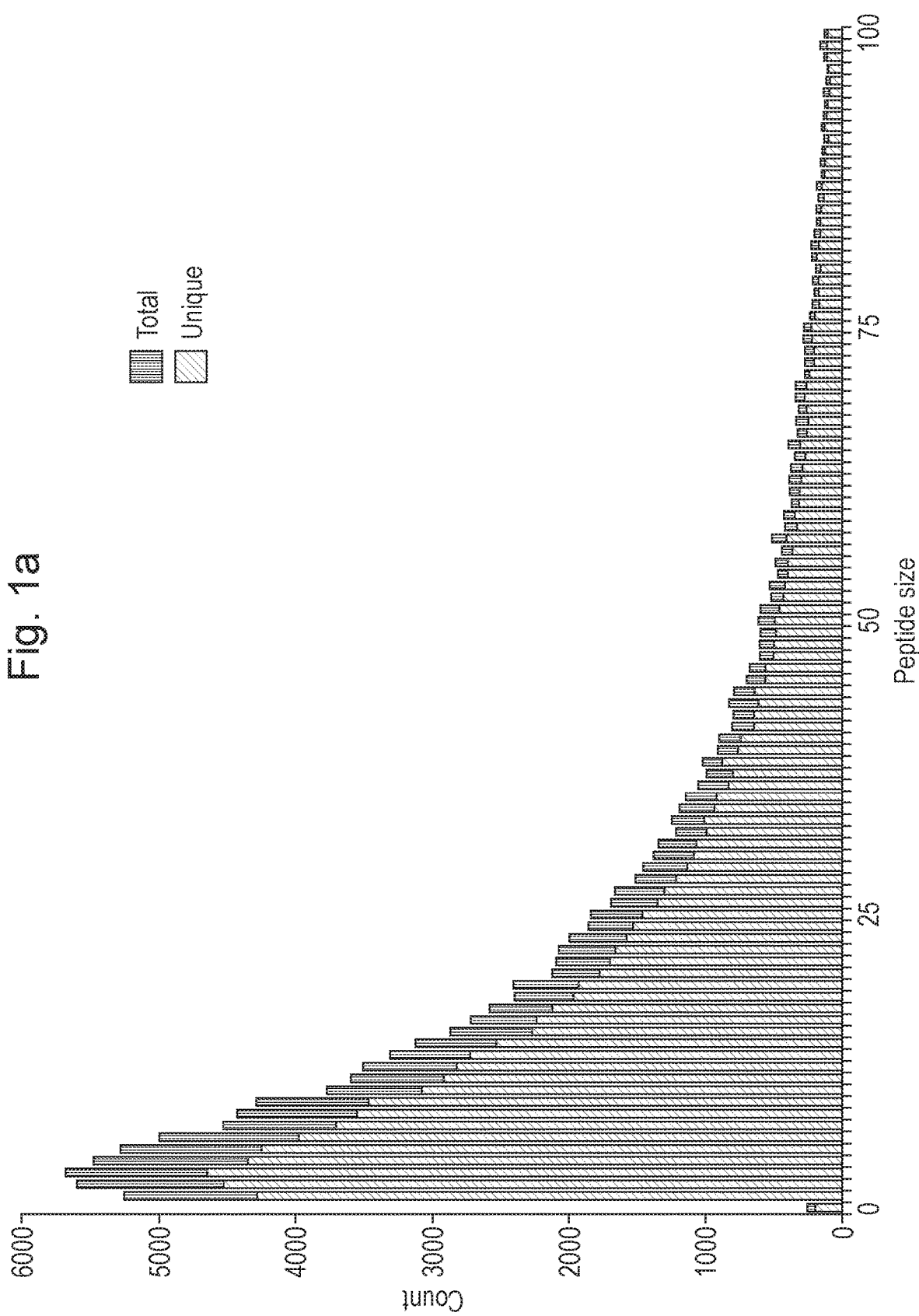

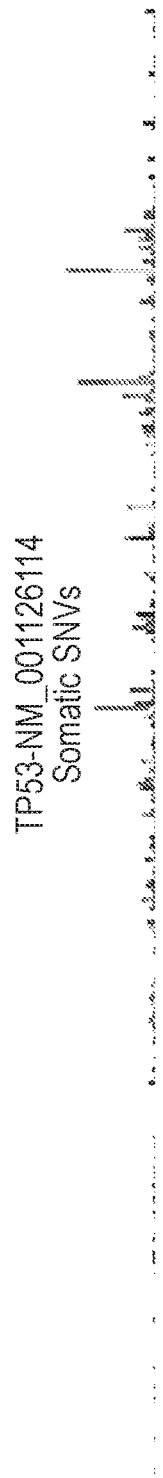

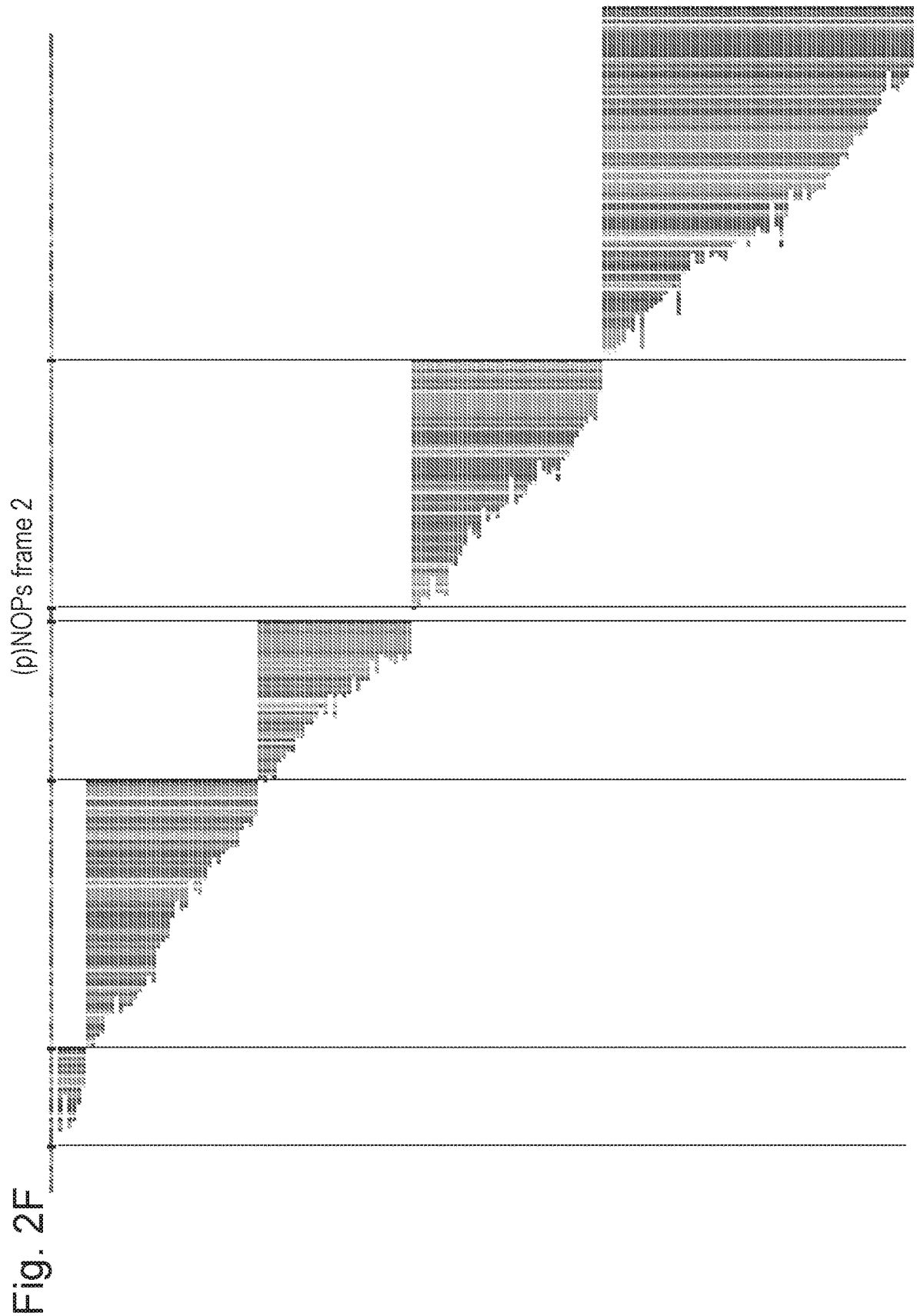

Fig. 8 (Cont. IIII)

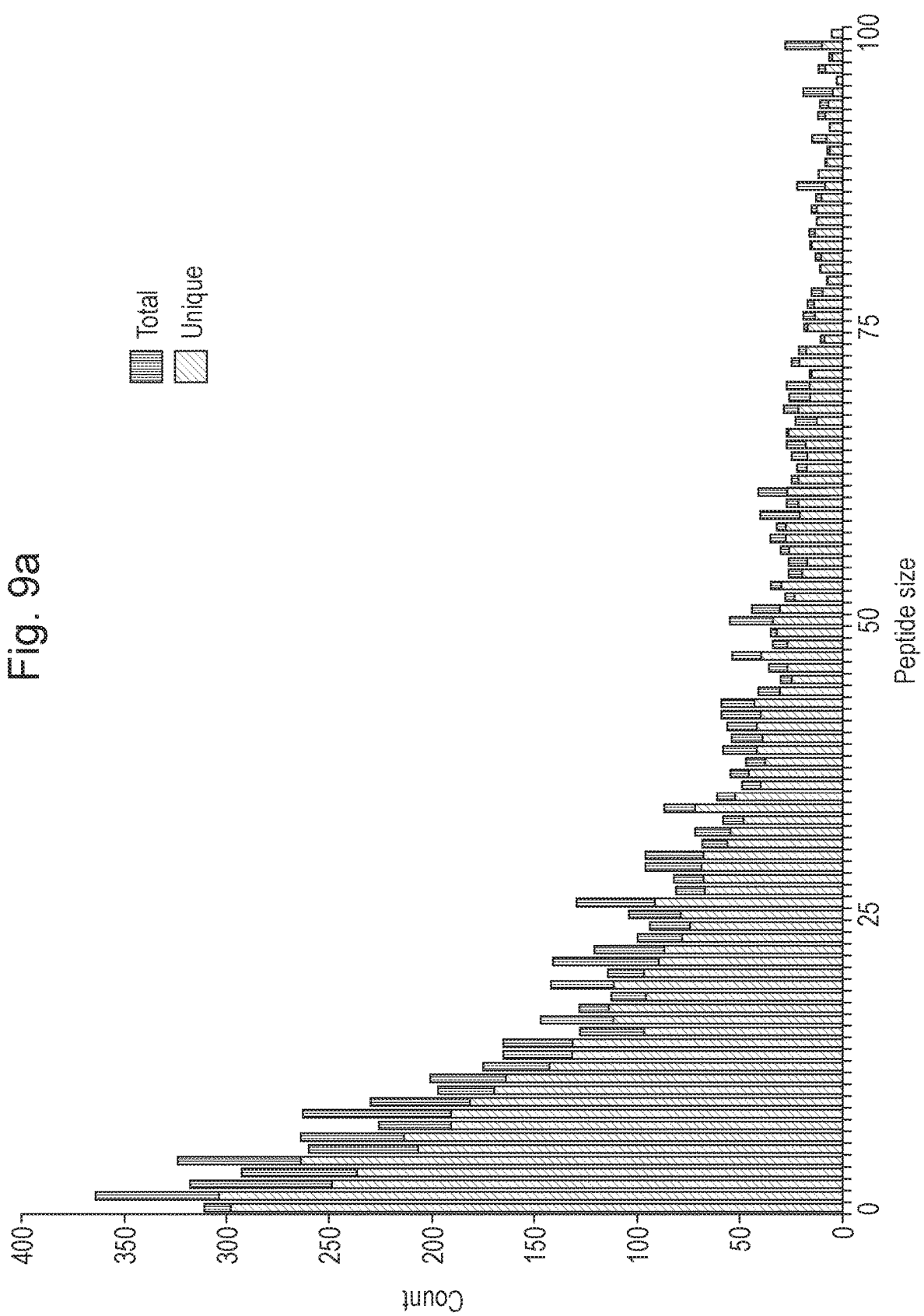

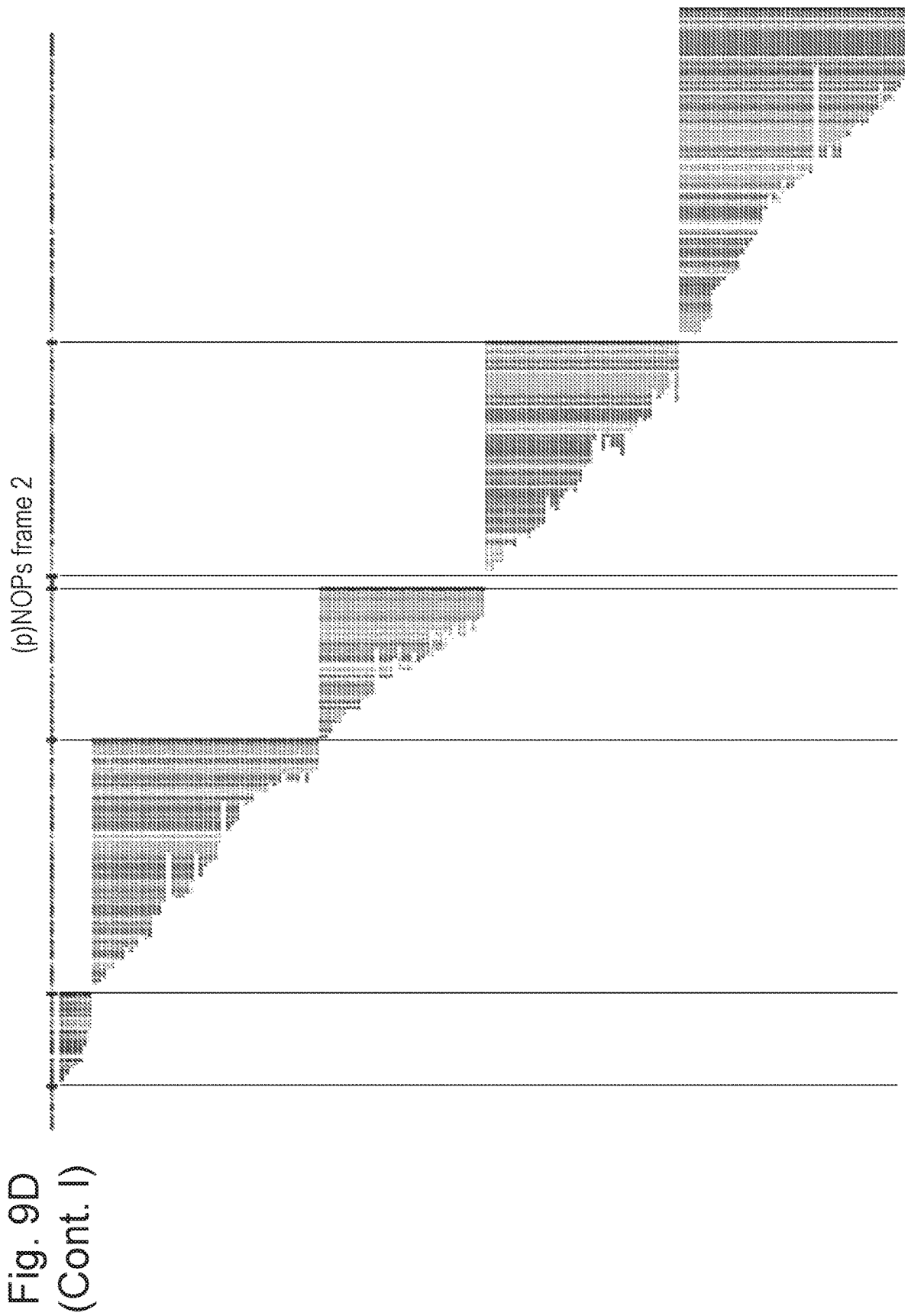
Fig. 9D (Cont. 1)

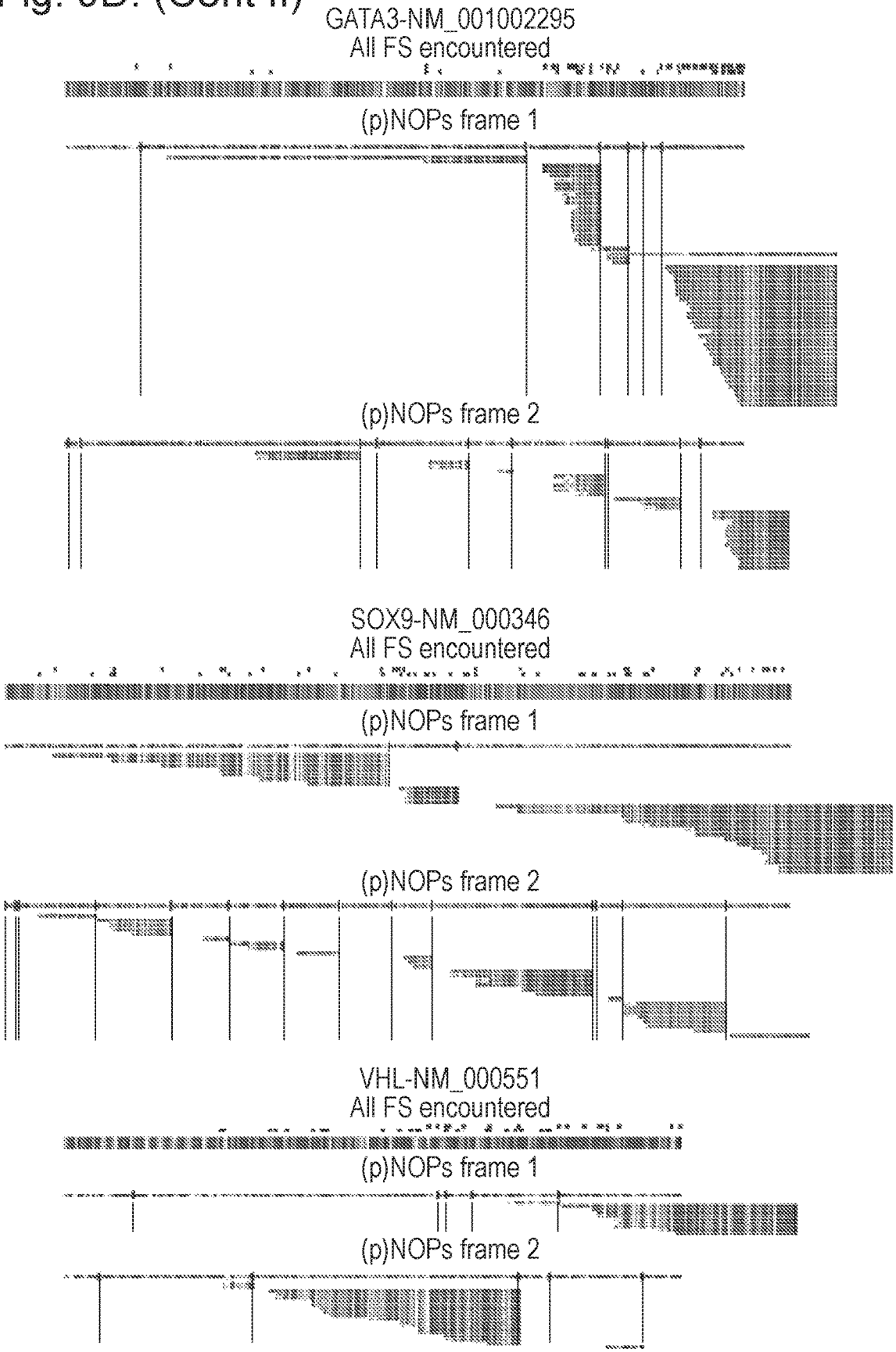
Fig. 9D. (Cont II)

KMT2D  All FS encountered   (p)NOPs frame 1   (p)NOPs frame 2

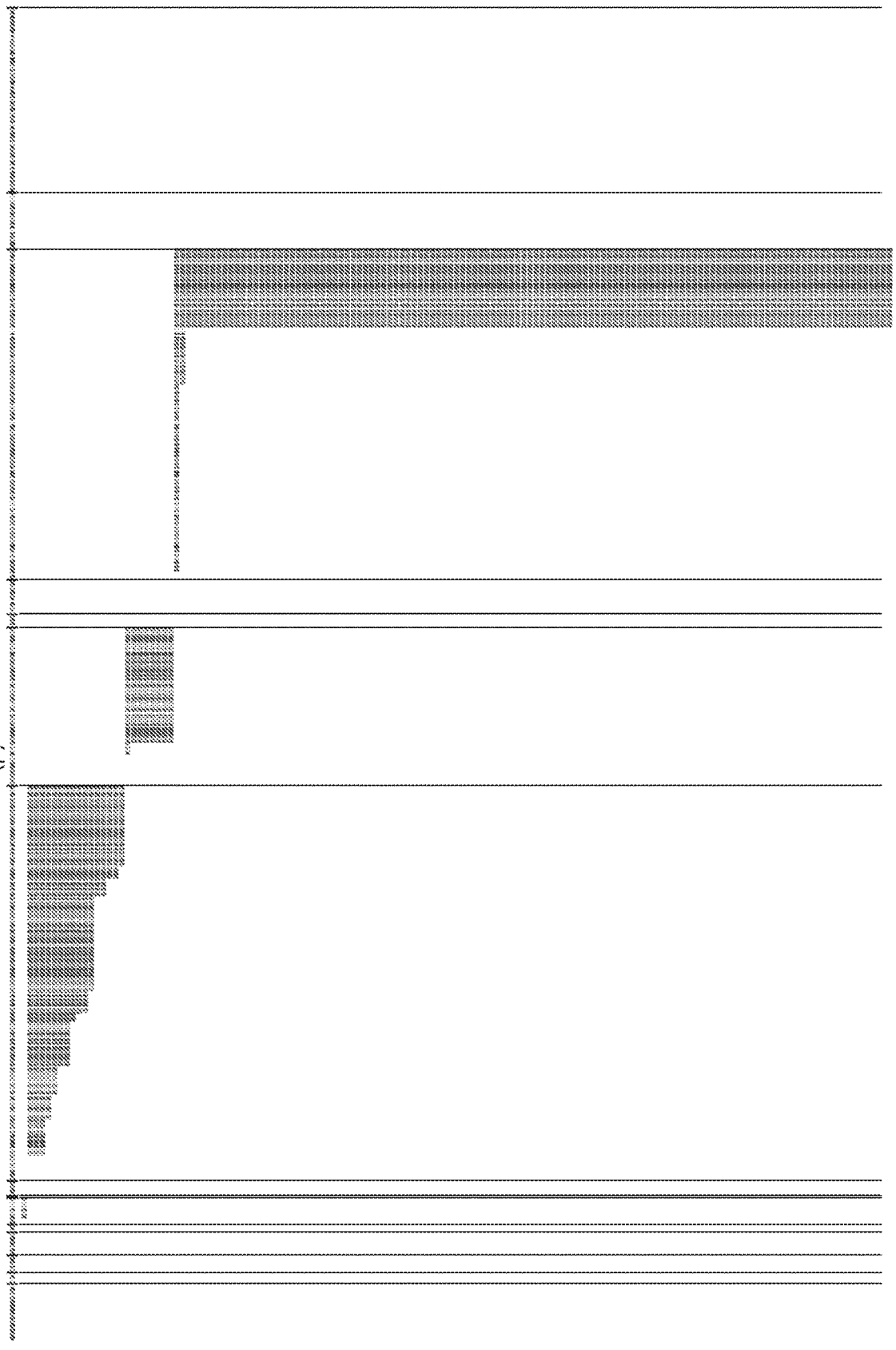

CANCER VACCINES FOR COLORECTAL CANCER

FIELD OF THE INVENTION

The invention relates to the field of cancer, in particular colorectal cancer. In particular, it relates to the field of immune system directed approaches for tumor reduction and control. Some aspects of the invention relate to vaccines, vaccinations and other means of stimulating an antigen specific immune response against a tumor in individuals. Such vaccines comprise neoantigens resulting from frameshift mutations that bring out-of-frame sequences of the APC, ARID1A, KMT2D, RNF43, SOX9, TCF7L2, TP53, and ZFP36L2 genes in-frame. Such vaccines are also useful for 'off the shelf' use.

BACKGROUND OF THE INVENTION

There are a number of different existing cancer therapies, including ablation techniques (e.g., surgical procedures and radiation) and chemical techniques (e.g., pharmaceutical agents and antibodies), and various combinations of such techniques. Despite intensive research such therapies are still frequently associated with serious risk, adverse or toxic side effects, as well as varying efficacy.

There is a growing interest in cancer therapies that aim to target cancer cells with a patient's own immune system (such as cancer vaccines or checkpoint inhibitors, or T-cell based immunotherapy). Such therapies may indeed eliminate some of the known disadvantages of existing therapies, or be used in addition to the existing therapies for additional therapeutic effect. Cancer vaccines or immunogenic compositions intended to treat an existing cancer by strengthening the body's natural defenses against the cancer and based on tumor-specific neoantigens hold great promise as next-generation of personalized cancer immunotherapy. Evidence shows that such neoantigen-based vaccination can elicit T-cell responses and can cause tumor regression in patients.

Typically the immunogenic compositions/vaccines are composed of tumor antigens (antigenic peptides or nucleic acids encoding them) and may include immune stimulatory molecules like cytokines that work together to induce antigen-specific cytotoxic T-cells that target and destroy tumor cells. Vaccines containing tumor-specific and patient-specific neoantigens require the sequencing of the patients' genome and tumor genome in order to determine whether the neoantigen is tumor specific, followed by the production of personalized compositions. Sequencing, identifying the patient's specific neoantigens and preparing such personalized compositions may require a substantial amount of time, time which may unfortunately not be available to the patient, given that for some tumors the average survival time after diagnosis is short, sometimes around a year or less.

Accordingly, there is a need for improved methods and compositions for providing subject-specific immunogenic compositions/cancer vaccines. In particular it would be desirable to have available a vaccine for use in the treatment of cancer, wherein such vaccine is suitable for treatment of a larger number of patients, and can thus be prepared in advance and provided off the shelf. There is a clear need in the art for personalized vaccines which induce an immune response to tumor specific neoantigens. One of the objects of the present disclosure is to provide personalized cancer vaccines that can be provided off the shelf. An additional object of the present disclosure is to provide cancer vaccines that can be provided prophylactically. Such vaccines are especially useful for individuals that are at risk of developing cancer.

SUMMARY OF THE INVENTION

In a preferred embodiment, the disclosure provides a vaccine or collection of vaccines for use in the treatment of colorectal cancer, said vaccine comprising:
(i) a peptide, or a collection of tiled peptides, having the amino acid sequence selected from Sequence 1, an amino acid sequence having 90% identity to Sequence 1, or a fragment thereof comprising at least 10 consecutive amino acids of Sequence 1; and
a peptide, or a collection of tiled peptides, having the amino acid sequence selected from Sequence 2, an amino acid sequence having 90% identity to Sequence 2, or a fragment thereof comprising at least 10 consecutive amino acids of Sequence 2; preferably also comprising
a peptide, or a collection of tiled peptides, having the amino acid sequence selected from Sequence 3, an amino acid sequence having 90% identity to Sequence 3, or a fragment thereof comprising at least 10 consecutive amino acids of Sequence 3;
a peptide, or a collection of tiled peptides, having the amino acid sequence selected from Sequence 4, an amino acid sequence having 90% identity to Sequence 4, or a fragment thereof comprising at least 10 consecutive amino acids of Sequence 4;
a peptide, or a collection of tiled peptides, having the amino acid sequence selected from Sequence 5, an amino acid sequence having 90% identity to Sequence 5, or a fragment thereof comprising at least 10 consecutive amino acids of Sequence 5; and/or
a peptide, or a collection of tiled peptides, having the amino acid sequence selected from Sequence 6, an amino acid sequence having 90% identity to Sequence 6, or a fragment thereof comprising at least 10 consecutive amino acids of Sequence 6;
(ii) a peptide, or a collection of tiled peptides, having the amino acid sequence selected from Sequence 197, an amino acid sequence having 90% identity to Sequence 197, or a fragment thereof comprising at least 10 consecutive amino acids of Sequence 197; and
a peptide, or a collection of tiled peptides, having the amino acid sequence selected from Sequence 198, an amino acid sequence having 90% identity to Sequence 198, or a fragment thereof comprising at least 10 consecutive amino acids of Sequence 198; preferably also comprising
a peptide, or a collection of tiled peptides, having the amino acid sequence selected from Sequence 199, an amino acid sequence having 90% identity to Sequence 199, or a fragment thereof comprising at least 10 consecutive amino acids of Sequence 199; and/or
a peptide, or a collection of tiled peptides, having the amino acid sequence selected from Sequence 200, an amino acid sequence having 90% identity to Sequence 200, or a fragment thereof comprising at least 10 consecutive amino acids of Sequence 200;
(iii) a peptide, or a collection of tiled peptides, having the amino acid sequence selected from Sequence 298, an amino acid sequence having 90% identity to Sequence 298, or a fragment thereof comprising at least 10 consecutive amino acids of Sequence 298; and a peptide, or a collection of tiled peptides, having the amino acid sequence selected from Sequence 299, an amino acid sequence having 90% identity to Sequence 299, or a fragment thereof comprising at least 10 consecutive amino acids of Sequence 299; preferably also comprising a peptide, or a collection of tiled peptides, having the amino acid sequence selected from Sequence 300, an amino acid sequence having 90% identity to Sequence 300, or a fragment thereof comprising at least 10 consecutive amino acids of Sequence 300;

(iv) a peptide, or a collection of tiled peptides, having the amino acid sequence selected from Sequence 553, an amino acid sequence having 90% identity to Sequence 553, or a fragment thereof comprising at least 10 consecutive amino acids of Sequence 553; and a peptide, or a collection of tiled peptides, having the amino acid sequence selected from Sequences 554-555, an amino acid sequence having 90% identity to Sequences 554-555, or a fragment thereof comprising at least 10 consecutive amino acids of Sequences 554-555;

(v) a peptide, or a collection of tiled peptides, having the amino acid sequence selected from Sequence 596, an amino acid sequence having 90% identity to Sequence 596, or a fragment thereof comprising at least 10 consecutive amino acids of Sequence 596; and a peptide, or a collection of tiled peptides, having the amino acid sequence selected from Sequence 597, an amino acid sequence having 90% identity to Sequence 597, or a fragment thereof comprising at least 10 consecutive amino acids of Sequence 597; preferably also comprising a peptide, or a collection of tiled peptides, having the amino acid sequence selected from Sequence 598, an amino acid sequence having 90% identity to Sequence 598, or a fragment thereof comprising at least 10 consecutive amino acids of Sequence 598;

a peptide, or a collection of tiled peptides, having the amino acid sequence selected from Sequence 599, an amino acid sequence having 90% identity to Sequence 599, or a fragment thereof comprising at least 10 consecutive amino acids of Sequence 599;

a peptide, or a collection of tiled peptides, having the amino acid sequence selected from Sequence 600, an amino acid sequence having 90% identity to Sequence 600, or a fragment thereof comprising at least 10 consecutive amino acids of Sequence 600; and/or a peptide, or a collection of tiled peptides, having the amino acid sequence selected from Sequence 601, an amino acid sequence having 90% identity to Sequence 601, or a fragment thereof comprising at least 10 consecutive amino acids of Sequence 601;

(vi) a peptide, or a collection of tiled peptides, having the amino acid sequence selected from Sequence 610, an amino acid sequence having 90% identity to Sequence 610, or a fragment thereof comprising at least 10 consecutive amino acids of Sequence 610; and a peptide, or a collection of tiled peptides, having the amino acid sequence selected from Sequence 611, an amino acid sequence having 90% identity to Sequence 611, or a fragment thereof comprising at least 10 consecutive amino acids of Sequence 611; preferably also comprising a peptide, or a collection of tiled peptides, having the amino acid sequence selected from Sequence 612, an amino acid sequence having 90% identity to Sequence 612, or a fragment thereof comprising at least 10 consecutive amino acids of Sequence 612;

a peptide, or a collection of tiled peptides, having the amino acid sequence selected from Sequence 613, an amino acid sequence having 90% identity to Sequence 613, or a fragment thereof comprising at least 10 consecutive amino acids of Sequence 613;

a peptide, or a collection of tiled peptides, having the amino acid sequence selected from Sequence 614, an amino acid sequence having 90% identity to Sequence 614, or a fragment thereof comprising at least 10 consecutive amino acids of Sequence 614; and/or a peptide, or a collection of tiled peptides, having the amino acid sequence selected from Sequence 615, an amino acid sequence having 90% identity to Sequence 615, or a fragment thereof comprising at least 10 consecutive amino acids of Sequence 615;

(vii) a peptide, or a collection of tiled peptides, having the amino acid sequence selected from Sequence 681, an amino acid sequence having 90% identity to Sequence 681, or a fragment thereof comprising at least 10 consecutive amino acids of Sequence 681; and a peptide, or a collection of tiled peptides, having the amino acid sequence selected from Sequence 682, an amino acid sequence having 90% identity to Sequence 682, or a fragment thereof comprising at least 10 consecutive amino acids of Sequence 682; preferably also comprising a peptide, or a collection of tiled peptides, having the amino acid sequence selected from Sequence 683, an amino acid sequence having 90% identity to Sequence 683, or a fragment thereof comprising at least 10 consecutive amino acids of Sequence 683;

a peptide, or a collection of tiled peptides, having the amino acid sequence selected from Sequence 684, an amino acid sequence having 90% identity to Sequence 684, or a fragment thereof comprising at least 10 consecutive amino acids of Sequence 684;

a peptide, or a collection of tiled peptides, having the amino acid sequence selected from Sequence 685, an amino acid sequence having 90% identity to Sequence 685, or a fragment thereof comprising at least 10 consecutive amino acids of Sequence 685; and/or a peptide, or a collection of tiled peptides, having the amino acid sequence selected from Sequence 686, an amino acid sequence having 90% identity to Sequence 686, or a fragment thereof comprising at least 10 consecutive amino acids of Sequence 686; and/or the vaccine comprises (viii) a peptide, or a collection of tiled peptides, having the amino acid sequence selected from Sequence 709, an amino acid sequence having 90% identity to Sequence 709, or a fragment thereof comprising at least 10 consecutive amino acids of Sequence 709; and a peptide, or a collection of tiled peptides, having the amino acid sequence selected from Sequence 710, an amino acid sequence having 90% identity to Sequence 710, or a fragment thereof comprising at least 10 consecutive amino acids of Sequence 710; preferably also comprising a peptide, or a collection of tiled peptides, having the amino acid sequence selected from Sequence 711, an amino acid sequence having 90% identity to Sequence 711, or a fragment thereof comprising at least 10 consecutive amino acids of Sequence 711; and/or a peptide, or a collection of tiled peptides, having the amino acid sequence selected from Sequence 712, an amino acid sequence having 90% identity to Sequence 712, or a fragment thereof comprising at least 10 consecutive amino acids of Sequence 712.

In a preferred embodiment, the disclosure provides a collection of frameshift-mutation peptides comprising:

(i) a peptide, or a collection of tiled peptides, having the amino acid sequence selected from Sequence 1, an amino acid sequence having 90% identity to Sequence 1, or a fragment thereof comprising at least 10 consecutive amino acids of Sequence 1; and a peptide, or a collection of tiled peptides, having the amino acid sequence selected from Sequence 2, an amino acid sequence having 90% identity to Sequence 2, or a fragment thereof comprising at least 10 consecutive amino acids of Sequence 2; preferably also comprising a peptide, or a collection of tiled peptides, having the amino acid sequence selected from Sequence 3, an amino acid sequence having 90% identity to Sequence 3, or a fragment thereof comprising at least 10 consecutive amino acids of Sequence 3;

a peptide, or a collection of tiled peptides, having the amino acid sequence selected from Sequence 4, an amino acid sequence having 90% identity to Sequence 4, or a fragment thereof comprising at least 10 consecutive amino acids of Sequence 4;

a peptide, or a collection of tiled peptides, having the amino acid sequence selected from Sequence 5, an amino acid sequence having 90% identity to Sequence 5, or a fragment thereof comprising at least 10 consecutive amino acids of Sequence 5; and/or a peptide, or a collection of tiled peptides, having the amino acid sequence selected from Sequence 6, an amino acid sequence having 90% identity to Sequence 6, or a fragment thereof comprising at least 10 consecutive amino acids of Sequence 6;

(ii) a peptide, or a collection of tiled peptides, having the amino acid sequence selected from Sequence 197, an amino acid sequence having 90% identity to Sequence 197, or a fragment thereof comprising at least 10 consecutive amino acids of Sequence 197; and a peptide, or a collection of tiled peptides, having the amino acid sequence selected from Sequence 198, an amino acid sequence having 90% identity to Sequence 198, or a fragment thereof comprising at least 10 consecutive amino acids of Sequence 198; preferably also comprising a peptide, or a collection of tiled peptides, having the amino acid sequence selected from Sequence 199, an amino acid sequence having 90% identity to Sequence 199, or a fragment thereof comprising at least 10 consecutive amino acids of Sequence 199; and/or a peptide, or a collection of tiled peptides, having the amino acid sequence selected from Sequence 200, an amino acid sequence having 90% identity to Sequence 200, or a fragment thereof comprising at least 10 consecutive amino acids of Sequence 200;

(iii) a peptide, or a collection of tiled peptides, having the amino acid sequence selected from Sequence 298, an amino acid sequence having 90% identity to Sequence 298, or a fragment thereof comprising at least 10 consecutive amino acids of Sequence 298; and a peptide, or a collection of tiled peptides, having the amino acid sequence selected from Sequence 299, an amino acid sequence having 90% identity to Sequence 299, or a fragment thereof comprising at least 10 consecutive amino acids of Sequence 299; preferably also comprising a peptide, or a collection of tiled peptides, having the amino acid sequence selected from Sequence 300, an amino acid sequence having 90% identity to Sequence 300, or a fragment thereof comprising at least 10 consecutive amino acids of Sequence 300;

(iv) a peptide, or a collection of tiled peptides, having the amino acid sequence selected from Sequence 553, an amino acid sequence having 90% identity to Sequence 553, or a fragment thereof comprising at least 10 consecutive amino acids of Sequence 553; and a peptide, or a collection of tiled peptides, having the amino acid sequence selected from Sequences 554-555, an amino acid sequence having 90% identity to Sequences 554-555, or a fragment thereof comprising at least 10 consecutive amino acids of Sequences 554-555;

(v) a peptide, or a collection of tiled peptides, having the amino acid sequence selected from Sequence 596, an amino acid sequence having 90% identity to Sequence 596, or a fragment thereof comprising at least 10 consecutive amino acids of Sequence 596; and a peptide, or a collection of tiled peptides, having the amino acid sequence selected from Sequence 597, an amino acid sequence having 90% identity to Sequence 597, or a fragment thereof comprising at least 10 consecutive amino acids of Sequence 597; preferably also comprising a peptide, or a collection of tiled peptides, having the amino acid sequence selected from Sequence 598, an amino acid sequence having 90% identity to Sequence 598, or a fragment thereof comprising at least 10 consecutive amino acids of Sequence 598;

a peptide, or a collection of tiled peptides, having the amino acid sequence selected from Sequence 599, an amino acid sequence having 90% identity to Sequence 599, or a fragment thereof comprising at least 10 consecutive amino acids of Sequence 599;

a peptide, or a collection of tiled peptides, having the amino acid sequence selected from Sequence 600, an amino acid sequence having 90% identity to Sequence 600, or a fragment thereof comprising at least 10 consecutive amino acids of Sequence 600; and/or a peptide, or a collection of tiled peptides, having the amino acid sequence selected from Sequence 601, an amino acid sequence having 90% identity to Sequence 601, or a fragment thereof comprising at least 10 consecutive amino acids of Sequence 601;

(vi) a peptide, or a collection of tiled peptides, having the amino acid sequence selected from Sequence 610, an amino acid sequence having 90% identity to Sequence 610, or a fragment thereof comprising at least 10 consecutive amino acids of Sequence 610; and a peptide, or a collection of tiled peptides, having the amino acid sequence selected from Sequence 611, an amino acid sequence having 90% identity to Sequence 611, or a fragment thereof comprising at least 10 consecutive amino acids of Sequence 611; preferably also comprising a peptide, or a collection of tiled peptides, having the amino acid sequence selected from Sequence 612, an amino acid sequence having 90% identity to Sequence 612, or a fragment thereof comprising at least 10 consecutive amino acids of Sequence 612;

a peptide, or a collection of tiled peptides, having the amino acid sequence selected from Sequence 613, an amino acid sequence having 90% identity to Sequence 613, or a fragment thereof comprising at least 10 consecutive amino acids of Sequence 613;

a peptide, or a collection of tiled peptides, having the amino acid sequence selected from Sequence 614, an amino acid sequence having 90% identity to Sequence 614, or a fragment thereof comprising at least 10 consecutive amino acids of Sequence 614; and/or a peptide, or a collection of tiled peptides, having the amino acid sequence selected from Sequence 615, an amino acid sequence having 90% identity to Sequence 615, or a fragment thereof comprising at least 10 consecutive amino acids of Sequence 615;

(vii) a peptide, or a collection of tiled peptides, having the amino acid sequence selected from Sequence 681, an amino acid sequence having 90% identity to Sequence 681, or a fragment thereof comprising at least 10 consecutive amino acids of Sequence 681; and a peptide, or a collection of tiled peptides, having the amino acid sequence selected from Sequence 682, an amino acid sequence having 90% identity to Sequence 682, or a fragment thereof comprising at least 10 consecutive amino acids of Sequence 682; preferably also comprising a peptide, or a collection of tiled peptides, having the amino acid sequence selected from Sequence 683, an amino acid sequence having 90% identity to Sequence 683, or a fragment thereof comprising at least 10 consecutive amino acids of Sequence 683;

a peptide, or a collection of tiled peptides, having the amino acid sequence selected from Sequence 684, an amino acid sequence having 90% identity to Sequence 684, or a fragment thereof comprising at least 10 consecutive amino acids of Sequence 684;

a peptide, or a collection of tiled peptides, having the amino acid sequence selected from Sequence 685, an amino acid sequence having 90% identity to Sequence 685, or a fragment thereof comprising at least 10 consecutive amino acids of Sequence 685; and/or a peptide, or a collection of tiled peptides, having the amino acid sequence selected from Sequence 686, an amino acid sequence having 90% identity to Sequence 686, or a fragment thereof comprising at least 10 consecutive amino acids of Sequence 686; and/or the collection comprising (viii) a peptide, or a collection of tiled peptides, having the amino acid sequence selected from Sequence 709, an amino acid sequence having 90% identity to Sequence 709, or a fragment thereof comprising at least 10 consecutive amino acids of Sequence 709; and a peptide, or a collection of tiled peptides, having the amino acid sequence selected from Sequence 710, an amino acid sequence having 90% identity to Sequence 710, or a fragment thereof comprising at least 10 consecutive amino acids of Sequence 710; preferably also comprising a peptide, or a collection of tiled peptides, having the amino acid sequence selected from Sequence 711, an amino acid sequence having 90% identity to Sequence 711, or a fragment thereof comprising at least 10 consecutive amino acids of Sequence 711; and/or a peptide, or a collection of tiled peptides, having the amino acid sequence selected from Sequence 712, an amino acid sequence having 90% identity to Sequence 712, or a fragment thereof comprising at least 10 consecutive amino acids of Sequence 712.

In a preferred embodiment, the disclosure provides a peptide comprising an amino acid sequence selected from the groups:

(i) Sequences 1-196, an amino acid sequence having 90% identity to Sequences 1-196, or a fragment thereof comprising at least 10 consecutive amino acids of Sequences 1-196;

(ii) Sequences 197-297, an amino acid sequence having 90% identity to Sequences 197-297, or a fragment thereof comprising at least 10 consecutive amino acids of Sequences 197-297;

(iii) Sequences 298-552, an amino acid sequence having 90% identity to Sequences 298-552, or a fragment thereof comprising at least 10 consecutive amino acids of Sequences 298-552;

(iv) Sequences 553-595, an amino acid sequence having 90% identity to Sequences 553-595, or a fragment thereof comprising at least 10 consecutive amino acids of Sequences 553-595; and (v) Sequences 596-609, an amino acid sequence having 90% identity to Sequences 596-609, or a fragment thereof comprising at least 10 consecutive amino acids of Sequences 596-609;

(vi) Sequences 610-680, an amino acid sequence having 90% identity to Sequences 610-680, or a fragment thereof comprising at least 10 consecutive amino acids of Sequences 610-680;

(vii) Sequences 681-708, an amino acid sequence having 90% identity to Sequences 681-708, or a fragment thereof comprising at least 10 consecutive amino acids of Sequences 681-708; and (viii) Sequences 709-717, an amino acid sequence having 90% identity to Sequences 709-717, or a fragment thereof comprising at least 10 consecutive amino acids of Sequences 709-717.

A preferred peptide is Sequence 201, an amino acid sequence having 90% identity to Sequence 201, or a fragment thereof comprising at least 10 consecutive amino acids of Sequence 201; as well as collections comprising said peptide.

A preferred collection comprises Sequences 298-299, an amino acid sequence having 90% identity to Sequences 298-299, or a fragment thereof comprising at least 10 consecutive amino acids of Sequences 298-299.

In some embodiments of the disclosure, the peptides are linked, preferably wherein said peptides are comprised within the same polypeptide.

In a preferred embodiment, the disclosure provides one more isolated nucleic acid molecules encoding the peptides or collection of peptides as disclosed herein. In a preferred embodiment, the disclosure provides one or more vectors comprising the nucleic acid molecules disclosed herein, preferably wherein the vector is a viral vector. In a preferred embodiment, the disclosure provides a host cell comprising the isolated nucleic acid molecules or the vectors as disclosed herein.

In a preferred embodiment, the disclosure provides a binding molecule or a collection of binding molecules that bind the peptide or collection of peptides disclosed herein, where in the binding molecule is an antibody, a T-cell receptor, or an antigen binding fragment thereof.

In a preferred embodiment, the disclosure provides a chimeric antigen receptor or collection of chimeric antigen receptors each comprising i) a T cell activation molecule; ii) a transmembrane region; and iii) an antigen recognition moiety; wherein said antigen recognition moieties bind the peptide or collection of peptides disclosed herein. In a preferred embodiment, the disclosure provides a host cell or combination of host cells that express the binding molecule or collection of binding molecules, or the chimeric antigen receptor or collection of chimeric antigen receptors as disclosed herein.

In a preferred embodiment, the disclosure provides a vaccine or collection of vaccines comprising the peptide or collection of peptides, the nucleic acid molecules, the vectors, or the host cells as disclosed herein; and a pharmaceutically acceptable excipient and/or adjuvant, preferably an immune-effective amount of adjuvant.

In a preferred embodiment, the disclosure provides the vaccines or collection of vaccines as disclosed herein for use in the treatment of colorectal cancer in an individual. In a preferred embodiment, the disclosure provides the vaccines as disclosed herein for prophylactic use in the prevention of colorectal cancer in an individual. In a preferred embodiment, the disclosure provides the vaccines as disclosed herein for use in the preparation of a medicament for treatment of colorectal cancer in an individual or for prophylactic use. In a preferred embodiment, the disclosure provides methods of treating an individual for colorectal cancer or reducing the risk of developing said cancer, the method comprising administering to the individual in need thereof a therapeutically effective amount of a vaccine as disclosed herein.

In a preferred embodiment, the individual has colorectal cancer and one or more cancer cells of the individual:
  (i) expresses a peptide having the amino acid sequence selected from Sequences 1-717, an amino acid sequence having 90% identity to any one of Sequences 1-717, or a fragment thereof comprising at least 10 consecutive amino acids of amino acid sequence selected from Sequences 1-717;
  (ii) or comprises a DNA or RNA sequence encoding an amino acid sequences of (i).

In one embodiment, the individual has a germline mutation in the MSH2, MLH1, FANCA, FANCB, FANCD1 (BRCA2), FANCD2, FANCE, FANCF, FANCG, FANCI, FANCJ (BRIP1), FANCN (PALB2), FANCP (SLX4), FANCS (BRCA1), RAD51C, XPF, POLE, POLD1, NTHL1, MSH3, RNF43, SMAD4, BMPR1A, STK11, PTEN, GREM1, AXIN2, GREM1, BLM, AKT1, ENG, CDH1, BUB1B, GALNT12, MLH3, RPS20, GJB2, CHEK2, MUTYH, FANCL, FANCM, COL7A1, APC, ERCC2, FANCC, MPL, SBDS, ATM, FAH, MSHG, NTHL1, and/or WRN gene, preferably in the GJB2, CHEK2, MUTYH, FANCL, FANCM, COL7A1, APC, ERCC2, FANCC, MPL, SBDS, ATM, FAH, MSH6, NTHL1, and/or WRN gene. In a preferred embodiment, the method, preferably the prophylactic method, further comprises determining whether said individual has a germline mutation in the MSH2, MLH1, FANCA, FANCB, FANCD1 (BRCA2), FANCD2, FANCE, FANCF, FANCG, FANCI, FANCJ (BRIM), FANCN (PALB2), FANCP (SLX4), FANCS (BRCA1), RAD51C, XPF, POLE, POLD1, NTHL1, MSH3, RNF43, SMAD4, BMPR1A, STK11, PTEN, GREM1, AXIN2, GREM1, BLM, AKT1, ENG, CDH1, BUB1B, GALNT12, MLH3, RPS20, GJB2, CHEK2, MUTYH, FANCL, FANCM, COL7A1, APC, ERCC2, FANCC, MPL, SBDS, ATM, FAH, MSH6, NTHL1, and/or WRN gene, preferably in the GJB2, CHEK2, MUTYH, FANCL, FANCM, COL7A1, APC, ERCC2, FANCC, MPL, SBDS, ATM, FAH, MSH6, NTHL1, and/or WRN gene. In some embodiments, the individual prophylactically administered a vaccine as disclosed herein has not been diagnosed with colorectal cancer.

In a preferred embodiment, the disclosure provides a method of stimulating the proliferation of human T-cells, comprising contacting said T-cells with the peptide or collection of peptides, the nucleic acid molecules, the vectors, the host cell, or the vaccine as disclosed herein.

In a preferred embodiment, the disclosure provides a storage facility for storing vaccines. Preferably the facility stores at least two different cancer vaccines as disclosed herein. Preferably the storing facility stores:
  a vaccine comprising:
    (i) a peptide, or a collection of tiled peptides, having the amino acid sequence selected from Sequence 1, an amino acid sequence having 90% identity to Sequence 1, or a fragment thereof comprising at least 10 consecutive amino acids of Sequence 1; and
    a peptide, or a collection of tiled peptides, having the amino acid sequence selected from Sequence 2, an amino acid sequence having 90% identity to Sequence 2, or a fragment thereof comprising at least 10 consecutive amino acids of Sequence 2; preferably also comprising
    a peptide, or a collection of tiled peptides, having the amino acid sequence selected from Sequence 3, an amino acid sequence having 90% identity to Sequence 3, or a fragment thereof comprising at least 10 consecutive amino acids of Sequence 3;
    a peptide, or a collection of tiled peptides, having the amino acid sequence selected from Sequence 4, an amino acid sequence having 90% identity to Sequence 4, or a fragment thereof comprising at least 10 consecutive amino acids of Sequence 4;
    a peptide, or a collection of tiled peptides, having the amino acid sequence selected from Sequence 5, an amino acid sequence having 90% identity to Sequence 5, or a fragment thereof comprising at least 10 consecutive amino acids of Sequence 5; and/or
    a peptide, or a collection of tiled peptides, having the amino acid sequence selected from Sequence 6, an amino acid sequence having 90% identity to Sequence 6, or a fragment thereof comprising at least 10 consecutive amino acids of Sequence 6;
    and one or more vaccines selected from:
  a vaccine comprising:
    (ii) a peptide, or a collection of tiled peptides, having the amino acid sequence selected from Sequence 197, an amino acid sequence having 90% identity to Sequence 197, or a fragment thereof comprising at least 10 consecutive amino acids of Sequence 197; and
    a peptide, or a collection of tiled peptides, having the amino acid sequence selected from Sequence 198, an amino acid sequence having 90% identity to Sequence 198, or a fragment thereof comprising at least 10 consecutive amino acids of Sequence 198; preferably also comprising
    a peptide, or a collection of tiled peptides, having the amino acid sequence selected from Sequence 199, an amino acid sequence having 90% identity to Sequence 199, or a fragment thereof comprising at least 10 consecutive amino acids of Sequence 199; and/or
    a peptide, or a collection of tiled peptides, having the amino acid sequence selected from Sequence 200, an amino acid sequence having 90% identity to Sequence 200, or a fragment thereof comprising at least 10 consecutive amino acids of Sequence 200;
a vaccine comprising:
(iii) a peptide, or a collection of tiled peptides, having the amino acid sequence selected from Sequence 298, an amino acid sequence having 90% identity to Sequence 298, or a fragment thereof comprising at least 10 consecutive amino acids of Sequence 298; and
a peptide, or a collection of tiled peptides, having the amino acid sequence selected from Sequence 299, an amino acid sequence having 90% identity to Sequence 299, or a fragment thereof comprising at least 10 consecutive amino acids of Sequence 299; preferably also comprising
a peptide, or a collection of tiled peptides, having the amino acid sequence selected from Sequence 300, an amino acid sequence having 90% identity to Sequence 300, or a fragment thereof comprising at least 10 consecutive amino acids of Sequence 300;
a vaccine comprising:
(iv) a peptide, or a collection of tiled peptides, having the amino acid sequence selected from Sequence 553, an amino acid sequence having 90% identity to Sequence 553, or a fragment thereof comprising at least 10 consecutive amino acids of Sequence 553; and
a peptide, or a collection of tiled peptides, having the amino acid sequence selected from Sequences 554-555, an amino acid sequence having 90% identity to Sequences 554-555, or a fragment thereof comprising at least 10 consecutive amino acids of Sequences 554-555;
a vaccine comprising:
(v) a peptide, or a collection of tiled peptides, having the amino acid sequence selected from Sequence 596, an amino acid sequence having 90% identity to Sequence 596, or a fragment thereof comprising at least 10 consecutive amino acids of Sequence 596; and
a peptide, or a collection of tiled peptides, having the amino acid sequence selected from Sequence 597, an amino acid sequence having 90% identity to Sequence 597, or a fragment thereof comprising at least 10 consecutive amino acids of Sequence 597; preferably also comprising
a peptide, or a collection of tiled peptides, having the amino acid sequence selected from Sequence 598, an amino acid sequence having 90% identity to Sequence 598, or a fragment thereof comprising at least 10 consecutive amino acids of Sequence 598; ad
a peptide, or a collection of tiled peptides, having the amino acid sequence selected from Sequence 599, an amino acid sequence having 90% identity to Sequence 599, or a fragment thereof comprising at least 10 consecutive amino acids of Sequence 599;
a peptide, or a collection of tiled peptides, having the amino acid sequence selected from Sequence 600, an amino acid sequence having 90% identity to Sequence 600, or a fragment thereof comprising at least 10 consecutive amino acids of Sequence 600; and/or
a peptide, or a collection of tiled peptides, having the amino acid sequence selected from Sequence 601, an amino acid sequence having 90% identity to Sequence 601, or a fragment thereof comprising at least 10 consecutive amino acids of Sequence 601;
a vaccine comprising:
(vi) a peptide, or a collection of tiled peptides, having the amino acid sequence selected from Sequence 610, an amino acid sequence having 90% identity to Sequence 610, or a fragment thereof comprising at least 10 consecutive amino acids of Sequence 610; and
a peptide, or a collection of tiled peptides, having the amino acid sequence selected from Sequence 611, an amino acid sequence having 90% identity to Sequence 611, or a fragment thereof comprising at least 10 consecutive amino acids of Sequence 611; preferably also comprising
a peptide, or a collection of tiled peptides, having the amino acid sequence selected from Sequence 612, an amino acid sequence having 90% identity to Sequence 612, or a fragment thereof comprising at least 10 consecutive amino acids of Sequence 612;
a peptide, or a collection of tiled peptides, having the amino acid sequence selected from Sequence 613, an amino acid sequence having 90% identity to Sequence 613, or a fragment thereof comprising at least 10 consecutive amino acids of Sequence 613;
a peptide, or a collection of tiled peptides, having the amino acid sequence selected from Sequence 614, an amino acid sequence having 90% identity to Sequence 614, or a fragment thereof comprising at least 10 consecutive amino acids of Sequence 614; and/or
a peptide, or a collection of tiled peptides, having the amino acid sequence selected from Sequence 615, an amino acid sequence having 90% identity to Sequence 615, or a fragment thereof comprising at least 10 consecutive amino acids of Sequence 615;
a vaccine comprising:
(vii) a peptide, or a collection of tiled peptides, having the amino acid sequence selected from Sequence 681, an amino acid sequence having 90% identity to Sequence 681, or a fragment thereof comprising at least 10 consecutive amino acids of Sequence 681; and
a peptide, or a collection of tiled peptides, having the amino acid sequence selected from Sequence 682, an amino acid sequence having 90% identity to Sequence 682, or a fragment thereof comprising at least 10 consecutive amino acids of Sequence 682; preferably also comprising
a peptide, or a collection of tiled peptides, having the amino acid sequence selected from Sequence 683, an amino acid sequence having 90% identity to Sequence 683, or a fragment thereof comprising at least 10 consecutive amino acids of Sequence 683;
a peptide, or a collection of tiled peptides, having the amino acid sequence selected from Sequence 684, an amino acid sequence having 90% identity to Sequence 684, or a fragment thereof comprising at least 10 consecutive amino acids of Sequence 684;
a peptide, or a collection of tiled peptides, having the amino acid sequence selected from Sequence 685, an amino acid sequence having 90% identity to Sequence 685, or a fragment thereof comprising at least 10 consecutive amino acids of Sequence 685; and/or
a peptide, or a collection of tiled peptides, having the amino acid sequence selected from Sequence 686, an amino acid sequence having 90% identity to Sequence 686, or a fragment thereof comprising at least 10 consecutive amino acids of Sequence 686;
a vaccine comprising:
(viii) a peptide, or a collection of tiled peptides, having the amino acid sequence selected from Sequence 709, an amino acid sequence having 90% identity to Sequence 709, or a fragment thereof comprising at least 10 consecutive amino acids of Sequence 709; and
a peptide, or a collection of tiled peptides, having the amino acid sequence selected from Sequence 710, an amino acid sequence having 90% identity to Sequence 710, or a fragment thereof comprising at least 10 consecutive amino acids of Sequence 710; preferably also comprising
a peptide, or a collection of tiled peptides, having the amino acid sequence selected from Sequence 711, an amino acid sequence having 90% identity to Sequence 711, or a fragment thereof comprising at least 10 consecutive amino acids of Sequence 711; and/or
a peptide, or a collection of tiled peptides, having the amino acid sequence selected from Sequence 712, an amino acid sequence having 90% identity to Sequence 712, or a fragment thereof comprising at least 10 consecutive amino acids of Sequence 712. Preferably, the storage facility comprises at least 5, at least 10, or at least 20 vaccines as disclosed herein.

In a preferred embodiment, the disclosure provides a method for providing a vaccine for immunizing a patient against a cancer in said patient comprising determining the sequence of APC, ARID1A, KMT2D, RNF43, SOX9, TCF7L2, TP53, and/or ZFP36L2 in cancer cells of said cancer and when the determined sequence comprises a frameshift mutation that produces a neoantigen of Sequence 1-717 or a fragment thereof, providing a vaccine comprising said neoantigen or a fragment thereof. Preferably, the vaccine is obtained from a storage facility as disclosed herein.

REFERENCE TO A SEQUENCE LISTING

The Sequence listing, which is a part of the present disclosure, includes a text file comprising amino acid and/or nucleic acid sequences. The subject matter of the Sequence listing is incorporated herein by reference in its entirety. The information recorded in computer readable form is identical to the written sequence listing. In the event of a discrepancy between the Sequence listing and the description, e.g., in regard to a sequence or sequence numbering, the description (e.g., Table 1) is leading.

DETAILED DESCRIPTION OF THE DISCLOSED EMBODIMENTS

One issue that may arise when considering personalized cancer vaccines is that once a tumor from a patient has been analysed (e.g. by whole genome or exome sequencing), neoantigens need to be selected and made in a vaccine. This may be a time consuming process, while time is something the cancer patient usually lacks as the disease progresses.

Somatic mutations in cancer can result in neoantigens against which patients can be vaccinated. Unfortunately, the quest for tumor specific neoantigens has yielded no targets that are common to all tumors, yet foreign to healthy cells. Single base pair substitutions (SNVs) at best can alter 1 amino acid which can result in a neoantigen. However, with the exception of rare site-specific oncogenic driver mutations (such as RAS or BRAF) such mutations are private and thus not generalizable.

An "off-the-shelf" solution, where vaccines are available against each potential—neoantigen would be beneficial. The present disclosure is based on the surprising finding that, despite the fact that there are infinite possibilities for frame shift mutations in the human genome, a vaccine can be developed that targets the novel amino acid sequence following a frame shift mutation in a tumor with potential use in a large population of cancer patients.

Neoantigens resulting from frame shift mutations have been previously described as potential cancer vaccines. See, for example, WO95/32731, WO2016172722 (Nantomics), WO2016/187508 (Broad), WO2017/173321 (Neon Therapeutics), US2018340944 (University of Connecticut), and WO2019/012082 (Nouscom), as well as Rahma et al. (Journal of Translational Medicine 2010 8:8) which describes peptides resulting from frame shift mutations in the von Hippel-Lindau tumor suppressor gene (VHL) and Rajasagi et al. (Blood 2014 124(3):453-462) which reports the systematic identification of personal tumor specific neoantigens.

The present disclosure provides a unique set of sequences resulting from frame shift mutations and that are shared among colorectal cancer patients. The finding of shared frame shift sequences is used to define an off-the-shelf colorectal cancer vaccine that can be used for both therapeutic and prophylactic use in a large number of individuals.

In the present disclosure we provide a source of common neoantigens induced by frame shift mutations, based on analysis of 10,186 TCGA tumor samples and 2774 tumor samples (see Priestley et al. 2019 at https://doi.org/10.1101/415133). We find that these frame shift mutations can produce long neoantigens. These neoantigens are typically new to the body, and can be highly immunogenic. The heterogeneity in the mutations that are found in tumors of different organs or tumors from a single organ in different individuals has always hampered the development of specific medicaments directed towards such mutations. The number of possible different tumorigenic mutations, even in a single gene as P53 was regarded prohibitive for the development of specific treatments. In the present disclosure it was found that many of the possible different frame shift mutations in a gene converge to the same small set of 3' neo open reading frame peptides (neopeptides or NOPs). We find a fixed set of only 1,244 neopeptides in as much as 30% of all TCGA cancer patients. For some tumor classes this is higher; e.g. for colon and cervical cancer, peptides derived from only ten genes (saturated at 90 peptides) can be applied to 39% of all patients. 50% of all TCGA patients can be targeted at saturation (using all those peptides in the library found more than once). A pre-fabricated library of vaccines (peptide, RNA or DNA) based on this set can provide off the shelf, quality certified, 'personalized' vaccines within hours, saving months of vaccine preparation. This is important for critically ill cancer patients with short average survival expectancy after diagnosis.

The concept of utilizing the immune system to battle cancer is very attractive and studied extensively. Indeed, neoantigens can result from somatic mutations, against which patients can be vaccinated[1-11]. Recent evidence suggests that frame shift mutations, that result in peptides which are completely new to the body, can be highly immunogenic[12-15]. The immune response to neoantigen vaccination, including the possible predictive value of epitope selection has been studied in great detail[8, 13, 16-21]

and WO2007/101227, and there is no doubt about the promise of neoantigen-directed immunotherapy. Some approaches find subject-specific neoantigens based on alternative reading frames caused by errors in translation/transcription (WO2004/111075). Others identify subject specific neoantigens based on mutational analysis of the subjects tumor that is to be treated (WO1999/058552; WO2011/143656; US20140170178; WO2016/187508; WO2017/173321). The quest for common antigens, however, has been disappointing, since virtually all mutations are private. For SNV-derived amino acid changes, one can derive algorithms that predict likely good epitopes, but still every case is different.

A change of one amino acid in an otherwise wild-type protein may or may not be immunogenic. The antigenicity depends on a number of factors including the degree of fit of the proteasome-produced peptides in the MHC and ultimately on the repertoire of the finite T-cell system of the patient. In regards to both of these points, novel peptide sequences resulting from a frame shift mutation (referred to herein as novel open reading frames or pNOPs) are a priori expected to score much higher. For example, a fifty amino acid long novel open reading frame sequence is as foreign to the body as a viral antigen. In addition, novel open reading frames can be processed by the proteasome in many ways, thus increasing the chance of producing peptides that bind MHC molecules, and increasing the number of epitopes will be seen by T-cell in the body repertoire.

It is has been established that novel proteins/peptides can arise from frameshift mutations[32-36]. Furthermore, tumors with a high load of frameshift mutations (micro-satellite instable tumors) have a high density of tumor infiltrating CD8+ T cells[33]. In fact, it has been shown that neo-antigens derived from frameshift mutations can elicit cytotoxic T cell responses[32,34,33]. A recent study demonstrated that a high load of frameshift indels or other mutation types correlates with response to checkpoint inhibitors[35].

Binding affinity to MHC class-I molecules was systematically predicted for frameshift indel and point mutations derived neoantigens[35]. Based on this analysis, neoantigens derived from frameshifts indels result in 3 times more high-affinity MHC binders compared to point mutation derived neoantigens, consistent with earlier work[31]. Almost all frameshift derived neoantigens are so-called mutant-specific binders, which means that cells with reactive T cell receptors for those frameshift neoantigens are (likely) not cleared by immune tolerance mechanisms[35]. These data are all in favour of neo-peptides from frameshift being superior antigens.

Here we report that frame shift mutations, which are also mostly unique among patients and tumors, nevertheless converge to neo open reading frame peptides (NOPs) from their translation products that surprisingly result in common neoantigens in large groups of cancer patients. The disclosure is based, in part, on the identification of common, tumor specific novel open reading frames resulting from frame shift mutations. Accordingly, the present disclosure provides novel tumor neoantigens and vaccines for the treatment of cancer. In some embodiments, multiple neoantigens corresponding to multiple NOPs can be combined, preferably within a single peptide or a nucleic acid molecule encoding such single peptide. This has the advantage that a large percentage of the patients can be treated with a single vaccine.

While not wishing to be bound by theory, the surprisingly high number of frame shift induced novel open reading frames shared by cancer patients can be explained, at least in part, as follows. Firstly, on the molecular level, different frame shift mutations can lead to the generation of shared novel open reading frames (or sharing at least part of a novel open reading frame). Secondly, the data presented herein suggests that frame shift mutations are strong loss-of-function mutations. This is illustrated in FIG. 2A, where it can be seen that the SNVs in the TCGA database are clustered within the p53 gene, presumably because mutations elsewhere in the gene do not inactive gene function. In contrast, frame shift mutations occur throughout the p53 gene (FIG. 2B). This suggests that frame shift mutations virtually anywhere in the p53 ORF reduce function (splice variants possibly excluded), while not all point mutations in p53 are expected to reduce function. Finally, the process of tumorigenesis naturally selects for loss of function mutations in genes that may suppress tumorigenesis. Interestingly, the present disclosure identifies frame shift mutations in genes that were not previously known as classic tumor suppressors, or that apparently do so only in some tissue tumor types (see, e.g., FIG. 8). These three factors are likely to contribute to the surprisingly high number of frame shift induced novel open reading frames shared by cancer patients; in particular, while frame shift mutations generally represent less than 10% of the mutations in cancer cells, their contribution to neoantigens and potential as vaccines is much higher. The high immunogenic potential of peptides resulting from frameshifts is to a large part attributable to their unique sequence, which is not part of any native protein sequence in humans, and would therefore not be recognised as 'self' by the immune system, which would lead to immune tolerance effects. The high immunogenic potential of out-of-frame peptides has been demonstrated in several recent papers.

Neoantigens are antigens that have at least one alteration that makes them distinct from the corresponding wild-type, parental antigen, e.g., via mutation in a tumor cell. A neoantigen can include a polypeptide sequence or a nucleotide sequence As used herein the term "ORF" refers to an open reading frame. As used herein the term "neoORF" is a tumor-specific ORF (i.e., neoantigen) arising from a frame shift mutation. Peptides arising from such neo ORFs are also referred to herein as neo open reading frame peptides (NOPs) and neoantigens.

A "frame shift mutation" is a mutation causing a change in the frame of the protein, for example as the consequence of an insertion or deletion mutation (other than insertion or deletion of 3 nucleotides, or multitudes thereof). Such frameshift mutations result in new amino acid sequences in the C-terminal part of the protein. These new amino acid sequences generally do not exist in the absence of the frameshift mutation and thus only exist in cells having the mutation (e.g., in tumor cells and pre-malignant progenitor cells).

FIGS. 3 and 4 and the data discussed above provide the answer to the question: how many cancer patients exhibit in their tumor a frame shift in region x or gene y of the genome. The patterns result from the summation of all cancer patients. The disclosure surprisingly demonstrates that within a single cancer type (i.e. colorectal cancer), the fraction of patients with a frame shift in a subset of genes is much higher than the fractions identified when looking at all cancer patients. We find that careful analysis of the data shows that frame shift mutations in one gene are found in 14% of all colorectal cancers and frameshift mutations in 8 genes together are found in up to 50% of all colorectal cancers.

Novel 3' neo open reading frame peptides (i.e., NOPs) of APC, ARID1A, KMT2D, RNF43, SOX9, TCF7L2, TP53, and ZFP36L2 are depicted in table 1. The NOPs, are defined as the amino acid sequences encoded by the longest neo open reading frame sequence identified. Sequences of these NOPs are represented in table 1 as follows:

APC: Sequences 1-196, more preferably sequences 1-60.
ARID1A: Sequences 197-297, more preferably sequences 197-232.
KMT2D: Sequences 298-552, more preferably sequences 298-337.
RNF43: Sequences 553-595, more preferably sequences 553-566.
SOX9: Sequences 596-608.
TCF7L2: Sequences 610-680, more preferably sequences 610-630.
TP53: Sequences 681-708, more preferably sequences 681-696.
ZFP36L2: Sequences 709-717, more preferably sequences 709-714.

The most preferred neoantigens are APC frameshift mutation peptides, followed by TCF7L2 frameshift mutation peptides, followed by TP53 frameshift mutation peptides, followed by RNF43 frameshift mutation peptides, followed by ZFP36L2 frameshift mutation peptides, followed by SOX9 frameshift mutation peptides, followed by KMT2D frameshift mutation peptides, followed by ARID frameshift mutation peptides.

The preference for individual neoantigens directly correlates with the frequency of their occurrence in colorectal cancer patients, with APC frameshift mutation peptides covering 14.2% of colorectal cancer patients,
TCF7L2 frameshift mutation peptides covering 6.5% of colorectal cancer patients,
TP53 frameshift mutation peptides covering 6.3% of colorectal cancer patients,
RNF43 frameshift mutation peptides covering 5.8% of colorectal cancer patients,
ZFP36L2 frameshift mutation peptides covering 5.7% of colorectal cancer patients,
SOX9 frameshift mutation peptides covering 4.8% of colorectal cancer patients,
KMT2D frameshift mutation peptides covering 4.7% of colorectal cancer patients,
and ARID1A frameshift mutation peptides covering 3.5% of colorectal cancer patients.

TABLE 1

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 1 | pNOP255295 | APC | MLQFRGSRFFQMLILYYILPRKVLQMDFLVHPA | 2.822 |
| 2 | pNOP124349 | APC | APVIFQIALDKCHQAEVKHLHHLLKQLKPSEKYLKIKHLLLKRERVDLSKLQ | 2.555 |
| 3 | pNOP344680 | APC | YFITFCHGKYSRWIFLFIQPECSEPR | 1.335 |
| 4 | pNOP39262 | APC | AKFQQCHTLEPNPADCRVLVVLQNQPCTKLLNFLQERNLPPKVLRHPKVHLNTMFRRPHSCLADVLLSVHLIVLRVVRLPAPFRVNHAVEW | 1.068 |
| 5 | pNOP200871 | APC | CLQFRKMTMGMKQNQSSLKNQMKTKRKRQKKLLILKRTY | 0.648 |
| 6 | pNOP68492 | APC | KNVLFLPCQQSHHVKQKSQPRLLQNYLHLMQGNQVSCLCTNFYHHKTGCNPKSMLVLHRGICHGCIVLKGHL | 0.61 |
| 7 | pNOP433821 | APC | IFFRSEISLQKWCSDTQKST | 0.381 |
| 8 | pNOP53481 | APC | NMPQFLHHKNSHFMSQKVHLDAVKPNICLQAVKIKPHLHEMPKGRISSIQVLHRVEVVSLKKLPLAKFLLLTKKQYRLIV | 0.381 |
| 9 | pNOP212577 | APC | QMREMHLEEALLPIHIQTLTISLSRKIQIGHVLCLMPN | 0.305 |
| 10 | pNOP475043 | APC | IVLVLKKIEVWRENAELV | 0.305 |
| 11 | pNOP620105 | APC | YPANSRNKRDWN | 0.229 |
| 12 | pNOP22093 | APC | LCLAPKTAVYPCDSLDVFLSSSSFYMAMTKTLYCWEIPGAVKRLGPGPVQHSTTSFTHSLMTREAGVKSESFIFWNRYALTVKPVGSGRKLMNQ AWTRTIKQCQLLLNIRSVLLCVF | 0.191 |
| 13 | pNOP441505 | APC | RLTAGYCECFEEFVLASRCK | 0.191 |
| 14 | pNOP632151 | APC | KKRLELGQLKIL | 0.191 |
| 15 | pNOP89454 | APC | NKVSKDNQGIKVQLILFILRALMINTSSSNHILDSRNVFLHTGHGEPMVQKQIEWVLIMELIKM | 0.191 |
| 16 | pNOP100473 | APC | KFGERTRNWSRQLPSSNRKSRNFFKARFADLHHCSPDCQSHGRSVSHSYLSGRQKFWVYH | 0.153 |
| 17 | pNOP108458 | APC | SKANQSCDGRTTRYLPGYGKTSTAKNSQNSANRKGHTSYTTAFTVPSNRSREVISEQA | 0.153 |
| 18 | pNOP120488 | APC | ATTIQQQKIQELLQSEVCRSPPLQPRLPKSWKKCQPFIPLRKTEVIGLPLNYIV | 0.153 |
| 19 | pNOP296350 | APC | HTLCTSKADKSSGNQGGNGVFIVVNAWYS | 0.153 |
| 20 | pNOP471295 | APC | ETKSPRSRIRCSALIRNF | 0.153 |
| 21 | pNOP515199 | APC | DVIRRHRKQILLIPCK | 0.153 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 22 | pNOP154897 | APC | QVIWEPRYALTVKPVGSGRKLMNQAWTRTKIQCQLLLNIRSVLLCVF | 0.114 |
| 23 | pNOP252656 | APC | GISWQIGLRSRPILCLLAWACHLFMLGNKKP | 0.114 |
| 24 | pNOP331017 | APC | YWQHDCPFTIPEYYSVTQLLFIKRKLR | 0.114 |
| 25 | pNOP333709 | APC | FKICHRYSFITETVIFILKEFIWTKQ | 0.114 |
| 26 | pNOP396063 | APC | GPQANPKREQLSTNFITTLKIS | 0.114 |
| 27 | pNOP458837 | APC | PEGNWNMKQGKSELRWKNN | 0.114 |
| 28 | pNOP525451 | APC | NTRRMYFCHANKVIT | 0.114 |
| 29 | pNOP68811 | APC | PEFSKSKRTYPVYDSFYSPKQQKQRGHLRTSMKPAHMMLSGRMKVKEWEKSTWQLLVMVRVQLHEWTMKQPVF | 0.076 |
| 30 | pNOP105449 | APC | VPARIWKNEHRGHLRTSMKPAHMMLSGRMKVKEWEKSTWQLLVMVRVQLHEWTMKQPVF | 0.076 |
| 31 | pNOP113394 | APC | FPWSKTAVKNVPPFLMKPGRICIKPFWRVQSCSYGFISKKRVCKWKQRKYWIFRRT | 0.076 |
| 32 | pNOP244561 | APC | KNLRKRGHCFLLILTKKKRKKTGITLNFRISLKE | 0.076 |
| 33 | pNOP269190 | APC | TPQVPTTFWTAGMCFSIQVTGSQWFRNKSSGF | 0.076 |
| 34 | pNOP330901 | APC | YMCCRWCTCIFGWHSYLPEPDKHFSHY | 0.076 |
| 35 | pNOP368169 | APC | NPRLNPILKMMKVSFAVMVNTQPT | 0.076 |
| 36 | pNOP456502 | APC | PRNNTDLLCRRYSNMFFKM | 0.076 |
| 37 | pNOP514964 | APC | DMFYALCQIRIQEIFK | 0.076 |
| 38 | pNOP525461 | APC | NTSTTSSNSNSNQARST | 0.076 |
| 39 | pNOP536966 | APC | AKTIKESKYNLSCLY | 0.076 |
| 40 | pNOP545659 | APC | KFFLTNRYDQKAIGI | 0.076 |
| 41 | pNOP612365 | APC | RSCERSSSSVTAP | 0.076 |
| 42 | pNOP69534 | APC | VLSVTLTKKTTIKKMNLSKRLSLTHRENQVNLKHQAMLLNHFMLKIPQFVSQETVLSVLLVLTLKMTCCRNV | 0.076 |
| 43 | pNOP138480 | APC | IEVSLNPYFRNNPLFPSHPKTYQTEGQQLMKSYRILLLKIILRRFAFLIIPL | 0.038 |
| 44 | pNOP152447 | APC | FIFQEFEIAPQVQLFLKKAHPLRLQPPKALVKVKQPPLLLEEPSHL | 0.038 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 45 | pNOP198985 | APC | SVMHVELCGISQQEILKTRKHYGTWGQLACSRTSFIQSTK | 0.038 |
| 46 | pNOP207088 | APC | VPRHLIVVSRDTSKVSMVIMFLTPIDMMIIGQTILILAT | 0.038 |
| 47 | pNOP208063 | APC | ASLCVKKMTMKMISLPIIVNVTLKKNSMKKKRDQQIIA | 0.038 |
| 48 | pNOP211063 | APC | LLEKELEEGHSQVNLKNEIPPLQKAEVQMRLKEEKPHL | 0.038 |
| 49 | pNOP211568 | APC | NCGQKCPSVLMEAGKDLYQAVLESAVLFLWVHFQEEGL | 0.038 |
| 50 | pNOP398231 | APC | KILQYVFQDVVHYHLCHQLKMK | 0.038 |
| 51 | pNOP454649 | APC | KDVARSWKCESIDGMCFRS | 0.038 |
| 52 | pNOP466104 | APC | VPYGICQHIALRIKLIYVL | 0.038 |
| 53 | pNOP486470 | APC | TLEGKVLHRMKDGQDPNT | 0.038 |
| 54 | pNOP524901 | APC | NIMKRNVMWISLLIIV | 0.038 |
| 55 | pNOP526125 | APC | PIKYIVQIIWMIMMEN | 0.038 |
| 56 | pNOP547138 | APC | KWSASKGCHLQSFFY | 0.038 |
| 57 | pNOP559516 | APC | TSDLSCCVCSNETFI | 0.038 |
| 58 | pNOP640763 | APC | QRLCIVGKFPGQ | 0.038 |
| 59 | pNOP641160 | APC | QYRQFKSQGISS | 0.038 |
| 60 | pNOP717530 | APC | TLCSGDPTHV | 0.038 |
| 61 | pNOP109202 | APC | YVRLPLGSGRPFARFCTTLSSRVLEHRRQQELRPAGDEEPGRRSYFWPLGERLAGST | <0.01 |
| 62 | pNOP164140 | APC | KIIPRSSMISSQIMKIESEEVLLLIHLIITRLLKELLTVFHEMIL | <0.01 |
| 63 | pNOP166473 | APC | SIMMEDQQSAMILHGLILKVLLDFQSIGQEPGNVSTANIHHPFLE | <0.01 |
| 64 | pNOP171017 | APC | PLQYYTKTICWNGFDKLDFWRCSQQGYAMLYERLHESTCGPTKI | <0.01 |
| 65 | pNOP198614 | APC | SKKASPDCFKITSTCGKETKSAACVQTSTITKQVATPKAC | <0.01 |
| 66 | pNOP203842 | APC | LTVFQKRQIQTLKIQKIIRQNKMWVAFPCVPWVWKIA | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 67 | pNOP209147 | APC | FCYAQREKQAFPCEKDNGPGPASICVFFCTQQKSVRM | <0.01 |
| 68 | pNOP223140 | APC | WKELLGMRERGGGRKYLNNYKEVLKMKLWLLLDRLIY | <0.01 |
| 69 | pNOP231193 | APC | VLLTNYLNFQGHHPLVLLQLSPQVLEKCHIHLQVDR | <0.01 |
| 70 | pNOP246740 | APC | PYLNWMTIKQRKVIFLQNALILLCPKGKVTSLSV | <0.01 |
| 71 | pNOP262357 | APC | FRNFRPNETAPSSKHAFNLSRQDNDSSRSSK | <0.01 |
| 72 | pNOP262906 | APC | GRGFQGDYRPLQNYCKWTVKCMGLLMTTTVLH | <0.01 |
| 73 | pNOP270883 | APC | AQQTFIIPSSSKHLEKNWKFIFNSFCFIRIQ | <0.01 |
| 74 | pNOP272083 | APC | EENWRNLLHLNLFLHHLDQLLPLGPRHKLQF | <0.01 |
| 75 | pNOP274267 | APC | IRKTCISTPVNFHQRSSKPNLKKKIGGICFI | <0.01 |
| 76 | pNOP281689 | APC | ALGEELEVHLQFFLLHQNPVKKQKVRMKNM | <0.01 |
| 77 | pNOP283121 | APC | EGYPGHFITGARAGAFRGTTGHCRIIASGL | <0.01 |
| 78 | pNOP285366 | APC | ITTQRSEIPKLTAQNPVEPKVLSAILGLTL | <0.01 |
| 79 | pNOP285606 | APC | KIYRDQIQNMVYPLIQKILIGKLFRKVQIP | <0.01 |
| 80 | pNOP288797 | APC | QVIWEPRWKWCIHCCQCLVLMIRMICRELC | <0.01 |
| 81 | pNOP290267 | APC | SKANQSCDGRTTRYLPGYGKTSTEVISEQA | <0.01 |
| 82 | pNOP291694 | APC | VLPFLICLYPHIRLFRLVDGENSHLISVPL | <0.01 |
| 83 | pNOP299057 | APC | NQESLWDHHFILHLIKKKNPLQVIKAHEF | <0.01 |
| 84 | pNOP305102 | APC | APQCQKRKSLQDSRVIMKNIVPEIWVAY | <0.01 |
| 85 | pNOP317504 | APC | ANRTLPNKQVYPRMPVVFQESVLPPKD | <0.01 |
| 86 | pNOP320163 | APC | GDYRPLQNYCKWTVKCMGLLMTTTVLH | <0.01 |
| 87 | pNOP321066 | APC | HAQEPHSFKAQNDCYGKCSSFKESHGK | <0.01 |
| 88 | pNOP322417 | APC | KKMNFLPQIVLLRPFPQVLQMVLNQRL | <0.01 |
| 89 | pNOP323347 | APC | LLLITTQALGKAAQIALQLGHLRSQLQ | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 90 | pNOP358839 | APC | VVYIKLLLHVYLDKLRLIQIPSFP | <0.01 |
| 91 | pNOP360210 | APC | APFWVLPCDICLKERKNETKKLC | <0.01 |
| 92 | pNOP366823 | APC | LPRQLYIHATVMSSSPHPAFTWQ | <0.01 |
| 93 | pNOP370727 | APC | RKYLNNYKEVLKMKLWLLLDRLIY | <0.01 |
| 94 | pNOP371340 | APC | RSQAICEIRIKPCCQADIPNRWVK | <0.01 |
| 95 | pNOP373907 | APC | VGQVKHLLDQDLEIRPLQDLPSNH | <0.01 |
| 96 | pNOP374715 | APC | WNVPHSVLAAQANTVHLVGLLLPE | <0.01 |
| 97 | pNOP389496 | APC | THTSETIHFSPVIQRHTRQRGSN | <0.01 |
| 98 | pNOP391151 | APC | WQCSHAYRGFGKSPELLYSGGCP | <0.01 |
| 99 | pNOP394532 | APC | ELRTVPLTILDLEDLPQVILPR | <0.01 |
| 100 | pNOP400812 | APC | NFLECLQLNQVEVNLIDQKDLY | <0.01 |
| 101 | pNOP406915 | APC | TLFQEPNKVKTKYPQKEHGEK | <0.01 |
| 102 | pNOP409301 | APC | ACEVQGCQYVVSWLKLAISSC | <0.01 |
| 103 | pNOP412763 | APC | FRFHPFPEIRNLSGITISSYT | <0.01 |
| 104 | pNOP420385 | APC | PVAGMYKLRNAKKEKAFKTQG | <0.01 |
| 105 | pNOP433641 | APC | HTLCTSKADKSSGNQDTRLL | <0.01 |
| 106 | pNOP434724 | APC | KGINPQKRIECLMEFCSTLH | <0.01 |
| 107 | pNOP457669 | APC | MVHLHFWLALLLTGARQTL | <0.01 |
| 108 | pNOP467541 | APC | YVSIHTFVCSGWWMAKTPT | <0.01 |
| 109 | pNOP468037 | APC | AIYTERCGIKNNASSSGK | <0.01 |
| 110 | pNOP471165 | APC | ERQKKIRNQRLKLPATQN | <0.01 |
| 111 | pNOP482475 | APC | RGSGQQCSTPQHHSLTA | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 112 | pNOP486128 | APC | TDEPTEPYQTNRFIQECQ | <0.01 |
| 113 | pNOP487292 | APC | VDLYSLLAETQFPLVEME | <0.01 |
| 114 | pNOP488775 | APC | WTRSSKHLRLLLHPTKIS | <0.01 |
| 115 | pNOP490250 | APC | ASCSKCCSSEGPGSSRC | <0.01 |
| 116 | pNOP501789 | APC | NQDKILLSLYQRLMKVL | <0.01 |
| 117 | pNOP502953 | APC | PPTNNQLIRHKLLQSSQ | <0.01 |
| 118 | pNOP504281 | APC | QRRKGKRLVLRSTSESH | <0.01 |
| 119 | pNOP516184 | APC | ESFLRQQRFKETEFEK | <0.01 |
| 120 | pNOP521009 | APC | KIIPIILQNWKLRHLI | <0.01 |
| 121 | pNOP522194 | APC | KWRWDITECVQLDSYK | <0.01 |
| 122 | pNOP524270 | APC | MLREFSQTTKIQRNRI | <0.01 |
| 123 | pNOP525002 | APC | NLKVKESKEEKKFIKV | <0.01 |
| 124 | pNOP525366 | APC | NSPFKQTCLQSLEAGQ | <0.01 |
| 125 | pNOP529050 | APC | RKPSIRKRNMEKNKRK | <0.01 |
| 126 | pNOP540192 | APC | EKETNFTSKTYTTKY | <0.01 |
| 127 | pNOP541018 | APC | FERYTETRFRTWSIP | <0.01 |
| 128 | pNOP541108 | APC | FIKWHLLFLKQRMFG | <0.01 |
| 129 | pNOP543049 | APC | GTEDGELKSSTRARR | <0.01 |
| 130 | pNOP544730 | APC | ILMMMLTFPGKRLN | <0.01 |
| 131 | pNOP546033 | APC | KKLCCPYTFKHLQFH | <0.01 |
| 132 | pNOP551509 | APC | PLLKVEVGYGMCPA | <0.01 |
| 133 | pNOP555084 | APC | RPTNSKTRGEKYIGN | <0.01 |
| 134 | pNOP556098 | APC | RYPSLFLKKQFSQFS | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 135 | pNOP559222 | APC | TPLFRWMPLTKKELR | <0.01 |
| 136 | pNOP559389 | APC | TRGTTGHCRIIASGL | <0.01 |
| 137 | pNOP564648 | APC | CQEAESAPSKFCTE | <0.01 |
| 138 | pNOP565904 | APC | DTSYCKAANKSRSA | <0.01 |
| 139 | pNOP571486 | APC | ILQCYPAPLHQEEA | <0.01 |
| 140 | pNOP571991 | APC | IVSVVMVMKEVK | <0.01 |
| 141 | pNOP574858 | APC | LLEKFDLIQKFQAK | <0.01 |
| 142 | pNOP577317 | APC | NLKVKTYSRLLRVF | <0.01 |
| 143 | pNOP577487 | APC | NPSPSSFGTDTRLL | <0.01 |
| 144 | pNOP586031 | APC | SYQPHRTNLQPTIS | <0.01 |
| 145 | pNOP587088 | APC | TRHGPGQKSNASSC | <0.01 |
| 146 | pNOP589723 | APC | YASQLSKKLQAQP | <0.01 |
| 147 | pNOP59141 | APC | CTPPWARVRSPLCPLLYHPQFSGPGAPAAAGAASGRRRRARAALVLLATGRASGRKYLNNYKEVLKMKLWLLLDRLIY | <0.01 |
| 148 | pNOP592613 | APC | CMWNFVESLSKKS | <0.01 |
| 149 | pNOP598578 | APC | HFSSAISDPNSSE | <0.01 |
| 150 | pNOP599868 | APC | IKDSNLSNGTCCF | <0.01 |
| 151 | pNOP602641 | APC | KTRYHSYRRQKYR | <0.01 |
| 152 | pNOP603193 | APC | LESYSGRCKFHSK | <0.01 |
| 153 | pNOP610345 | APC | RDTYKLFHSYISK | <0.01 |
| 154 | pNOP610470 | APC | RFDPFKTCPATIK | <0.01 |
| 155 | pNOP612555 | APC | RSRSGRNQHGNFW | <0.01 |
| 156 | pNOP616618 | APC | TMQWNGKWHYKPQ | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 157 | pNOP617519 | APC | TYTVSWPKLNFPW | <0.01 |
| 158 | pNOP618023 | APC | VLQLWSIPSRPSP | <0.01 |
| 159 | pNOP618027 | APC | VLRFWKNVIYISR | <0.01 |
| 160 | pNOP618122 | APC | VPARIWKNEHSEE | <0.01 |
| 161 | pNOP618153 | APC | VPGTNSSFKSFPS | <0.01 |
| 162 | pNOP619854 | APC | YFSDRFLRCYKWC | <0.01 |
| 163 | pNOP621732 | APC | ASMSHLYRKMWN | <0.01 |
| 164 | pNOP621939 | APC | AVELWKAKSFTE | <0.01 |
| 165 | pNOP625526 | APC | ERTTVYKLYYNT | <0.01 |
| 166 | pNOP628448 | APC | GSRRKNLICNHT | <0.01 |
| 167 | pNOP633163 | APC | KTCELYFRNQTK | <0.01 |
| 168 | pNOP637232 | APC | NLYHKILNIGHV | <0.01 |
| 169 | pNOP637386 | APC | NQGRKVHWKLKR | <0.01 |
| 170 | pNOP649061 | APC | VGRLPGAFHHRS | <0.01 |
| 171 | pNOP655968 | APC | DTCKKKCRLKK | <0.01 |
| 172 | pNOP658090 | APC | FIFRISQAQSC | <0.01 |
| 173 | pNOP658639 | APC | FTSSCCCCMFI | <0.01 |
| 174 | pNOP663444 | APC | IVKRRCEKLEV | <0.01 |
| 175 | pNOP664052 | APC | KFYSGTYPIQF | <0.01 |
| 176 | pNOP664687 | APC | KLKRNQPSKAY | <0.01 |
| 177 | pNOP664820 | APC | KMGKTQTHNRR | <0.01 |
| 178 | pNOP668825 | APC | MLSTYQKLLTI | <0.01 |
| 179 | pNOP669525 | APC | NFHLMKSIDMQ | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 180 | pNOP673249 | APC | QISTSKDIIP | <0.01 |
| 181 | pNOP676143 | APC | RPGSIMGHGGS | <0.01 |
| 182 | pNOP678565 | APC | SKCKPVFVSRR | <0.01 |
| 183 | pNOP683285 | APC | VLVAHTLHLEG | <0.01 |
| 184 | pNOP687997 | APC | CESSGKSYWG | <0.01 |
| 185 | pNOP691856 | APC | ESFDCQLRSE | <0.01 |
| 186 | pNOP697423 | APC | IIVLNIQMSS | <0.01 |
| 187 | pNOP700014 | APC | KPRERGRKNY | <0.01 |
| 188 | pNOP703850 | APC | MIQMMMILKY | <0.01 |
| 189 | pNOP704337 | APC | MVRKRNQLHQ | <0.01 |
| 190 | pNOP708330 | APC | PWTNHATKQK | <0.01 |
| 191 | pNOP708440 | APC | QCFRKGKSKH | <0.01 |
| 192 | pNOP708789 | APC | QHRIQWNPKS | <0.01 |
| 193 | pNOP713466 | APC | RWRTQIPDKS | <0.01 |
| 194 | pNOP718963 | APC | VCLQRTKSDE | <0.01 |
| 195 | pNOP720338 | APC | WDCCCQSDSF | <0.01 |
| 196 | pNOP721298 | APC | WSGFNYTNGP | <0.01 |
| 197 | pNOP82315 | ARID1A | RSYRRMIHLWWTAQISLGVCRSLTVACCTGGLVGGTPLSISRPTSRARQSCCLPGLTHPAHQPLGSM | 0.725 |
| 198 | pNOP6110 | ARID1A | ALGPHSRISCLPTQTRGCILLAATPRSSSSSSSNDMIPMAISSPPKAPLLAAPSPASRLQCINSNSRITSGQWMAHMALLPSGTGRCTACHTALGRGSLSSSSCPQQPSPSLLPASNKLPSLPLSKMYTTSMAMPILPLPQLLLSADQQAAPRTNFHSSLAETVSLHPLAPMPSKTCHHK | 0.496 |
| 199 | pNOP16341 | ARID1A | APREVALRAPARRRLPAPSRLPPPAPPPPRRLRPSLLSSASGPWGEAAPPRPAGELPSPPPPPSTNCSRRPARPATRATPGATTVAGPRTGAPARARRTWPRSVGGLRRRQLRRRPPREGPNKGATTRP | 0.343 |
| 200 | pNOP8860 | ARID1A | FWPHPPSAAWRSCIALWCASSVTERTRCAGRWLWYCWPTWLRGTAWQLVPLQCRRAVSATSWAS | 0.343 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 201 | pNOP1299 | ARID1A | PHGAAPRRRWRQQRWGGASSLSRGRLAAPSLRLRATLRPPVCRRRRGRRLPTTWRTTKPWPGSAAFRRRGPGAIRGAPAELSRPRLP QPPVQLLLPQQPRLPPARPGLRAEELPERWHSGLRRGGGCRLQAASLLQRLRLLVVFVLRSAALRGHGGRRPLRGRRGNSPAHRHPHPQPTAHV AQLGPGLPGLPRGRLQWRAPGRGRRGQPGGHGLAVLGGCGGSCGGRLGRGPTKEPPRAHEPREQRRGAAARPDPSAIQSNGSDGQDE TSAIWRD | 0.229 |
| 202 | pNOP5538 | ARID1A | PCRAGRVPWAASLIHSRFLLMDNKAPAGMVNRARLHITTSKVLTLSSSSHPTPSNHRPPLMPNLRISSSHSLNHHSSSPLSLHTPSSHPSLHISS PRLHTPSSRRHSSTPRASPPTHSRHLSLLTSSSNLSSQHPRRSPRLRILSPSLSSPSKLPIPSSASLHRRSYLKIHLGLRHPQPPQ | 0.229 |
| 203 | pNOP323677 | ARID1A | LRSTRTKNGGNLQPTSMWAHQAVLPAP | 0.191 |
| 204 | pNOP43369 | ARID1A | TNQALPKIEVICRGTPRCPSTVPPSPAQPYLRSLPEDRYTQAWAPTSRTPWGAMVPRGVSMAHKVATPGSQTIMPCPMPTTPVQAWLEA | 0.191 |
| 205 | pNOP160041 | ARID1A | QGPLHLTTSPHQACRITFLRYPALLPCPGQWRTAPLLASLHSCTLG | 0.153 |
| 206 | pNOP81513 | ARID1A | KSSISSVSMPLNARLNGEKTLPQTSLQLLIPRSPSPSRSSLPLLRDQDLCRGRLPSQPAVPWQKEET | 0.153 |
| 207 | pNOP13360 | ARID1A | SSSVSFLSSYLPSPAWHPRPPPVPCWLSRQCCSVSLRTTLACCSARQPDATSATQWPVGQHHASFHEPIKHCPRSRLYAEEPPDAPVQFPPARLS LISASAAFRRTDTHRHGLLPAELHGELWSPGGVWPTRMLPQAAKL | 0.114 |
| 208 | pNOP109934 | ARID1A | ETSGPLSPLCVCEGDWWIDSGQQEQKMAGTCNQPQCGHIKQCCQLLEKAVVPVSLCL | 0.076 |
| 209 | pNOP205126 | ARID1A | QQQRVHQGQQTRRGPHLMDLQKNGSQPLWMTCCLLGLAP | 0.076 |
| 210 | pNOP3000 | ARID1A | PILAATGTSVRTAARTWVPRAAIRVPDPAAVPDDHAGPGAECHGRPLLYTADSSLWTTRPQRVWSTGPDSILQPAKSSPSAAAATLLPATTVPD PSCPTFVSAAATVSTTTAPVLSASILPAAIPASTSAVPGSIPLPAVDDTAAPPEPAPLLITATGSVSLPAAATSAASTLDALPAGCVSSAPVSAVPANCL FPAALPSTAGAISRFIWVSGILSPLNDLQ | 0.076 |
| 211 | pNOP317526 | ARID1A | APGAAAAGGSRSPGPLSHPVQMIRWAR | 0.076 |
| 212 | pNOP40276 | ARID1A | AATKWSGGGTAWRCSGKTPWLHSPTSRGSWTYLHTPRAFACLSWTDSYTGAFALQLKPRTPFPPWAPMPSFPRRDWSWKPSANSASRTTM WT | 0.076 |
| 213 | pNOP120573 | ARID1A | CLAWCQLPQCRHGWRHKPHGCRRSNAWTAWHPTLWHTPSREDESRLHGQPALWP | 0.038 |
| 214 | pNOP140600 | ARID1A | SGPLFHPGPQCRPFPAETGLGNPQQTQHPGQQCGPDSGHTPLQPPGEVV | 0.038 |
| 215 | pNOP141882 | ARID1A | CGHDAAGCPRAACLGQQGREPLRVYSVRITAVGHLGITVDELIGFTSHL | 0.038 |
| 216 | pNOP162214 | ARID1A | APTSRPPEPISIPVWPRPCLCTPWHQCPAKAHATTNDGRPHTGIS | 0.038 |
| 217 | pNOP204073 | ARID1A | NAAHRSEGQPRRLVAFPWHTPAPIWSLCPCAPHDKAPSI | 0.038 |
| 218 | pNOP221454 | ARID1A | RSMRWTQDRERYWILGGSARCLVQLPWRVGKKKKNF | 0.038 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 219 | pNOP22341 | ARID1A | TITSRSRPAAAVAAAAMGWGRLLTQPRPPCRPQPTASGNPTAGARLPSPPRPPPSSTNNMADNKALAWQRCRAAAAGAWSPTRGPSRTLTT TASPTTSTTPTTPTAAPTPRPRPTR | 0.038 |
| 220 | pNOP26533 | ARID1A | HGRAGRPRRRQQPGQPAAAALGAEESRAAAAGGGGRGGGGSGRARGNEGSRRAGKRGPRRGAAAAGKGAAAGRGREQWGRRRR SRQRRRARRGAGPEELERERGP | 0.038 |
| 221 | pNOP271959 | ARID1A | DVQTPRAAAHPCGQADPAAPQAPRTEAGTTNL | 0.038 |
| 222 | pNOP28543 | ARID1A | FLWQSVLHPRHPFWQPLPQPADYNVSTATAELQAANGWHIWPSCQAARRGDVQRAIQHWAGAASAAAVAPSPAPACQOPATSCPAPPSARC IQPVWQCLSHCHSCY | 0.038 |
| 223 | pNOP339133 | ARID1A | PPHGDRRSSESWSEHIRDFQQPRRAE | 0.038 |
| 224 | pNOP355250 | ARID1A | RKPSSSSGRRRGARRRRRQRPSAGK | 0.038 |
| 225 | pNOP390796 | ARID1A | WAAPYRHQLRLLSKAPCGRGVMT | 0.038 |
| 226 | pNOP419746 | ARID1A | PIIMPTGRARALPPRAPPIMA | 0.038 |
| 227 | pNOP450666 | ARID1A | EMWRWDHDSTIPMEVLMTE | 0.038 |
| 228 | pNOP484623 | ARID1A | SHQLQHPHHTVRSPHCQA | 0.038 |
| 229 | pNOP709605 | ARID1A | QSEDGAWNRA | 0.038 |
| 230 | pNOP78127 | ARID1A | YGWHDQPSGTPIFHGWNHGQQFCRDGSQPRDDGPWGCKVNSSHQNEQQGRMDTQDRIQIQEIQFFYYNQ | 0.038 |
| 231 | pNOP84384 | ARID1A | PKEPGVPGDGCCTAGQPGSGGQPGSSCHCSAEGQYRQPPGLPRGQPCRHTVPAEPCQPPPHAEPTL | 0.038 |
| 232 | pNOP86506 | ARID1A | KGGGTGPRGELQQSGVVVGLLGDAPGKHLGYTRQHLGAVGPISIPREHLPACPGRTPTLGSLPFS | 0.038 |
| 233 | pNOP108335 | ARID1A | RTNPTVRMRPHCVPFWTGRILLIPSAASVCPIPFEACHLCQAMTLRCPNTQGCCSSWAS | <0.01 |
| 234 | pNOP115908 | ARID1A | TTRQMGHPRQNPNPRNPVLLLQPMRRSPSCMSWVVSLRGRCGWTVIWPSLRRRPWA | <0.01 |
| 235 | pNOP144966 | ARID1A | RQPPGRKARAPPWGRRSRWERSCRTGPRAMGVAAAAEPAAAAGPARSRT | <0.01 |
| 236 | pNOP145255 | ARID1A | SHTACVEAEEAAHNERHWNPGGMAGNDVPQVWSPGREHMGIRYHQHPAV | <0.01 |
| 237 | pNOP152466 | ARID1A | FLWQSVLHPRHPFWQPLPQPADYNVSTATAGIQPCSPAPANGEPHLS | <0.01 |
| 238 | pNOP157058 | ARID1A | AYPDDLREQDRAAAFPASRTLPTSPSEACDNSRGYTRDNRPGGAPT | <0.01 |
| 239 | pNOP171474 | ARID1A | QVSIPALWDENAEGRSPSTCLAHSTCPCAAPHDSAGYHLPTWLC | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 240 | pNOP187097 | ARID1A | DLSHMAGLTHTRSNRDLRQDRSKDMGTQGSHTGPRPRSGTR | <0.01 |
| 241 | pNOP222331 | ARID1A | TEQMKCCTQIRGPTTKARGLPMAHASPHMVPLPLCPP | <0.01 |
| 242 | pNOP232518 | ARID1A | CGGLPARCLPWPRWTRTTQSLLCTNHGCWTSRYHR | <0.01 |
| 243 | pNOP251638 | ARID1A | DPTVYPSGLAGPSCQALRLCVQYHSKPVICARQ | <0.01 |
| 244 | pNOP266437 | ARID1A | PRMELRVQRPSRRAASFHLALAQHRATGTSRS | <0.01 |
| 245 | pNOP272985 | ARID1A | GKLQGVIPSCPQGRAPTAGWVTPTVVLPALG | <0.01 |
| 246 | pNOP280686 | ARID1A | VTPPWATGLMALTWPICHLRLGQGCVPHQGA | <0.01 |
| 247 | pNOP28463 | ARID1A | CTVFDWPVMTAVGHLPPPCVCACVENLETDCCPLFMQNHLRIQFTLCCPASPLGKSLSCFSLLLPPPLPPSPHAFLFLVLTLLPSGPYPTLFEKTKLC LHRRLFLF | <0.01 |
| 248 | pNOP286473 | ARID1A | LPAPTKHAESHSSGIQPCSPAPANGEPHLS | <0.01 |
| 249 | pNOP289760 | ARID1A | RTALPPHSSSRARPASSTCRTHPLSQLVWT | <0.01 |
| 250 | pNOP325333 | ARID1A | PLQSCCRPWARKCGDGTTTALSLWRSL | <0.01 |
| 251 | pNOP326245 | ARID1A | QQHHDLQPQSAPRVARAPCRIFPTMPD | <0.01 |
| 252 | pNOP329083 | ARID1A | TGKPKLLSPCMLLPTLSKTGRQATPI | <0.01 |
| 253 | pNOP342491 | ARID1A | STLRDPHIPWVEPWPTILQGWQPAQR | <0.01 |
| 254 | pNOP345053 | ARID1A | AGAIQLGSRMPLMMEVTPHSRSGIP | <0.01 |
| 255 | pNOP357957 | ARID1A | TPWVPEVKCMDSLASHLMAHSLQGG | <0.01 |
| 256 | pNOP363287 | ARID1A | GKHEHWGPTAESHAFQPRLGDVFS | <0.01 |
| 257 | pNOP366177 | ARID1A | LASHDSRGTPPPVCVCVCGELRN | <0.01 |
| 258 | pNOP382230 | ARID1A | LCQQAEHGLCPPGPRLSWREPNR | <0.01 |
| 259 | pNOP391130 | ARID1A | WPRRSPPPPAAWATRRRRRPRS | <0.01 |
| 260 | pNOP39264 | ARID1A | ALGPHSRISCLPTQTRGCILLAATPRSSSSSSNDMIPMAISSPPKAPLLAAPSPASRLQCINSNSRYPALLPCPGQWRTAPLLASLHSCTLG | <0.01 |
| 261 | pNOP399373 | ARID1A | LHIPEAEFHDSKPWVSAQYEYL | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 262 | pNOP460168 | ARID1A | QICLLWVGNLWTSIASMCL | <0.01 |
| 263 | pNOP471545 | ARID1A | FGGISPSHLALLKPHSLC | <0.01 |
| 264 | pNOP472965 | ARID1A | GRARRYEPEPSVKTLQLA | <0.01 |
| 265 | pNOP503306 | ARID1A | PSTEPPEHQDPRGRTPQ | <0.01 |
| 266 | pNOP525902 | ARID1A | PFQARTSQLQRIVRRS | <0.01 |
| 267 | pNOP526697 | ARID1A | PRTENATGSWEVQQGV | <0.01 |
| 268 | pNOP532250 | ARID1A | SSSHGGWGRRRRTSRS | <0.01 |
| 269 | pNOP535077 | ARID1A | WELDLLMDKGLIVWLA | <0.01 |
| 270 | pNOP536697 | ARID1A | APSQDPPACLIYLVQ | <0.01 |
| 271 | pNOP539995 | ARID1A | EPRGHQGEQQVSIWH | <0.01 |
| 272 | pNOP561120 | ARID1A | WGACPMSQIRILMAA | <0.01 |
| 273 | pNOP564630 | ARID1A | CPSSLVSWQRAHGH | <0.01 |
| 274 | pNOP568326 | ARID1A | GDSLFRQGQASFRE | <0.01 |
| 275 | pNOP57388 | ARID1A | AHQGFPAAAKESRVIQLSLSLLIPPLTCLASEALPRPLLALPPVLLSLAQDHSRLLQCQATRCHLGHPVASRTASCILP | <0.01 |
| 276 | pNOP578746 | ARID1A | PLPPAAAAAAATT | <0.01 |
| 277 | pNOP580855 | ARID1A | QWPAALADWWGGHH | <0.01 |
| 278 | pNOP583798 | ARID1A | SCCTTSTQNGSRHH | <0.01 |
| 279 | pNOP584557 | ARID1A | SLHVLRAGPQRRDG | <0.01 |
| 280 | pNOP596649 | ARID1A | GEGHGHDKSACCG | <0.01 |
| 281 | pNOP600191 | ARID1A | IPSTSCCMMTTAS | <0.01 |
| 282 | pNOP600818 | ARID1A | KCRRQVPQYLPRT | <0.01 |
| 283 | pNOP616167 | ARID1A | TGRRPSPRHLCSC | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 284 | pNOP616285 | ARID1A | THWFHKSFVMYCF | <0.01 |
| 285 | pNOP624639 | ARID1A | EEDVGGPLSGLH | <0.01 |
| 286 | pNOP628397 | ARID1A | GSLWQHEESRE | <0.01 |
| 287 | pNOP643975 | ARID1A | RTRTGTRALGPP | <0.01 |
| 288 | pNOP650952 | ARID1A | WTSRKTDHSHYG | <0.01 |
| 289 | pNOP658966 | ARID1A | GCSARHHVAGA | <0.01 |
| 290 | pNOP667279 | ARID1A | LMKRRRNRTKG | <0.01 |
| 291 | pNOP700714 | ARID1A | KTLEPRRHGG | <0.01 |
| 292 | pNOP704301 | ARID1A | MTSPWGQKEL | <0.01 |
| 293 | pNOP708028 | ARID1A | PSTSVSQGC | <0.01 |
| 294 | pNOP708425 | ARID1A | QASSKDRTEE | <0.01 |
| 295 | pNOP718154 | ARID1A | TRRGRRRGSS | <0.01 |
| 296 | pNOP76377 | ARID1A | FQEVPAQDPASLSCGIRIYAGAPDSPVNQQFHGRRRRLKATNSSIHTTQSDPPIARHEQEQFSWDPGCL | <0.01 |
| 297 | pNOP91542 | ARID1A | HGQYATSGWVRDVSPTRGHEPENPRNCCRHACCCQLYPKQAARLPQYESRGHDGNWTSLWTRD | <0.01 |
| 298 | pNOP234091 | KMT2D | GPRSHPLPRLWHLLLQVTQTSFALAPTLTHMLSPH | 1.491 |
| 299 | pNOP134 | KMT2D | TRRCHCCPHLRSHPCPHLRNHPRPHLRNHPRPHLRHHACHHHLRNCPHPHFRHCTCPGRWRNRPSLRRLRSLLCLPLHLNHHLFLHWRSRPCLHRKSHP HLLHLRLYPHHLKHRPCPHHLKNLLCPRHLKHLACLHHLRSHPCPRHLKSHPCLHHRRHLVCSHHLKSLLCPLHLRSLPFPHHLRHH ACPHHLRTRLCPHHLKNHLCPPHLRYRAYPPCLWCHACLHRLRNLPCPHRLRSLPRPLHLRLHASPHHLRTPPHPHHLRTHLLPHHRRTRSCPCR WRSHPCCHYLRSRNSAPGPRGRTCHPGLRSTCPPGLRSHTYLRRLRSHTCPPSLRSHAYALCLRSHTCPPRLRDHICPLSLRNCTCPPRLRSRTCLL CLRSHACPPNLRNHTCPPSLRSHACPPGLRNRICPLLSRSHPCPLGLKSPLRSQANALHLRSCPCSLPLGNHPYLPCLESQPCLSLGNHLCPLCPRSC RCPHLGSHPCRLS | 0.972 |
| 300 | pNOP21934 | KMT2D | ARVMPVPVFLAQSPSQALQTRRGVAPCPWSWGSLRMLVQPEMRAPYGSVLTHCQRLMTHYCAMLGQLSAEAKLRGRRGGAAPQPVPAS NRVAAAVSQEDAGLVEEPMEDVVEDGPG | 0.648 |
| 301 | pNOP111349 | KMT2D | PTLRWGLGGSQQPCPRGQQVSSMPRSQVGSPPILSGPLGRVHLWAPPLPCVSLSLRQ | 0.259 |
| 302 | pNOP170800 | KMT2D | NRLMRLNGRPCCGWSQDPWALRSALPLLLMPLNPAWHLCSLR | 0.259 |
| 303 | pNOP58594 | KMT2D | SKSLASFSGENGCTCSVWGALCSTPSDSCCLTRWLTFIVPLPSIPWATRPRASIGASAPTIVAAAIAVLLVRTTGGRSL | 0.259 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 304 | pNOP17440 | KMT2D | WTARSWLVRIKIQNRQLMDLQLLRTQVPLSQTCPTHMWEERSLSLVLVGPGFRRLLRTAVGVRCGVVLSVTAGSPVTGSGSYGALSCHLIGPGV QWCPLGGAQGPMRQCCPVRTYHRLVSLRALHLPT | 0.194 |
| 305 | pNOP118816 | KMT2D | PTGPT5PHSPAARGTQPAPRCCPHHFHWQPHYPRRLVYLCGRVPEAAGGLGAWP | 0.13 |
| 306 | pNOP144483 | KMT2D | PVRLTDRPYISAFPRSQGHWAARPPLLPPPFSLAAPLPPPACLPLRTGS | 0.13 |
| 307 | pNOP189145 | KMT2D | LLGPNLRPLRAAVLCPLAHCPPTLSPECLPVLSPSPAPSLH | 0.13 |
| 308 | pNOP408074 | KMT2D | VTRRHHPRRCPPHPHRCSRRW | 0.13 |
| 309 | pNOP413106 | KMT2D | GEAKLPSPCSRPHLLGSPGRP | 0.13 |
| 310 | pNOP11179 | KMT2D | APCQGPKWAAPQFCPVPWDGCICGHPLSHAFHFPSSRGAFPKAPCPSAWSPATPWDQQPFWARPHLGQASKHKLHSSHRELPPIGQPPGA QQRVHRGELWAVPTTPSVGSATTCTRRIPPLPVPWSLTAIRHHLSCRKARRPRDWNG | 0.065 |
| 311 | pNOP129784 | KMT2D | KHCSCYAQSTRGLHIWRRLAVQCVRGQGSCVTCSSVPAVGITITGPAQTLL | 0.065 |
| 312 | pNOP139704 | KMT2D | PSPGCSVPPSWHSRVRALWDTGWSQPSSSSSNNSTNSKGPWQGCPIFSRV | 0.065 |
| 313 | pNOP143520 | KMT2D | LCLLPALRGKACGACCTSRAGAHEGERARAPVLSRRCVADRNWHGLAA | 0.065 |
| 314 | pNOP16127 | KMT2D | KAAVRHCRGPFFKVDSLWAICPPAAQWTPTQASASPRSWILGSAGASLARNPVSPTAPGRAQVAPRPPPQPPRRVRATDSPITSGVFSAGRR MRSWASCPPSHLCSMPTLIFLISSKTTQTGQAVANKS | 0.065 |
| 315 | pNOP17996 | KMT2D | ALPQAPTGARPSAFAGPLWTGPCLSPGAPLPHGTAHLSPLS | 0.065 |
| 316 | pNOP187538 | KMT2D | FGSRSSATPCGRRRKQLQQLQEQWGLQAAGVLSPAALPLSS | 0.065 |
| 317 | pNOP20115 | KMT2D | GLFSQPGWVPTAAFPGSCRCPTARFAPATDAHPATSSCPPATPGSIHGYVQSRAYAKWAAWRAGRIGTPAFLTASAITFAHGHHATFHHVHFA AAIGNAAAAGKQLLPRYRPGQICCRRYH | 0.065 |
| 318 | pNOP209010 | KMT2D | EPWGRGRQSFRAPALAPTFWGVPEGPRGEEGRAWGILS | 0.065 |
| 319 | pNOP22159 | KMT2D | PCHHCTSGANGEDGLASQARQDWRVLSPQMPLALMTRRMGTWTPMSCSRVKVVWSTWSAKLNWRAPSALMWSLAKRRPRKAKNASVN HIGLALVVSWCDSGNPTHARKRGLLHRRRC | 0.065 |
| 320 | pNOP248474 | KMT2D | SPLSLSLVRHPMGSTAILGPAPPWASLKAQTTQ | 0.065 |
| 321 | pNOP251217 | KMT2D | CQCQFSWLRAPPGLSRPGGGWLPVHGVGGLYGC | 0.065 |
| 322 | pNOP264714 | KMT2D | LHTLWALCQPGDLPYLSCSLRRRGPTPVPPL | 0.065 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 323 | pNOP28077 | KMT2D | PQGTSTHRAAPWGPAAGPQGRAMGCPHYALRRFCHHLHPTDPSPTCMEPHSDQASPLLSKEKTQGLEWVALWRQLNSQVPRTQACPALAKQSWRSNGSASDYESC | 0.065 |
| 324 | pNOP29324 | KMT2D | GQGLDLRAHPGSLPHQEPYLQDQSLALSIPHLHHPALKSQRDLHNYLPPAPSFPLRPSSLPPIQGPPNLRGQPWSRLLGGSHLLPSLQIPCLARVWDLGIPQTT | 0.065 |
| 325 | pNOP224899 | KMT2D | PADTTLVAAPHPTPIGAAEDGEWRHPI | 0.065 |
| 326 | pNOP363170 | KMT2D | GGPLEVGRCPLALTTIPSCLPRIT | 0.065 |
| 327 | pNOP36658 | KMT2D | GPYTCPPRTWRVLLGSPLVCCMVGRRMGAGGPRTMWCGQGHLLRDLTALLPLHQARCLHPLPLITWMSTALPLPLRDCQRPLPIHENTAAAMPRAQ | 0.065 |
| 328 | pNOP412059 | KMT2D | ELLSLSPLSQSPGRSDYPLRC | 0.065 |
| 329 | pNOP421083 | KMT2D | QRGQNHHHLQPANPQRRGANL | 0.065 |
| 330 | pNOP43053 | KMT2D | PLGVWHYLDSLVAPSLIQLWPNSSNSNILVGLDPWLALQGASSLATLLFEASDLIQGFYRKGSCSCSSNVCSWPRNCSSSSSNSSSSTF | 0.065 |
| 331 | pNOP44838 | KMT2D | CCSRAGVVWSVLCVRCVARPPTPHACCSVMTVILATTHTAWTPHCSPSPRAAGSASGVCPVCSVGLLPLASTVNGRIVTHTVGPVPAW | 0.065 |
| 332 | pNOP483870 | KMT2D | RTLPAPFPLGTFSCQSPY | 0.065 |
| 333 | pNOP580931 | KMT2D | RAGGAPQGCCLCPG | 0.065 |
| 334 | pNOP596763 | KMT2D | GGCISGGGSLCSV | 0.065 |
| 335 | pNOP68935 | KMT2D | PTLPATSTSHAPLYGCEQPATCRRLPSFLSATLSWVPALITAATATTVAATTGNSSNLHAICHVSSLSINSWT | 0.065 |
| 336 | pNOP69709 | KMT2D | ACPPYDPSPISRLPSGAGSHPDGAPSSSFATPSAPPGSPKLPSFPVLSSCPTTVRSLPVESHREGSGGLR | 0.065 |
| 337 | pNOP8118 | KMT2D | YRATTSQTRTCPPVWAGSAWGWNHAYGGSASSTAPRSPGQKPTAAALKSSAAAATGTPHAAAAAESGSTPDPTLPGAWDPDLSPPGPPGLPTSTWGLPWTTDRPPPGARGRASTSGPTPAPCPTRSLIYRTSPWPCPSHTSTIQPSRAKETFTITFPQLPASH | 0.065 |
| 338 | pNOP102126 | KMT2D | TTVFIQHPTPRVLPCQLVWSWSTGPRRALSLAAPILMPWKLGSCPVRIPSWMTILMTPRP | <0.01 |
| 339 | pNOP106859 | KMT2D | HPGLCLLKLFAHHPLPLASSPLTLILAHPHALSPVTHLPHCISHPDPSPLKLPLRLGL | <0.01 |
| 340 | pNOP1069 | KMT2D | FKAFTGKAAAAAAATYAAGPETAAAAAATAAAAPSRTGPAATAAGSWSTDKPSGSGQAPGPYASQQPPRPPGPAAVPSTTPGAPGHAGPCPGGCVAAAAPQSFGPPGPSQTGAYDPVPGAWFPPAGTAGSGPYGTQAGHSPAAAAATTAPTARVHGRAVPSSAESDVTQMAAQTERSAHGLFTAASAAAAAATATATSAAAAATTATATSAATAATASTAATAAAASTAATAAAASTAAATAATAADGPFKPESNFTVSSATTAAASGTWPWHASKASSTLF | <0.01 |
| 341 | pNOP108932 | KMT2D | VPRWREPPVCQALVSQCLVQLVLPSSLSCGTMYRKDWDLGALRFLVRAHLRDPVFTL | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 342 | pNOP109806 | KMT2D | EAPKLSISEHPILGPCPYSSNSNNCGSNNRQQQQPPCDLPCQLAFHQLLDLNLAAKP | <0.01 |
| 343 | pNOP110054 | KMT2D | GEAQGGGWTPPFSLPIHHCYPQGRARTCCFWPGAKARTEHDGQPGYPDGHRAIF | <0.01 |
| 344 | pNOP114830 | KMT2D | PSAPCASELVPPAAAIACVAPMSTILLVPSVPSACSSRTRPCCVQCIRSRGPVSKS | <0.01 |
| 345 | pNOP116135 | KMT2D | WGSMRLSCTRWRLRKFQNLNAQPWNPVPPVLSLPQWGTFPAPPPALPQPWMTSLA | <0.01 |
| 346 | pNOP118654 | KMT2D | PGSSPHQQGAEARGTGQPAPRCCPHHFHWQPHYPRRLVYLCGRVPEAAGGLGAWP | <0.01 |
| 347 | pNOP118804 | KMT2D | PSRRAVGGRRMSGKWQSLMSSLAQPCDLTRYRETCVAAVSVMRRVTGPLMGLPVC | <0.01 |
| 348 | pNOP127343 | KMT2D | SGPCKIIQGHNLPNQDLSSSLGRVCLGLESCLRWVSFEHSSKESWPKTHSCGT | <0.01 |
| 349 | pNOP127724 | KMT2D | TRTASGLWNPWPRRQPYATAEALSSRWTPFGQSALQQPNGLLPRPLPVPVPGF | <0.01 |
| 350 | pNOP137298 | KMT2D | CLQSPDPDPSGISGRAPEPGLGPKAPGATPCPFGTFSSKSPRHLSPWLLH | <0.01 |
| 351 | pNOP137386 | KMT2D | CSVAWLYPEEPTRHLEPPETGEPRPRATHSAQLYLQCLQSGCATALGPTS | <0.01 |
| 352 | pNOP142770 | KMT2D | GPQKPREMEAQKGRNSPHRRKEMMVQILQMKNPVASRAKPIHQDLRMGA | <0.01 |
| 353 | pNOP144316 | KMT2D | PNRAGEATAAPATTRAADSAADPAQHPAAGEGNSCSCRSSGASRQLGC | <0.01 |
| 354 | pNOP152835 | KMT2D | GRSAQDPLPLWSLELSEMDELRSFEATRQGSPPTHNLFPPERDEGEER | <0.01 |
| 355 | pNOP154481 | KMT2D | PLWRSTPNASRQQGRAHHVKNRKSHVHRWPPHHPLSSNPTSLTRSLI | <0.01 |
| 356 | pNOP155302 | KMT2D | RSPTPMRCCSQRAPPQALSQRRGKLRVLVGRKRVWKARAQTLALIG | <0.01 |
| 357 | pNOP161094 | KMT2D | SSGERFQQLTKPPTCKRPKITGQLTASTRCRSRLRARSTSRPRWAT | <0.01 |
| 358 | pNOP165656 | KMT2D | QRIPYFLPKTTHGGTACSLLEVQGVPGVPGLWGGLSRTESQLGVV | <0.01 |
| 359 | pNOP169094 | KMT2D | GKTQPLWMGLMLRVHSQSLLDRPLAVMLVNLKAPLCSWPRSWPL | <0.01 |
| 360 | pNOP172213 | KMT2D | SHCKGQDGGFERHQESDGSGQHWGGTWYEQTASVSASPEALGGT | <0.01 |
| 361 | pNOP172370 | KMT2D | SQLLLPLRLWLLTLIALPVRRRRKKMMTPCRIPWFSSPTQTLS | <0.01 |
| 362 | pNOP172794 | KMT2D | TRRGKALTLWGLTTPACPTPAPASAQLSAAAATSEASRTTAAAS | <0.01 |
| 363 | pNOP17361 | KMT2D | RSRLVYTASPGRLCVPSSALPKKLAVSSQKLMLRSSSWLQSSRARSRNNWIRSGNSRRSTLISWQNIGTSSSNNSSSSNNNSNSTQLCWLSALPRV PGCPSSLVSCSLAMGCSHHRGLRVGKPEVFA | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 364 | pNOP174645 | KMT2D | EEGAAEAAAFSTVAACPAAAATAAARPTVCTRPCPGHVFAT | <0.01 |
| 365 | pNOP175361 | KMT2D | GVAVPYPAAPTDAAEGARGADWCTPQVPEGSVCQAAHCQKSWP | <0.01 |
| 366 | pNOP178870 | KMT2D | TISAWHWFHGATAEIPHTHEKGACCTGGGVEWGWAARRGDTC | <0.01 |
| 367 | pNOP182619 | KMT2D | LPANVLAGSALNAKCAKPAGNLGMTLRCWFVRRVTKDTILSA | <0.01 |
| 368 | pNOP183568 | KMT2D | PRGSRGDLAVICRTMWQLGVARSGVLVIPPSLVPTRPLLLRE | <0.01 |
| 369 | pNOP185368 | KMT2D | TRVELYCLLSNNSSSKWHLALACQQSLFNTFLALEPWVQPSS | <0.01 |
| 370 | pNOP18835 | KMT2D | KAAVRHCRGPFFKVDSLWAICPPAAQWTPTQASASPRSWILARNPVSPTAPGRAQVAPRPPPQPPPRRVRATDSPITSGVFSAGRRMRSWAS CPPSHLCSMPTLIFLISSKTTQTGQAVANKS | <0.01 |
| 371 | pNOP188940 | KMT2D | KTWRPMTPTWMTCSMETSLTCWHHILILSWTLGTRRISSMST | <0.01 |
| 372 | pNOP191904 | KMT2D | STPLVPKGTVTLSHRWLPPSWRHPSALHQKLTALTLSLSPL | <0.01 |
| 373 | pNOP193752 | KMT2D | CRTCVWYVAALAGGQRATSLPVRSALSAITLTVSTARSPR | <0.01 |
| 374 | pNOP194798 | KMT2D | GLICAPPAGSALCFLRGSAWHDPEPSGPPTAHARAAHAK | <0.01 |
| 375 | pNOP198849 | KMT2D | SRSNWQCSSSWQTASSQIQTWTNLLQKISLIPLQRPRWWL | <0.01 |
| 376 | pNOP198864 | KMT2D | SSAATVNGGCMQAVRASSQRTMWSRQPMKALTVSPASPTW | <0.01 |
| 377 | pNOP199023 | KMT2D | SYGGPCAAPDAGRLISSWGWPARGIPHYPTWHPQTPALHT | <0.01 |
| 378 | pNOP199159 | KMT2D | TISAWHWFHGATAEIPHTHEKGACCTGGGVEWGWAARRG | <0.01 |
| 379 | pNOP201536 | KMT2D | ELLCSAPSLTALRPFLPSACQSSVPVQLPVSTDTPASVC | <0.01 |
| 380 | pNOP20393 | KMT2D | TCWLPCLHPLTIRLRMSGWRVMRIAILITALCQLHPLRASWGRRPLVSLIWAQAGGSKRTSPSPSLSSPSFLGPASQSSQIPNLMGPLAWRSLESC LSQLGKRAKEVRCQSCSQSLLLQPRT | <0.01 |
| 381 | pNOP209424 | KMT2D | GGEGAAAQLPSPHPHQTGSQQQFPRKTPASWRSPWRTW | <0.01 |
| 382 | pNOP211037 | KMT2D | LKGMRRRSNSGEGARRANWRTCSLLTCRKPSLGRSCWT | <0.01 |
| 383 | pNOP211152 | KMT2D | LPHILPPTAHRPQGRLEVQVCVLYAVWGCFPWLPL | <0.01 |
| 384 | pNOP21288 | KMT2D | SRRRARCLALTRLVSSSSSHPRCPPKCLRRTPLDWPLPIPWSPASPRHRPPIPPILVLRGPLRSPRCWAPHLVLGLASQGNSTLPHLAPPDTSPPHL THSSNPAAPRWITWLCLRALG | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 385 | pNOP214330 | KMT2D | TGFPQKNCPRWNPRTCSSSSRMFWALNENSIWVVEPLA | <0.01 |
| 386 | pNOP215253 | KMT2D | WSPELLSVRHSFSIPWFPKTPLLPSALLLPYHCPFPPR | <0.01 |
| 387 | pNOP215460 | KMT2D | AAESRPDPLCWDTGAEQPCGVAPKQAEWPHPGARVLP | <0.01 |
| 388 | pNOP217529 | KMT2D | GPAPSHPSRDPQTSGANLGAASWEGLTCCCPACRYLV | <0.01 |
| 389 | pNOP217538 | KMT2D | GPFCSWGGPAKLWTRDPKSQGRWRLRKEGTPHIAERR | <0.01 |
| 390 | pNOP218359 | KMT2D | ITARGGELSKLFIPLWAPPYGAATHDQPHWLCPIRA | <0.01 |
| 391 | pNOP218743 | KMT2D | KSTQWLSSTLAPSFGTRWPTGGRKSTKSRIEASTCSE | <0.01 |
| 392 | pNOP220563 | KMT2D | QGSGTLGSPRQPSRNPEARAEQPGTWASGPGEWTGGA | <0.01 |
| 393 | pNOP223482 | KMT2D | YSSGPTAATATFWWGWIPGWPFRGLLPWQPCSSKPRT | <0.01 |
| 394 | pNOP224854 | KMT2D | EEATAARAQEEQTGGHVPCLLAGSLLWEGAAGPEP | <0.01 |
| 395 | pNOP23772 | KMT2D | NRRAPPQHPLSTAIPTMSPIWMCDSSRPHLLKNPPRPLPPWHLLLPVPLLSPWLNFPPNPWLSHPSPHLCHMPHPLNQPDPSPVPGPLKKVKI PVLLASRNGKECAGSGFGCC | <0.01 |
| 396 | pNOP240334 | KMT2D | WAAGIPGWAQGHFLAVGTQLRRPPLGPREDHQLTC | <0.01 |
| 397 | pNOP243509 | KMT2D | GVSHAHSLCCCSQEPEWRDGGSGGAAEHEDPQLL | <0.01 |
| 398 | pNOP245157 | KMT2D | LLTLIALPVRRRRKMMTPCRIPWFSSPTQTNLS | <0.01 |
| 399 | pNOP257143 | KMT2D | RPPSSSPQEMERSALEAASAAADHPEGQWAAGG | <0.01 |
| 400 | pNOP257396 | KMT2D | RLPCAPGPRGAGPCDPYGGLPRMQADSRAGLTM | <0.01 |
| 401 | pNOP257632 | KMT2D | RRKSLGHPLLAMGPQTWALLTHPPQAPTWVAWS | <0.01 |
| 402 | pNOP258695 | KMT2D | STPLAVPDQSLKSSHTTNAFSHPLSHLILTTL | <0.01 |
| 403 | pNOP259446 | KMT2D | VGSMEGRQAWYPSRAHSQCYHRSPWAPCHLPCA | <0.01 |
| 404 | pNOP261027 | KMT2D | CHCPLSRGLRGHAHLLEPPHQQSSLLLSLFYW | <0.01 |
| 405 | pNOP261872 | KMT2D | EGLLWGHGRTTSSPADPQPTEWPRRILPAGKV | <0.01 |
| 406 | pNOP269687 | KMT2D | VRTPTDWLLKGFGAWRYQVFPHRNPQPHRPLN | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 407 | pNOP270434 | KMT2D | AAAQCTERTGTWGHSVSWSGPTSETPFLPCK | <0.01 |
| 408 | pNOP276046 | KMT2D | MPSLGTQCHQSSPFPNGGPFLPRPQPCPSPG | <0.01 |
| 409 | pNOP277209 | KMT2D | PVLLYQLWASLSRGLPGHCSDCPQTCWLAVP | <0.01 |
| 410 | pNOP277754 | KMT2D | RARCSVRCMPPAAKGWARDLYATQGTRAPAM | <0.01 |
| 411 | pNOP279143 | KMT2D | SKSSSRAWRTWSSLTPLPRPCGIASLSLWLP | <0.01 |
| 412 | pNOP284778 | KMT2D | HHSAGRTAAHVPCGGPCVPRHRTAAASPDG | <0.01 |
| 413 | pNOP285042 | KMT2D | IEQQSSSNTPHQGSYPANWFGAGQPAPVEH | <0.01 |
| 414 | pNOP287872 | KMT2D | PLCPLWQWLPSQWAEPAEGGLMKWGAAHWP | <0.01 |
| 415 | pNOP298931 | KMT2D | NHPWRNCLLTLGSARRAGCAPVGRAQQN | <0.01 |
| 416 | pNOP302234 | KMT2D | SPHSLGTHNSLSNPSPSLSPALCSCSHL | <0.01 |
| 417 | pNOP303477 | KMT2D | VAPWGQGPSLAMTDSPGHLHQPRLPLWM | <0.01 |
| 418 | pNOP310713 | KMT2D | MDRWCLRHPNSASSRNLGKSHVPWEPSQ | <0.01 |
| 419 | pNOP318057 | KMT2D | CHQIPFLLHSHPSSQLRPHRPCLLWGS | <0.01 |
| 420 | pNOP318220 | KMT2D | CPPSHQLMPSSNAWLHPWLWPIKGIC | <0.01 |
| 421 | pNOP318964 | KMT2D | EAQAGYRAAEQDPETTGSGPETAEGAH | <0.01 |
| 422 | pNOP323435 | KMT2D | LNHCPGWRAVKTIYSAMGATPLWSCHS | <0.01 |
| 423 | pNOP323658 | KMT2D | LRQDFHRRTAWDGIQGPAAALQGCSGL | <0.01 |
| 424 | pNOP325001 | KMT2D | PDHVTTAQAAPTARTAWPPRRGRIGGF | <0.01 |
| 425 | pNOP325387 | KMT2D | PMTISLILRTISTRPATVEPGIVGNG | <0.01 |
| 426 | pNOP325875 | KMT2D | PWSPGSNPPDGQGTKHRRPSRFFRGH | <0.01 |
| 427 | pNOP334374 | KMT2D | GLTCPFTTGGLAHVPAAGGVTPVATT | <0.01 |
| 428 | pNOP336175 | KMT2D | KGTEGYFRGEESRPAGCLAYTPSQSD | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 429 | pNOP341158 | KMT2D | RSLLSPPILASLPPLAVAAQSMGRAS | <0.01 |
| 430 | pNOP343442 | KMT2D | TWTWTCGCTSTVPFGPRRCMRPRAGH | <0.01 |
| 431 | pNOP344075 | KMT2D | WACPSAEPGPVGAPQLCPLVHGGV | <0.01 |
| 432 | pNOP352206 | KMT2D | MASPHLKSWGSTPRMLPLPGIVKGH | <0.01 |
| 433 | pNOP356926 | KMT2D | SQARLPRLVKPLQTNHEALEKGSSS | <0.01 |
| 434 | pNOP362881 | KMT2D | FWESQASGDSSGLQWGSGAALCSL | <0.01 |
| 435 | pNOP363905 | KMT2D | GWVSSPHFAGGWGVPSSPARGASR | <0.01 |
| 436 | pNOP364735 | KMT2D | IITFFSTGGVALVSTGRVTPISCT | <0.01 |
| 437 | pNOP370861 | KMT2D | RMMKSLLTWVWVWMWPRVMMNLAP | <0.01 |
| 438 | pNOP37587 | KMT2D | GISELHLHRRDQHPLQQAVCALQVISVPAAAHRMEEQRVPGSLPYPGPGALCSQGPRKAHNGYRVHWHHHSERGGQPAGENLRRAESRHLHV PNKQ | <0.01 |
| 439 | pNOP376012 | KMT2D | ARQPLDGLRWHHALHPHNPHGG | <0.01 |
| 440 | pNOP378675 | KMT2D | GAALVPSPWGTILISLAWRASPV | <0.01 |
| 441 | pNOP378896 | KMT2D | GFQDNSSSKLACSTQQVEEAMGS | <0.01 |
| 442 | pNOP386633 | KMT2D | RHPQCPVTLRSQAPQVKGCLALT | <0.01 |
| 443 | pNOP388467 | KMT2D | SMKLTSGSMRSGCSIPSSSYRCS | <0.01 |
| 444 | pNOP390234 | KMT2D | VEARPLLGHRTRAALWGCPQAS | <0.01 |
| 445 | pNOP394670 | KMT2D | EQRAAGVCNQSHRAGPGGPGLH | <0.01 |
| 446 | pNOP404863 | KMT2D | RTGRATCTGGPHTTHSHQIRHR | <0.01 |
| 447 | pNOP405923 | KMT2D | SPRWRRVDATLLLANSPLLPPR | <0.01 |
| 448 | pNOP406378 | KMT2D | STPLAVPDQSLKSSHTTNGPIP | <0.01 |
| 449 | pNOP410165 | KMT2D | AVDHLLRPHLCPTCWLSPLFP | <0.01 |
| 450 | pNOP414691 | KMT2D | HLTKRTKSSSPAGESPKERS | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 451 | pNOP421373 | KMT2D | RASGPGGIRSSPTETLSPTGP | <0.01 |
| 452 | pNOP425823 | KMT2D | TWPPSPRPVGGNFHPSARPW | <0.01 |
| 453 | pNOP438522 | KMT2D | PAALPGTLTIPVPLITVWPKS | <0.01 |
| 454 | pNOP44778 | KMT2D | ALSPWALYSSFSSSSSCNSNSNFSSSSSSYNSNSNFSSNSSSFNNSSSNSSYNSNSNNNSSSFNSSSNSSRWAF | <0.01 |
| 455 | pNOP458695 | KMT2D | PAPHSRWRKPWAARQWIIF | <0.01 |
| 456 | pNOP465144 | KMT2D | TQPFLQRPLRGPLHIREGR | <0.01 |
| 457 | pNOP466225 | KMT2D | VSEGRGALWADGACRASHS | <0.01 |
| 458 | pNOP46646 | KMT2D | PASYPCSLRTCWSMRRRSCRRSSSFQHSCSLPSSSSNSSSSIPYCLHQALPRPCLCHMRALLPVWLGPNSSFPWVLQVPDSQVCPSH | <0.01 |
| 459 | pNOP468251 | KMT2D | APERSCCGRRTGSGPARPC | <0.01 |
| 460 | pNOP473253 | KMT2D | GSWWEGKGSGRQEPRHWP | <0.01 |
| 461 | pNOP481442 | KMT2D | QKPRSQSRAAWYLGIWTR | <0.01 |
| 462 | pNOP487229 | KMT2D | VAQEDPPCWKSLSSRVGL | <0.01 |
| 463 | pNOP487911 | KMT2D | VTVGCPHPGDTHQPSTRS | <0.01 |
| 464 | pNOP490058 | KMT2D | APVGGPPKRGDATAAPT | <0.01 |
| 465 | pNOP490152 | KMT2D | AREWGFDLAWTCSIWG | <0.01 |
| 466 | pNOP490194 | KMT2D | ARQDGELTGSQRVTPAH | <0.01 |
| 467 | pNOP493996 | KMT2D | GAATLPPVRGAAPVTPA | <0.01 |
| 468 | pNOP494542 | KMT2D | GIAPIPPACGVTPVSTA | <0.01 |
| 469 | pNOP494543 | KMT2D | GIAPVPAAGGIAPLSAA | <0.01 |
| 470 | pNOP501743 | KMT2D | NPHTLQTAPYPEQHQHV | <0.01 |
| 471 | pNOP502714 | KMT2D | PLCNPRNQGPCNVKPNH | <0.01 |
| 472 | pNOP506673 | KMT2D | RVTHVSTTGGISSVPTI | <0.01 |
| 473 | pNOP507548 | KMT2D | SLPASSQPAHFCSGSDQ | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 474 | pNOP508277 | KMT2D | SSQQPYEAPYPEQHQHV | <0.01 |
| 475 | pNOP512482 | KMT2D | AGSGRVVGAAWHSLAT | <0.01 |
| 476 | pNOP513338 | KMT2D | AVRPFLQLGWAGQALD | <0.01 |
| 477 | pNOP513379 | KMT2D | AWPPQSSGPGSWEVAL | <0.01 |
| 478 | pNOP513605 | KMT2D | CGAWQRGDRGKQKTQA | <0.01 |
| 479 | pNOP514247 | KMT2D | CSGFTARAWTDPWQFG | <0.01 |
| 480 | pNOP517078 | KMT2D | GALYTSGRAVSNRNYP | <0.01 |
| 481 | pNOP518512 | KMT2D | GVPAVHLTCALCQH | <0.01 |
| 482 | pNOP522295 | KMT2D | LAPVVSGVPWGEPRAQ | <0.01 |
| 483 | pNOP523824 | KMT2D | LTLLRHPPGWPGVKDT | <0.01 |
| 484 | pNOP52423 | KMT2D | SHGRISEQAAATTAAAATTATALSCAGSQPFPESPAAHQAPWSAAPWPWAAATTGASGWASRRSSPDPWGYGTTWTAWWPLP | <0.01 |
| 485 | pNOP526117 | KMT2D | PICSAPIDSSAPTSAP | <0.01 |
| 486 | pNOP530549 | KMT2D | SAEPCGSWEWPGAECW | <0.01 |
| 487 | pNOP530881 | KMT2D | SFPHLQAPQWGRLLPS | <0.01 |
| 488 | pNOP537026 | KMT2D | ALLLSSGGSTLSGTR | <0.01 |
| 489 | pNOP548556 | KMT2D | LRGAQSTRAAGATAL | <0.01 |
| 490 | pNOP548811 | KMT2D | LTIVRCWDSYQRRQS | <0.01 |
| 491 | pNOP550374 | KMT2D | NPHTLQTRFHIHYLI | <0.01 |
| 492 | pNOP55230 | KMT2D | QQAGWAGAETTGYPQQQGGCSSKEAFDTEAQAGTEGKRQVGELPKEAAEGGRGQGQRGLAETAETGAVPAAPNGACYHRQF | <0.01 |
| 493 | pNOP58727 | KMT2D | TGGPAAGGGARTLGP | <0.01 |
| 494 | pNOP56040 | KMT2D | DRWQSSNSSRVLEYRQTKLWVPSPRALCLPAATKASWSSSCPLNHPRGPRACWALPRWLCCSSSTLELWAPRALTDRCL | <0.01 |
| 495 | pNOP563434 | KMT2D | ARAELFCCLPAGLH | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 496 | pNOP566785 | KMT2D | EPDQQADQGGRHSP | <0.01 |
| 497 | pNOP568806 | KMT2D | GKQGSNLSPSWRPP | <0.01 |
| 498 | pNOP569843 | KMT2D | GVWPGLRPLTPAAL | <0.01 |
| 499 | pNOP570795 | KMT2D | HRSPGYRRQATGW | <0.01 |
| 500 | pNOP573651 | KMT2D | KSQSPSTFASKVCG | <0.01 |
| 501 | pNOP575068 | KMT2D | LLWPRGRHSPSGWD | <0.01 |
| 502 | pNOP580906 | KMT2D | RACSPSGCGCGQG | <0.01 |
| 503 | pNOP581766 | KMT2D | RIPWPRGQSYTRT | <0.01 |
| 504 | pNOP584053 | KMT2D | SFLPITRYPSLPVP | <0.01 |
| 505 | pNOP588394 | KMT2D | VRPAQPTCGRGLCP | <0.01 |
| 506 | pNOP589969 | KMT2D | YLLTCLQRAPWSRA | <0.01 |
| 507 | pNOP591792 | KMT2D | ATRPLTSATGLIP | <0.01 |
| 508 | pNOP594808 | KMT2D | EKRLTCCDSSLSI | <0.01 |
| 509 | pNOP594895 | KMT2D | ELPLSQWPLNQER | <0.01 |
| 510 | pNOP595078 | KMT2D | EPLHRGRCGAGSR | <0.01 |
| 511 | pNOP607374 | KMT2D | PGSSPHQQGAEAG | <0.01 |
| 512 | pNOP608986 | KMT2D | QGTARHASLLFLS | <0.01 |
| 513 | pNOP608941 | KMT2D | ENLEGPAGLTIGVLHGRQAYGGRRAQNYVVWTRPSSQGSHSAAPTAPGSVPPSLAAHLDVHGFTTSPARLPAVPSYP | <0.01 |
| 514 | pNOP61039 | KMT2D | GHQEPATTSCWQALAQKLGICSCRSYSGQRMCNSALGGGPRGCELRSTGTLTASWLGWSRNYRVPPATRRMQQQGSL | <0.01 |
| 515 | pNOP614310 | KMT2D | SLWRLLHLQSWCP | <0.01 |
| 516 | pNOP621656 | KMT2D | ASAWSWSCPVH | <0.01 |
| 517 | pNOP626830 | KMT2D | GAVPREPRPGRH | <0.01 |
| 518 | pNOP62730 | KMT2D | GIPTQHQAGTSGRAMCPGSPVSEEGGQWGANRGTRNQQPPPAGRPSLRSWASALAEATPGKECATQHWAGVRGAAS | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 519 | pNOP636166 | KMT2D | MQSVPLQETWE | <0.01 |
| 520 | pNOP637952 | KMT2D | PACGRRGAELS | <0.01 |
| 521 | pNOP638098 | KMT2D | PCLVDLQHLGMS | <0.01 |
| 522 | pNOP638632 | KMT2D | PLFSPTLTPSVP | <0.01 |
| 523 | pNOP640173 | KMT2D | QIFTPRAWRYPH | <0.01 |
| 524 | pNOP643882 | KMT2D | RTGPAKVNCFFH | <0.01 |
| 525 | pNOP645741 | KMT2D | SPHLLPIPLAWG | <0.01 |
| 526 | pNOP648045 | KMT2D | TPRYPGPRHVRP | <0.01 |
| 527 | pNOP652166 | KMT2D | AGHWGQEGYLQ | <0.01 |
| 528 | pNOP654960 | KMT2D | CYDRRPCQVH | <0.01 |
| 529 | pNOP660899 | KMT2D | GWGREGIPSAQ | <0.01 |
| 530 | pNOP663294 | KMT2D | ISPTQAPCPAP | <0.01 |
| 531 | pNOP671528 | KMT2D | PIPQTPLPLAG | <0.01 |
| 532 | pNOP672236 | KMT2D | PRTFWAPNSPC | <0.01 |
| 533 | pNOP675830 | KMT2D | RLSPGRVESHH | <0.01 |
| 534 | pNOP679479 | KMT2D | SQTTRESRGPT | <0.01 |
| 535 | pNOP679892 | KMT2D | SSLMQCCLAIP | <0.01 |
| 536 | pNOP682972 | KMT2D | VGMGSPTRVRR | <0.01 |
| 537 | pNOP684498 | KMT2D | WLRAALGWHLV | <0.01 |
| 538 | pNOP70346 | KMT2D | HHAEYRGSLLQHRQICPNAGHVCGMWQLWPGGRGPPPCLFAVLSVLSPLLCQQQDHQGDAAQGLALCGVYCV | <0.01 |
| 539 | pNOP704364 | KMT2D | MWRLPCTEDC | <0.01 |
| 540 | pNOP706242 | KMT2D | PAESSALGEG | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 541 | pNOP708910 | KMT2D | QKLAWPCCVT | <0.01 |
| 542 | pNOP709657 | KMT2D | QSPLPAKGQR | <0.01 |
| 543 | pNOP713389 | KMT2D | RWCGAHGVRN | <0.01 |
| 544 | pNOP715424 | KMT2D | SQLLLPLRLW | <0.01 |
| 545 | pNOP718753 | KMT2D | TWHLRKPGDQ | <0.01 |
| 546 | pNOP78569 | KMT2D | EHLGGGGSFPSGLRPVGARGPGPLPCHPPHSSGQHPSLPRYQTLWGPWPGGPWKAACHNLGKGQRK | <0.01 |
| 547 | pNOP81414 | KMT2D | IPTRSGLRTTLSTAVTKPREVRLSAPLLSSIPRCVADFHPQSLAIPPLTSPMLCTLHAKGSQRVGT | <0.01 |
| 548 | pNOP85659 | KMT2D | AWGTTSVPSARGAAVVPIWGAILVASADATRSPSSSTLTHHHSCGPTGPVSFGGVRVPLMCQRGQ | <0.01 |
| 549 | pNOP85855 | KMT2D | DPGRGTDECGGCPAPRTANQVLPVPANWCHQQLQSHALPQCLPFCLCHPCQVHVLQGQDHAVSNA | <0.01 |
| 550 | pNOP87579 | KMT2D | SSGERPQQLTKPPTCKRPKITGQLTASTRCRSQGHWAARPLLPPPFSLAAPLPPACLPLRTGS | <0.01 |
| 551 | pNOP96015 | KMT2D | VLSSSSSYRHSSCSGSCSRVRQYARPHPTRSLGPRPLPSRASWAANLNLGASLDHRQAPSRS | <0.01 |
| 552 | pNOP98767 | KMT2D | TAPACLRHIRAPSQARPTPPTASSLCTPSHLSTGGCAPNGRTTCTWLAPVSRAWGSMQPRT | <0.01 |
| 553 | pNOP6995 | RNF43 | PLGLVPWTRWCPQGKPRFPAMSTTTATGTTTTKSGSSGMAGSLAQKPESPSPGLLFLGHSPSQSHLLLISKSPDPTQQPLRGGSLTHSAPGPSLSQPLAQLTPPASAPVPAVCSTCKNPASLPDTHRGKGGVPPSPPLALGPRMQLCTQLARFFPITPPVWHILGPQRHTP | 3.852 |
| 554 | pNOP3856 | RNF43 | SSWLRCCASGAAPATAGRIRFSREQPGPSA5WPPGGTRPAAGRPGVSGQTQGAAAAQPLCVPSVWRSSLRGRSYGSFPAMSSIVTVWTPGYISIGLAPSACSTSQREIHFPSPWDPLDLTKNQVEDSTSFASIPAMPTTTSLLPTCWALPGVQWLGPHDLVPSCHPRSQAWALGITASPELHIPGLQESSSAWQEPSTPMHKAGD | 0.534 |
| 555 | pNOP66044 | RNF43 | CSPTRCTCAMPVMTTIWSLDSSASSWRVLDGPPAPACHWLARLGWRVSEEPVLSSLTSLRIELLLSSCSSRWG | 0.496 |
| 556 | pNOP22244 | RNF43 | RLQHLPQYQQSVQLAKIQPLCPTPTEEKAGGSLRAHPWLSAPGCNCAPSLPDFSPLHPQCGISLVPRGTPLDLWTSRPGQEAATRNPRPLLLKFTASVVVPDSSPAPGTTSTWGGAF | 0.267 |
| 557 | pNOP52830 | RNF43 | ATSNPPHSTLLLAQCPYAGPGPLTAVDLEKAIAQNAVGTWQMGQPVTPAQGPVMALPVTLMSTARTSAYRGSMAAVLLSAAP | 0.229 |
| 558 | pNOP12229 | RNF43 | LCGPLVTSASDLPPLHVQQHHRGRFIFVPGTLSILPRTRSKTPPHSPASRPCPLPPCCLPVGPPFPECSGSAPTTWSLPAIPGARHGPSASPLPQSCTSPGSRRAAAPGRSPARLCTRLGTEPPIHLTAPCCLPSAPTPGQAP | 0.153 |
| 559 | pNOP244428 | RNF43 | KISRTESYYQSDPLENGPHRKTESHFGRCVCWCC | 0.153 |
| 560 | pNOP102838 | RNF43 | CVDPNDSGGHHLCDHPGFGAAHPVPPPQQAGSASAENSLGHQPAGHQEVPGLQAGPG | 0.076 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 561 | pNOP327324 | RNF43 | RQSGAWIHQHRQAGESSTGPPPLPVTG | 0.076 |
| 562 | pNOP209936 | RNF43 | HEWWPPAAAGCPLALAADGYPAGRLWTHRTGTGSSGGV | 0.038 |
| 563 | pNOP269967 | RNF43 | WLPCRQALDAQDWYWQQRWSLKDQQNRKLLSE | 0.038 |
| 564 | pNOP336828 | RNF43 | LCGQLHGHQPTGGPWQQFYFLQLPKQ | 0.038 |
| 565 | pNOP407540 | RNF43 | VARLREQLQLSPCVCHLSGGVL | 0.038 |
| 566 | pNOP612507 | RNF43 | RSPRPGQIMMCGS | 0.038 |
| 567 | pNOP114240 | RNF43 | LLASPWNHIHLGRGLLNGVLTPQRAGHALIRTARCCRPSLSFQREVGVVGRGDYS | <0.01 |
| 568 | pNOP144417 | RNF43 | PSGQRIMLARVQEHPTSARCYPFSWQITGRSQGGAGVAEASERHLEGRV | <0.01 |
| 569 | pNOP295346 | RNF43 | GIRKALGRPGVMAHACNPRTLGGLGGWIP | <0.01 |
| 570 | pNOP296302 | RNF43 | HRRGQAMPLSALPGAVGPAWLRGGTRGAV | <0.01 |
| 571 | pNOP302630 | RNF43 | SVDLQAWTRGCYQKPQAPVTQIHSQCGCA | <0.01 |
| 572 | pNOP304307 | RNF43 | WRVSEBPVLSSLTSLRIELLLSSCSSRWG | <0.01 |
| 573 | pNOP32819 | RNF43 | TGCVRCSGLAPTKSVLQMCLGPTWHRVLLLGKERTTANTILFAVLPRSTGRGLIVMVEGERVPFPAPAPDLVCRKHLQCSKSMSSQATSCCLWRV WASLEG | <0.01 |
| 574 | pNOP36815 | RNF43 | LLASPWNHIHLGRGLLNGVLTPQRAGHALIRTARCCRPSLAQRRNSRSCVNRLCEMFRPSSNQECAPDVFGPYLAQSPAPGKGDHSKHHSFCR TS | <0.01 |
| 575 | pNOP395545 | RNF43 | GEETTAEYFRTGEVSQQRVDGS | <0.01 |
| 576 | pNOP403219 | RNF43 | QQWIWRKLLHRTQWVPGRWASQ | <0.01 |
| 577 | pNOP433557 | RNF43 | HRRGQAMPLSALPGAVGPAW | <0.01 |
| 578 | pNOP438085 | RNF43 | NNSSRRKINAVPPAVPVQCQ | <0.01 |
| 579 | pNOP489283 | RNF43 | AAAAAAGADLASGVDLG | <0.01 |
| 580 | pNOP491380 | RNF43 | CTAALKGIPSEWTCSLV | <0.01 |
| 581 | pNOP515288 | RNF43 | EADGVCVQEPKGPCED | <0.01 |
| 582 | pNOP530623 | RNF43 | SASHQLQLSSPFGAAL | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 583 | pNOP560805 | RNF43 | VVATSCSWLPSGPGC | <0.01 |
| 584 | pNOP574079 | RNF43 | LADHREVPGRCWCG | <0.01 |
| 585 | pNOP580384 | RNF43 | QPKYLTIGTAYHAG | <0.01 |
| 586 | pNOP600409 | RNF43 | ISLWKVCLLVLLK | <0.01 |
| 587 | pNOP613170 | RNF43 | SAGTPHLCQVLPL | <0.01 |
| 588 | pNOP650386 | RNF43 | WLMPVIPELWEA | <0.01 |
| 589 | pNOP656602 | RNF43 | EGYSRDDNQNT | <0.01 |
| 590 | pNOP658785 | RNF43 | GAGATGHFLPP | <0.01 |
| 591 | pNOP667654 | RNF43 | LQLRALSWLFQ | <0.01 |
| 592 | pNOP684894 | RNF43 | WSLCTRTKRPM | <0.01 |
| 593 | pNOP686213 | RNF43 | AEGAPGLARL | <0.01 |
| 594 | pNOP710735 | RNF43 | RGSPASGHAA | <0.01 |
| 595 | pNOP76090 | RNF43 | CDLSASFLGLGGAHRGNPGFQCPLPPPAPPLQKAVPVAWQEAWPRNRSPPVQASYSSDTAPARATFS | <0.01 |
| 596 | pNOP1314 | SOX9 | PVPAAQRPPGGAGHARPGHLHGQLRHQQHRGHPGERGPRVDVQAAGAAATPAAAPTGPAGPAGAPAAAGGAPTAAGGTPAAATGAHAD HAEQRAGPVPANAHQDGAAEPQPLQRAAAALAPTDRLQPLQPPTLQPLLPAHHPLTVRLHRPPELQLLLQPRGRPGHRPLLHLHLHEPRSAPH VHPHRRHLWGPFHPADPQPPALGTTRLHTAHSTLRRPPTKGEDGRDDPKNNRRKRGPTRIPFGHLCFFVFLFCFVFSSSSSLKTFKLKATRTQIS KTQT | 0.992 |
| 597 | pNOP30584 | SOX9 | AATSSPTSRPSMSTSLLTSTCRPTATRGCRPRTARSPTRAATASAAPRPPRRARATCGCPSSRRRRHPRSSPHRPRPRRRRPRSRRRPHSSRRHPR SSHRRTR | 0.877 |
| 598 | pNOP1997 | SOX9 | YESPGPLHEDDRRAGEGPVRRPQPHHVRGLRGLALPVGLRLGHREHAAPGEHVPQGRARSEEGERGGQVPRVHPRGGQPGAQRLRLDAGAH AGARQRLQQEQAARQAAHERLHGVGAGAQEARGPVPALAQRRQQDAGQALETSERREAALRGGGAAARAAQEGQOGKQVQAAAEE VGEERAGGGRGHGADAHLPQRHLQGAAGRLATLLLRHERGALPRRALGAIPGPTDPTHHPQNRRAAGQG | 0.648 |
| 599 | pNOP356358 | SOX9 | SERGAPCQRGADSPLSTSATWTSAS | 0.61 |
| 600 | pNOP83048 | SOX9 | APATTASSSSTRPNRSPTAPSTSHTTAPPTRPSPAHSTTTPTTRTPAPTTATRQARAPASTPPSPT | 0.572 |
| 601 | pNOP177083 | SOX9 | PEARGAPLARGGQTAPYRLPRRGHRRAEQRRHLQHRDLRCQRV | 0.534 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 602 | pNOP144465 | SOX9 | PTSRRRACPAPPAPPCPRTPRARPARRAPARTRGPRRTRSPRASPI | 0.267 |
| 603 | pNOP250754 | SOX9 | ARCTPPASTRGNPRAHRPHPPPKPTCSRARLT | 0.191 |
| 604 | pNOP512212 | SOX9 | AASRAGPSERTSRRSS | 0.076 |
| 605 | pNOP131867 | SOX9 | TPLSAPCTPSPTPLGSLPSRRPTAPSTGNNPSTHSSDLEEASHEGRRWPR | 0.038 |
| 606 | pNOP150040 | SOX9 | RRRARRTSSPCASARRSARCSKATTGRWCPCRCASTAPARTSRTSSGP | 0.038 |
| 607 | pNOP230868 | SOX9 | TPSWCGRRRAGSSRTSTRTCTTPSSARRWASSGDF | 0.038 |
| 608 | pNOP238602 | SOX9 | RTGRRRQRRPRSRRTSPPTPSSRRCRPTRHTPPPA | 0.038 |
| 609 | pNOP239820 | SOX9 | TRARSGPSWRRRSGCACSTRRTTRITSTSRGGGSR | 0.038 |
| 610 | pNOP23162 | TCF7L2 | KKARPSTRSLGGGGMHCPEKSKRNTTSWPGRSDSFICNCTPAGPRGITMERRRRGKGTSSREPMMQILQRSVGHCSGLTDRLYGANRAGEKK SAFATYKVKAAASAHPLQMEAY | 1.487 |
| 611 | pNOP146451 | TCF7L2 | ALLRNAERALALINRITGAALAGEKKSAFATYKVKAAASAHPLQMEAY | 1.259 |
| 612 | pNOP9620 | TCF7L2 | LWKEEEEKGQAAGRDQWRKKKCVRYIQGEGSCLSPPSSDGSLLDSPPPSPNLLGSPPRDAKSQTTQPLSLSLKPDPLAHLSMPPPPALLLA EATHKASALCPNGALDLPPAALQPAAPSSSIAQPSTSSLHSHSSLAGTQPQPLSLVTKSLE | 0.648 |
| 613 | pNOP9889 | TCF7L2 | TQRMPPKSLPFTSSDYRRKKKCVRYIQGEGSCLSPPSSDGSLLDSPPPSPNLLGSPPRDAKSQTEQTQPLSLSLKPDPLAHLSMPPPPALLLAEAT HKASALCPNGALDLPPAALQPAAPSSSIAQPSTSSLHSHSSLAGTQPQPLSLVTKSLE | 0.648 |
| 614 | pNOP119014 | TCF7L2 | RAPTSPTDRSRPPPEPLTKCQWCSTLTMSTPSRLLSRTAMNTSRRETHLHTYQPT | 0.42 |
| 615 | pNOP77071 | TCF7L2 | NGHCLMSRQGASRVDKPSRMPGPHHRHTLSLTKCQWCSTLTMSTPSRLLSRTAMNTSRRETHLHTYQPT | 0.42 |
| 616 | pNOP117898 | TCF7L2 | KGATPYKKLGSPGVLSLTKCQWCSTLTMSTPSRLLSRTANTSRRETHLHTYQPT | 0.381 |
| 617 | pNOP181832 | TCF7L2 | IAGLTKCQWCSTLTMSTPSRLLSRTAMNTSRRETHLHTYQPT | 0.381 |
| 618 | pNOP193656 | TCF7L2 | CLTKCQWCSTLTMSTPSRLLSRTAMNTSRRETHLHTYQPT | 0.381 |
| 619 | pNOP22344 | TCF7L2 | TLHAGKPTSLTSRRRPQNRNPTASAPSRYIPVLPTIAWHRRTNPPSARMVSTTARSTSVPNHDRRIQTPLPHSSDRQCFHVQVSPYGPTTSYAT HDGHSASGHSHTNSQTGIVPE | 0.114 |
| 620 | pNOP169706 | TCF7L2 | IRNESKQLLRFRGGKTASASLRKFPRQIPGKFGRSQEARWRAL | 0.076 |
| 621 | pNOP238936 | TCF7L2 | SHQQSNRNRPRVMSAHSIVQSIRTPKRKKKRRSPT | 0.076 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 622 | pNOP24554 | TCF7L2 | TLHAGKPTSTLTSRRPQNRNPTASAPSRYIPVLPTIAWHRRTNPPSARMARSTSVPNHDRRIQTPLPHSSDRQCFHVQVPSPYGPTTSYATHDG HSASGHSHTNSQTGIVPE | 0.076 |
| 623 | pNOP395162 | TCF7L2 | FPSKTRANRRRAPKTPRQRGI | 0.076 |
| 624 | pNOP76119 | TCF7L2 | CLRHPPSCSLRPPTRPPSVPTGPWTCPQPLCSLPPPHQLHSRRLLYIPTAPWPGPSPSRCRSSPSL | 0.076 |
| 625 | pNOP108508 | TCF7L2 | SMNQKRIKTAPPIPRRKDGLRLAPKVSETNPGKVWKKRPRGKMEGSLRGHRIPATPSS | 0.038 |
| 626 | pNOP246621 | TCF7L2 | PSMLPCPAFCLLGSLPIWSHHIIRYTRRAFRIRP | 0.038 |
| 627 | pNOP249601 | TCF7L2 | VPSPYGPTTSYATHDGHSASGHSHTNSQTGIVPE | 0.038 |
| 628 | pNOP391533 | TCF7L2 | YHSKVNQCTQSRQEDSDTPTPQL | 0.038 |
| 629 | pNOP403210 | TCF7L2 | QSASGAAPSPCPPPHASYHVQQ | 0.038 |
| 630 | pNOP86123 | TCF7L2 | GPHQGLRPLSQRGPGPAPSRFAACRPLLINCTAVDFFLTPQLPGRDPAPAAVARHQVRIALAS | <0.01 |
| 631 | pNOP100389 | TCF7L2 | ILAFHFLRLQMQILQRSVGHCSGLTDRLYGANRAGEKKSAFATYKVKAAASAHPLQMLEAY | <0.01 |
| 632 | pNOP100945 | TCF7L2 | NGHCLMSRQGASRVDKPSRMPGPHHRHTLSAPSLAALRDMTVSTSTPPQTSLSALKSSGT | <0.01 |
| 633 | pNOP114399 | TCF7L2 | LVRPLQMQILQRSVGHCSGLTDRLYGANRAGEKKSAFATKVKAAASAHPLQMEAY | <0.01 |
| 634 | pNOP141050 | TCF7L2 | VHVERKRGHQPDPWAEVACTVQRRASEILRAGPEGATASYATVPRLVRAG | <0.01 |
| 635 | pNOP152548 | TCF7L2 | GATVSRLPLHHDPRPDEPLPPQRIALAHRPNPPFSVRQHTLLCVQND | <0.01 |
| 636 | pNOP182797 | TCF7L2 | LVRPLQMQILQRSVGHCSGLTDRLYGANRAGEKKKVRSLHTR | <0.01 |
| 637 | pNOP184017 | TCF7L2 | RAPTSPTDRSRPPPEPSIFSPAAHITLRTKRLNTRLQFSISR | <0.01 |
| 638 | pNOP194610 | TCF7L2 | GATVSRLPLHHDPRPDEPLPPQRIALAHRPNLSPDEMATA | <0.01 |
| 639 | pNOP196518 | TCF7L2 | LVRPLQSLNLEYNGEKKSAFATYKVKAAASAHPLQMEAY | <0.01 |
| 640 | pNOP236046 | TCF7L2 | LSALLPPLRLHCQHSSLQGHEKEPLLTKSWGALVY | <0.01 |
| 641 | pNOP238356 | TCF7L2 | RQLPQPTLFRWKLTRFASPLPEPARLDSPRRQVTD | <0.01 |
| 642 | pNOP262475 | TCF7L2 | GATVSRLPLHHDPRPDEPLPPQRIALAHRPNL | <0.01 |
| 643 | pNOP277062 | TCF7L2 | PRRQRRTDFLQRRGRTGGEELRKLLGREGFS | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 644 | pNOP291285 | TCF7L2 | TQRMPPKSLPFTSSDYRCKIYSKEVSGTVRA | <0.01 |
| 645 | pNOP292673 | TCF7L2 | ADPASVAVPEARPPGPPVHDASATRPPAR | <0.01 |
| 646 | pNOP299871 | TCF7L2 | PSMLPCPGSLPIWSHHIIRYTRRAFRIRP | <0.01 |
| 647 | pNOP343264 | TCF7L2 | TSPQGCPVPITGTHCPEPPPLLHSGT | <0.01 |
| 648 | pNOP348748 | TCF7L2 | GRRSGLRGLSVPAVGRLAPQFELLV | <0.01 |
| 649 | pNOP357917 | TCF7L2 | TPKQESHGLRTLQIYPRITHYRLAP | <0.01 |
| 650 | pNOP358118 | TCF7L2 | TSPQGCPVPITGTHCQPPPLLHSGT | <0.01 |
| 651 | pNOP390758 | TCF7L2 | VVREAQWPPGSLCSSSWAVGTSI | <0.01 |
| 652 | pNOP393746 | TCF7L2 | DGKVNQCTQSRQEDSDTPTPQL | <0.01 |
| 653 | pNOP412605 | TCF7L2 | FKASGLQKGRRKEEAPHKETS | <0.01 |
| 654 | pNOP415243 | TCF7L2 | ILAFHLRLQEKKVRSLHTR | <0.01 |
| 655 | pNOP41787 | TCF7L2 | KKARPSTRSLGGGGMHCPEKSKRNTTSWPGRSDSFICNCTPAGPRGITMERRRGKGTSSRERMVKKKSAFATYKVKAAASAHPLQMEAY | <0.01 |
| 656 | pNOP420332 | TCF7L2 | PTDFMVQTVQEKKKVRSLHTR | <0.01 |
| 657 | pNOP425448 | TCF7L2 | TQRMPPKSLPFTSSDYRPERS | <0.01 |
| 658 | pNOP428234 | TCF7L2 | APLPETSHRLSRPSLCRCP | <0.01 |
| 659 | pNOP458391 | TCF7L2 | NSFSVVNPAALFMVLFHFS | <0.01 |
| 660 | pNOP460845 | TCF7L2 | RAPTSPTDRSRPPPEPISR | <0.01 |
| 661 | pNOP47070 | TCF7L2 | TLHAGKPTSTLTSRRRPQNRNPTASAPSRYIPVLPTIAQHRRTNPPSARMVSTTARSTSVPNHDRRIQTPLPHSSDRQFHVQLSVF | <0.01 |
| 662 | pNOP478102 | TCF7L2 | LWKEEEEKGQAAGRDQW | <0.01 |
| 663 | pNOP500461 | TCF7L2 | LVRPLQEKKKVRSLHTR | <0.01 |
| 664 | pNOP500497 | TCF7L2 | LWKEEEEKGQAAGRDQ | <0.01 |
| 665 | pNOP52551 | TCF7L2 | TLHAGKPTSTLTSRRRPQNRNPTASAPSRYIPVLPTIAWHRRTNPPSARMARSTSVPNHDRRIQTPLPHSSDRQCFHVQLSVF | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 666 | pNOP533731 | TCF7L2 | TSPQGCPVPITGTHCL | <0.01 |
| 667 | pNOP538111 | TCF7L2 | CIHVVYEGNESKGRS | <0.01 |
| 668 | pNOP5491 | TCF7L2 | ALLRNAERALALINRITGAALADANTPKKCRALFGLDRQTWCKPCRRKKKCVRYIQEGEGSCLSPPSSDGSLLDSPPPSPNLLGSPPRDAKSQTEQT QPLSLSLKPDPLAHLSMMPPPPALLLAEATHKASALCPNGALDLPPAALQPAASSSIAQPSTSSLHSHSSLLAGTQPQPLSLVTKSLE | <0.01 |
| 669 | pNOP559194 | TCF7L2 | TPDCSSVSPDEMATA | <0.01 |
| 670 | pNOP592448 | TCF7L2 | CKYSKEVSGTVRA | <0.01 |
| 671 | pNOP627331 | TCF7L2 | GHNFSGNGRFEW | <0.01 |
| 672 | pNOP62995 | TCF7L2 | KKARPSTRSLGGGGMHCPEKSKRNTTSWPGRSDSFICNCTPAGPRGITMERRRRGKGTSSRERPMEKKKVRSLHTR | <0.01 |
| 673 | pNOP662684 | TCF7L2 | IAFHFLRLQT | <0.01 |
| 674 | pNOP699373 | TCF7L2 | KKKVRSLHTR | <0.01 |
| 675 | pNOP704386 | TCF7L2 | NAAAERRWRG | <0.01 |
| 676 | pNOP711788 | TCF7L2 | RNLLMHSCCI | <0.01 |
| 677 | pNOP72480 | TCF7L2 | KKARPSTRSLGGGGMHCPEKSKRNTTSWPGRSDSFICNCTPAGPRGITMERRRRGKGTSSRERPMNTANVS | <0.01 |
| 678 | pNOP7370 | TCF7L2 | ALLRNAERALALINRITGAALAVEFGLLQWRKKKCVRYIQEGEGSCLSPPSSDGSLLDSPPPSPNLLGSPPRDAKSQTEQTQPLSLSLKPDPLAHLSM MPPPPALLLAEATHKASALCPNGALDLPPAALQPAASSSIAQPSTSSLHSHSSLLAGTQPQPLSLVTKSLE | <0.01 |
| 679 | pNOP83888 | TCF7L2 | KKARPSTRSLGGGGMHCPEKSKRNTTSWPGRSDSFICNCTPAGPRGITMERRRRGKGTSSRERPMT | <0.01 |
| 680 | pNOP97816 | TCF7L2 | NGHCLMSRQGASRVDKPSRMPGPHHRHTLSRAPSLAALRDMTVSTSTPPQTSLSALKSSGT | <0.01 |
| 681 | pNOP49591 | TP53 | SSQNARCGSPRGPCTSSSYTGPCTSPLLAPVIFCPFPENLPGQLRFPSGLLAFWDSQVCDLHVLPCPQQDVLPTGQDLPCAAVG | 1.259 |
| 682 | pNOP31232 | TP53 | TGGPSSPSSHWKTPVVIYWDGTALRCVVPVLGETGAQRKRLSARKGSLTTSCPQGALSEHCPTTPAPLPSQRRNHWMENISPFRTRPAFKKKIV KESMKMVL | 0.877 |
| 683 | pNOP158914 | TP53 | LARTPLPSTRCFANWPRPALCSCGLIPHPRPAPASAPWPSTSSHST | 0.763 |
| 684 | pNOP59073 | TP53 | CCPRTILNNGSLKTQVQMKLPECQRLLPPWPLHQQLLHRRPLHQPPGPCHLLSLPRKPTRAATVSVWASCILGQPSL | 0.763 |
| 685 | pNOP224126 | TP53 | CFANWPRPALCSCGLIPHPRPAPASAPWPSTSSHST | 0.572 |
| 686 | pNOP70126 | TP53 | GAAPTMSAAQIAMVWPLLSILSEWKEICVWSIWMTETLFDIVWWCPMSRLRLALIVPPSTTTCVTVPAWAA | 0.496 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 687 | pNOP272502 | TP53 | FHTPAHPRPHGHLQAVTAHDGGCEALPPP | 0.458 |
| 688 | pNOP136003 | TP53 | SPKRVSLPPAIKNSCSRQKGLTQTDILHFLFPTDSLPPPSLPPLPFWVLGL | 0.267 |
| 689 | pNOP405064 | TP53 | RWSGPSSASYSGRKFACGVFG | 0.229 |
| 690 | pNOP193414 | TP53 | ASTAQQHQLLSPAKEETTGWRIFHPSGPDQLSKRKLLKRA | 0.153 |
| 691 | pNOP316190 | TP53 | VRKHFQTYGNYFLKTTFCPPCRPKQMMI | 0.114 |
| 692 | pNOP252394 | TP53 | GACLCLSWERPAHRGRESPQERGASPRAAPREH | 0.076 |
| 693 | pNOP36301 | TP53 | TGGPSSPSSHWKTPVVIYWDGTALRCVFVPVLGETGAQRKRISARKGLTTSCPQGALSEHCPTTPAPLPSQRRNHWMENISPFRSVGVSASRCSES | 0.076 |
| 694 | pNOP385655 | TP53 | QFLHGRHEPEAHPHHHHTGRLQW | 0.076 |
| 695 | pNOP433152 | TP53 | HGHLQAVTAHDGGCEALPPP | 0.076 |
| 696 | pNOP602122 | TP53 | KQRSVPLAVPSNG | 0.038 |
| 697 | pNOP243169 | TP53 | GLGTQGCPGWEGARGEQGSLQPPEVQKGSVVLPP | <0.01 |
| 698 | pNOP281999 | TP53 | ASTAQQHQLLSPAKEETTGWRIFHPSDPWA | <0.01 |
| 699 | pNOP293143 | TP53 | ASTAQQHQLLSPAKEETTGWRIFHPSDAT | <0.01 |
| 700 | pNOP367554 | TP53 | MRPWNSRMPRLGRSQGGAGLTPAT | <0.01 |
| 701 | pNOP38141 | TP53 | TGGPSSPSSHWKTPVVIYWDGTALRCVFVPVLGETGAQRKRISARKGSLTTSCPQGALSEHCPTTPAPLPSQRRNHWMENISPFRCYLITYDGVTS | <0.01 |
| 702 | pNOP445026 | TP53 | TRRKLKILSVGVSASRCSES | <0.01 |
| 703 | pNOP483390 | TP53 | RRAPSESGNIFRPMETTS | <0.01 |
| 704 | pNOP539666 | TP53 | DVLPTGQDLPCAAVG | <0.01 |
| 705 | pNOP59708 | TP53 | LRLTFSTSCSPLTASHPHLSLPCHFGFWVFEPLLAIGVRQKHPGLPFALSRGSTEQVGLHWCFVVGRRMGSRTYQLRF | <0.01 |
| 706 | pNOP604680 | TP53 | LTMVLLPDKLVVS | <0.01 |
| 707 | pNOP619453 | TP53 | WRSRSQILASSPL | <0.01 |
| 708 | pNOP703537 | TP53 | LYHHPLQLHV | <0.01 |

TABLE 1-continued

Library of NOP sequences

Sequences of NOPs including the percentage of colorectal cancer (CRC) patients identified in the present study with each NOP. The sequences referred to herein correspond to the sequence numbering in the table below.

| Sequence | Peptide ID | gene | Peptide Sequence | % CRC patients |
|---|---|---|---|---|
| 709 | pNOP9298 | ZFP36L2 | TTCWTRRRWGRLWPPPARASRRDSDGTRPATCMHSPTPRPAPAAARPSSRAPLTAAAAARRPAVRPPTAPLRSRRGAAAQPCSTRRTNS GTARLARTAIAASTSCTCSSSRRGAAAPRSTPRATPRATRPSCAGPSRRAARASTAKSASSMASTSCAA | 2.407 |
| 710 | pNOP610 | ZFP36L2 | RERRSQPAPPAPAAAAEGGRRLPDQLHALQDRAVPALRGERHVQVRRKVPVRAWLPRAAQPDSPEVQDRAVPHLSYHRLLPLWAALPLHPQ RGRAAARAVGGRLRGPACLWHARCVAPGLPAGAAAQVAPQPQLLGLPVGPPSAPGRPRVAAAARQPHVAHAAAALLLFGLVLLLRLLLFLGL RGLHALGRPDMLRLRGGRGCGRSAVRHRGRRGPAGAGGPVRGLLVGLIVRQQORLRLRSGAQQPHHAARHPDPQLCRRGRRRLLPQSAAAAAA GPGAPRAAAGAAQRDPPRRGRRTSLAALQLPAAAPPVRLARVRRAPQPPGLAVGPRQLPKRLPELRQPQRL | 2.063 |
| 711 | pNOP395419 | ZFP36L2 | GAVGGRRHSPAQQGEQIPGPLV | 0.619 |
| 712 | pNOP53232 | ZFP36L2 | HVDHTSVRLLRCRLLVQDREIPGQPQPEQHAGQEGGGDACGRRPQLGLRAGIPPTALGAAPACTRPPRAQPRQLLAQVPGRR | 0.344 |
| 713 | pNOP1471 | ZFP36L2 | LAIRSTRPSCAAPFIPSASAPMGRAATSSTTRTSGGPRRRGAPPGTCVPLARAMRCTWASRGSRGPSCTTASASRASRRATISPRAASSRRCCSTA PRRARRRRPALRPRPAPPPPVPRRPRPRPRAPRHAAPPRRPRRPRLRPLCCTAPGAPRTCWRRGPRARPARRPRAPTTPSPVRSAASSRRSP SRPTTLPWPPPTTAVSSSSRAWRPPRSRRRPARPSPPGPPHLPRRPSASSCRAACPTRPCSTRPAPRTRCRTATAT | 0.275 |
| 714 | pNOP223799 | ZFP36L2 | APAASAALLPASTLAAACQSSAASPSTTEARGRQ | 0.069 |
| 715 | pNOP116065 | ZFP36L2 | VSQPRPWPPPANLQPPLHLRRLRQEGASEEEGKAVQRCWRTPLAISPLLGAREWGG | <0.01 |
| 716 | pNOP332322 | ZFP36L2 | CRPHFCPPSTMSTSCARQRNPWPTST | <0.01 |
| 717 | pNOP483342 | ZFP36L2 | RQQLRQRGGRRSDLLRHP | <0.01 |

In a preferred embodiment the disclosure provides one or more frameshift-mutation peptides (also referred to herein as 'neoantigens') comprising an amino acid sequence selected from the groups:
  i) Sequences 1-196, an amino acid sequence having 90% identity to Sequences 1-196, or a fragment thereof comprising at least 10 consecutive amino acids of Sequences 1-196;
  (ii) Sequences 197-297, an amino acid sequence having 90% identity to Sequences 197-297, or a fragment thereof comprising at least 10 consecutive amino acids of Sequences 197-297;
  (iii) Sequences 298-552, an amino acid sequence having 90% identity to Sequences 298-552, or a fragment thereof comprising at least 10 consecutive amino acids of Sequences 298-552;
  (iv) Sequences 553-595, an amino acid sequence having 90% identity to Sequences 553-595, or a fragment thereof comprising at least 10 consecutive amino acids of Sequences 553-595; and
  (v) Sequences 596-609, an amino acid sequence having 90% identity to Sequences 596-609, or a fragment thereof comprising at least 10 consecutive amino acids of Sequences 596-609;
  (vi) Sequences 610-680, an amino acid sequence having 90% identity to Sequences 610-680, or a fragment thereof comprising at least 10 consecutive amino acids of Sequences 610-680;
  (vii) Sequences 681-708, an amino acid sequence having 90% identity to Sequences 681-708, or a fragment thereof comprising at least 10 consecutive amino acids of Sequences 681-708; and
  (viii) Sequences 709-717, an amino acid sequence having 90% identity to Sequences 709-717, or a fragment thereof comprising at least 10 consecutive amino acids of Sequences 709-717.

As will be clear to a skilled person, the preferred amino acid sequences may also be provided as a collection of tiled sequences, wherein such a collection comprises two or more peptides that have an overlapping sequence. Such 'tiled' peptides have the advantage that several peptides can be easily synthetically produced, while still covering a large portion of the NOP. In an exemplary embodiment, a collection comprising at least 3, 4, 5, 6, 10, or more tiled peptides each having between 10-50, preferably 12-45, more preferably 15-35 amino acids, is provided. As described further herein, such tiled peptides are preferably directed to the C-terminus of a pNOP. As will be clear to a skilled person, a collection of tiled peptides comprising an amino acid sequence of Sequence X, indicates that when aligning the tiled peptides and removing the overlapping sequences, the resulting tiled peptides provide the amino acid sequence of Sequence X, albeit present on separate peptides. As is also clear to a skilled person, a collection of tiled peptides comprising a fragment of 10 consecutive amino acids of Sequence X, indicates that when aligning the tiled peptides and removing the overlapping sequences, the resulting tiled peptides provide the amino acid sequence of the fragment, albeit present on separate peptides. When providing tiled peptides, the fragment preferably comprises at least 20 consecutive amino acids of a sequence as disclosed herein.

Specific NOP sequences cover a large percentage of colorectal cancer patients. Preferred NOP sequences, or subsequences of NOP sequence, are those that target the largest percentage of colorectal cancer patients. Preferred sequences are preferably in this order of preference, Sequence 553 (3.9% of colorectal cancer patients), Sequence 1 (2.8% of colorectal cancer patients), Sequence 2 (2.6% of colorectal cancer patients), Sequence 709 (2.4% of colorectal cancer patients), Sequence 710 (2.1% of colorectal cancer patients), Sequence 298, 610 (each covering 1.5% of colorectal cancer patients), Sequence 3, 611, 681 (1.3% of colorectal cancer patients), Sequence 4 (1.1% of colorectal cancer patients), Sequence 596, 299 (each covering 1% of colorectal cancer patients), Sequence 597, 682 (each covering 0.9% of colorectal cancer patients), Sequence 683-684 (each covering 0.8% of colorectal cancer patients), Sequence 197 (covering 0.7% of colorectal cancer patients), Sequence 5, 6, 300, 598-600, 612-613, 685, 711 (each covering 0.6% of colorectal cancer patients), Sequence 198, 554-555, 601, 686-687 (each covering 0.5% of colorectal cancer patients), Sequence 7-8, 614-618 (each covering 0.4% of colorectal cancer patients), Sequence 9-10, 199-200, 301-303, 556, 602, 688, 712-713 (each covering 0.3% of colorectal cancer patients), Sequence 11-21, 201-206, 304, 557-559, 603, 689-690 (each covering 0.2% of colorectal cancer patients), Sequence 22-29, 207, 305-309, 619, 691 (each covering 0.1% of colorectal cancer patients), all other Sequences listed in Table 1 and not mentioned in this paragraph (each covering less than 0.1% of colorectal cancer patients). As discussed further herein, neoantigens also include the nucleic acid molecules (such as DNA and RNA) encoding said amino acid sequences. The preferred sequences listed above are also the preferred sequences for the embodiments described further herein.

Preferably, the neoantigens and vaccines disclosed herein induce an immune response, or rather the neoantigens are immunogenic. Preferably, the neoantigens bind to an antibody or a T-cell receptor. In preferred embodiments, the neoantigens comprise an MHCI or MHCII ligand.

The major histocompatibility complex (MHC) is a set of cell surface molecules encoded by a large gene family in vertebrates. In humans, MHC is also referred to as human leukocyte antigen (HLA). An MHC molecule displays an antigen and presents it to the immune system of the vertebrate. Antigens (also referred to herein as 'MHC ligands') bind MHC molecules via a binding motif specific for the MHC molecule. Such binding motifs have been characterized and can be identified in proteins. See for a review Meydan et al. 2013 BMC Bioinformatics 14:S13.

MHC-class I molecules typically present the antigen to CD8 positive T-cells whereas MHC-class II molecules present the antigen to CD4 positive T-cells. The terms "cellular immune response" and "cellular response" or similar terms refer to an immune response directed to cells characterized by presentation of an antigen with class I or class II MHC involving T cells or T-lymphocytes which act as either "helpers" or "killers". The helper T cells (also termed CD4+ T cells) play a central role by regulating the immune response and the killer cells (also termed cytotoxic T cells, cytolytic T cells, CD8+ T cells or CTLs) kill diseased cells such as cancer cells, preventing the production of more diseased cells.

In preferred embodiments, the present disclosure involves the stimulation of an anti-tumor CTL response against tumor cells expressing one or more tumor-expressed antigens (i.e., NOPs) and preferably presenting such tumor-expressed antigens with class I MHC.

In some embodiments, an entire NOP (e.g., Sequence 1) may be provided as the neoantigen (i.e., peptide). The length of the NOPs identified herein vary from around 10 to around 494 amino acids. Preferred NOPs are at least 20 amino acids in length, more preferably at least 30 amino acids, and most preferably at least 50 amino acids in length. While not wishing to be bound by theory, it is believed that neoantigens longer than 10 amino acids can be processed into shorter peptides, e.g., by antigen presenting cells, which then bind to MHC molecules.

In some embodiments, fragments of a NOP can also be presented as the neoantigen. The fragments comprise at least 8 consecutive amino acids of the NOP, preferably at least 10 consecutive amino acids, and more preferably at least 20 consecutive amino acids, and most preferably at least 30 amino acids. In some embodiments, the fragments can be about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 60, about 70, about 80, about 90, about 100, about 110, or about 120 amino acids or greater. Preferably, the fragment is between 8-50, between 8-30, or between 10-20 amino acids. As will be understood by the skilled person, fragments greater than about 10 amino acids can be processed to shorter peptides, e.g., by antigen presenting cells.

The specific mutations resulting in the generation of a neo open reading frame may differ between individuals resulting in differing NOP lengths. However, as depicted in, e.g., FIG. 2, such individuals share common NOP sequences, in particular at the C-terminus of an NOP. While suitable fragments for use as neoantigens may be located at any position along the length of an NOP, fragments located near the C-terminus are preferred as they are expected to benefit a larger number of patients. Preferably, fragments of a NOP correspond to the C-terminal (3') portion of the NOP, preferably the C-terminal 10 consecutive amino acids, more preferably the C-terminal 20 consecutive amino acids, more preferably the C-terminal 30 consecutive amino acids, more preferably the C-terminal 40 consecutive amino acids, more preferably the C-terminal 50 consecutive amino acids, more preferably the C-terminal 60 consecutive amino acids, more preferably the C-terminal 70 consecutive amino acids, more preferably the C-terminal 80 consecutive amino acids, more preferably the C-terminal 90 consecutive amino acids, and most preferably the C-terminal 100 or more consecutive amino acids. As is clear to a skilled person, the C-terminal amino acids need not include the, e.g., 1-most C-terminal amino acids. In some embodiments a subsequence of the preferred C-terminal portion of the NOP may be highly preferred for reasons of manufacturability, solubility and MHC binding strength.

Suitable fragments for use as neoantigens can be readily determined. The NOPs disclosed herein may be analysed by known means in the art in order to identify potential MHC binding peptides (i.e., MHC ligands). Suitable methods are described herein in the examples and include in silico prediction methods (e.g., ANNPRED, BIMAS, EPIMHC, HLABIND, IEDB, KISS, MULTIPRED, NetMHC, PEPVAC, POPI, PREDEP, RANKPEP, SVMHC, SVRMHC, and SYFFPEITHI, see Lundegaard 2010 130:309-318 for a review). MHC binding predictions depend on HLA genotypes, furthermore it is well known in the art that different MHC binding prediction programs predict different MHC affinities for a given epitope. While not wishing to be limited by such predictions, at least 60% of NOP sequences as defined herein, contain one or more predicted high affinity MHC class I binding epitope of 10 amino acids, based on allele HLA-A0201 and using NetMHC4.0.

A skilled person will appreciate that natural variations may occur in the genome resulting in variations in the sequence of an NOP. Accordingly, a neoantigen of the disclosure may comprise minor sequence variations, including, e.g., conservative amino acid substitutions. Conservative substitutions are well known in the art and refer to the substitution of one or more amino acids by similar amino acids. For example, a conservative substitution can be the substitution of an amino acid for another amino acid within the same general class (e.g., an acidic amino acid, a basic amino acid, or a neutral amino acid). A skilled person can readily determine whether such variants retain their immunogenicity, e.g., by determining their ability to bind MHC molecules.

Preferably, a neoantigen has at least 90% sequence identity to the NOPs disclosed herein. Preferably, the neoantigen has at least 95% or 98% sequence identity. The term "% sequence identity" is defined herein as the percentage of nucleotides in a nucleic acid sequence, or amino acids in an amino acid sequence, that are identical with the nucleotides, resp amino acids, in a nucleic acid or amino acid sequence of interest, after aligning the sequences and optionally introducing gaps, if necessary, to achieve the maximum percent sequence identity. The skilled person understands that consecutive amino acid residues in one amino acid sequence are compared to consecutive amino acid residues in another amino acid sequence. Methods and computer programs for alignments are well known in the art. Sequence identity is calculated over substantially the whole length, preferably the whole (full) length, of a sequence of interest.

The disclosure also provides at least two frameshift-mutation derived peptides (i.e., neoantigens), also referred to herein as a 'collection' of peptides. Preferably the collection comprises at least 3, at least 4, at least 5, at least 10, at least 15, or at least 20, or at least 50 neoantigens. In some embodiments, the collections comprise less than 20, preferably less than 15 neoantigens. Preferably, the collections comprise the top 20, more preferably the top 15 most frequently occurring neoantigens in cancer patients. The neoantigens are selected from:
(i) Sequences 1-196, an amino acid sequence having 90% identity to Sequences 1-196, or a fragment thereof comprising at least 10 consecutive amino acids of Sequences 1-196;
(ii) Sequences 197-297, an amino acid sequence having 90% identity to Sequences 197-297, or a fragment thereof comprising at least 10 consecutive amino acids of Sequences 197-297;
(iii) Sequences 298-552, an amino acid sequence having 90% identity to Sequences 298-552, or a fragment thereof comprising at least 10 consecutive amino acids of Sequences 298-552;
(iv) Sequences 553-595, an amino acid sequence having 90% identity to Sequences 553-595, or a fragment thereof comprising at least 10 consecutive amino acids of Sequences 553-595; and
(v) Sequences 596-609, an amino acid sequence having 90% identity to Sequences 596-609, or a fragment thereof comprising at least 10 consecutive amino acids of Sequences 596-609;
(vi) Sequences 610-680, an amino acid sequence having 90% identity to Sequences 610-680, or a fragment thereof comprising at least 10 consecutive amino acids of Sequences 610-680;
(vii) Sequences 681-708, an amino acid sequence having 90% identity to Sequences 681-708, or a fragment thereof comprising at least 10 consecutive amino acids of Sequences 681-708; and (viii) Sequences 709-717, an amino acid sequence having 90% identity to Sequences 709-717, or a fragment thereof comprising at least 10 consecutive amino acids of Sequences 709-717.

Preferably, the collection comprises at least two frameshift-mutation derived peptides corresponding to the same gene. Preferably, a collection is provided comprising:

(i) a peptide, or a collection of tiled peptides, having the amino acid sequence selected from Sequence 1, an amino acid sequence having 90% identity to Sequence 1, or a fragment thereof comprising at least 10 consecutive amino acids of Sequence 1; and a peptide, or a collection of tiled peptides, having the amino acid sequence selected from Sequence 2, an amino acid sequence having 90% identity to Sequence 2, or a fragment thereof comprising at least 10 consecutive amino acids of Sequence 2; preferably also comprising a peptide, or a collection of tiled peptides, having the amino acid sequence selected from Sequence 3, an amino acid sequence having 90% identity to Sequence 3, or a fragment thereof comprising at least 10 consecutive amino acids of Sequence 3;

a peptide, or a collection of tiled peptides, having the amino acid sequence selected from Sequence 4, an amino acid sequence having 90% identity to Sequence 4, or a fragment thereof comprising at least 10 consecutive amino acids of Sequence 4;

a peptide, or a collection of tiled peptides, having the amino acid sequence selected from Sequence 5, an amino acid sequence having 90% identity to Sequence 5, or a fragment thereof comprising at least 10 consecutive amino acids of Sequence 5; and/or a peptide, or a collection of tiled peptides, having the amino acid sequence selected from Sequence 6, an amino acid sequence having 90% identity to Sequence 6, or a fragment thereof comprising at least 10 consecutive amino acids of Sequence 6;

(ii) a peptide, or a collection of tiled peptides, having the amino acid sequence selected from Sequence 197, an amino acid sequence having 90% identity to Sequence 197, or a fragment thereof comprising at least 10 consecutive amino acids of Sequence 197; and a peptide, or a collection of tiled peptides, having the amino acid sequence selected from Sequence 198, an amino acid sequence having 90% identity to Sequence 198, or a fragment thereof comprising at least 10 consecutive amino acids of Sequence 198; preferably also comprising a peptide, or a collection of tiled peptides, having the amino acid sequence selected from Sequence 199, an amino acid sequence having 90% identity to Sequence 199, or a fragment thereof comprising at least 10 consecutive amino acids of Sequence 199; and/or a peptide, or a collection of tiled peptides, having the amino acid sequence selected from Sequence 200, an amino acid sequence having 90% identity to Sequence 200, or a fragment thereof comprising at least 10 consecutive amino acids of Sequence 200;

(iii) a peptide, or a collection of tiled peptides, having the amino acid sequence selected from Sequence 298, an amino acid sequence having 90% identity to Sequence 298, or a fragment thereof comprising at least 10 consecutive amino acids of Sequence 298; and a peptide, or a collection of tiled peptides, having the amino acid sequence selected from Sequence 299, an amino acid sequence having 90% identity to Sequence 299, or a fragment thereof comprising at least 10 consecutive amino acids of Sequence 299; preferably also comprising a peptide, or a collection of tiled peptides, having the amino acid sequence selected from Sequence 300, an amino acid sequence having 90% identity to Sequence 300, or a fragment thereof comprising at least 10 consecutive amino acids of Sequence 300;

(iv) a peptide, or a collection of tiled peptides, having the amino acid sequence selected from Sequence 553, an amino acid sequence having 90% identity to Sequence 553, or a fragment thereof comprising at least 10 consecutive amino acids of Sequence 553; and a peptide, or a collection of tiled peptides, having the amino acid sequence selected from Sequences 554-555, an amino acid sequence having 90% identity to Sequences 554-555, or a fragment thereof comprising at least 10 consecutive amino acids of Sequences 554-555;

(v) a peptide, or a collection of tiled peptides, having the amino acid sequence selected from Sequence 596, an amino acid sequence having 90% identity to Sequence 596, or a fragment thereof comprising at least 10 consecutive amino acids of Sequence 596; and a peptide, or a collection of tiled peptides, having the amino acid sequence selected from Sequence 597, an amino acid sequence having 90% identity to Sequence 597, or a fragment thereof comprising at least 10 consecutive amino acids of Sequence 597; preferably also comprising a peptide, or a collection of tiled peptides, having the amino acid sequence selected from Sequence 598, an amino acid sequence having 90% identity to Sequence 598, or a fragment thereof comprising at least 10 consecutive amino acids of Sequence 598;

a peptide, or a collection of tiled peptides, having the amino acid sequence selected from Sequence 599, an amino acid sequence having 90% identity to Sequence 599, or a fragment thereof comprising at least 10 consecutive amino acids of Sequence 599;

a peptide, or a collection of tiled peptides, having the amino acid sequence selected from Sequence 600, an amino acid sequence having 90% identity to Sequence 600, or a fragment thereof comprising at least 10 consecutive amino acids of Sequence 600; and/or a peptide, or a collection of tiled peptides, having the amino acid sequence selected from Sequence 601, an amino acid sequence having 90% identity to Sequence 601, or a fragment thereof comprising at least 10 consecutive amino acids of Sequence 601;

(vi) a peptide, or a collection of tiled peptides, having the amino acid sequence selected from Sequence 610, an amino acid sequence having 90% identity to Sequence 610, or a fragment thereof comprising at least 10 consecutive amino acids of Sequence 610; and a peptide, or a collection of tiled peptides, having the amino acid sequence selected from Sequence 611, an amino acid sequence having 90% identity to Sequence 611, or a fragment thereof comprising at least 10 consecutive amino acids of Sequence 611; preferably also comprising a peptide, or a collection of tiled peptides, having the amino acid sequence selected from Sequence 612, an amino acid sequence having 90% identity to Sequence 612, or a fragment thereof comprising at least 10 consecutive amino acids of Sequence 612;
a peptide, or a collection of tiled peptides, having the amino acid sequence selected from Sequence 613, an amino acid sequence having 90% identity to Sequence 613, or a fragment thereof comprising at least 10 consecutive amino acids of Sequence 613;
a peptide, or a collection of tiled peptides, having the amino acid sequence selected from Sequence 614, an amino acid sequence having 90% identity to Sequence 614, or a fragment thereof comprising at least 10 consecutive amino acids of Sequence 614; and/or
a peptide, or a collection of tiled peptides, having the amino acid sequence selected from Sequence 615, an amino acid sequence having 90% identity to Sequence 615, or a fragment thereof comprising at least 10 consecutive amino acids of Sequence 615;
(vii) a peptide, or a collection of tiled peptides, having the amino acid sequence selected from Sequence 681, an amino acid sequence having 90% identity to Sequence 681, or a fragment thereof comprising at least 10 consecutive amino acids of Sequence 681; and
a peptide, or a collection of tiled peptides, having the amino acid sequence selected from Sequence 682, an amino acid sequence having 90% identity to Sequence 682, or a fragment thereof comprising at least 10 consecutive amino acids of Sequence 682; preferably also comprising
a peptide, or a collection of tiled peptides, having the amino acid sequence selected from Sequence 683, an amino acid sequence having 90% identity to Sequence 683, or a fragment thereof comprising at least 10 consecutive amino acids of Sequence 683;
a peptide, or a collection of tiled peptides, having the amino acid sequence selected from Sequence 684, an amino acid sequence having 90% identity to Sequence 684, or a fragment thereof comprising at least 10 consecutive amino acids of Sequence 684;
a peptide, or a collection of tiled peptides, having the amino acid sequence selected from Sequence 685, an amino acid sequence having 90% identity to Sequence 685, or a fragment thereof comprising at least 10 consecutive amino acids of Sequence 685; and/or
a peptide, or a collection of tiled peptides, having the amino acid sequence selected from Sequence 686, an amino acid sequence having 90% identity to Sequence 686, or a fragment thereof comprising at least 10 consecutive amino acids of Sequence 686; and/or the collection comprising
(viii) a peptide, or a collection of tiled peptides, having the amino acid sequence selected from Sequence 709, an amino acid sequence having 90% identity to Sequence 709, or a fragment thereof comprising at least 10 consecutive amino acids of Sequence 709; and
a peptide, or a collection of tiled peptides, having the amino acid sequence selected from Sequence 710, an amino acid sequence having 90% identity to Sequence 710, or a fragment thereof comprising at least 10 consecutive amino acids of Sequence 710; preferably also comprising
a peptide, or a collection of tiled peptides, having the amino acid sequence selected from Sequence 711, an amino acid sequence having 90% identity to Sequence 711, or a fragment thereof comprising at least 10 consecutive amino acids of Sequence 711; and/or
a peptide, or a collection of tiled peptides, having the amino acid sequence selected from Sequence 712, an amino acid sequence having 90% identity to Sequence 712, or a fragment thereof comprising at least 10 consecutive amino acids of Sequence 712.

In some embodiments, the collection comprises two or more neoantigens corresponding to the same NOR For example, the collection may comprise two (or more) fragments of Sequence 1 or the collection may comprise a peptide having Sequence 1 and a peptide having 95% identity to Sequence 1.

Preferably, the collection comprises two or more neoantigens corresponding to different NOPs. In some embodiments, the collection comprises two or more neoantigens corresponding to different NOPs of the same gene. For example the peptide may comprise the amino acid sequence of Sequence 1 (or a fragment or collection of tiled fragments thereof) and the amino acid sequence of Sequence 2 (or a fragment or collection of tiled fragments thereof).

Preferably, the collection comprises Sequences 1-4, preferably 1-6, more preferably 1-29, most preferably 1-96 (or a fragment or collection of tiled fragments thereof). Preferably, the collection comprises Sequences 197-200, preferably 197-202, more preferably 197-207 (or a fragment or collection of tiled fragments thereof). Preferably, the collection comprises Sequences 298-300, preferably 298-303, more preferably 298-309 (or a fragment or collection of tiled fragments thereof). Preferably, the collection comprises Sequences 553-555, preferably 553-559, more preferably 553-566 (or a fragment or collection of tiled fragments thereof). Preferably, the collection comprises Sequences 596-599, preferably 596-602, more preferably 596-609 (or a fragment or collection of tiled fragments thereof). Preferably, the collection comprises Sequences 610-613, preferably 610-618, more preferably 610-624 (or a fragment or collection of tiled fragments thereof). Preferably, the collection comprises Sequences 681-684, preferably 681-687, more preferably 681-695 (or a fragment or collection of tiled fragments thereof). Preferably, the collection comprises Sequences 709-711, preferably 709-714 (or a fragment or collection of tiled fragments thereof).

In some embodiments, the collection comprises two or more neoantigens corresponding to different NOPs of different genes. For example the collection may comprise a peptide having the amino acid sequence of Sequence 1 (or a fragment or collection of tiled fragments thereof) and a peptide having the amino acid sequence of Sequence 43 (or a fragment or collection of tiled fragments thereof). Preferably, the collection comprises at least one neoantigen from group (i) and at least one neoantigen from group (ii); at least one neoantigen from group (i) and at least one neoantigen from group (iii); at least one neoantigen from group (i) and at least one neoantigen from group (iv); at least one neoantigen from group (i) and at least one neoantigen from group (v); at least one neoantigen from group (i) and at least one neoantigen from group (vi); at least one neoantigen from group (i) and at least one neoantigen from group (vii); at least one neoantigen from group (i) and at least one neoantigen from group (viii); at least one neoantigen from group (ii) and at least one neoantigen from group (iii); at least one neoantigen from group (ii) and at least one neoantigen from group (iv); at least one neoantigen from group (ii) and at least one neoantigen from group (v); at least one neoantigen from group (ii) and at least one neoantigen from group (vi); at least one neoantigen from group (ii) and at least one neoantigen from group (vii); at least one neoantigen from group (ii) and at least one neoantigen from group (viii); at least one neoantigen from group (iii) and at least one neoantigen from group (iv); at least one neoantigen from group (iii) and at least one neoantigen from group (v); at least one neoantigen from group (iii) and at least one neoantigen from group (vi); at least one neoantigen from group (iii) and at least one neoantigen from group (vii); at least one neoantigen from group (iii) and at least one neoantigen from group (viii); at least one neoantigen from group (iv) and at least one neoantigen from group (v), at least one neoantigen from group (iv) and at least one neoantigen from group (vi), at least one neoantigen from group (iv) and at least one neoantigen from group (vii), at least one neoantigen from group (iv) and at least one neoantigen from group (viii), at least one neoantigen from group (v) and at least one neoantigen from group (vi), (v) and at least one neoantigen from group (vii), (v) and at least one neoantigen from group (viii), (vi) and at least one neoantigen from group (vii), (vi) and at least one neoantigen from group (viii), (vii) and at least one neoantigen from group (viii). Preferably, the collection comprises at least one neoantigen from group (i), at least one neoantigen from group (ii), and at least one neoantigen from group (iii). Preferably, the collection comprises at least one neoantigen from each of groups (i) to (v). Preferably, the collection comprises at least one neoantigen from each of groups (i) to (viii).

In a preferred embodiment, the collections disclosed herein include Sequence 553 and Sequence 1 (or a variant or fragment or collection of tiled fragments thereof as disclosed herein). In preferred embodiments, the collection further includes one, two or all three of Sequences 2, 709, and 710 (or a variant or fragment or collection of tiled fragments thereof as disclosed herein). In preferred embodiments, the collection further includes, at least one, two, three, or all of Sequence 298, 610, 3, 611, 681 (or a variant or fragment or collection of tiled fragments thereof as disclosed herein). In preferred embodiments, the collection further includes at least one or all of Sequences 4, 526, 299, 597, 682 (or a variant or fragment or collection of tiled fragments thereof as disclosed herein). In preferred embodiments, the collection further includes, at least one, two or more of Sequences 683-684, 197, 5, 6, 300, 598-600, 612-613, 685, 711, 198, 554-555, 601, 686-687 (or a variant or fragment or collection of tiled fragments thereof as disclosed herein). In preferred embodiments, the collection further includes, Sequences 614-618, 7-21, 199-200, 301-303, 556, 602-603, 712-713, 201-206, 304, 557-559, 688-691, 22-29, 207, 305-309, 619 (or a variant or fragment or collection of tiled fragments thereof as disclosed herein). In preferred embodiments, the collection further includes all other Sequences listed in Table 1 and not mentioned earlier in this paragraph (or a variant or fragment or collection of tiled fragments thereof as disclosed herein). Preferably, such collections, or nucleic acid molecules encoding said collections, are useful in treating colorectal cancer.

Such collections comprising multiple neoantigens have the advantage that a single collection (e.g, when used as a vaccine) can benefit a larger group of patients having different frameshift mutations. This makes it feasible to construct and/or test the vaccine in advance and have the vaccine available for off-the-shelf use. This also greatly reduces the time from screening a tumor from a patient to administering a potential vaccine for said tumor to the patient, as it eliminates the time of production, testing and approval. In addition, a single collection consisting of multiple neoantigens corresponding to different genes will limit possible resistance mechanisms of the tumor, e.g. by losing one or more of the targeted neoantigens.

In preferred embodiments, the neoantigens (i.e., peptides) are directly linked. Preferably, the neoantigens are linked by peptide bonds, or rather, the neoantigens are present in a single polypeptide. Accordingly, the disclosure provides polypeptides comprising at least two peptides (i.e., neoantigens) as disclosed herein. In some embodiments, the polypeptide comprises 3, 4, 5, 6, 7, 8, 9, 10 or more peptides as disclosed herein (i.e., neoantigens). Such polypeptides are also referred to herein as 'polyNOPs'. A collection of peptides can have one or more peptides and one or more polypeptides comprising the respective neoantigens.

In an exemplary embodiment, a polypeptide of the disclosure may comprise 10 different neoantigens, each neoantigen having between 10-400 amino acids. Thus, the polypeptide of the disclosure may comprise between 100-4000 amino acids, or more. As is clear to a skilled person, the final length of the polypeptide is determined by the number of neoantigens selected and their respective lengths. A collection may comprise two or more polypeptides comprising the neoantigens which can be used to reduce the size of each of the polypeptides.

In preferred embodiments, the amino acid sequences of the neoantigens are located directly adjacent to each other in the polypeptide. For example, a nucleic acid molecule may be provided that encodes multiple neoantigens in the same reading frame. In some embodiments, a linker amino acid sequence may be present. Preferably a linker has a length of 1, 2, 3, 4 or 5, or more amino acids. The use of linker may be beneficial, for example for introducing, among others, signal peptides or cleavage sites. In some embodiments at least one, preferably all of the linker amino acid sequences have the amino acid sequence VDD.

As will be appreciated by the skilled person, the peptides and polypeptides disclosed herein may contain additional amino acids, for example at the N- or C-terminus. Such additional amino acids include, e.g., purification or affinity tags or hydrophilic amino acids in order to decrease the hydrophobicity of the peptide. In some embodiments, the neoantigens may comprise amino acids corresponding to the adjacent, wild-type amino acid sequences of the relevant gene, i.e., amino acid sequences located 5' to the frame shift mutation that results in the neo open reading frame. Preferably, each neoantigen comprises no more than 20, more preferably no more than 10, and most preferably no more than 5 of such wild-type amino acid sequences.

In preferred embodiments, the peptides and polypeptides disclosed herein have a sequence depicted as follows:

A-B-C-(D-E)$_n$, wherein

A, C, and E are independently 0-100 amino acids

B and D are amino acid sequences as disclosed herein and selected from sequences 1-717, or an amino acid sequence having 90% identity to Sequences 1-717, or a fragment thereof comprising at least 10 consecutive amino acids of Sequences 1-717, n is an integer from 0 to 500.

Preferably, B and D are different amino acid sequences. Preferably, n is an integer from 0-200. Preferably A, C, and E are independently 0-50 amino acids, more preferably independently 0-20 amino acids.

The peptides and polypeptides disclosed herein can be produced by any method known to a skilled person. In some embodiments, the peptides and polypeptide are chemically synthesized. The peptides and polypeptide can also be produced using molecular genetic techniques, such as by inserting a nucleic acid into an expression vector, introducing the expression vector into a host cell, and expressing the peptide. Preferably, such peptides and polypeptide are isolated, or rather, substantially isolated from other polypeptides, cellular components, or impurities. The peptide and polypeptide can be isolated from other (poly)peptides as a result of solid phase protein synthesis, for example. Alternatively, the peptides and polypeptide can be substantially isolated from other proteins after cell lysis from recombinant production (e.g., using HPLC).

The disclosure further provides nucleic acid molecules encoding the peptides and polypeptide disclosed herein. Based on the genetic code, a skilled person can determine the nucleic acid sequences which encode the (poly)peptides disclosed herein. Based on the degeneracy of the genetic code, sixty-four codons may be used to encode twenty amino acids and translation termination signal.

In a preferred embodiment, the nucleic acid molecules are codon optimized. As is known to a skilled person, codon usage bias in different organisms can effect gene expression level. Various computational tools are available to the skilled person in order to optimize codon usage depending on which organism the desired nucleic acid will be expressed. Preferably, the nucleic acid molecules are optimized for expression in mammalian cells, preferably in human cells. Table 2 lists for each acid amino acid (and the stop codon) the most frequently used codon as encountered in the human exome.

TABLE 2 most frequently used codon for each amino acid and most frequently used stop codon.

| A | GCC |
| C | TGC |
| D | GAC |
| E | GAG |
| F | TTC |
| G | GGC |
| H | CAC |
| I | ATC |
| K | AAG |
| L | CTG |
| M | ATG |
| N | AAC |
| P | CCC |
| Q | CAG |
| R | CGG |
| S | AGC |
| T | ACC |
| V | GTG |
| W | TGG |
| Y | TAC |
| Stop | TGA |

In preferred embodiments, at least 50%, 60%, 70%, 80%, 90%, or 100% of the amino acids are encoded by a codon corresponding to a codon presented in Table 2.

In preferred embodiments, the nucleic acid molecule encodes for a linker amino acid sequence in the peptide. Preferably, the nucleic acid sequence encoding the linker comprises at least one codon triplet that codes for a stop codon when a frameshift occurs. Preferably, said codon triplet is chosen from the group consisting of: ATA, CTA, GTA, TTA, ATG, CTG, GTG, TTG, AAA, AAC, AAG, AAT, AGA, AGC, AGG, AGT, GAA, GAC, GAG, and GAT. These codons do not code for a stop codon, but could create a stop codon in case of a frame shift, such as when read in the +1, +2, +4, +, 5, etc. reading frame. For example, two amino acid encoding sequences are linked by a linker amino acid encoding sequence as follows (linker amino acid encoding sequence in bold):

CTATACAGGCGAATGAGATTATG

Resulting in the following amino acid sequence (amino acid linker sequence in bold): LYRRMRL In case of a +1 frame shift, the following sequence is encoded:

YTGE [stop] DY

This embodiment has the advantage that if a frame shift occurs in the nucleotide sequence encoding the peptide, the nucleic acid sequence encoding the linker will terminate translation, thereby preventing expression of (part of) the native protein sequence for the gene related to peptide sequence encoded by the nucleotide sequence.

In some preferred embodiments, the linker amino acid sequences are encoded by the nucleotide sequence (TAGATGAC. This linker has the advantage that it contains two out of frame stop codons (TAG and TGA), one in the +1 and one in the −1 reading frame. The amino acid sequence encoded by this nucleotide sequence is VDD. The added advantage of using a nucleotide sequence encoding for this linker amino acid sequence is that any frame shift will result in a stop codon.

The disclosure also provides binding molecules and a collection of binding molecules that bind the neoantigens disclosed herein and or a neoantigen/MHC complex. In some embodiments the binding molecule is an antibody, a T-cell receptor, or an antigen binding fragment thereof. In some embodiments the binding molecule is a chimeric antigen receptor comprising i) a T cell activation molecule; ii) a transmembrane region; and iii) an antigen recognition moiety; wherein said antigen recognition moieties bind the neoantigens disclosed herein and or a neoantigen/MHC complex.

The term "antibody" as used herein refers to an immunoglobulin molecule that is typically composed of two identical pairs of polypeptide chains, each pair of chains consisting of one "heavy" chain with one "light" chain. The human light chains are classified as kappa and lambda. The heavy chains comprise different classes namely: mu, delta, gamma, alpha or epsilon. These classes define the isotype of the antibody, such as IgM, IgD, IgG IgA and IgE, respectively. These classes are important for the function of the antibody and help to regulate the immune response. Both the heavy chain and the light chain comprise a variable domain and a constant region. Each heavy chain variable region (VH) and light chain variable region (VL) comprises complementary determining regions (CDR) interspersed by framework regions (FR). The variable region has in total four FRs and three CDRs. These are arranged from the amino- to the carboxyl-terminus as follows: FR1. CDR1, FR2, CDR2, FR3, CDR3, FR4. The variable regions of the light and heavy chain together form the antibody binding site and define the specificity for the epitope.

The term "antibody" encompasses murine, humanized, deimmunized, human, and chimeric antibodies, and an antibody that is a multimeric form of antibodies, such as dimers, trimers, or higher-order multimers of monomeric antibodies. The term antibody also encompasses monospecific, bispecific or multi-specific antibodies, and any other modified configuration of the immunoglobulin molecule that comprises an antigen recognition site of the required specificity.

Preferably, an antibody or antigen binding fragment thereof as disclosed herein is a humanized antibody or antigen binding fragment thereof. The term "humanized antibody" refers to an antibody that contains some or all of the CDRs from a non-human animal antibody while the framework and constant regions of the antibody contain amino acid residues derived from human antibody sequences. Humanized antibodies are typically produced by grafting CDRs from a mouse antibody into human framework sequences followed by back substitution of certain human framework residues for the corresponding mouse residues from the source antibody. The term "deimmunized antibody" also refers to an antibody of non-human origin in which, typically in one or more variable regions, one or more epitopes have been removed, that have a high propensity of constituting a human T-cell and/or B-cell epitope, for purposes of reducing immunogenicity. The amino acid sequence of the epitope can be removed in full or in part. However, typically the amino acid sequence is altered by substituting one or more of the amino acids constituting the epitope for one or more other amino acids, thereby changing the amino acid sequence into a sequence that does not constitute a human T-cell and/or B-cell epitope. The amino acids are substituted by amino acids that are present at the corresponding position(s) in a corresponding human variable heavy or variable light chain as the case may be.

In some embodiments, an antibody or antigen binding fragment thereof as disclosed herein is a human antibody or antigen binding fragment thereof. The term "human antibody" refers to an antibody consisting of amino acid sequences of human immunoglobulin sequences only. Human antibodies may be prepared in a variety of ways known in the art.

As used herein, antigen-binding fragments include Fab, F(ab'), F(ab')2, complementarity determining region (CDR) fragments, single-chain antibodies (scFv), bivalent single-chain antibodies, and other antigen recognizing immunoglobulin fragments.

In some embodiments, the antibody or antigen binding fragment thereof is an isolated antibody or antigen binding fragment thereof. The term "isolated", as used herein, refers to material which is substantially or essentially free from components which normally accompany it in nature.

In some embodiments, the antibody or antigen binding fragment thereof is linked or attached to a non-antibody moiety. In preferred embodiments, the non-antibody moiety is a cytotoxic moiety such as auristatins, maytanasines, calicheasmicins, duocarymycins, a-amanitin, doxorubicin, and centanamycin. Other suitable cytotoxins and methods for preparing such antibody drug conjugates are known in the art; see, e.g., WO2013085925A1 and WO2016133927A1.

Antibodies which bind a particular epitope can be generated by methods known in the art. For example, polyclonal antibodies can be made by the conventional method of immunizing a mammal (e.g., rabbits, mice, rats, sheep, goats). Polyclonal antibodies are then contained in the sera of the immunized animals and can be isolated using standard procedures (e.g., affinity chromatography, immunoprecipitation, size exclusion chromatography, and ion exchange chromatography). Monoclonal antibodies can be made by the conventional method of immunization of a mammal, followed by isolation of plasma B cells producing the monoclonal antibodies of interest and fusion with a myeloma cell (see, e.g., Mishell, B. B., et al., Selected Methods In Cellular Immunology, (W.H. Freeman, ed.) San Francisco (1980)). Peptides corresponding to the neoantiens disclosed herein may be used for immunization in order to produce antibodies which recognize a particular epitope. Screening for recognition of the epitope can be performed using standard immunoassay methods including ELISA techniques, radioimmunoassays, immunofluorescence, immunohistochemistry, and Western blotting. See, Short Protocols in Molecular Biology, Chapter 11, Green Publishing Associates and John Wiley & Sons, Edited by Ausubel, F. M et al., 1992. In vitro methods of antibody selection, such as antibody phage display, may also be used to generate antibodies recognizing the neoantigens disclosed herein (see, e.g., Schirrmann et al. Molecules 2011 16:412-426).

T-cell receptors (TCRs) are expressed on the surface of T-cells and consist of an α chain and a β chain. TCRs recognize antigens bound to MHC molecules expressed on the surface of antigen-presenting cells. The T-cell receptor (TCR) is a heterodimeric protein, in the majority of cases (95%) consisting of a variable alpha (α) and beta (β) chain, and is expressed on the plasma membrane of T-cells. The TCR is subdivided in three domains: an extracellular domain, a transmembrane domain and a short intracellular domain. The extracellular domain of both α and β chains have an immunoglobulin-like structure, containing a variable and a constant region. The variable region recognizes processed peptides, among which neoantigens, presented by major histocompatibility complex (MHC) molecules, and is highly variable. The intracellular domain of the TCR is very short, and needs to interact with CD3 to allow for signal propagation upon ligation of the extracellular domain.

With the focus of cancer treatment shifted towards more targeted therapies, among which immunotherapy, the potential of therapeutic application of tumor-directed T-cells is increasingly explored. One such application is adoptive T-cell therapy (ATCT) using genetically modified T-cells that carry chimeric antigen receptors (CARs) recognizing a particular epitope (Ref Gomes-Silva 2018). The extracellular domain of the CAR is commonly formed by the antigen-specific subunit of (scFv) of a monoclonal antibody that recognizes a tumor-antigen (Ref Abate-Daga 2016). This enables the CAR T-cell to recognize epitopes independent of MHC-molecules, thus widely applicable, as their functionality is not restricted to individuals expressing the specific MHC-molecule recognized by the TCR. Methods for engineering TCRs that bind a particular epitope are known to a skilled person. See, for example, US20100009863A1, which describes methods of modifying one or more structural loop regions. The intracellular domain of the CAR can be a TCR intracellular domain or a modified peptide to enable induction of a signaling cascade without the need for interaction with accessory proteins. This is accomplished by inclusion of the CD3-signalling domain, often in combination with one or more co-stimulatory domains, such as CD28 and 4-1BB, which further enhance CAR T-cell functioning and persistence (Ref Abate-Daga 2016).

The engineering of the extracellular domain towards an scFv limits CAR T-cell to the recognition of molecules that are expressed on the cell-surface. Peptides derived from proteins that are expressed intracellularly can be recognized upon their presentation on the plasma membrane by MHC molecules, of which human form is called human leukocyte antigen (HLA). The HLA-haplotype generally differs among individuals, but some HLA types, like HLA-A*02:01, are globally common. Engineering of CAR T-cell extracellular domains recognizing tumor-derived peptides or neoantigens presented by a commonly shared HLA molecule enables recognition of tumor antigens that remain intracellular. Indeed CAR T-cells expressing a CAR with a TCR-like extracellular domain have been shown to be able to recognize tumor-derived antigens in the context of HLA-A*02:01 (Refs Zhang 2014, Ma 2016, Liu 2017).

In some embodiments, the binding molecules are mono-specific, or rather they bind one of the neoantigens disclosed herein. In some embodiments, the binding molecules are bispecific, e.g., bispecific antibodies and bispecific chimeric antigen receptors.

In some embodiments, the disclosure provides a first antigen binding domain that binds a first neoantigen described herein and a second antigen binding domain that binds a second neoantigen described herein. The first and second antigen binding domains may be part of a single molecule, e.g., as a bispecific antibody or bispecific chimeric antigen receptor or they may be provided on separate molecules, e.g., as a collection of antibodies, T-cell receptors, or chimeric antigen receptors. In some embodiments, 3, 4, 5 or more antigen binding domains are provided each binding a different neoantigen disclosed herein. As used herein, an antigen binding domain includes the variable (antigen binding) domain of a T-cell receptor and the variable domain of an antibody (e.g., comprising a light chain variable region and a heavy chain variable region).

The disclosure further provides nucleic acid molecules encoding the antibodies, TCRs, and CARs disclosed herein. In a preferred embodiment, the nucleic acid molecules are codon optimized as disclosed herein.

The disclosure further provides vectors comprising the nucleic acids molecules disclosed herein. A "vector" is a recombinant nucleic acid construct, such as plasmid, phase genome, virus genome, cosmid, or artificial chromosome, to which another nucleic acid segment may be attached. The term "vector" includes both viral and non-viral means for introducing the nucleic acid into a cell in vitro, ex vivo or in vivo. The disclosure contemplates both DNA and RNA vectors. The disclosure further includes self-replicating RNA with (virus-derived) replicons, including but not limited to mRNA molecules derived from mRNA molecules from alphavirus genomes, such as the Sindbis, Semliki Forest and Venezuelan equine encephalitis viruses.

Vectors, including plasmid vectors, eukaryotic viral vectors and expression vectors are known to the skilled person. Vectors may be used to express a recombinant gene construct in eukaryotic cells depending on the preference and judgment of the skilled practitioner (see, for example, Sambrook et al., Chapter 16). For example, many viral vectors are known in the art including, for example, retroviruses, adeno-associated viruses, and adenoviruses. Other viruses useful for introduction of a gene into a cell include, but a not limited to, arenavirus, herpes virus, mumps virus, poliovirus, Sindbis virus, and vaccinia virus, such as, canary pox virus. The methods for producing replication-deficient viral particles and for manipulating the viral genomes are well known. In some embodiments, the vaccine comprises an attenuated or inactivated viral vector comprising a nucleic acid disclosed herein.

Preferred vectors are expression vectors. It is within the purview of a skilled person to prepare suitable expression vectors for expressing the inhibitors disclosed hereon. An "expression vector" is generally a DNA element, often of circular structure, having the ability to replicate autonomously in a desired host cell, or to integrate into a host cell genome and also possessing certain well-known features which, for example, permit expression of a coding DNA inserted into the vector sequence at the proper site and in proper orientation. Such features can include, but are not limited to, one or more promoter sequences to direct transcription initiation of the coding DNA and other DNA elements such as enhancers, polyadenylation sites and the like, all as well known in the art. Suitable regulatory sequences including enhancers, promoters, translation initiation signals, and polyadenylation signals may be included. Additionally, depending on the host cell chosen and the vector employed, other sequences, such as an origin of replication, additional DNA restriction sites, enhancers, and sequences conferring inducibility of transcription may be incorporated into the expression vector. The expression vectors may also contain a selectable marker gene which facilitates the selection of host cells transformed or transfected. Examples of selectable marker genes are genes encoding a protein such as G418 and hygromycin which confer resistance to certain drugs, β-galactosidase, chloramphenicol acetyltransferase, and firefly luciferase.

The expression vector can also be an RNA element that contains the sequences required to initiate translation in the desired reading frame, and possibly additional elements that are known to stabilize or contribute to replicate the RNA molecules after administration. Therefore when used herein the term DNA when referring to an isolated nucleic acid encoding the peptide according to the invention should be interpreted as referring to DNA from which the peptide can be transcribed or RNA molecules from which the peptide can be translated.

Also provided for is a host cell comprising an nucleic acid molecule or a vector as disclosed herein. The nucleic acid molecule may be introduced into a cell (prokaryotic or eukaryotic) by standard methods. As used herein, the terms "transformation" and "transfection" are intended to refer to a variety of art recognized techniques to introduce a DNA into a host cell. Such methods include, for example, transfection, including, but not limited to, liposome-polybrene, DEAE dextran-mediated transfection, electroporation, calcium phosphate precipitation, microinjection, or velocity driven microprojectiles ("biolistics"). Such techniques are well known by one skilled in the art. See, Sambrook et al. (1989) Molecular Cloning: A Laboratory Manaual (2 ed. Cold Spring Harbor Lab Press, Plainview, N.Y.). Alternatively, one could use a system that delivers the DNA construct in a gene delivery vehicle. The gene delivery vehicle may be viral or chemical. Various viral gene delivery vehicles can be used with the present invention. In general, viral vectors are composed of viral particles derived from naturally occurring viruses. The naturally occurring virus has been genetically modified to be replication defective and does not generate additional infectious viruses, or it may be a virus that is known to be attenuated and does not have unacceptable side effects.

Preferably, the host cell is a mammalian cell, such as MRCS cells (human cell line derived from lung tissue), HuH7 cells (human liver cell line), CHO-cells (Chinese Hamster Ovary), COS-cells (derived from monkey kidney (African green monkey), Vero-cells (kidney epithelial cells extracted from African green monkey), Hela-cells (human cell line), BHK-cells (baby hamster kidney cells, HEK-cells (Human Embryonic Kidney), NSO-cells (Murine myeloma cell line), C127-cells (nontumorigenic mouse cell line), PerC6®-cells (human cell line, Crucell), and Madin-Darby Canine Kidney (MDCK) cells. In some embodiments, the disclosure comprises an in vitro cell culture of mammalian cells expressing the neoantigens disclosed herein. Such cultures are useful, for example, in the production of cell-based vaccines, such as viral vectors expressing the neoantigens disclosed herein.

In some embodiments the host cells express the antibodies, TCRs, or CARs as disclosed herein. As will be clear to a skilled person, individual polypeptide chains (e.g., immunoglobulin heavy and light chains) may be provided on the same or different nucleic acid molecules and expressed by the same or different vectors. For example, in some embodiments, a host cell is transfected with a nucleic acid encoding an α-TCR polypeptide chain and a nucleic acid encoding a β-polypeptide chain.

In preferred embodiments, the disclosure provides T-cells expressing a TCR or CAR as disclosed herein. T cells may be obtained from, e.g., peripheral blood mononuclear cells, bone marrow, lymph node tissue, cord blood, thymus tissue, spleen tissue, and tumors. Preferably, the T-cells are obtained from the individual to be treated (autologous T-cells). T-cells may also be obtained from healthy donors (allogenic T-cells). Isolated T-cells are expanded in vitro using established methods, such as stimulation with cytokines (IL-2). Methods for obtaining and expanding T-cells for adoptive therapy are well known in the art and are also described, e.g., in EP2872533A1.

The disclosure also provides vaccines comprising one or more neoantigens as disclosed herein. In particular, the vaccine comprises one or more (poly)peptides, antibodies or antigen binding fragments thereof, TCRs, CARS, nucleic acid molecules, vectors, or cells (or cell cultures) as disclosed herein.

The vaccine may be prepared so that the selection, number and/or amount of neoantigens (e.g., peptides or nucleic acids encoding said peptides) present in the composition is patient-specific. Selection of one or more neoantigens may be based on sequencing information from the tumor of the patient. For any frame shift mutation found, a corresponding NOP is selected. Preferably, the vaccine comprises more than one neoantigen corresponding to the NOP selected. In case multiple frame shift mutations (multiple NOPs) are found, multiple neoantigens corresponding to each NOP may be selected for the vaccine.

The selection may also be dependent on the specific type of cancer, the status of the disease, earlier treatment regimens, the immune status of the patient, and, HLA-haplotype of the patient. Furthermore, the vaccine can contain individualized components, according to personal needs of the particular patient.

As is clear to a skilled person, if multiple neoantigens are used, they may be provided in a single vaccine composition or in several different vaccines to make up a vaccine collection. The disclosure thus provides vaccine collections comprising a collection of tiled peptides, collection of peptides as disclosed herein, as well as nucleic acid molecules, vectors, or host cells as disclosed herein. As is clear to a skilled person, such vaccine collections may be administered to an individual simultaneously or consecutively (e.g., on the same day) or they may be administered several days or weeks apart.

Various known methods may be used to administer the vaccines to an individual in need thereof. For instance, one or more neoantigens can be provided as a nucleic acid molecule directly, as "naked DNA". Neoantigens can also be expressed by attenuated viral hosts, such as vaccinia or fowlpox. This approach involves the use of a virus as a vector to express nucleotide sequences that encode the neoantigen. Upon introduction into the individual, the recombinant virus expresses the neoantigen peptide, and thereby elicits a host CTL response. Vaccination using viral vectors is well-known to a skilled person and vaccinia vectors and methods useful in immunization protocols are described in, e.g., U.S. Patent No. 4722848. Another vector is BCG (Bacille Calmette Guerin) as described in Stover et al. (Nature 351:456-460 (1991)).

Preferably, the vaccine comprises a pharmaceutically acceptable excipient and/or an adjuvant. The compositions may contain pharmaceutically acceptable auxiliary substances as required to approximate physiological conditions, such as pH adjusting and buffering agents, tonicity adjusting agents, wetting agents and the like. Suitable adjuvants are well-known in the art and include, aluminum (or a salt thereof, e.g., aluminium phosphate and aluminium hydroxide), monophosphoryl lipid A, squalene (e.g., MF59), and cytosine phosphoguanine (CpG), montanide, liposomes (e.g. CAF adjuvants, cationic adjuvant formulations and variations thereof), lipoprotein conjugates (e.g. Amplivant), Resiquimod, Iscomatrix, hiltonol, poly-ICLC (polyriboinosinic-polyribocytidylic acid-polylysine carboxymethylcellulose). A skilled person is able to determine the appropriate adjuvant, if necessary, and an immune-effective amount thereof. As used herein, an immune-effective amount of adjuvant refers to the amount needed to increase the vaccine's immunogenicity in order to achieve the desired effect.

The disclosure also provides the use of the neoantigens disclosed herein for the treatment of disease, in particular for the treatment of colorectal cancer in an individual. Colorectal cancer refers to cancer that develops in the colon or rectum. In preferred embodiments, the colorectal cancer is colon cancer, such as colon adenocarcinoma (COAD). In preferred embodiments, the colorectal cancer is rectal cancer, such as rectal adenocarcinoma (READ). Adenocarcinomas make up approximately 95% of colorectal cancers. It is within the purview of a skilled person to diagnose an individual with as having colorectal cancer.

As used herein, the terms "treatment," "treat," and "treating" refer to reversing, alleviating, or inhibiting the progress of a disease, or reversing, alleviating, delaying the onset of, or inhibiting one or more symptoms thereof. Treatment includes, e.g., slowing the growth of a tumor, reducing the size of a tumor, and/or slowing or preventing tumor metastasis.

The term 'individual' includes mammals, both humans and non-humans and includes but is not limited to humans, non-human primates, canines, felines, murines, bovines, equines, and porcines. Preferably, the human is a mammal.

As used herein, administration or administering in the context of treatment or therapy of a subject is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

The optimum amount of each neoantigen to be included in the vaccine composition and the optimum dosing regimen can be determined by one skilled in the art without undue experimentation. The composition may be prepared for injection of the peptide, nucleic acid molecule encoding the peptide, or any other carrier comprising such (such as a virus or liposomes). For example, doses of between 1 and 500 mg 50 µg and 1.5 mg, preferably 125 µg to 500 µg, of peptide or DNA may be given and will depend from the respective peptide or DNA. Other methods of administration are known to the skilled person. Preferably, the vaccines may be administered parenterally, e.g., intravenously, subcutaneously, intradermally, intramuscularly, or otherwise.

For therapeutic use, administration may begin at or shortly after the surgical removal of tumors. This can be followed by boosting doses until at least symptoms are substantially abated and for a period thereafter.

In some embodiments, the vaccines may be provided as a neoadjuvant therapy, e.g., prior to the removal of tumors or prior to treatment with radiation or chemotherapy. Neoadjuvant therapy is intended to reduce the size of the tumor before more radical treatment is used. For that reason being able to provide the vaccine off-the-shelf or in a short period of time is very important.

Also disclosed herein, the vaccine is capable of initiating a specific T-cell response. It is within the purview of a skilled person to measure such T-cell responses either in vivo or in vitro, e.g. by analyzing IFN-γ production or tumor killing by T-cells. In therapeutic applications, vaccines are administered to a patient in an amount sufficient to elicit an effective CTL response to the tumor antigen and to cure or at least partially arrest symptoms and/or complications.

The vaccine disclosed herein can be administered alone or in combination with other therapeutic agents. The therapeutic agent is for example, a chemotherapeutic agent, radiation, or immunotherapy, including but not limited to checkpoint inhibitors, such as nivolumab, ipilimumab, pembrolizumab, or the like. Any suitable therapeutic treatment for a particular, cancer may be administered.

The term "chemotherapeutic agent" refers to a compound that inhibits or prevents the viability and/or function of cells, and/or causes destruction of cells (cell death), and/or exerts anti-tumor/anti-proliferative effects. The term also includes agents that cause a cytostatic effect only and not a mere cytotoxic effect. Examples of chemotherapeutic agents include, but are not limited to bleomycin, capecitabine, carboplatin, cisplatin, cyclophosphamide, docetaxel, doxorubicin, etoposide, interferon alpha, irinotecan, lansoprazole, levamisole, methotrexate, metoclopramide, mitomycin, omeprazole, ondansetron, paclitaxel, pilocarpine, rituxitnab, tamoxifen, taxol, trastuzumab, vinblastine, and vinorelbine tartrate.

Preferably, the other therapeutic agent is an anti-immunosuppressive/immunostimulatory agent, such as anti-CTLA antibody or anti-PD-1 or anti-PD-L1. Blockade of CTLA-4 or PD-L1 by antibodies can enhance the immune response to cancerous cells. In particular, CTLA-4 blockade has been shown effective when following a vaccination protocol.

As is understood by a skilled person the vaccine and other therapeutic agents may be provided simultaneously, separately, or sequentially. In some embodiments, the vaccine may be provided several days or several weeks prior to or following treatment with one or more other therapeutic agents. The combination therapy may result in an additive or synergistic therapeutic effect.

As disclosed herein, the present disclosure provides vaccines which can be prepared as off-the-shelf vaccines. As used herein "off-the-shelf" means a vaccine as disclosed herein that is available and ready for administration to a patient. For example, when a certain frame shift mutation is identified in a patient, the term "off-the-shelf" would refer to a vaccine according to the disclosure that is ready for use in the treatment of the patient, meaning that, if the vaccine is peptide based, the corresponding polyNOP peptide may, for example already be expressed and for example stored with the required excipients and stored appropriately, for example at −20° C. or −80° C. Preferably the term "off-the-shelf" also means that the vaccine has been tested, for example for safety or toxicity. More preferably the term also means that the vaccine has also been approved for use in the treatment or prevention in a patient. Accordingly, the disclosure also provides a storage facility for storing the vaccines disclosed herein. Depending on the final formulation, the vaccines may be stored frozen or at room temperature, e.g., as dried preparations. Preferably, the storage facility stores at least 20 or at least 50 different vaccines, each recognizing a neoantigen disclosed herein.

The present disclosure also contemplates methods which include determining the presence of NOPs in a tumor sample. In a preferred embodiment, a tumor of a patient can be screened for the presence of frame shift mutations and an NOP can be identified that results from such a frame shift mutation. Based on the NOP(s) identified in the tumor, a vaccine comprising the relevant NOP(s) can be provided to immunize the patient, so the immune system of the patient will target the tumor cells expressing the neoantigen. An exemplary workflow for providing a neoantigen as disclosed herein is as follows. When a patient is diagnosed with a cancer, a biopsy may be taken from the tumor or a sample set is taken of the tumor after resection. The genome, exome and/or transcriptome is sequenced by any method known to a skilled person. The outcome is compared, for example using a web interface or software, to the library of NOPs disclosed herein. A patient whose tumor expresses one of the NOPs disclosed herein is thus a candidate for a vaccine comprising the NOP (or a fragment thereof).

Accordingly, the disclosure provides a method for determining a therapeutic treatment for an individual afflicted with cancer, said method comprising determining the presence of a frame shift mutation which results in the expression of an NOP selected from sequences 1-717. Identification of the expression of an NOP indicates that said individual should be treated with a vaccine corresponding to the identified NOP. For example, if it is determined that tumor cells from an individual express Sequence 1, then a vaccine comprising Sequence 1 or a fragment thereof is indicated as a treatment for said individual.

Accordingly, the disclosure provides a method for determining a therapeutic treatment for an individual afflicted with cancer, said method comprising
 a. performing complete, targeted or partial genome, exome, ORFeome, or transcriptome sequencing of at least one tumor sample obtained from the individual to obtain a set of sequences of the subject-specific tumor genome, exome, ORFeome, or transcriptome;
 b. comparing at least one sequence or portion thereof from the set of sequences with one or more sequences selected from:
  (i) APC: Sequences 1-196, more preferably sequences 1-60.
  (ii) ARID1A: Sequences 197-297, more preferably sequences 197-232.
  (iii) KMT2D: Sequences 298-552, more preferably sequences 298-337.
  (iv) RNF43: Sequences 553-595, more preferably sequences 553-566.
  (v) SOX9: Sequences 596-608.
  (vi) TCF7L2: Sequences 610-680, more preferably sequences 610-630.
  (vii) TP53: Sequences 681-708, more preferably sequences 681-696.
  (viii) ZFP36L2: Sequences 709-717, more preferably sequences 709-714.
 c. identifying a match between the at least one sequence or portion thereof from the set of sequences and a sequence from groups (i) to (v) when the sequences have a string in common representative of at least 8 amino acids to identify a neoantigen encoded by a frameshift mutation;
  wherein a match indicates that said individual is to be treated with the vaccine as disclosed herein.

As used herein the term "sequence" can refer to a peptide sequence, DNA sequence or RNA sequence. The term "sequence" will be understood by the skilled person to mean either or any of these, and will be clear in the context provided. For example, when comparing sequences to identify a match, the comparison may be between DNA sequences, RNA sequences or peptide sequences, but also between DNA sequences and peptide sequences. In the latter case the skilled person is capable of first converting such DNA sequence or such peptide sequence into, respectively, a peptide sequence and a DNA sequence in order to make the comparison and to identify the match. As is clear to a skilled person, when sequences are obtained from the genome or exome, the DNA sequences are preferably converted to the predicted peptide sequences. In this way, neo open reading frame peptides are identified.

As used herein the term "exome" is a subset of the genome that codes for proteins. An exome can be the collective exons of a genome, or also refer to a subset of the exons in a genome, for example all exons of known cancer genes.

As used herein the term "transcriptome" is the set of all RNA molecules is a cell or population of cells. In a preferred embodiment the transcriptome refers to all mRNA.

In some preferred embodiments the genome is sequenced. In some preferred embodiments the exome is sequenced. In some preferred embodiments the transcriptome is sequenced. In some preferred embodiments a panel of genes is sequenced, for example APC, ARID1A, KMT2D, RNF43, SOX9, TCF7L2, TP53, and/or ZFP36L2. In some preferred embodiments a single gene is sequenced. Preferably the transcriptome is sequenced, in particular the mRNA present in a sample from a tumor of the patient. The transcriptome is representative of genes and neo open reading frame peptides as defined herein being expressed in the tumor in the patient.

As used herein the term "sample" can include a single cell or multiple cells or fragments of cells or an aliquot of body fluid, taken from an individual, by means including venipuncture, excretion, ejaculation, massage, biopsy, needle aspirate, lavage sample, scraping, surgical incision, or intervention or other means known in the art. The DNA and/or RNA for sequencing is preferably obtained by taking a sample from a tumor of the patient. The skilled person knowns how to obtain samples from a tumor of a patient and depending on the nature, for example location or size, of the tumor. Preferably the tumor is a tumor of the colon or rectum. Preferably the sample is obtained from the patient by biopsy or resection. The sample is obtained in such manner that is allows for sequencing of the genetic material obtained therein. In order to prevent a less accurate identification of at least one antigen, preferably the sequence of the tumor sample obtained from the patient is compared to the sequence of other non-tumor tissue of the patient, usually blood, obtained by known techniques (e.g. venipuncture).

Identification of frame shift mutations can be done by sequencing of RNA or DNA using methods known to the skilled person. Sequencing of the genome, exome, ORFeome, or transcriptome may be complete, targeted or partial. In some embodiments the sequencing is complete (whole sequencing). In some embodiments the sequencing is targeted. With targeted sequencing is meant that purposively certain region or portion of the genome, exome, ORFeome or transcriptome are sequenced. For example targeted sequencing may be directed to only sequencing for sequences in the set of sequences obtained from the cancer patient that would provide for a match with one or more of the sequences in the sequence listing, for example by using specific primers. In some embodiment only portion of the genome, exome, ORFeome or transcriptome is sequenced. The skilled person is well-aware of methods that allow for whole, targeted or partial sequencing of the genome, exome, ORFeome or transcriptome of a tumor sample of a patient. For example any suitable sequencing-by-synthesis platform can be used including the Genome Sequencers from Illumina/Solexa, the Ion Torrent system from Applied BioSystems, and the RSII or Sequel systems from Pacific Biosciences. Alternatively Nanopore sequencing may be used, such as the MinION, GridION or PromethION platform offered by Oxford Nanopore Technologies. The method of sequencing the genome, exome, ORFeome or transcriptome is not in particular limited within the context of the present invention.

Sequence comparison can be performed by any suitable means available to the skilled person. Indeed the skilled person is well equipped with methods to perform such comparison, for example using software tools like BLAST and the like, or specific software to align short or long sequence reads, accurate or noisy sequence reads to a reference genome, e.g. the human reference genome GRCh37 or GRCh38. A match is identified when a sequence identified in the patients material and a sequence as disclosed herein have a string, i.e. a peptide sequence (or RNA or DNA sequence encoding such peptide (sequence) in case the comparison is on the level of RNA or DNA) in common representative of at least 8, preferably at least 10 adjacent amino acids. Furthermore, sequence reads derived from a patients cancer genome (or transcriptome) can partially match the genomic DNA sequences encoding the amino acid sequences as disclosed herein, for example if such sequence reads are derived from exon/intron boundaries or exon/exon junctions, or if part of the sequence aligns upstream (to the 5' end of the gene) of the position of a frameshift mutation. Analysis of sequence reads and identification of frameshift mutations will occur through standard methods in the field. For sequence alignment, aligners specific for short or long reads can be used, e.g. BWA (Li and Durbin, Bioinformatics. 2009 Jul. 15; 25(14):1754-60) or Minimap2 (Li, Bioinformatics. 2018 Sep. 15; 34(18):3094-3100). Subsequently, frameshift mutations can be derived from the read alignments and their comparison to a reference genome sequence (e.g. the human reference genome GRCh37) using variant calling tools, for example Genome Analysis ToolKit (GATK), and the like (McKenna et al. Genome Res. 2010 September; 20(9):1297-303).

A match between an individual patient's tumor sample genome or transcriptome sequence and one or more NOPs disclosed herein indicates that said tumor expresses said NOP and that said patient would likely benefit from treatment with a vaccine comprising said NOP (or a fragment thereof). More specifically, a match occurs if a frameshift mutation is identified in said patient's tumor genome sequence and said frameshift leads to a novel reading frame (+1 or −1 with respect to the native reading from of a gene). In such instance, the predicted out-of-frame peptide derived from the frameshift mutation matches any of the sequences 1-717 as disclosed herein. In some embodiments, said patient is administered said NOP (e.g., by administering the peptides, nucleic acid molecules, vectors, host cells or vaccines as disclosed herein).

In some embodiments, the methods further comprise sequencing the genome, exome, ORFeome, or transcriptome (or a part thereof) from a normal, non-tumor sample from said individual and determining whether there is a match with one or more NOPs identified in the tumor sample. Although the neoantigens disclosed herein appear to be specific to tumors, such methods may be employed to confirm that the neoantigen is tumor specific and not, e.g., a germline mutation.

The disclosure further provides the use of the neoantigens and vaccines disclosed herein in prophylactic methods from preventing or delaying the onset of colorectal cancer. Approximately 4%-4.5% of women and men, respectively, will develop colorectal cancer and the neo open reading frames disclosed herein occur in up to 50% of colorectal cancer patients. Prophylactic vaccination based on frameshift resulting peptides disclosed herein would thus provide possible protection to approximately 2% of the general population. The vaccine may be specifically used in a prophylactic setting for individuals that have an increased risk of developing colorectal cancer. For example, prophylactic vaccination based on out-of-frame peptides sequences for APC, SOX9 and TP53 together, as disclosed herein, is expected to provide possible protection to around 18% of individuals having a germline predisposition mutation as referred to in FIG. 12, and who would have developed colorectal cancer as a result of their predisposing mutation. In some embodiments, the prophylactic methods are useful for individuals who are genetically related to individuals afflicted with colorectal cancer. In some embodiments, the prophylactic methods are useful for the general population.

In some embodiments, the individual is at risk of developing cancer. It is understood to a skilled person that being at risk of developing cancer indicates that the individual has a higher risk of developing cancer than the general population; or rather the individual has an increased risk over the average of developing cancer. Such risk factors are known to a skilled person and include; increased age, in particular being 50 years or older, obesity, smoking, lack of physical exercise, diet high in red meat or processed meats, a history of adenomatous polyps, having inflammatory bowel disease (e.g., ulcerative colitis or Crohn's disease), family history of colorectal cancer or adenomatous polyps, and having a mutation in a gene that predisposes an individual to colorectal cancer. A number of genetic syndromes are also associated with increased risk of colorectal cancer including Gardner syndrome, hereditary non-polyposis colorectal cancer (HNPCC), and familial adenomatous polyposis.

In some embodiments, said individual has a germline mutation in a gene that increases the chance that the individual will develop colorectal cancer, preferably the mutation is in MSH2, MLH1, FANCA, FANCB, FANCD1 (BRCA2), FANCD2, FANCE, FANCF, FANCG, FANCI, FANCJ (BRIP1), FANCN (PALB2), FANCP (SLX4), FANCS (BRCA1), PMS2, RAD51C, XPF, POLE, POLD1, NTHL1, MSH3, RNF43, SMAD4, BMPR1A, STK11, PTEN, GREM1, AXIN2, GREM1, BLM, AKT1, ENG, CDH1, BUB1B, GALNT12, MLH3, RPS20, GJB2, CHEK2, MUTYH, FANCL, FANCM, COL7A1, APC, ERCC2, FANCC, MPL, SBDS, ATM, FAH, MSHG, NTHL1, and/or WRN gene, preferably in the GJB2, CHEK2, MUTYH, FANCL, FANCM, COL7A1, APC, ERCC2, FANCC, MPL, SBDS, ATM, FAH, MSHG, NTHL1, and/or WRN gene. Predisposing mutations in said genes are known to a skilled person and such mutations can be identified in individuals. Preferably, the prophylactic methods disclosed herein comprise determining the presence of a predisposing mutation in one or more of MSH2, MLH1, FANCA, FANCB, FANCD1 (BRCA2), FANCD2, FANCE, FANCF, FANCG, FANCI, FANCJ (BRIP1), FANCN (PALB2), FANCP (SLX4), FANCS (BRCA1), PMS2, RAD51C, XPF, POLE, POLD1, NTHL1, MSH3, RNF43, SMAD4, BMPR1A, STK11, PTEN, GREM1, AXIN2, GREM1, BLM, AKT1, ENG, CDH1, BUB1B, GALNT12, MLH3, RPS20, GJB2, CHEK2, MUTYH, FANCL, FANCM, COL7A1, APC, ERCC2, FANCC, MPL, SBDS, ATM, FAH, MSH6, NTHL1, and/or WRN gene, preferably in the GJB2, CHEK2, MUTYH, FANCL, FANCM, COL7A1, APC, ERCC2, FANCC, MPL, SBDS, ATM, FAH, MSH6, NTHL1, and/or WRN genes and prophylactically administering the vaccine disclosed herein to an individual having said predisposing mutation in one or more of MSH2, MLH1, FANCA, FANCB, FANCD1 (BRCA2), FANCD2, FANCE, FANCF, FANCG, FANCI, FANCJ (BRIP1), FANCN (PALB2), FANCP (SLX4), FANCS (BRCA1), PMS2, RAD51C, XPF, POLE, POLD1, NTHL1, MSH3, RNF43, SMAD4, BMPR1A, STK11, PTEN, GREM1, AXIN2, GREM1, BLM, AKT1, ENG, CDH1, BUB1B, GALNT12, MLH3, RPS20, GJB2, CHEK2, MUTYH, FANCL, FANCM, COL7A1, APC, ERCC2, FANCC, MPL, SBDS, ATM, FAH, MSH6, NTHL1, and/or WRN gene, preferably in the GJB2, CHEK2, MUTYH, FANCL, FANCM, COL7A1, APC, ERCC2, FANCC, MPL, SBDS, ATM, FAH, MSH6, NTHL1, and/or WRN gene, or other genes with known predisposing mutations.

As used herein, "to comprise" and its conjugations is used in its non-limiting sense to mean that items following the word are included, but items not specifically mentioned are not excluded. In addition, the verb "to consist" may be replaced by "to consist essentially of" meaning that a compound or adjunct compound as defined herein may comprise additional component(s) than the ones specifically identified, said additional component(s) not altering the unique characteristic of the invention.

The articles "a" and "an" are used herein to refer to one or to more than one (i.e., to at least one) of the grammatical object of the article. By way of example, "an element" means one element or more than one element.

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety.

For the purpose of clarity and a concise description features are described herein as part of the same or separate embodiments, however, it will be appreciated that the scope of the invention may include embodiments having combinations of all or some of the features described.

positions of frame shift mutations on the −1 and the +1 frame C amino acid sequence of TP53. D. Peptide (10aa) library (n=1,000) selection. Peptides belonging to −1 or +1 frame are separated vertically E,F pNOPs for the different frames followed by all encountered frame shift mutations (rows), translated to a stop codon (lines) colored by amino acid.

Figure 3:
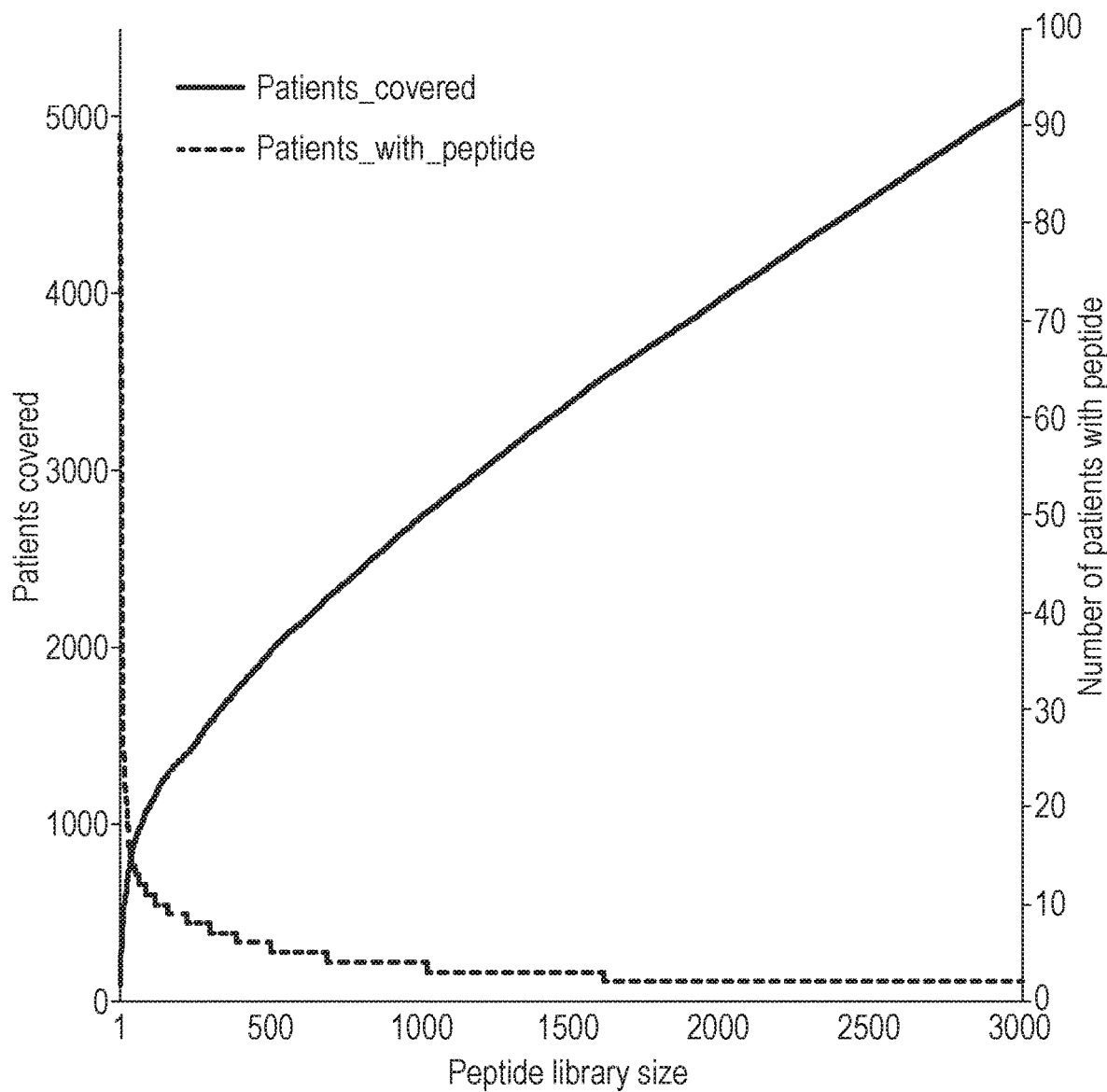

FIG. 3 A recurrent peptide selection procedure can generate a 'fixed' library to corer up to 50% of the TCGA cohort. Graph depicts the number of unique patients from the TCGA cohort (10,186 patients) accommodated by a growing library of 10-mer peptides, picked in descending order of the number patients with that sequence in their NOPs. A peptide is only added if it adds a new patient from the TCGA cohort. The dark blue line shows that an increasing number of 10-mer peptides covers an increasing number of patients from the TCGA cohort (up to 50% if using 3000 unique 10-mer peptides). Light shaded blue line depicts the number of patients containing the peptide that was included (right Y-axis). The best peptide covers 89 additional patients from the TCGA cohort (left side of the blue line), the worst peptide includes only 1 additional patient (right side of the blue line).

Figure 4:
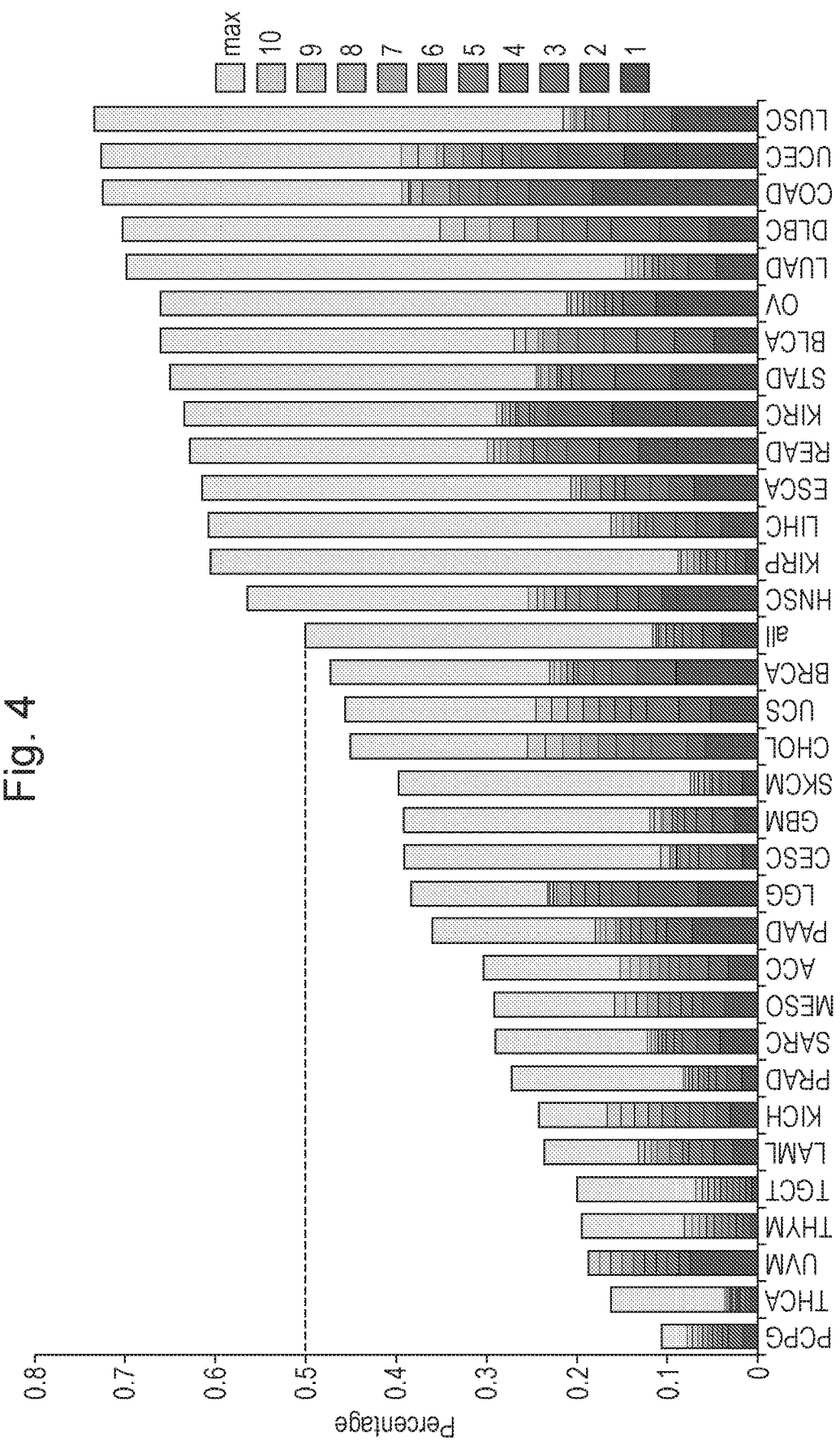
Figure 5A:
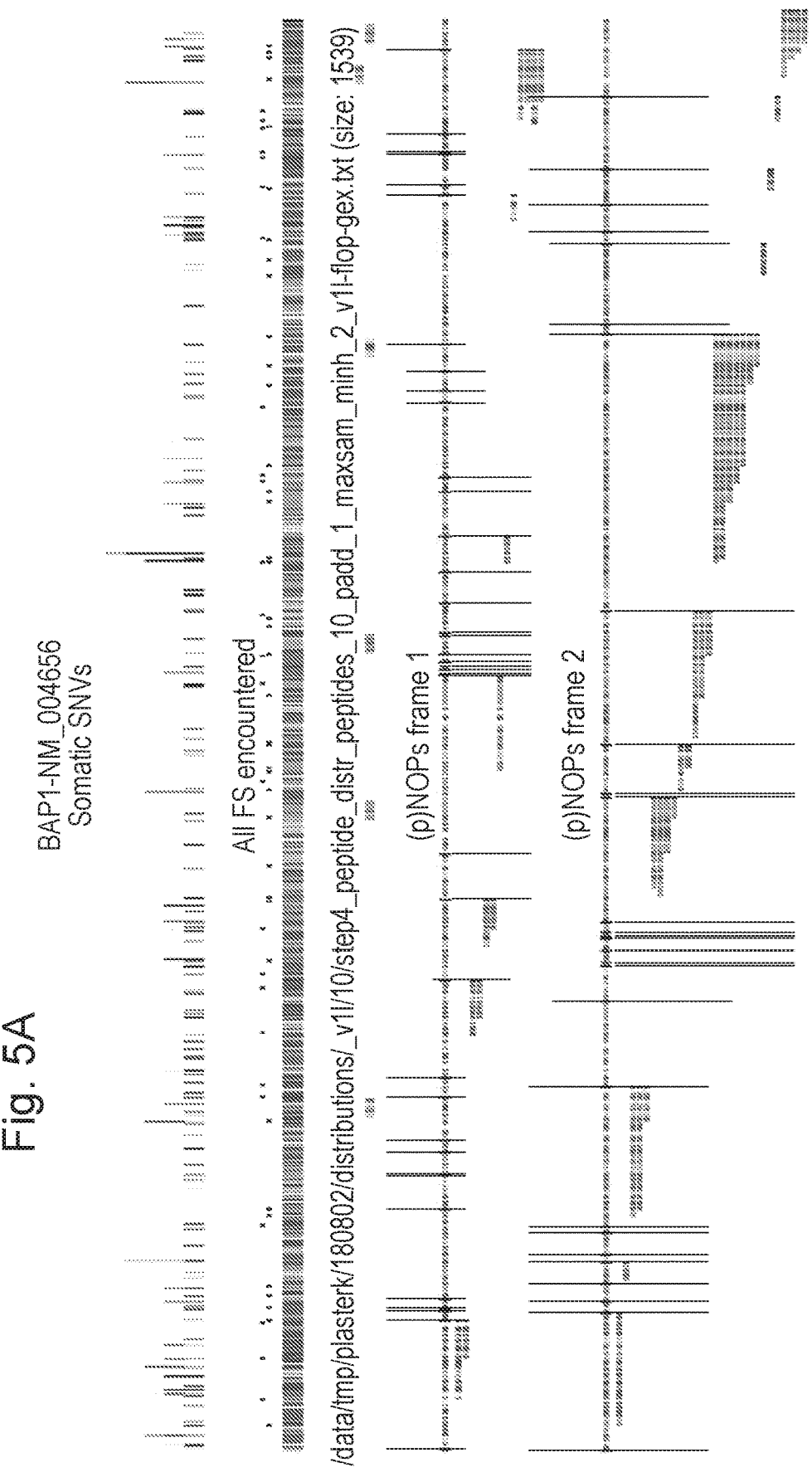
Figure 5B:
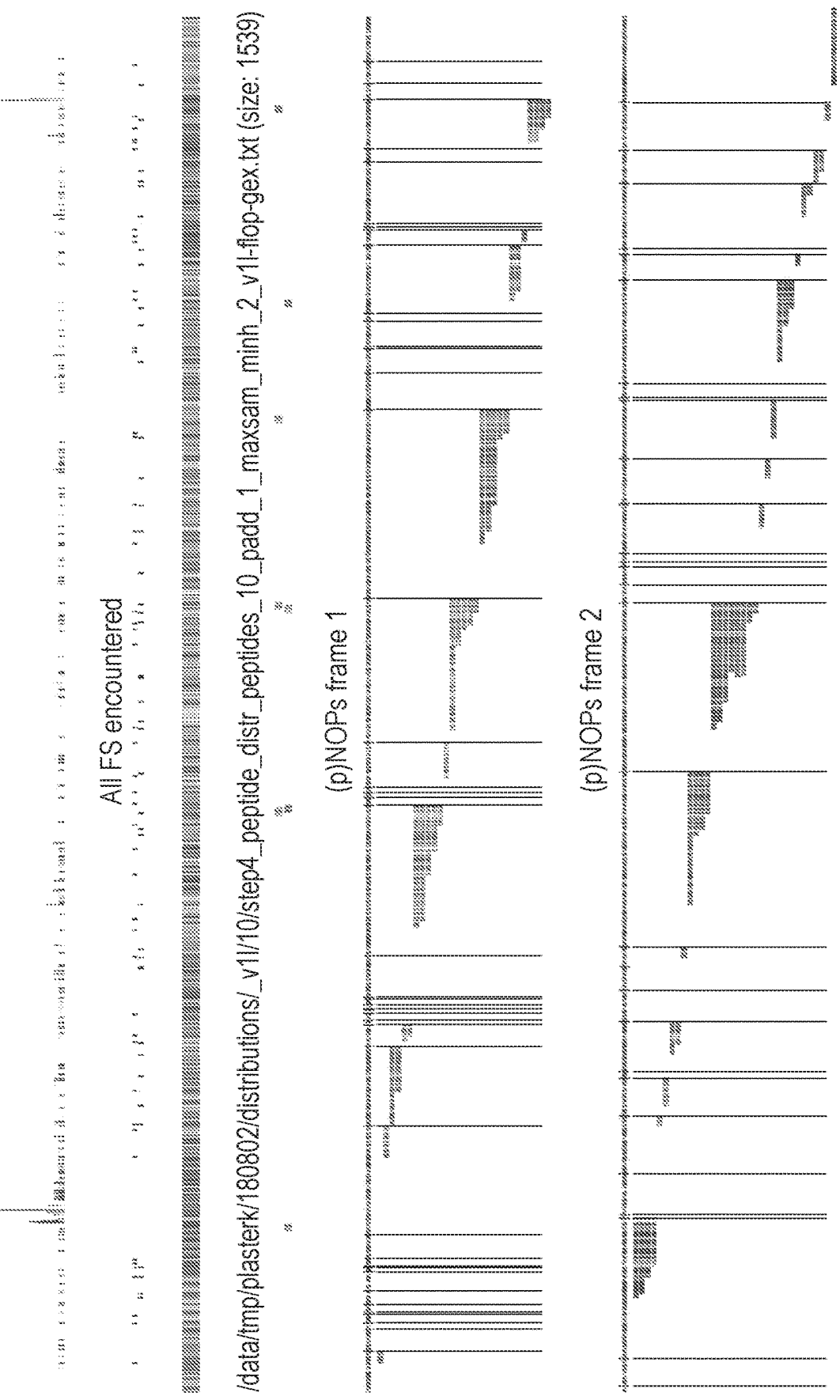
Figure 5C:
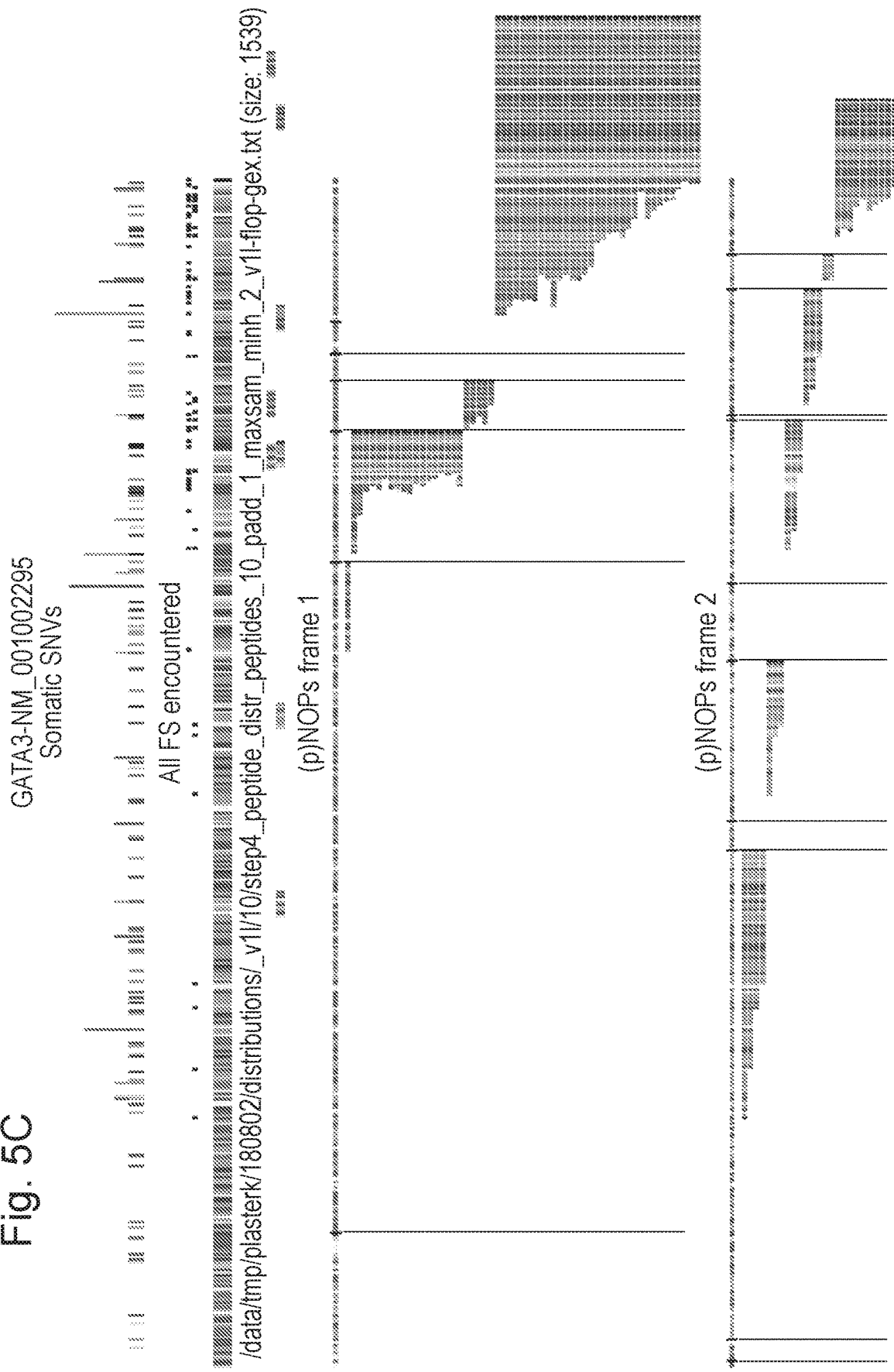
Figure 5D:
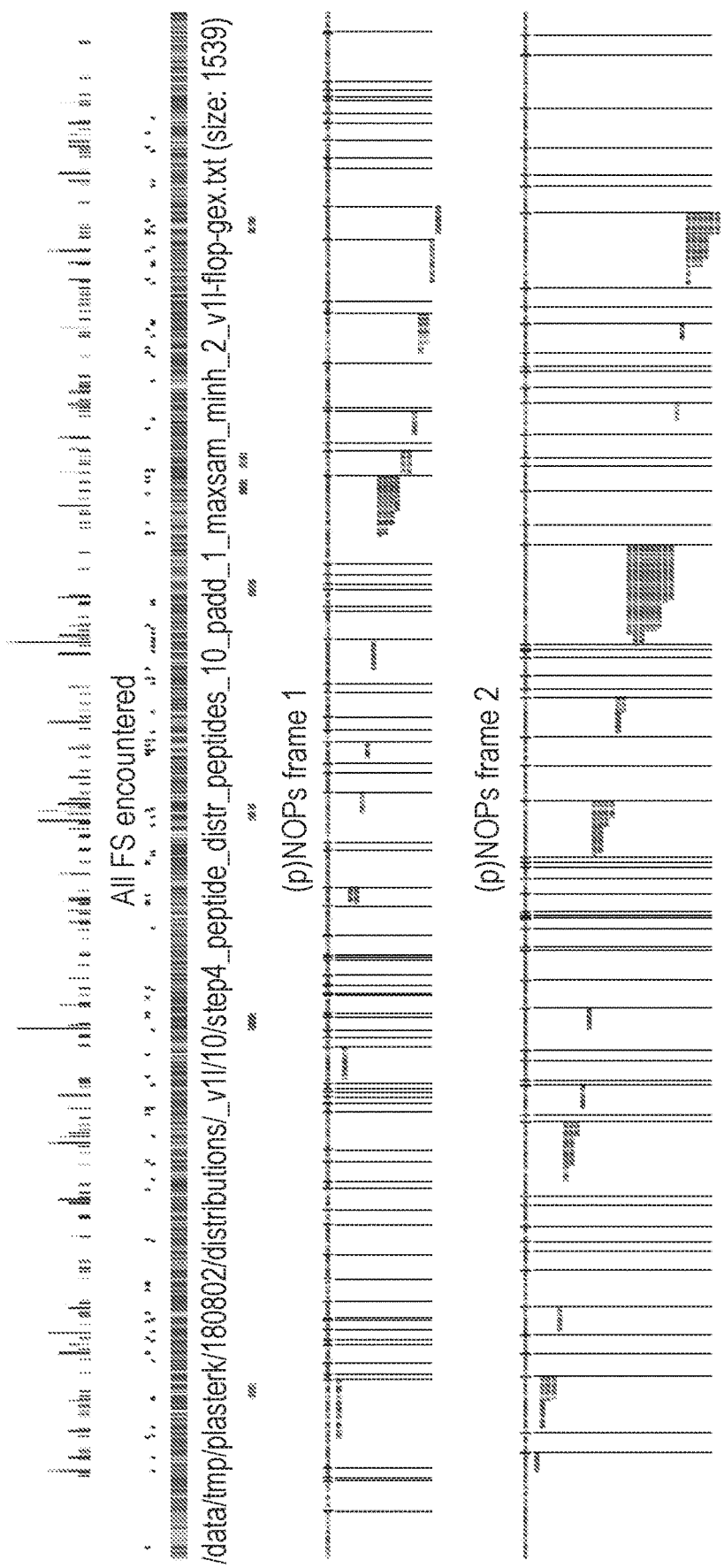
Figure 5E:
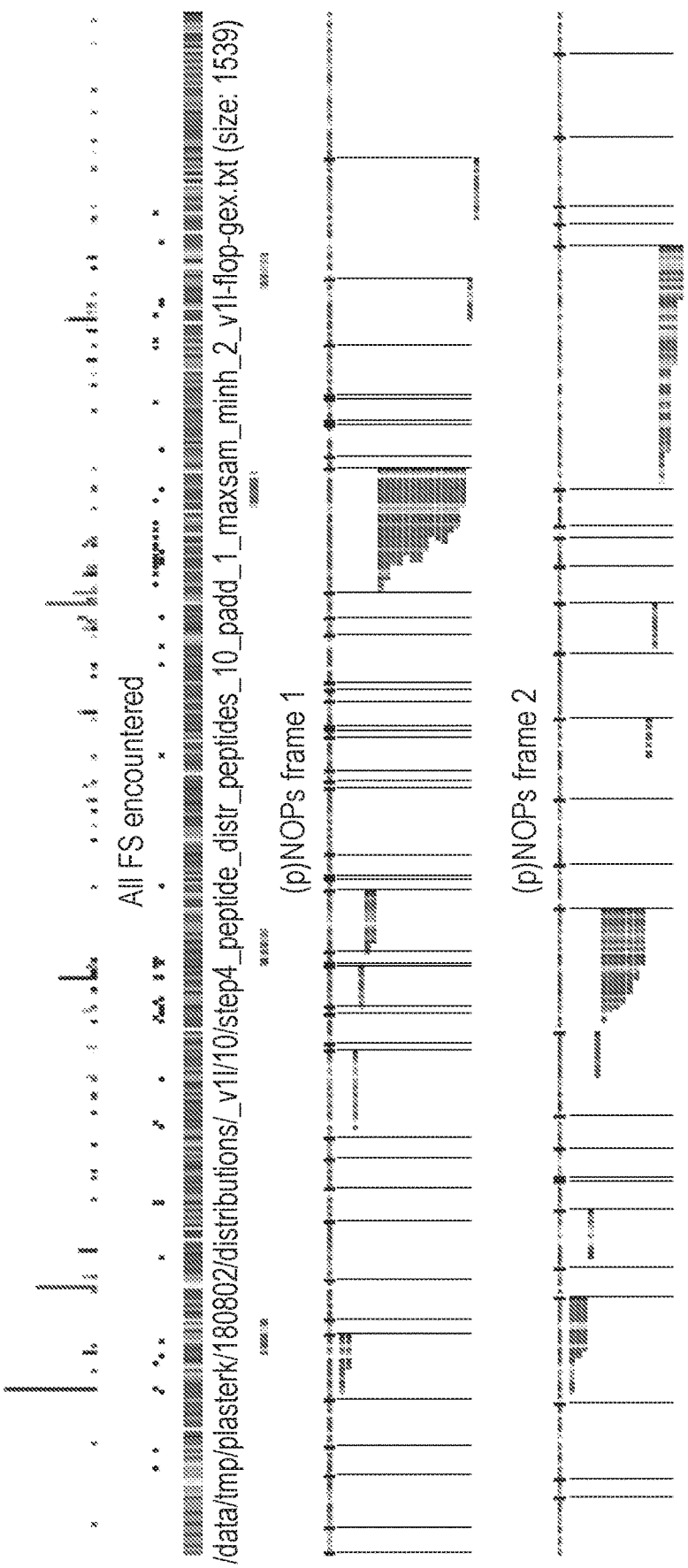
Figure 5F:
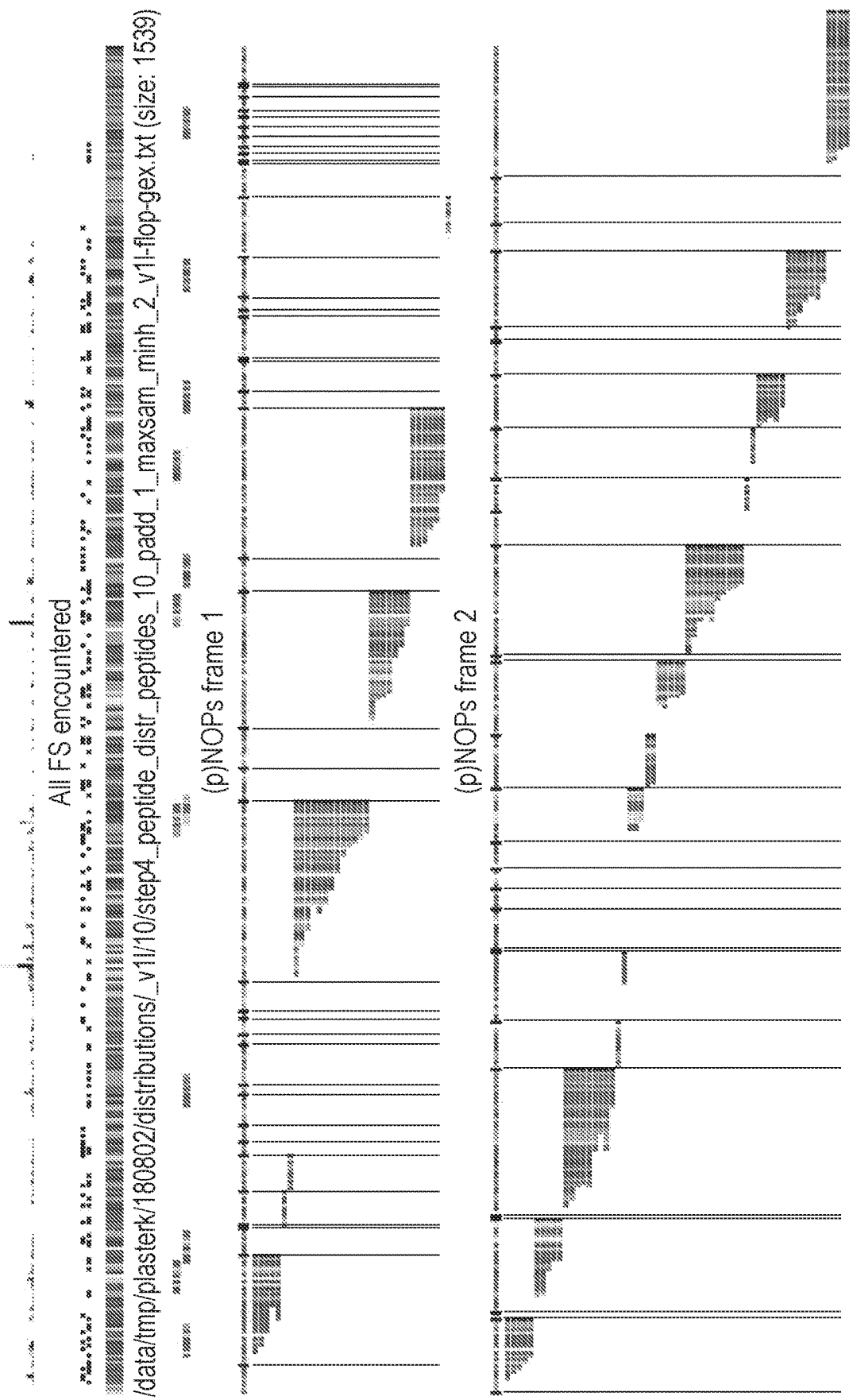
Figure 5G:
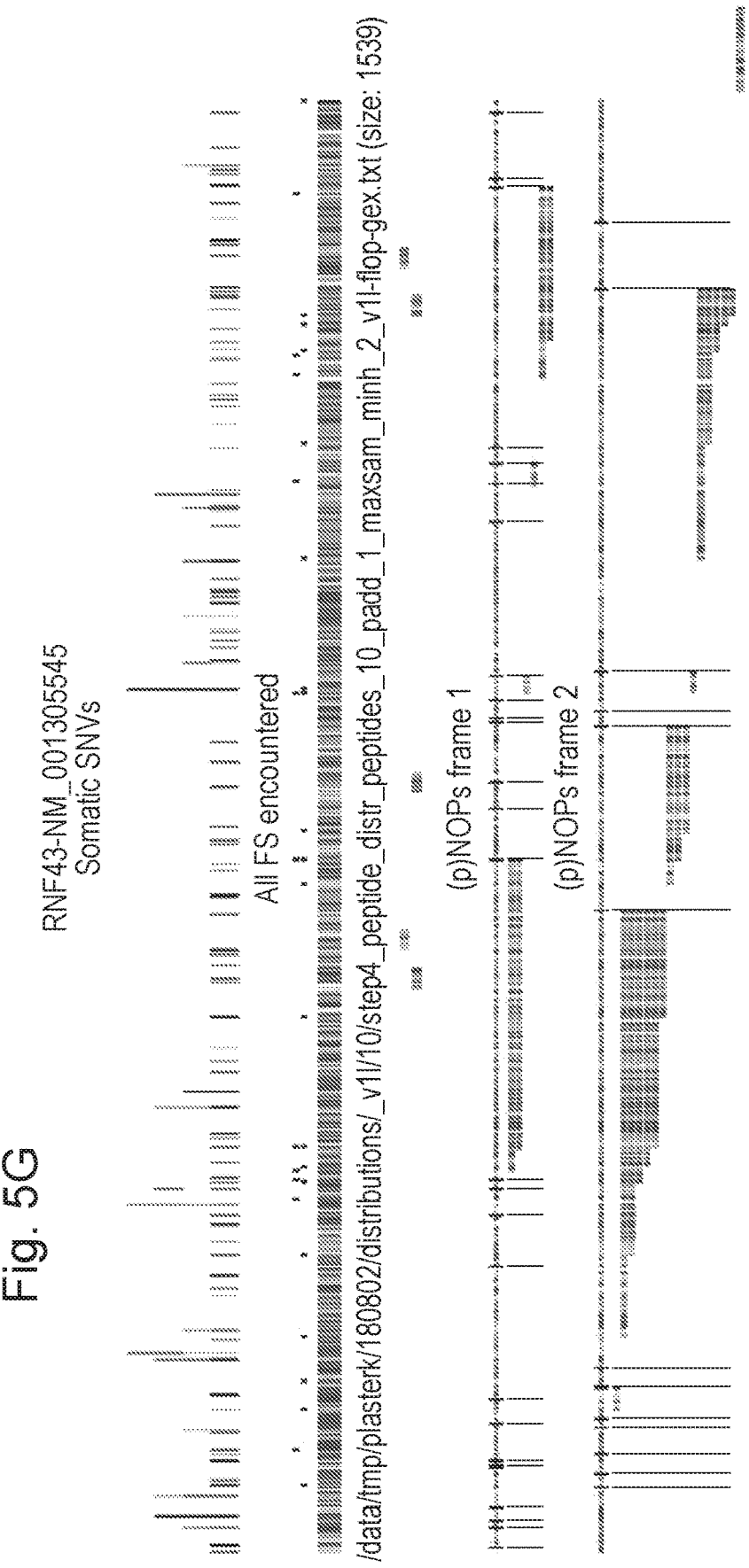
Figure 5H:
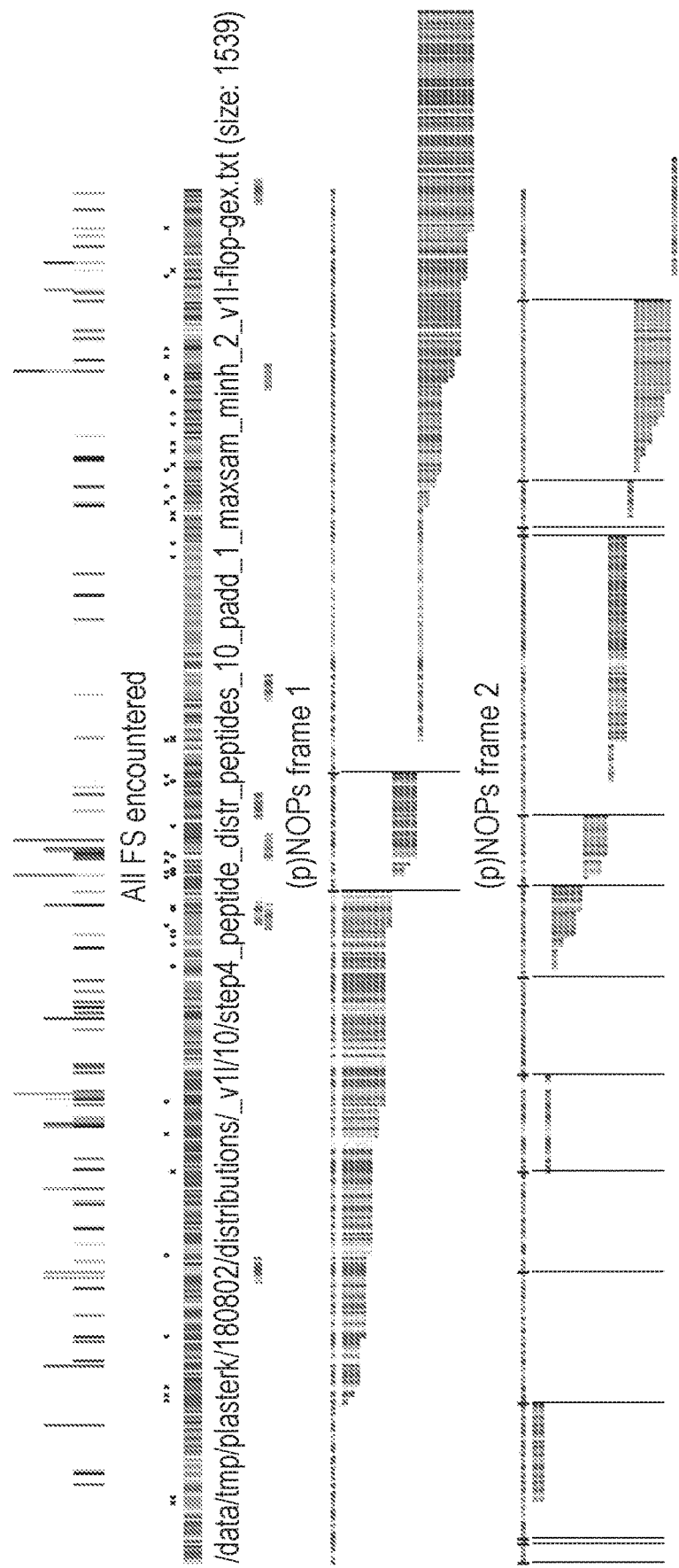
Figure 5I:
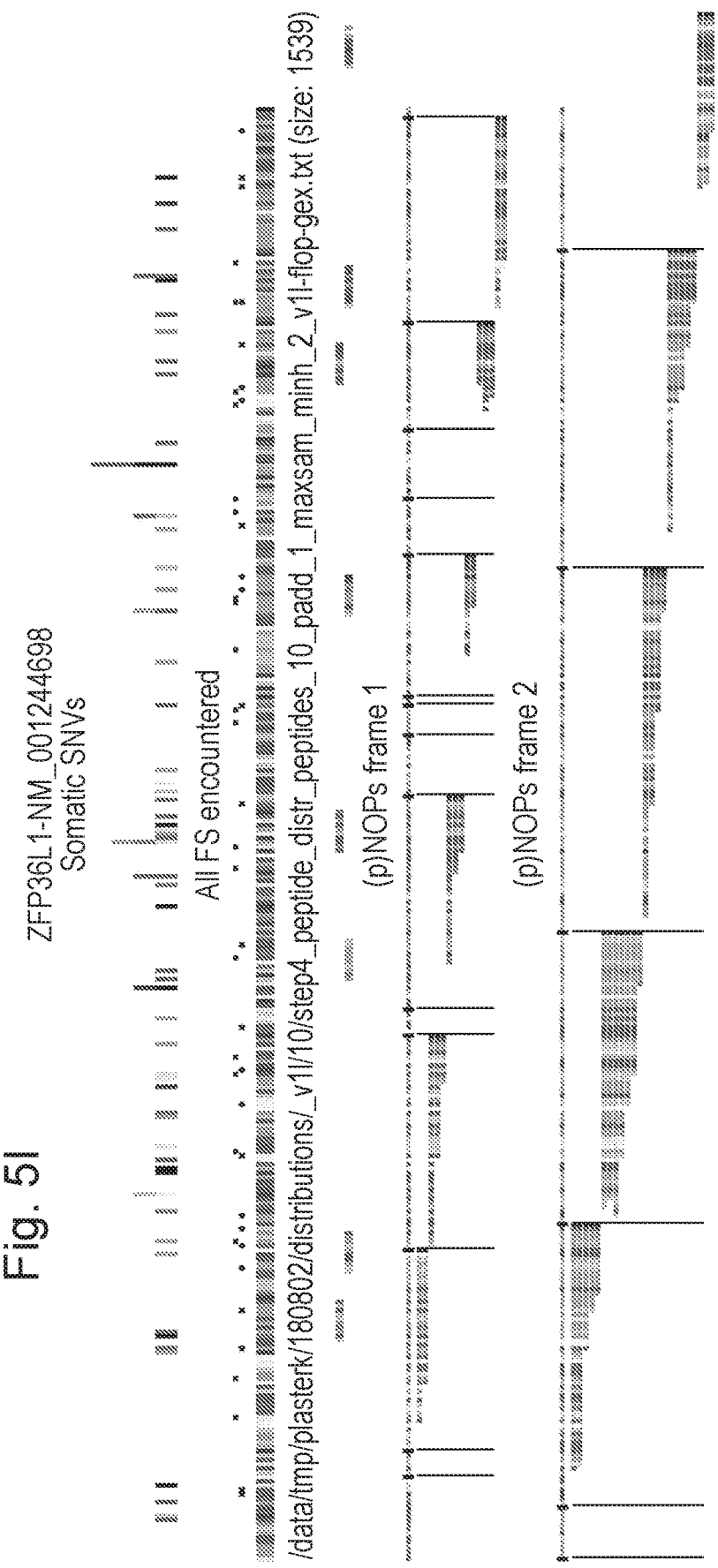
Figure 5J:
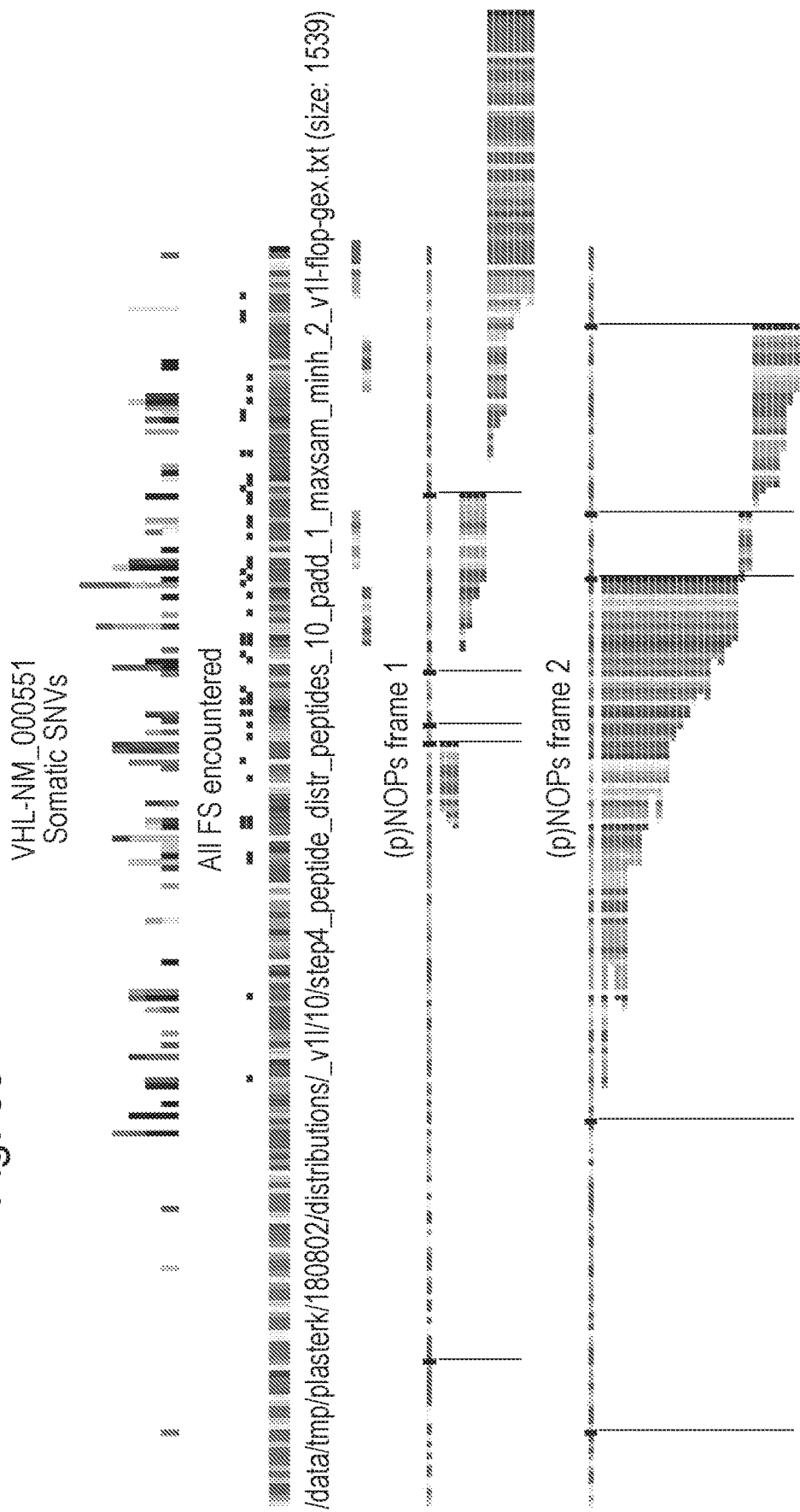
Figure 5K:
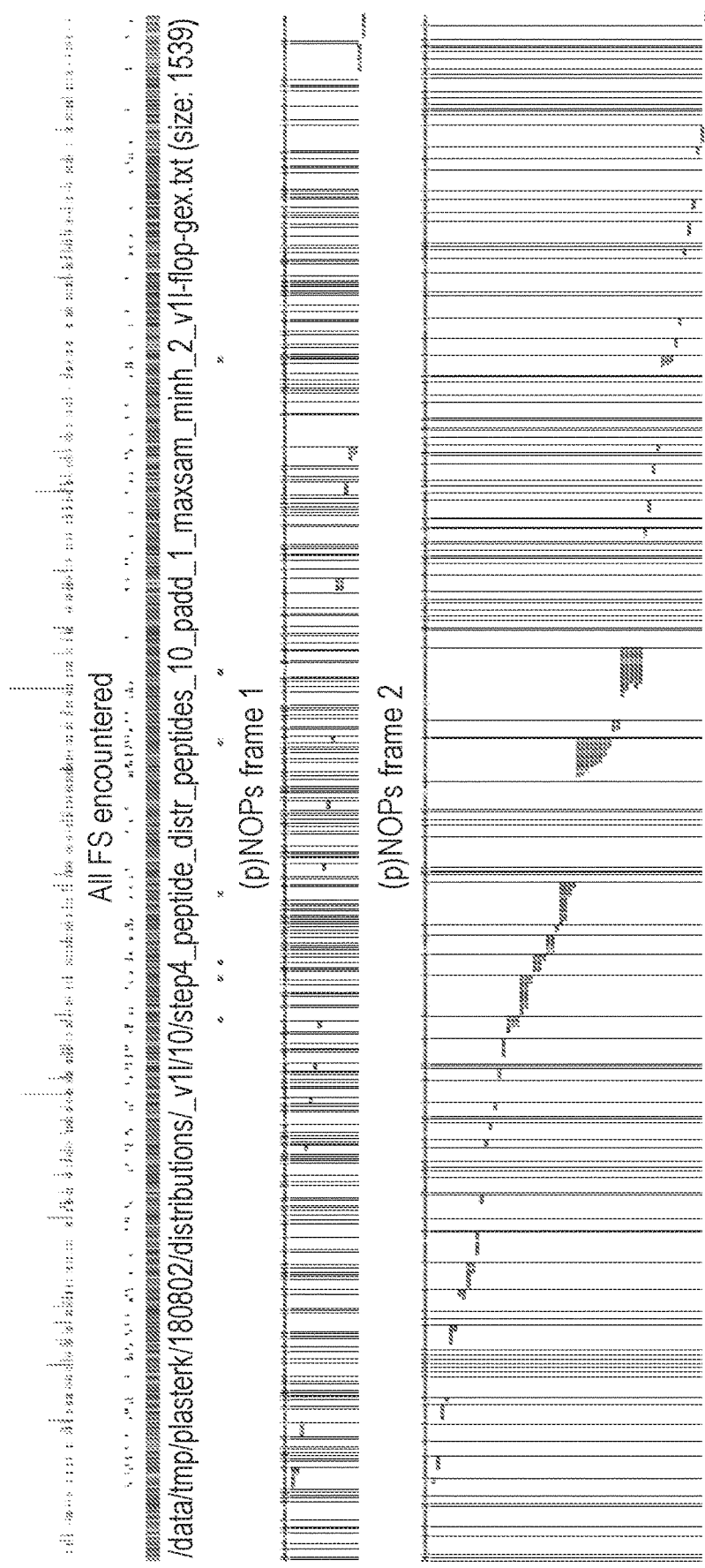

FIG. 4 For some cancers up to 70% of patients contain a recurrent NOP. TCGA cohort ratio of patients separated by tumor type that could be 'helped' using optimally selected peptides for genes encountered most often within a cancer. Coloring represents the ratio, using 1, 2 . . . 10 genes, or using all encountered genes (lightest shade)

FIG. 5 Examples of NOPs. Selection of genes containing NOPs of 10 or more amino acids.

Figure 6A:
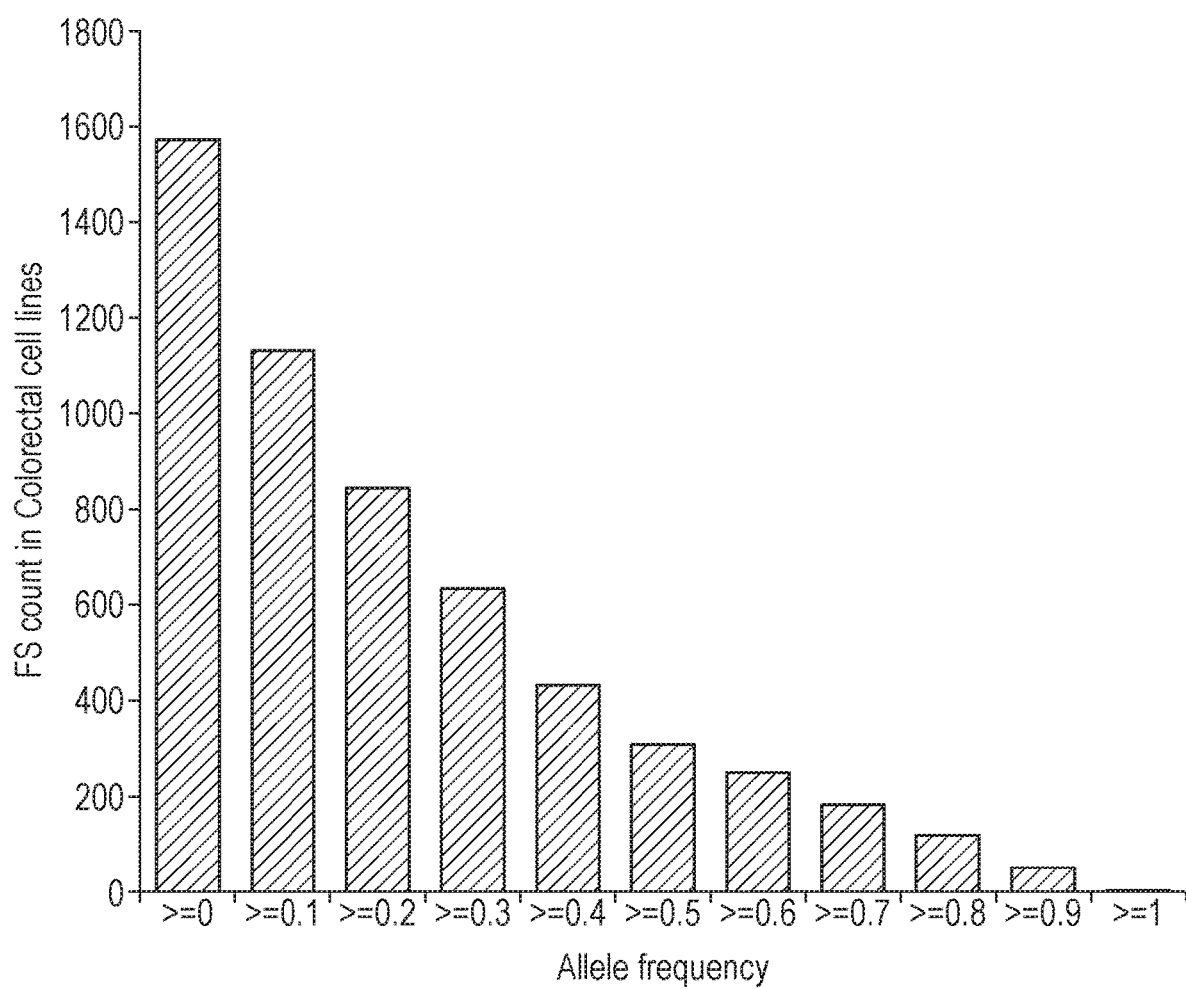
Figure 6B:
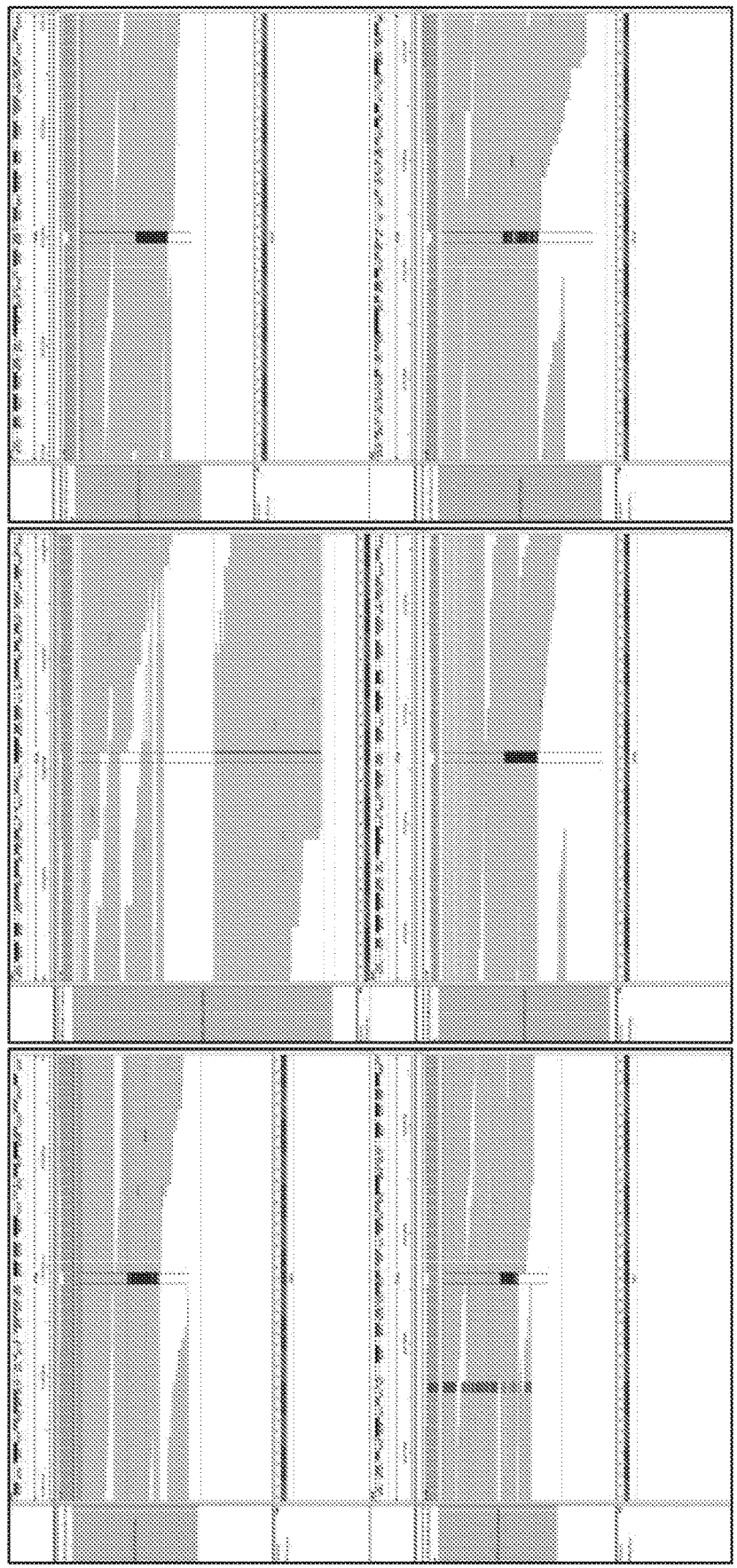

FIG. 6 Frame shift presence in mRNA from 58 CCLE colorectal cancer cell lines.
  a. Cumulative counting of RNAseq allele frequency (Samtools mpileup (XO:1/all)) at the genomic position of DNA detected frame shift mutations.
  b. IGV examples of frame shift mutations in the BAM files of CCLE cell lines.

Figure 7:
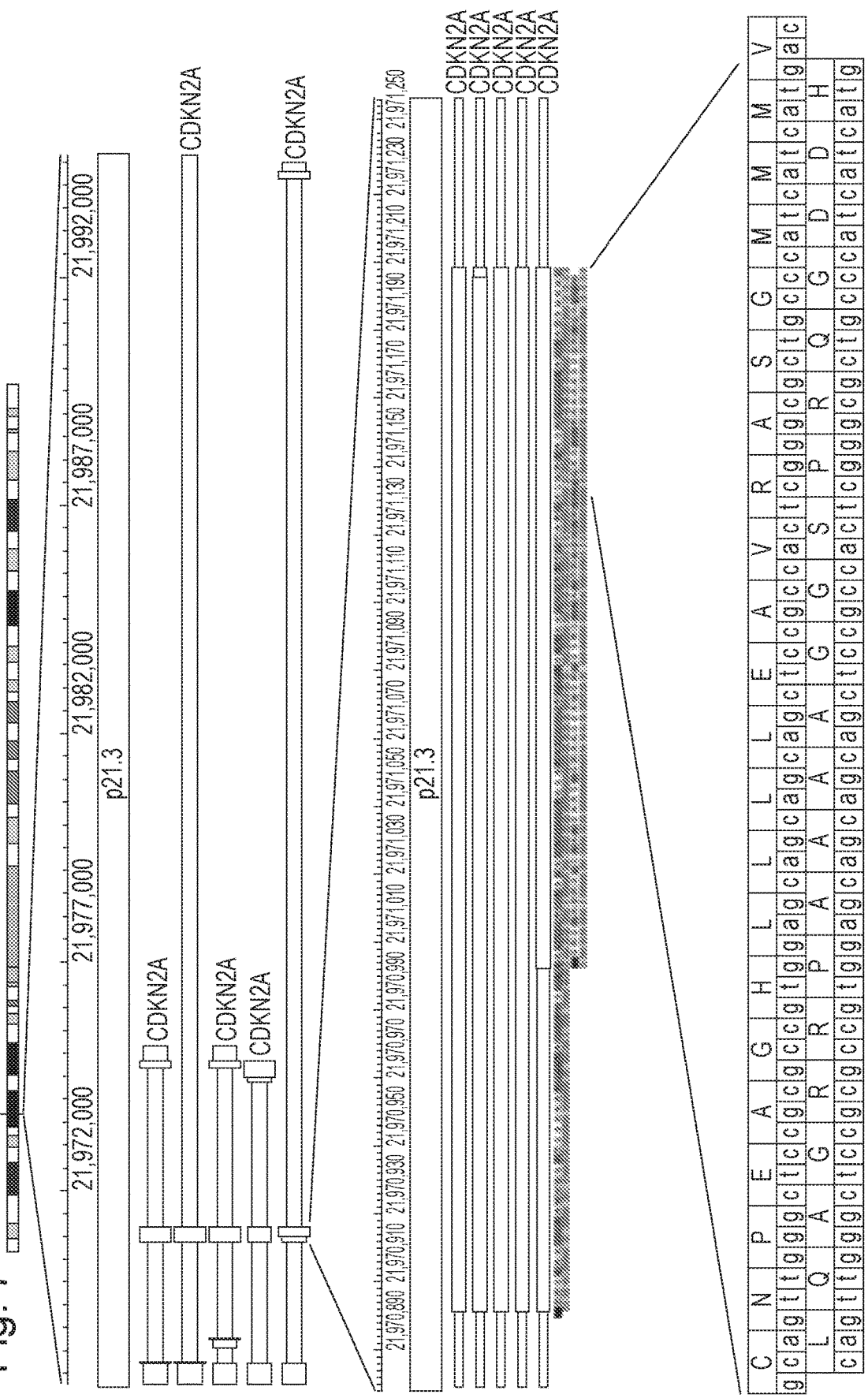

FIG. 7 Example of normal isoforms, using shifted frame. Genome model of CDKN2A with the different isoforms are shown on the minus strand of the genome. Zoom of the middle exon depicts the 2 reading frames that are encountered in the different isoforms.

Figure 8:
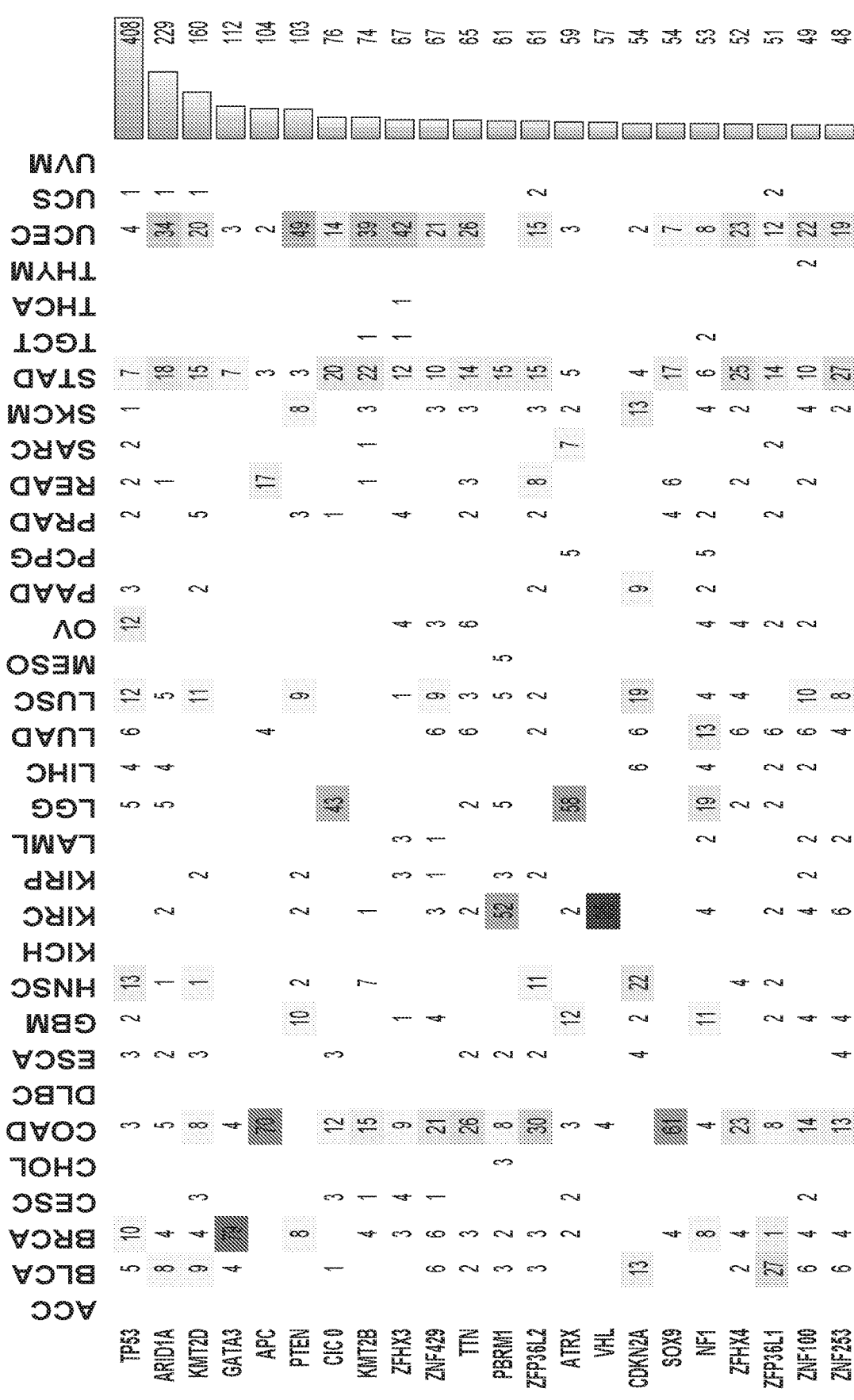

FIG. 8 Gene prevalence vs Cancer type. Percentage of frameshift mutations (resulting in peptides of 10 aa or longer), assessed by the type of cancer in the TCGA cohort. Genes where 50% or more of the frameshifts occur within a single tumor type are indicated in bold. Cancer type abbreviations are as follows:
  LAML Acute Myeloid Leukemia
  ACC Adrenocortical carcinoma
  BLCA Bladder Urothelial Carcinoma
  LGG Brain Lower Grade Glioma
  BRCA Breast invasive carcinoma
  CESC Cervical squamous cell carcinoma and endocervical adenocarcinoma
  CHOL Cholangiocarcinoma
  LCML Chronic Myelogenous Leukemia
  COAD Colon adenocarcinoma
  CNTL Controls
  ESCA Esophageal carcinoma
  GBM Glioblastoma multiforme
  HNSC Head and Neck squamous cell carcinoma
  KICH Kidney Chromophobe
  KIRC Kidney renal clear cell carcinoma
  KIRP Kidney renal papillary cell carcinoma
  LIHC Liver hepatocellular carcinoma
  LUAD Lung adenocarcinoma
  LUSC, Lung squamous cell carcinoma
  DLBC Lymphoid Neoplasm Diffuse Large B-cell Lymphoma
  MESO Mesothelioma
  MISC Miscellaneous
  OV Ovarian serous cystadenocarcinoma
  PAAD Pancreatic adenocarcinoma
  PCPG Pheochromocytoma and Paraganglioma
  PRAD Prostate adenocarcinoma
  READ Rectum adenocarcinoma
  SARC Sarcoma
  SKCM Skin Cutaneous Melanoma
  STAD Stomach adenocarcinoma
  TGCT Testicular Germ Cell Tumors
  THYM Thymoma
  THCA Thyroid carcinoma
  UCS Uterine Carcinosarcoma
  UCEC Uterine Corpus Endometrial Carcinoma
  UVM Uveal Melanoma FIG. 9 NOPs in the MSK-IMPACT study Frame shift analysis in the targeted sequencing panel of the MSK-IMPACT study, covering up to 410 genes in more 10,129 patients (with at least 1 somatic mutation). a. FS peptide length distribution, b. Gene count of patients containing NOPs of 10 or more amino acids. c. Ratio of patients separated by tumor type that possess a neo epitope using optimally selected peptides for genes encountered most often within a cancer. Coloring represents the ratio, using 1, 2, 10 genes, or using all encountered genes (lightest shade) d. Examples of NOPs for 4 genes.

Figure 10:
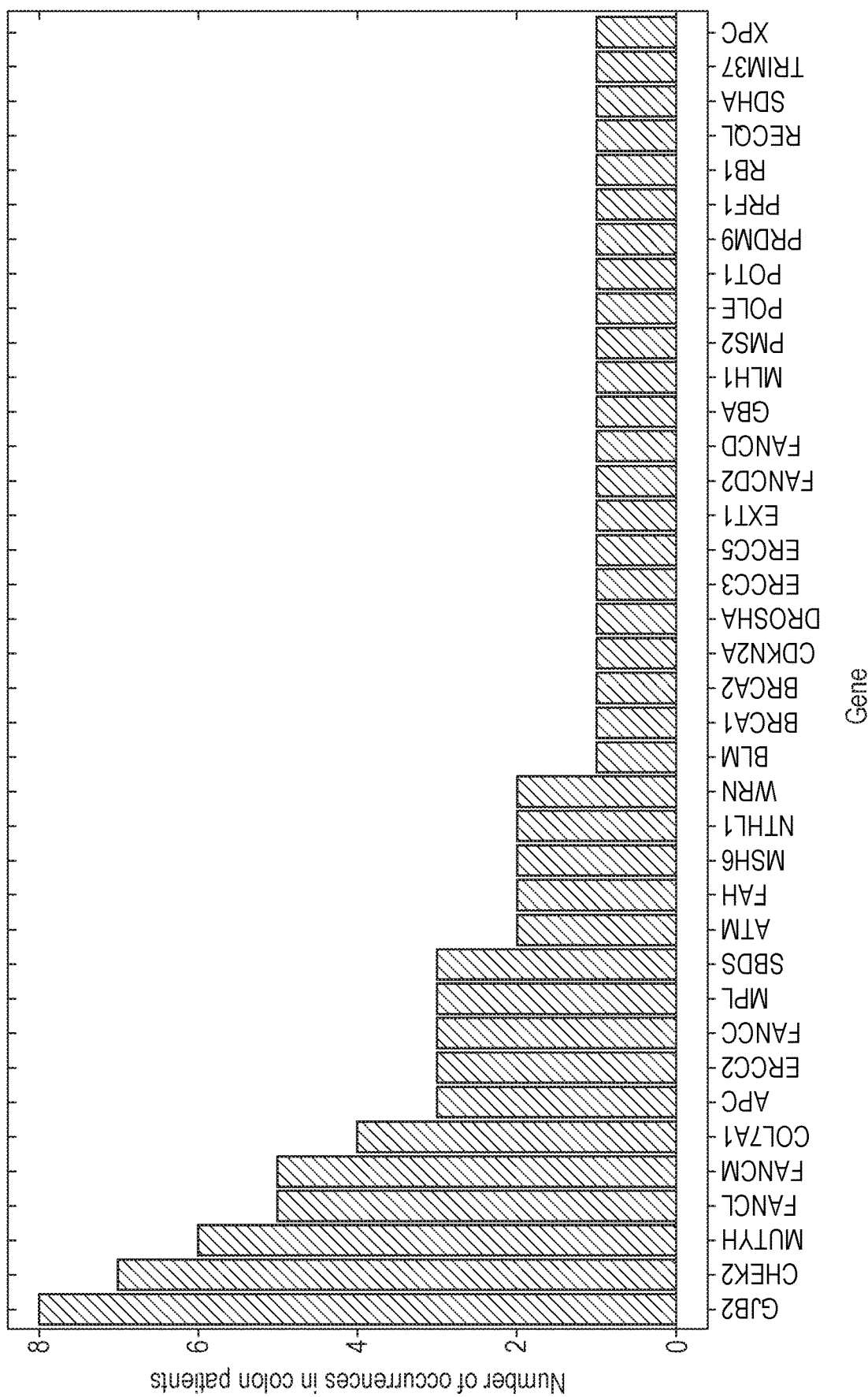

FIG. 10. Number of mutations in cancer susceptibility genes observed in patients with colon and rectum cancer from the Hartwig Medical Foundation database.

Figure 11:
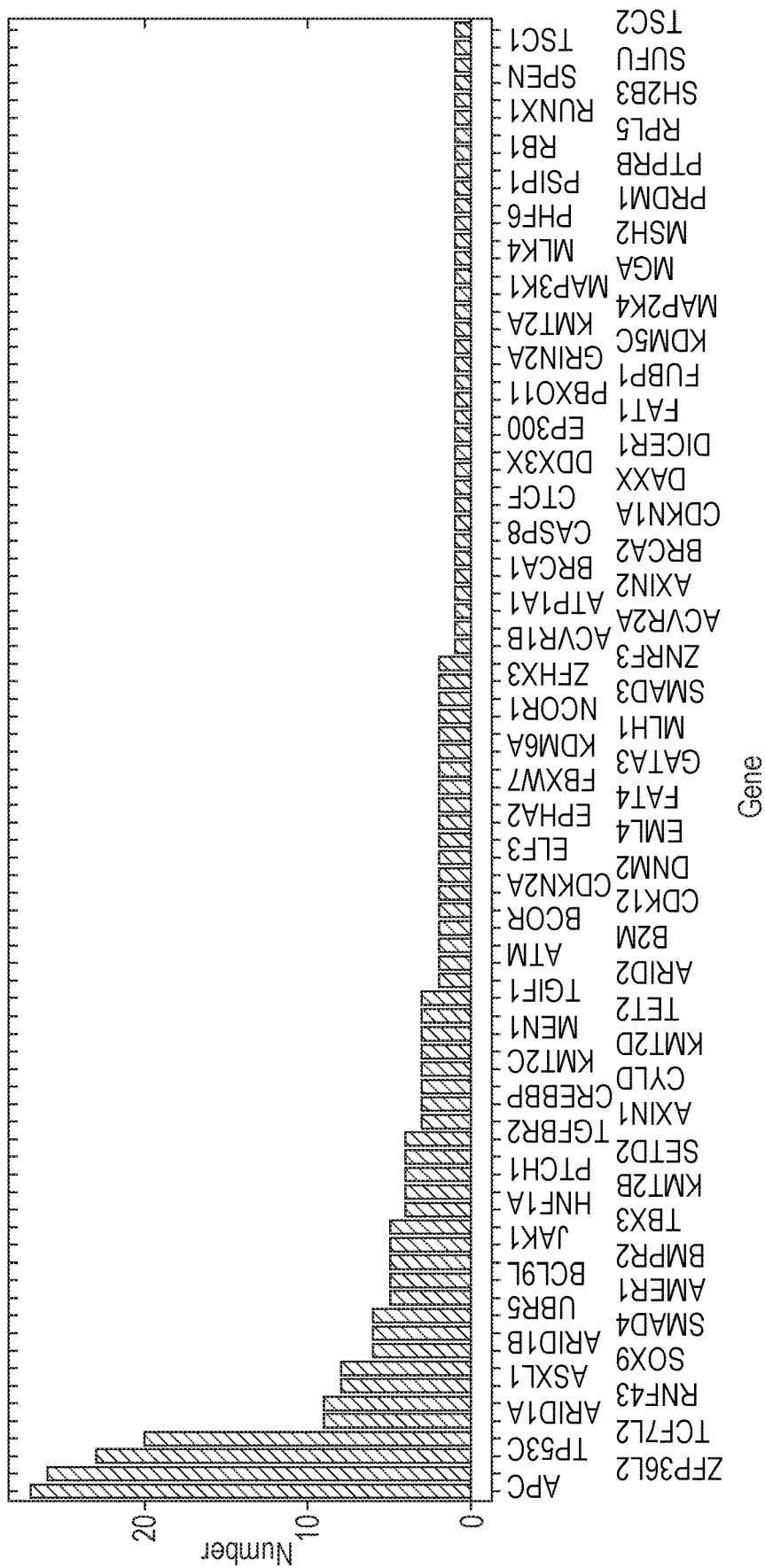

FIG. 11. Number of colon and rectum cancer patients with frameshift mutation counts per gene leading to neo-peptides >=10 amino acids.

Figure 12:
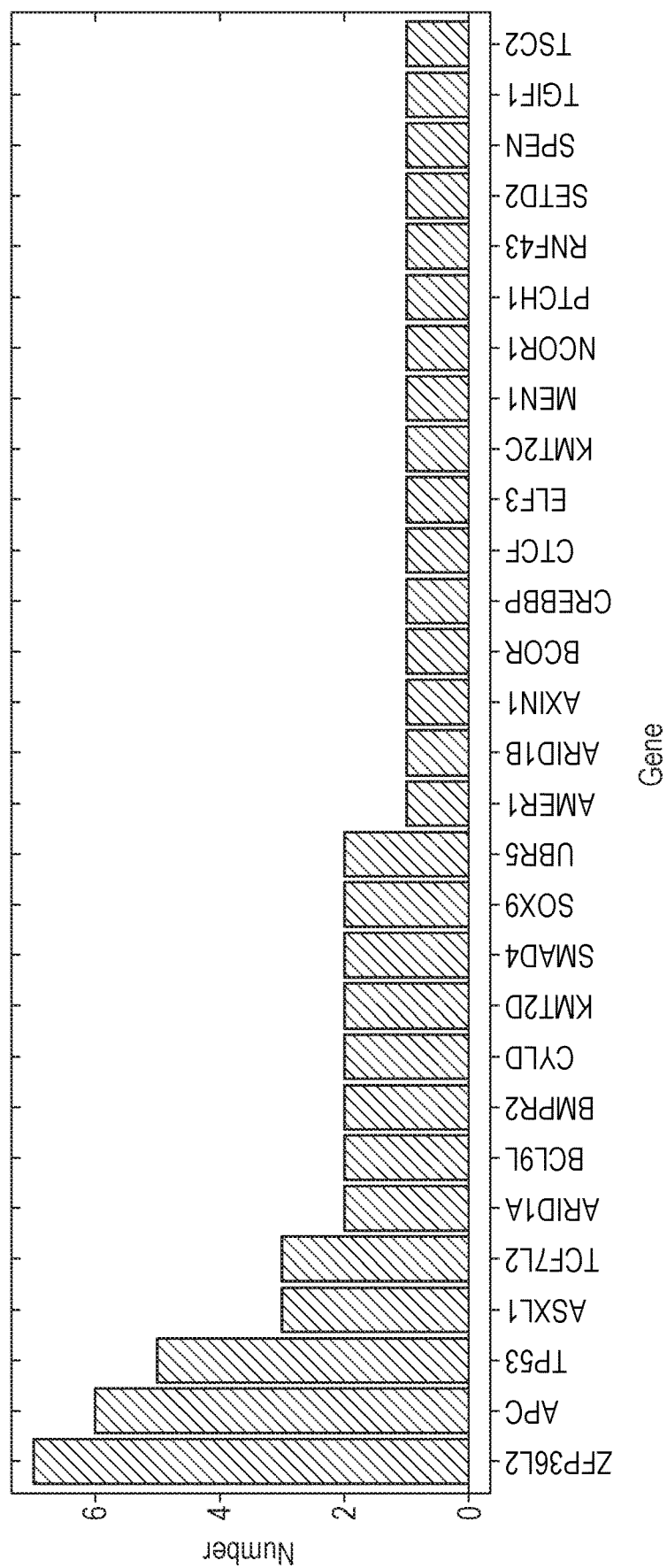

FIG. 12. Number of colon cancer patients with germline predisposition mutation, carrying somatic frameshift leading to neopeptide (>=10 amino acids) in the indicated genes (x-axis).

Figure 13:
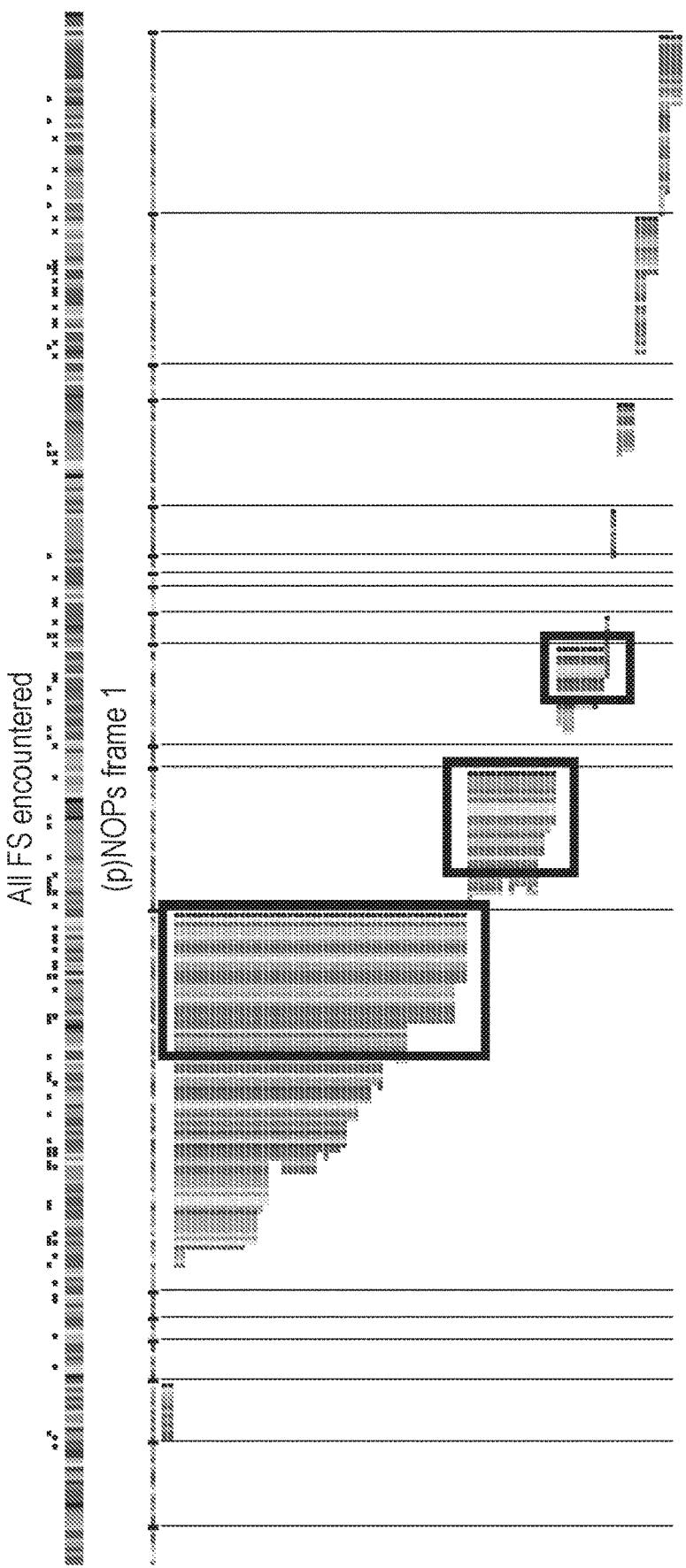
Figure 13:
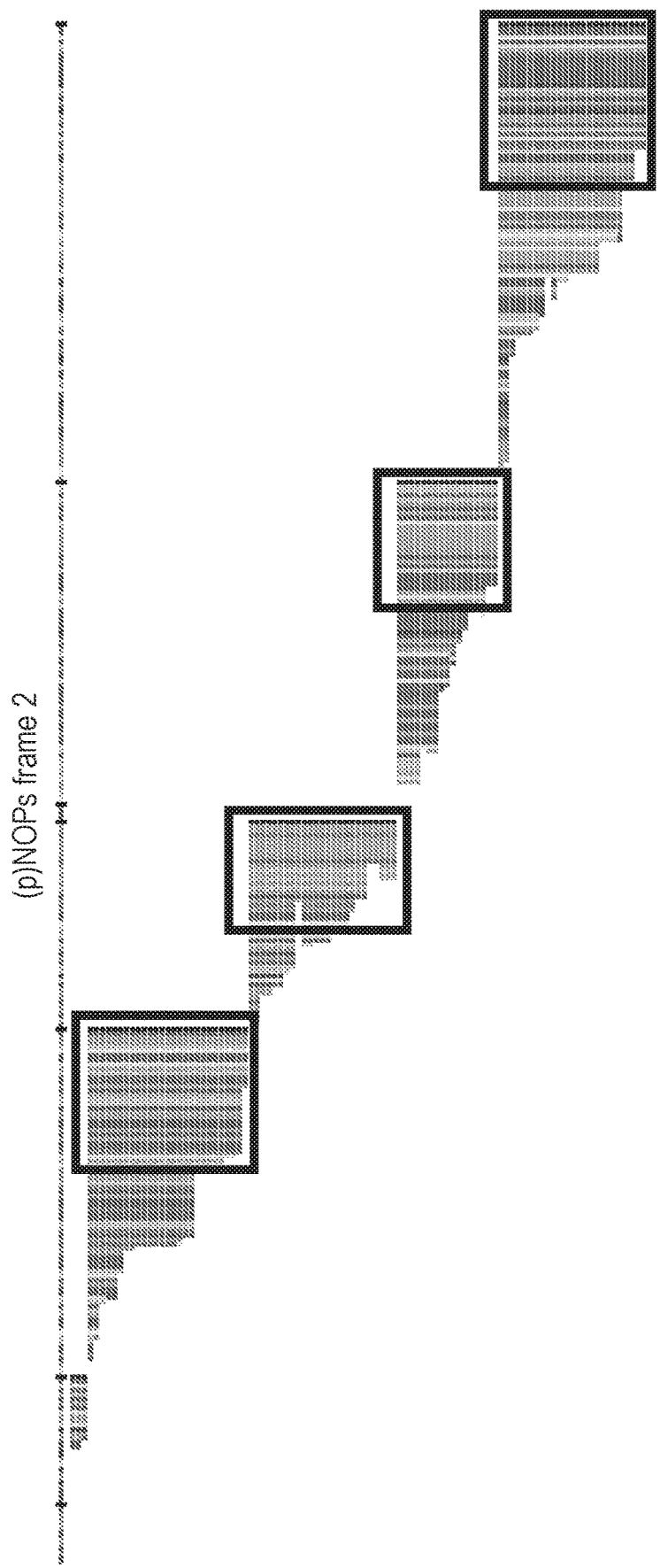
Figure 14:
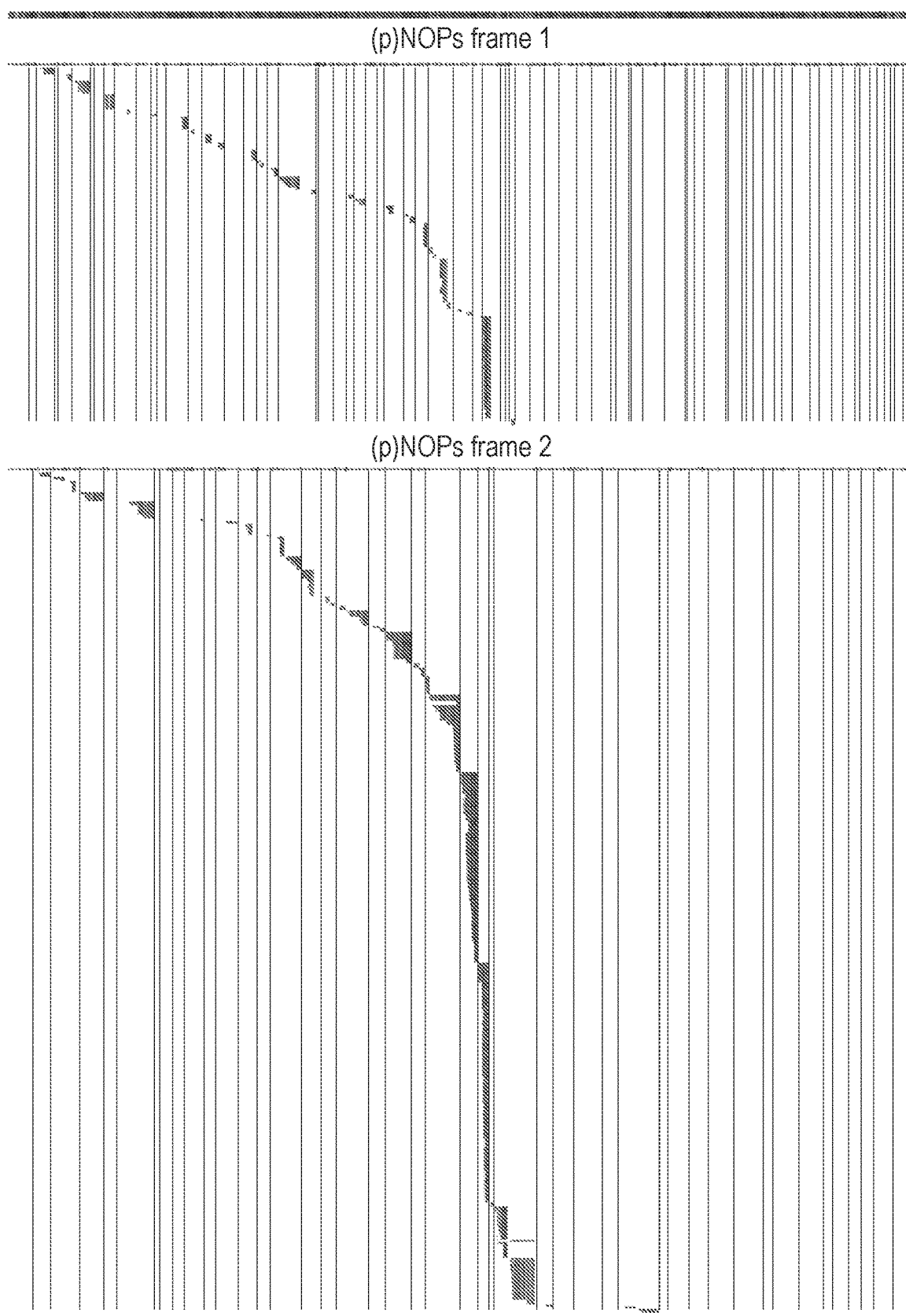
Figure 15:
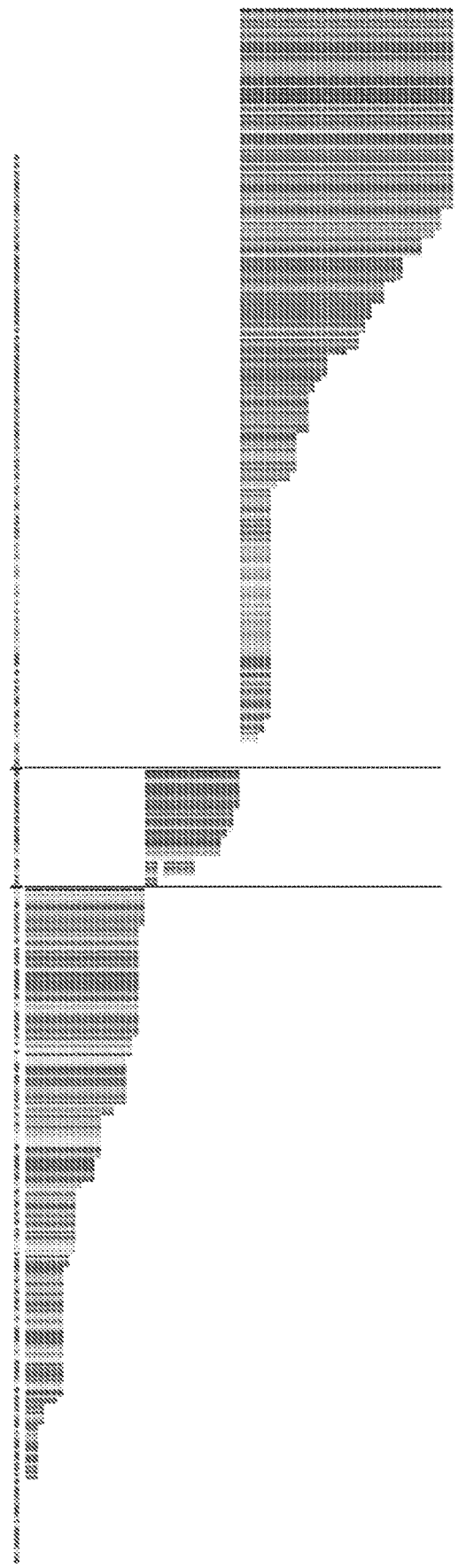
Figure 15:
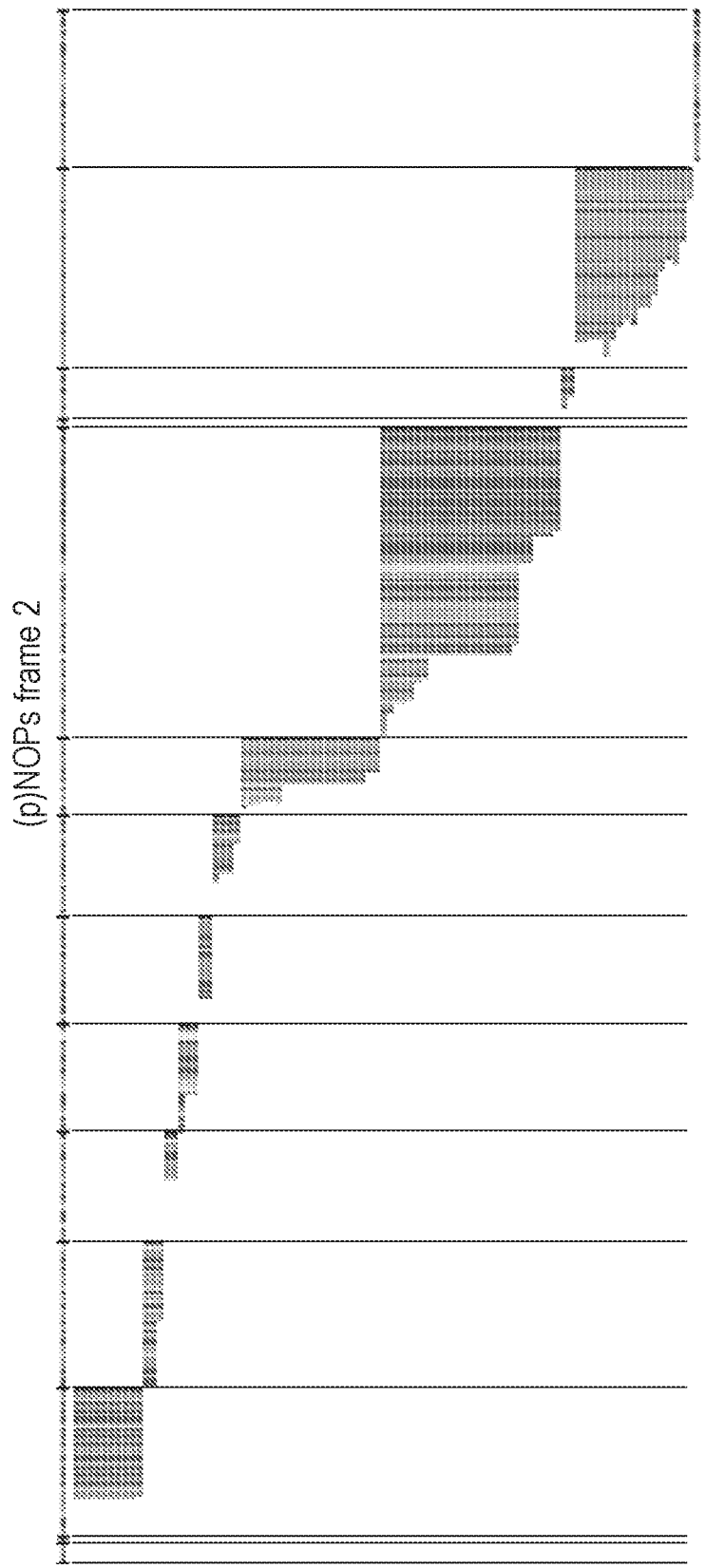
Figure 16:
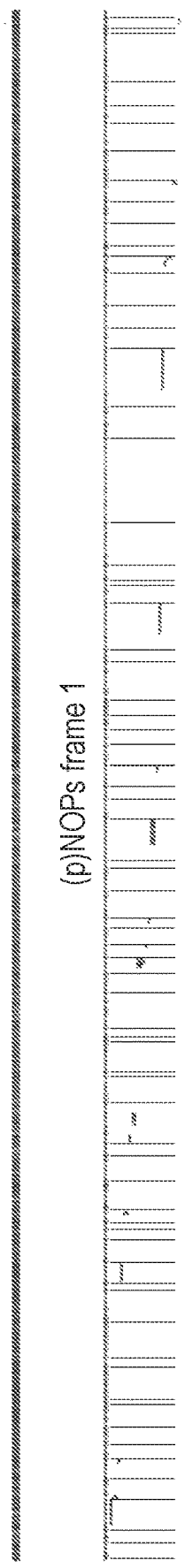
Figure 16:
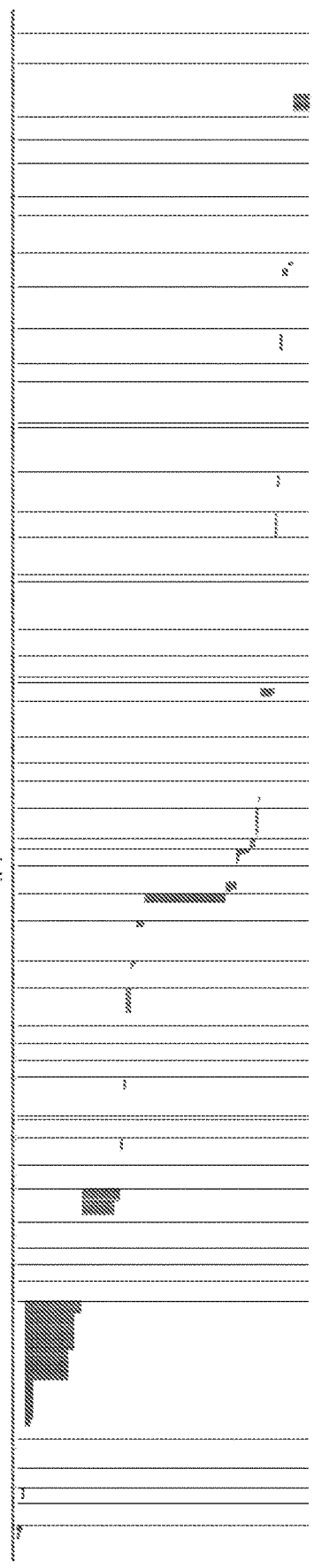
Figure 17:
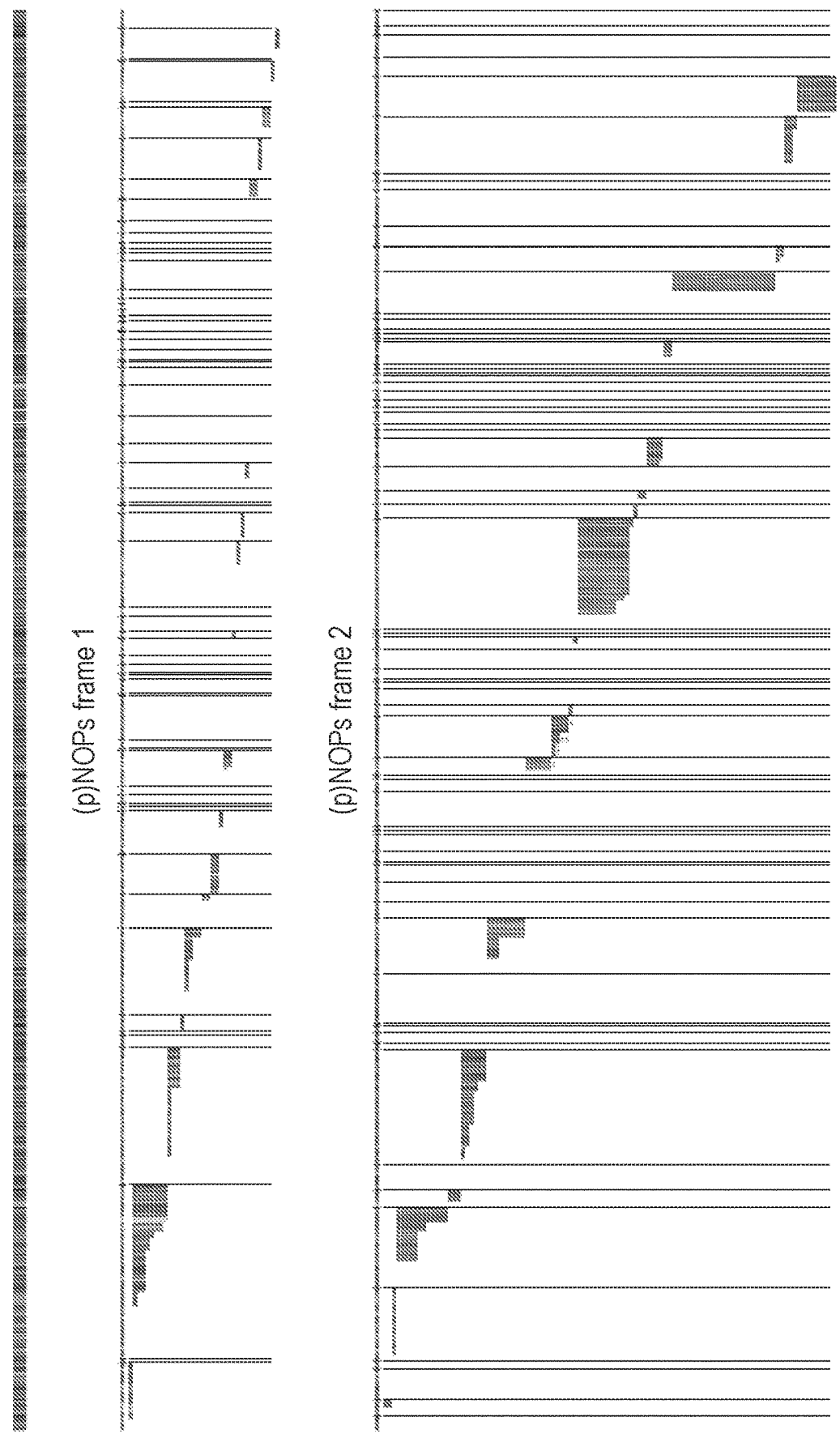
Figure 18:
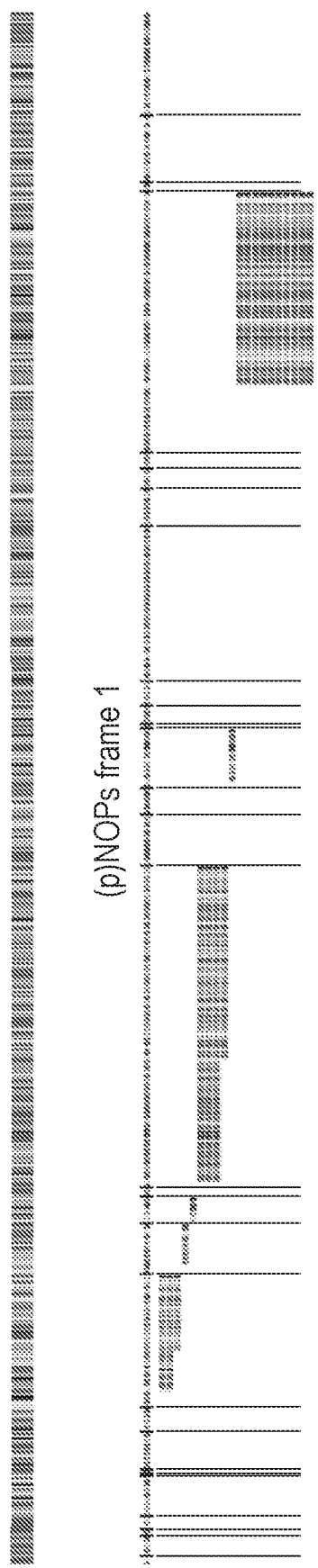
Figure 19:
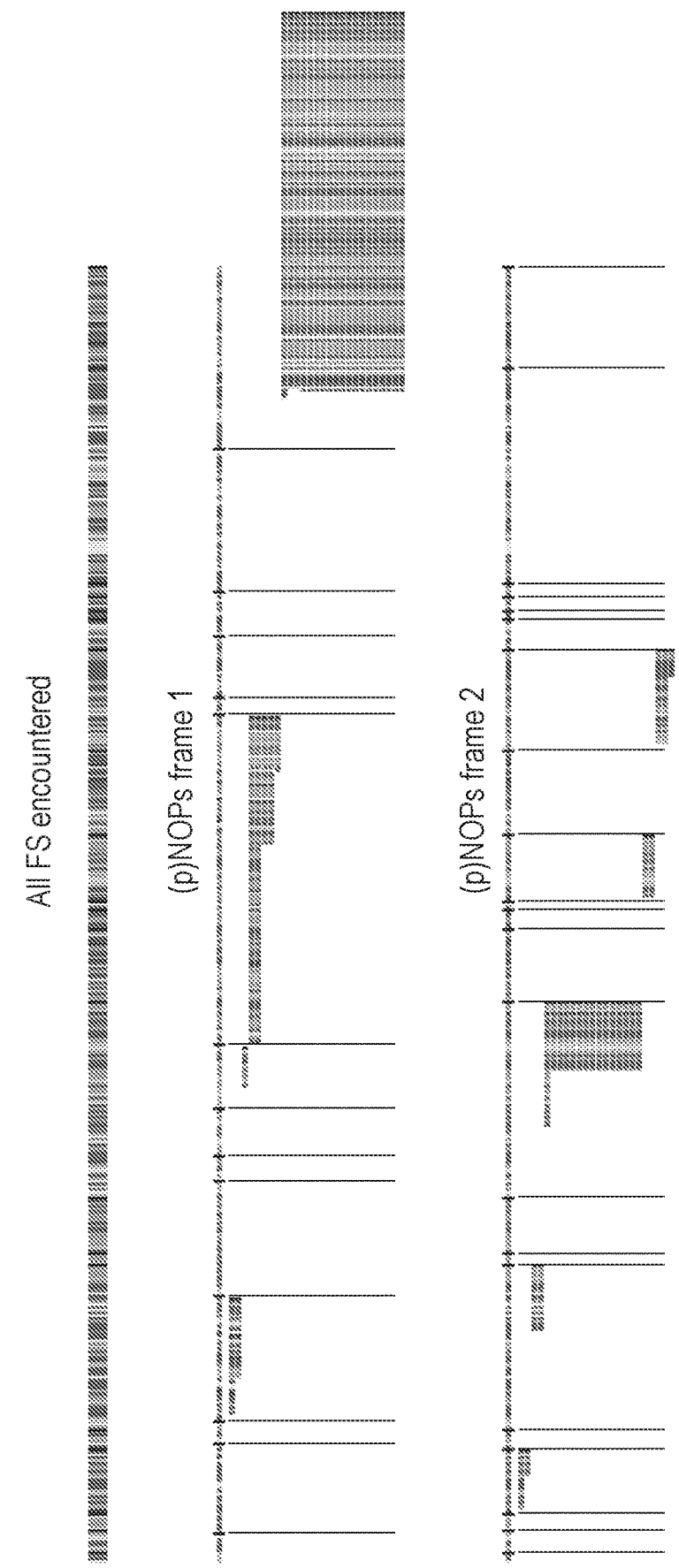
Figure 20:
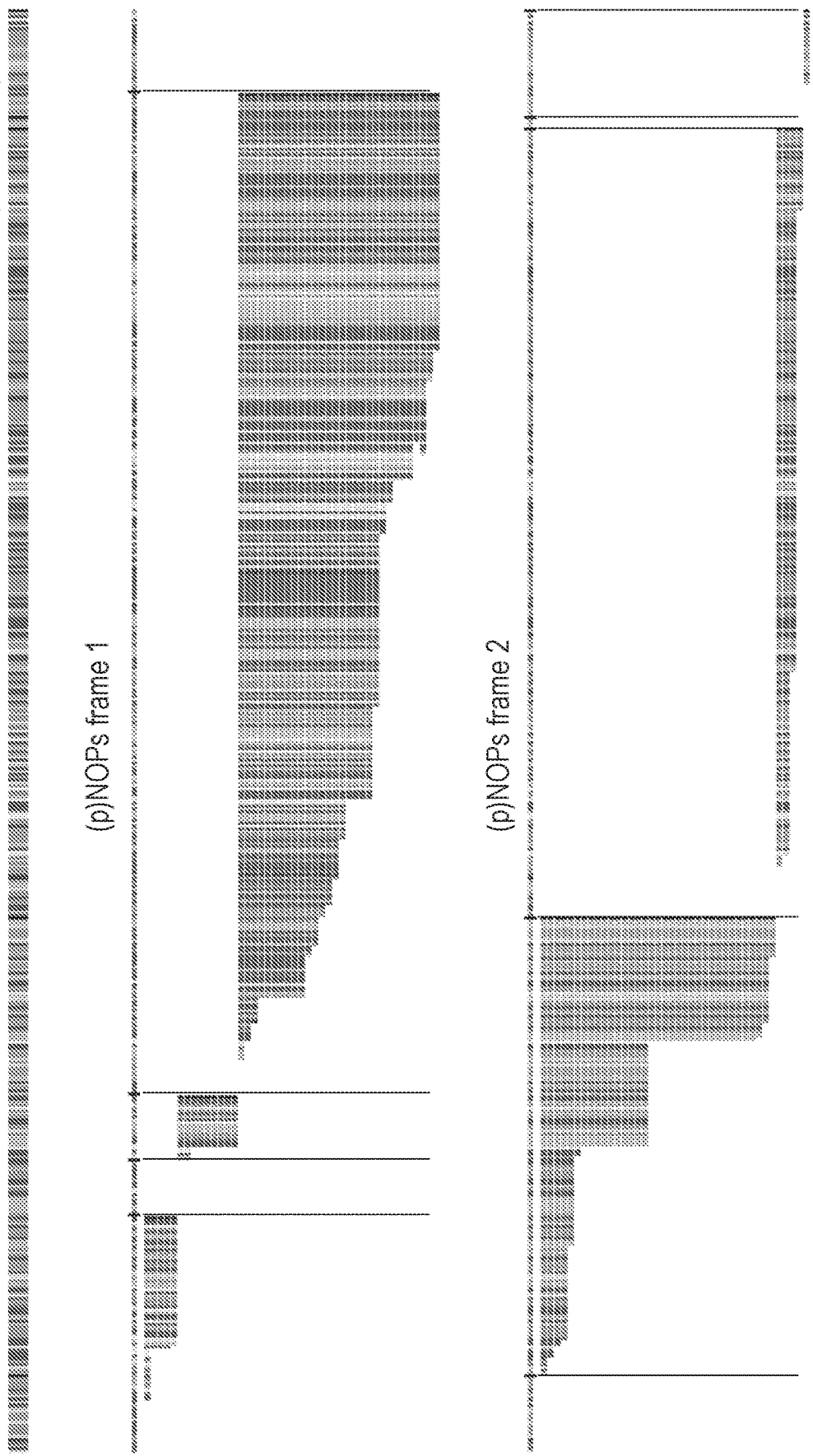

FIG. 13. TP53 out-of-frame peptide sequences based on frameshift mutations in colorectal cancer patients. Stacks of recurrent out-of-frame peptide subsequences are indicated with red boxes.

FIGS. 14-20. Out-of-frame peptide sequences based on frameshift mutations in colorectal cancer patients for APC, SOX9, KMT2D, ARID1A, RNF43, TCF7L2, and ZFP36L2, respectively.

EXAMPLES

Figure 1B:
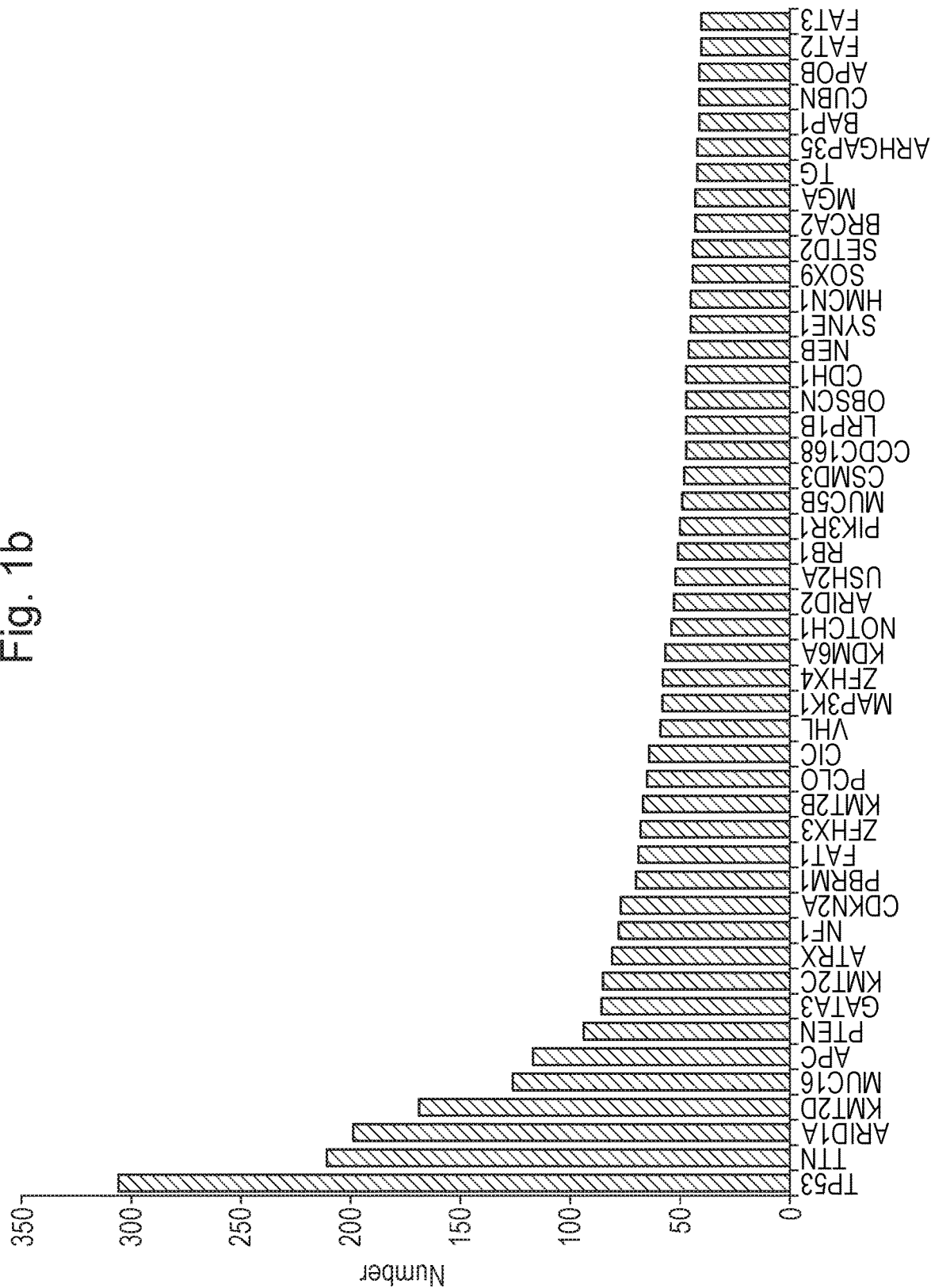
FIG. 1 Frame shift initiated translation in the TCGA (n=10,186) cohort is of sufficient size for immune presentation. A. Peptide length distribution of frame shift mutation initiated translation up to the first encountered stop codon. Dark shades are unique peptide sequences derived from frameshift mutations, light shade indicates the total sum (unique peptides derived from frameshifts multiplied by number of patients containing that frameshift). B. Gene distribution of peptides with length 10 or longer and encountered in up to 10 patients.
Figure 2E:
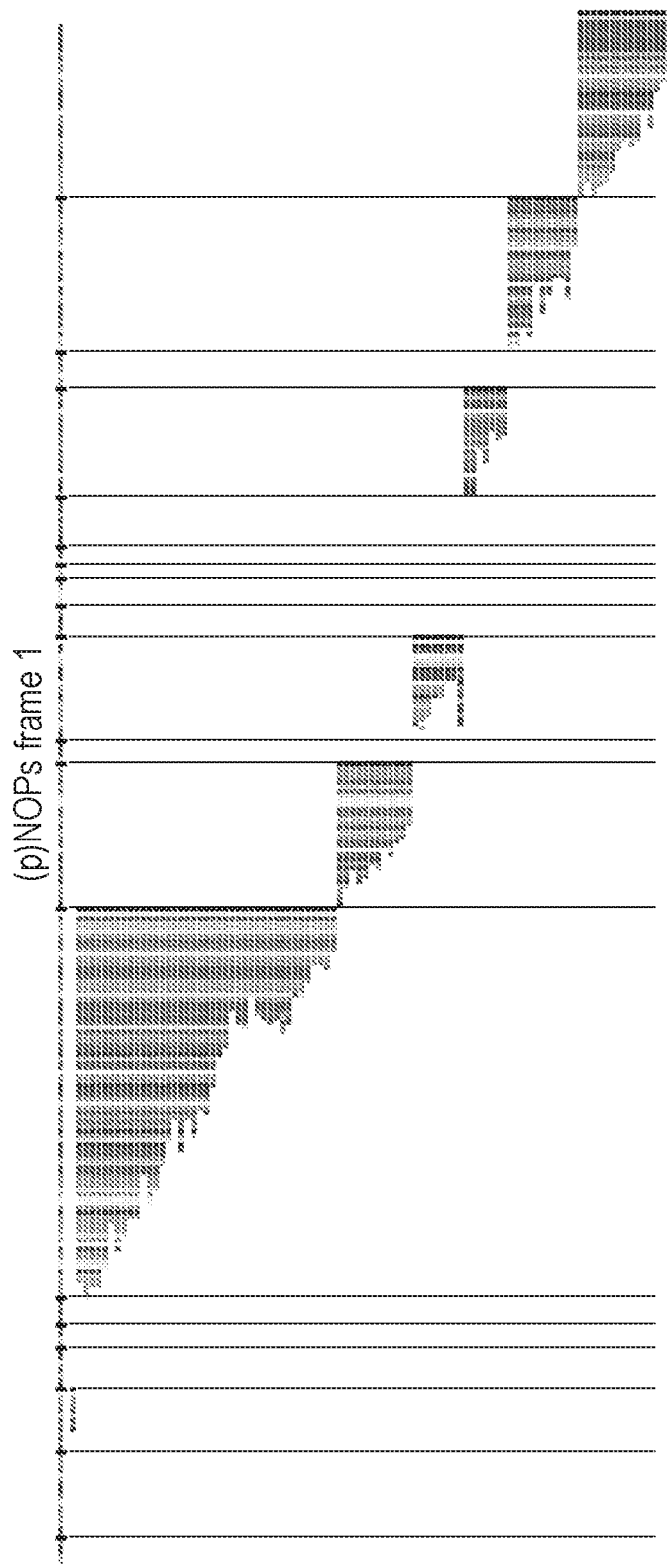
FIG. 2 Neo open reading frame peptides (TCGA cohort) converge on common peptide sequences. Graphical representation in an isoform of TP53, where amino acids are colored distinctly. A. somatic single nucleotide variants, B.
Figure 9B:
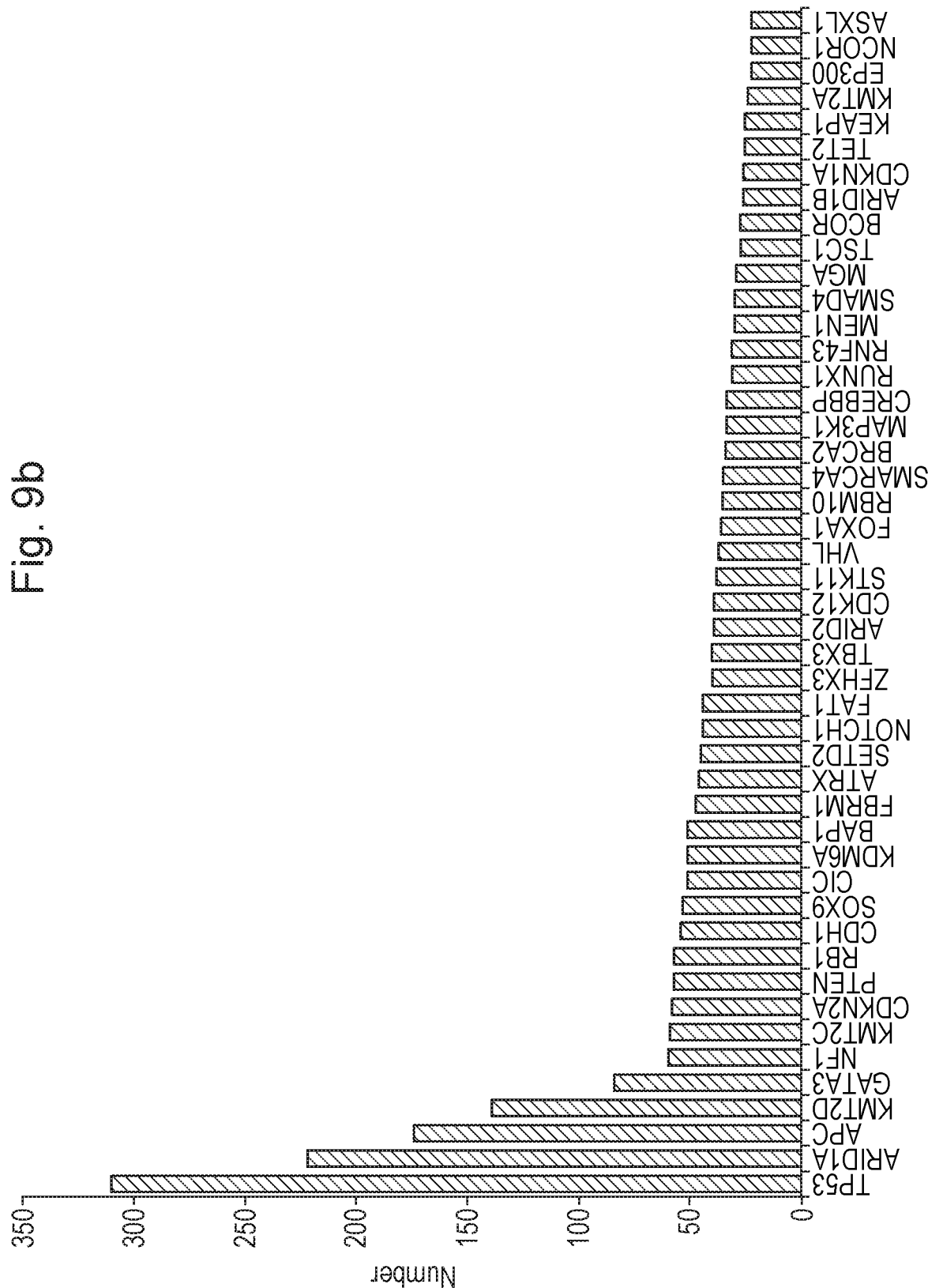
Figure 9C:
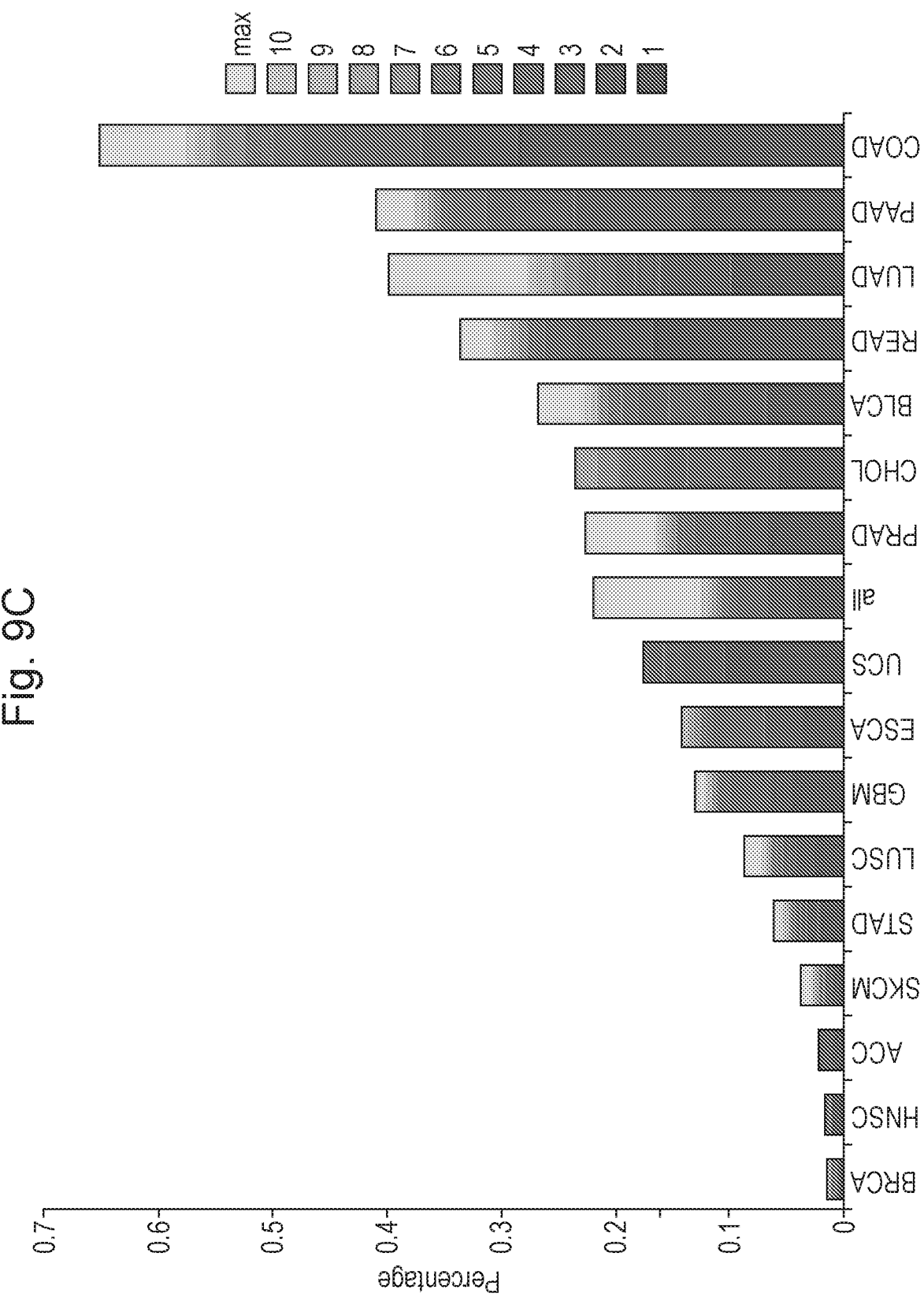
Figure 9D:
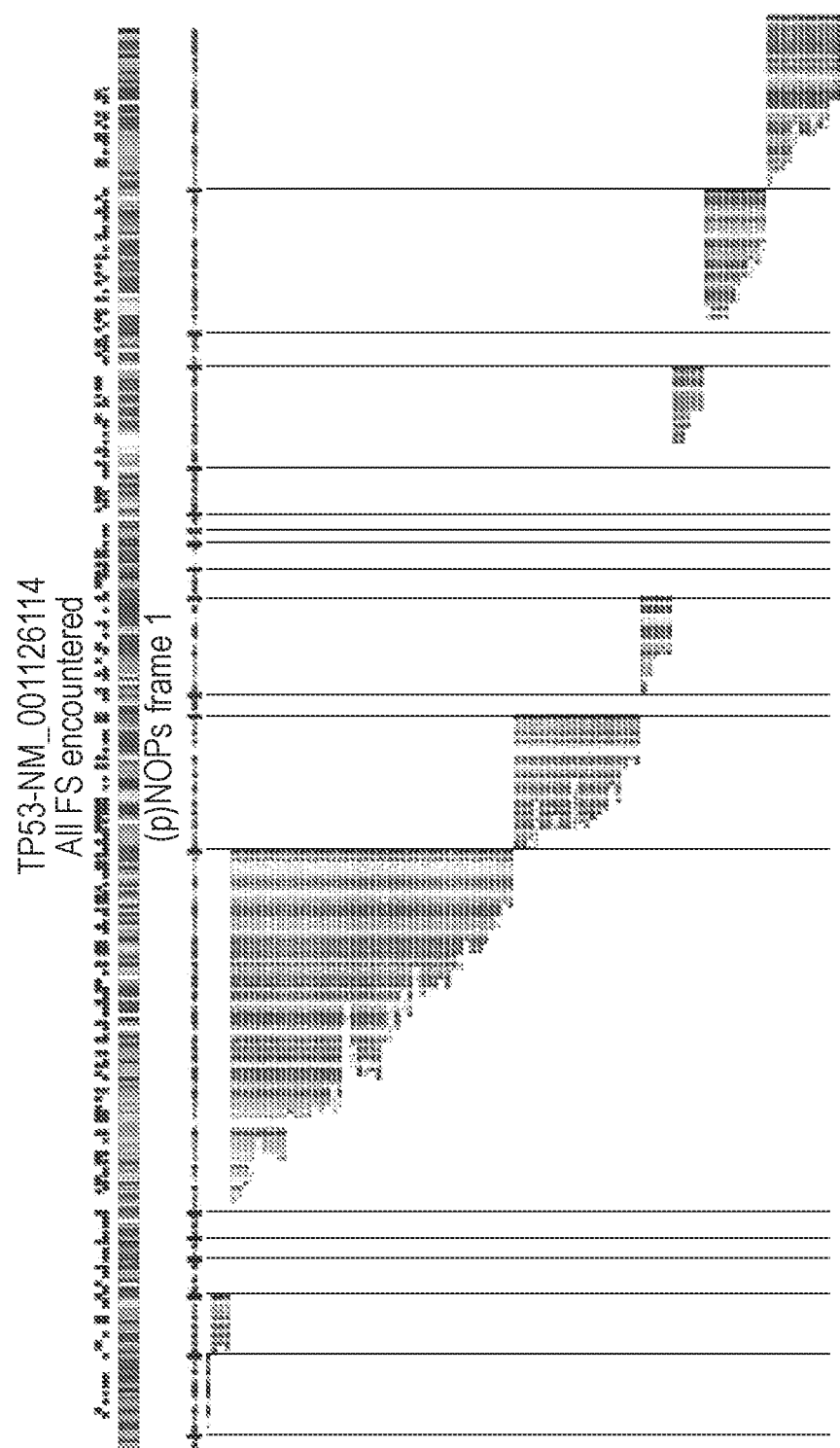

We have analyzed 10,186 cancer genomes from 33 tumor types of the 40 TCGA (The Cancer Genome Atlas 22) and focused on the 143,444 frame shift mutations represented in this cohort. Translation of these mutations after re-annotation to a RefSeq annotation, starting in the protein reading frame, can lead to 70,439 unique peptides that are 10 or more amino acids in length (a cut off we have set at a size sufficient to shape a distinct epitope in the context of MHC (FIG. 1a). The list of genes most commonly represented in the cohort and containing such frame shift mutations is headed nearly exclusively by tumor driver genes, such as NF1, RB, BRCA2 (FIG. 1b) whose whole or partial loss of function apparently contributes to tumorigenesis. Note that a priori frame shift mutations are expected to result in loss of gene function more than a random SNV, and more independent of the precise position. NOPs initiated from a frameshift mutation and of a significant size are prevalent in tumors, and are enriched in cancer driver genes. Alignment of the translated NOP products onto the protein sequence reveals that a wide array of different frame shift mutations translate in a common downstream stretch of neo open reading frame peptides ('NOPs'), as dictated by the −1 and +1 alternative reading frames. While we initially screened for NOPs of ten or more amino acids, their open reading frame in the out-of-frame genome often extends far beyond that search window. As a result we see (FIG. 2) that hundreds of different frame shift mutations all at different sites in the gene nevertheless converge on only a handful of NOPs. Similar patterns are found in other common driver genes (FIG. 5). FIG. 2 illustrates that the precise location of a frame shift does not seem to matter much; the more or less straight slope of the series of mutations found in these 10,186 tumors indicates that it is not relevant for the biological effect (presumably reduction/loss of gene function) where the precise frame shift is, as long as translation stalls in the gene before the downstream remainder of the protein is expressed. As can also be seen in FIG. 2, all frame shift mutations alter the reading frame to one of the two alternative frames. Therefore, for potential immunogenicity the relevant information is the sequence of the alternative ORFs and more precisely, the encoded peptide sequence between 2 stop codons. We term these peptides 'proto Neo Open Reading Frame peptides' or pNOPs, and generated a full list of all thus defined out of frame protein encoding regions in the human genome, of 10 amino acids or longer. We refer to the total sum of all Neo-ORFs as the Neo-ORFeome. The Neo-ORFeome contains all the peptide potential that the human genome can generate after simple frame-shift induced mutations. The size of the Neo-ORFeome is 46.6 Mb. To investigate whether or not Nonsense Mediated Decay would wipe out frame shift mRNAs, we turned to a public repository containing read coverage for a large collection of cell lines (CCLE). We processed the data in a similar fashion as for the TCGA, identified the locations of frame shifts and subsequently found that, in line with the previous literature[23-25], at least a large proportion of expressed genes also contained the frame shift mutation within the expressed mRNAs (FIG. 6). On the mRNA level, NOPs can be detected in RNAseq data. We next investigated how the number of patients relates to the number of NOPs. We sorted 10-mer peptides from NOPs by the number of new patients that contain the queried peptide. Assessed per tumor type, frame shift mutations in genes with very low to absent mRNA expression were removed to avoid overestimation. Of note NOP sequences are sometimes also encountered in the normal ORFeome, presumably as result of naturally occurring isoforms (e.g, FIG. 7). Also these peptides were excluded. We can create a library of possible 'vaccines' that is optimally geared towards covering the TCGA cohort, a cohort large enough that, also looking at the data presented here, it is representative of future patients (FIG. 10). Using this strategy 30% of all patients can be covered with a fixed collection of only 1,244 peptides of length 10 (FIG. 3). Since tumors will regularly have more than 1 frame shift mutation, one can use a 'cocktail' of different NOPs to optimally attack a tumor. Indeed, given a library of 1,244 peptides, 27% of the covered TCGA patients contain 2 or more 'vaccine' candidates. In conclusion, using a limited pool with optimal patient inclusion of vaccines, a large proportion of patients is covered. Strikingly, using only 6 genes (TP53, ARID1A, KMT2D, GATA3, APC, PTEN), already 10% of the complete TCGA cohort is covered. Separating this by the various tumor types, we find that for some cancers (like Pheochromocytoma and Paraganglioma (PCPG) or Thyroid carcinoma (THCA)) the hit rate is low, while for others up to 39% can be covered even with only 10 genes (Colon adenocarcinoma (COAD) using 60 peptides, Uterine Corpus Endometrial Carcinoma (UCEC) using 90 peptides), FIG. 4. At saturation (using all peptides encountered more than once) 50% of TCGA is covered and more than 70% can be achieved for specific cancer types (COAD, UCEC, Lung squamous cell carcinoma (LUSC) 72%, 73%, 73% respectively). As could be expected, these roughly follow the mutational load in the respective cancer types. In addition some frame shifted genes are highly enriched in specific tumor types (e.g. VHL, GATA3. FIG. 8). We conclude that at saturating peptide coverage, using only very limited set of genes, a large cohort of patients can be provided with off the shelf vaccines. To validate the presence of NOPs, we used the targeted sequencing data on 10,129 patients from the MSK-IMPACT cohort 26. For the 341-410 genes assessed in this cohort, we obtained strikingly similar results in terms of genes frequently affected by frame shifts and the NOPs that they create (FIG. 9). Even within this limited set of genes, 86% of the library peptides (in genes targeted by MSK-IMPACT) were encountered in the patient set. Since some cancers, like glioblastoma or pancreatic cancer, show survival expectancies after diagnosis measured in months rather than years (e.g. see 27), it is of importance to move as much of the work load and time line to the moment before diagnosis. Since the time of whole exome sequencing after biopsy is currently technically days, and since the scan of a resulting sequence against a public database describing these NOPs takes seconds, and the shipment of a peptide of choice days, a vaccination can be done theoretically within days and practically within a few weeks after biopsy. This makes it attractive to generate a stored and quality controlled peptide vaccine library based on the data presented here, possibly with replicates stored on several locations in the world. The synthesis in advance will—by economics of scale—reduce costs, allow for proper regulatory oversight, and can be quality certified, in addition to saving the patient time and thus provide chances. The present invention will likely not replace other therapies, but be an additional option in the treatment repertoire. The advantages of scale also apply to other means of vaccination against these common neoantigens, by RNA- or DNA-based approaches (e.g. 28), or recombinant bacteria (e.g. 29). The present invention also provides neoantigen directed application of the CAR-T therapy (For recent review see 30, and references therein), where the T-cells are directed not against a cell-type specific antigens (such as CD19 or CD20), but against a tumor specific neoantigen as provided herein. E.g. once one functional T-cell against any of the common p53 NOPs (FIG. 2) is identified, the recognition domains can be engineered into T-cells for any future patient with such a NOP, and the constructs could similarly be deposited in an off-the-shelf library.

In the present invention, we have identified that various frame shift mutations can result in a source for common neo open reading frame peptides, suitable as pre-synthesized vaccines. This may be combined with immune response stimulating measures such as but not limited checkpoint inhibition to help instruct our own immune system to defeat cancer.

About 5-10% of all colon cancers are a result of a heritable germline mutation. Two major types of heritable colon cancer are familial adenomatous polyposis (FAP) or Lynch syndrome (also known as hereditary nonpolyposis colorectal cancer (HNPCC)). In addition, there may be more rare forms of heritable colon cancer. For a review see: Short et al. J Med Genet. 2015 December; 52(12):791-6. Genetic testing can involve several genes, amongst others MLH1, MSH2, APC, MSH6, PMS2, and MUTYH. Several of these genes (MLH1, MSH2, MSH6, MUTYH), play a role in mismatch repair. Defects in mismatch genes can lead to hypermutation phenotypes in tumors.

Thus, there is an opportunity for prophylactic vaccination to reduce the risk of colon cancer in individuals with predisposition mutations in these genes. A prophylactic vaccine would be of highest efficacy if it vaccinates against (i) strongly immunogenic antigens, and (ii) antigens that are expected to be present in a large proportion of colon tumors observed in patients with predisposition mutations.

We exploited a recent data source from the Hartwig Medical Foundation (see Priestley et al. 2019 at https://doi.org/10.1101/415133) for the presence of targetable neoantigens in colon tumors in patients with germline mutations in a range of cancer predisposition genes.

Amongst 444 colon/rectum tumors, we found that 71 (15.9%) of the patients carrying those tumors have a mutation in one or more possible predisposition genes (FIG. 10). As can be seen in FIG. 10, germline predisposing mutations in GJB2 and CHEK2 are most frequently observed (8 and 7, respectively) in the HMF colon cancer cohort. The role of GJB2 in heritable colorectal cancer is known, while CHEK2 is a well-known cancer predisposition gene. Other well-known colorectal cancer predisposition genes are also observed in the HMF cohort, such as MUTYH, MSH6, MLH1, APC and fanconi anaemia genes (FANCL, FANCM).

Next, we explored the idea of using neo-open reading frame peptides, resulting from somatic frameshift mutations, as an attractive source of neoantigens in human cancers. Therefore, we calculated the number of colon cancer patients in the HMF data resource with frameshift mutations leading to possible out of frame neo-peptides (FIG. 11). Neo-peptides larger than or equal to 10 amino acids are most frequently found in APC (6%), ZFP36L2 (5.9%), TP53 (5.2%), TCF7L2 (4.5%), RNF43 (2%), ARID1A (2%), SOX9 (1.8%), ASXL2 (1.8%), KMT2D (0.7%).

The frequencies of these out-of-frame peptide sequences differs somewhat from those in the TCGA database, e.g. the frequent occurrence of ZFP36L2 frameshifts is not observed in the TCGA database. However, APC, TP53 and SOX9 are among the top-ranked genes, as expected.

To explore the possibility for prophylactic vaccination of individuals at risk for colorectal cancer based on germline predisposing mutations, we determined the genes for which out-of-frame peptide sequences are found among patients with germline predisposition mutations. Out of all 71 colorectal cancer patients with presumed germline predisposition mutations (in any possible predisposition gene), we found 13 (18%) patients that have a frameshift leading to a neo-peptide in TP53, APC or SOX9 (FIG. 12).

We conclude that a considerable fraction of colon/rectum cancer patients with predisposing germline mutations, may benefit from vaccination against frameshift-induced neopeptides. Within this group, 18% develops tumors for which vaccines derived from only three genes (APC, TP53 and SOX9) would be relevant."

Methods:

TCGA frameshift mutations—Frame shift mutations were retrieved from Varscan and mutect files per tumor type via https://portal.gdc.cancer.gov/. Frame shift mutations contained within these files were extracted using custom perl scripts and used for the further processing steps using HG38 as reference genome build.

CCLE frameshift mutations—For the CCLE cell line cohort, somatic mutations were retrieved from http://www-.broadinstitute.org/ccle/data/ browseData?conversationPropagation=begin (CCLE_hybrid_capture1650_hg19_NoCommonSNPs_ NoNeutralVariants_CDS_2012.02.20.maf). Frame shift mutations were extracted using custom perl scripts using hg19 as reference genome.

Refseq annotation—To have full control over the sequences used within our analyses, we downloaded the reference sequences from the NCBI website (2018-02-27) and extracted mRNA and coding sequences from the gbff files using custom perl scripts. Subsequently, mRNA and every exon defined within the mRNA sequences were aligned to the genome (hg19 and hg38) using the BLAT suite. The best mapping locations from the psl files were subsequently used to place every mRNA on the genome, using the separate exons to perform fine placement of the exonic borders. Using this procedure we also keep track of the offsets to enable placement of the amino acid sequences onto the genome.

Mapping genome coordinate onto Refseq—To assess the effect of every mentioned frame shift mutation within the cohorts (CCLE or TCGA), we used the genome coordinates of the frameshifts to obtain the exact protein position on our reference sequence database, which were aligned to the genome builds. This step was performed using custom perl scripts taking into account the codon offsets and strand orientation, necessary for the translation step described below.

Translation of FS peptides—Using the reference sequence annotation and the positions on the genome where a frame shift mutation was identified, the frame shift mutations were used to translate peptides until a stop codon was encountered. The NOP sequences were recorded and used in downstream analyses as described in the text.

Verification of FS mRNA expression in the CUE colorectal cancer cell lines—For a set of 59 colorectal cancer cell lines, the HG19 mapped bam files were downloaded from haps://portal.gde.cancer.govi. Furthermore, the locations of FS mutations were retrieved from CCLE_hybrid_capture1650_hg19_NoCommonSNPs_No NeutralVariants_CDS_2012.02.20.maf (http://www.broa-dinstitute.org/ccle/data/ browseData?conversationPropagation=beg in), by selection only frameshift entries. Entries were processed similarly to the TCGA data, but this time based on a HG19 reference genome. To get a rough indication that a particular location in the genome indeed contains an indel in the RNAseq data, we first extracted the count at the location of a frameshift by making use of the pileup function in samtools. Next we used the special tag XO:1 to isolate reads that contain an indel in it. On those bam files we again used the pileup function to count the number of reads containing an indel (assuming that the indel would primarily be found at the frameshift instructed location). Comparison of those 2 values can then be interpreted as a percentage of indel at that particular location. To reduce spurious results, at least 10 reads needed to be detected at the FS location in the original bam file.

Defining peptide library—To define peptide libraries that are maximized on performance (covering as many patients with the least amount of peptides) we followed the following procedure. From the complete TCGA cohort, FS translated peptides of size 10 or more (up to the encountering of a stop codon) were cut to produce any possible 10-mer. Then in descending order of patients containing a 10-mer, a library was constructed. A new peptide was added only if an additional patient in the cohort was included. peptides were only considered if they were seen 2 or more times in the TCGA cohort, if they were not filtered for low expression (see Filtering for low expression section), and if the peptide was not encountered in the orfeome (see Filtering for peptide presence orfeome). In addition, since we expect frame shift mutations to occur randomly and be composed of a large array of events (insertions and deletions of any non triplet combination), frame shift mutations being encountered in more than 10 patients were omitted to avoid focusing on potential artefacts. Manual inspection indicated that these were cases with e.g. long stretches of Cs, where sequencing errors are common.

Filtering for low expression—Frameshift mutations within genes that are not expressed are not likely to result in the expression of a peptide. To take this into account we calculated the average expression of all genes per TCGA entity and arbitrarily defined a cutoff of 2 log 2 units as a minimal expression. Any frameshift mutation where the average expression within that particular entity was below the cutoff was excluded from the library. This strategy was followed, since mRNA gene expression data was not available for every TCGA sample that was represented in the sequencing data set. Expression data (RNASEQ v2) was pooled and downloaded from the R2 platform (http://r2.amc.nl). In current sequencing of new tumors with the goal of neoantigen identification such mRNA expression studies are routine and allow routine verification of presence of mutant alleles in the mRNA pool.

Filtering for peptide presence orfeome—Since for a small percentage of genes, different isoforms can actually make use of the shifted reading frame, or by chance a 10-mer could be present in any other gene, we verified the absence of any picked peptide from peptides that can be defined in any entry of the reference sequence collection, once converted to a collection of tiled 10-mers.

Generation of cohort coverage by all peptides per gene To generate overviews of the proportion of patients harboring exhaustive FS peptides starting from the most mentioned gene, we first pooled all peptides of size 10 by gene and recorded the largest group of patients per tumor entity. Subsequently we picked peptides identified in the largest set of patients and kept on adding a new peptide in descending order, but only when at least 1 new patient was added. Once all patients containing a peptide in the first gene was covered, we progressed to the next gene and repeated the procedure until no patient with FS mutations leading to a peptide of size 10 was left.

proto-NOP (pNOP) and Neo-ORFeome proto—NOPs are those peptide products that result from the translation of the gene products when the reading frame is shifted by −1 or +1 base (so out of frame). Collectively, these pNOPs form the Neo-OrfeomeAs such we generated a pNOP reference base of any peptide with length of or more amino acids, from the RefSeq collection of sequences. Two notes: the minimal length of 10 amino acids is a choice; if one were to set the minimal window at 8 amino acids the total numbers go up a bit, e.g. the 30% patient covery of the library goes up. On a second note: we limited our definition to ORFs that can become in frame after a single insertion deletion on that location; this includes obviously also longer insertion or deletion stretches than +1 or −1. The definition has not taken account more complex events that get an out-of-frame ORF in frame, such as mutations creating or deleting splice sites, or a combination of two frame shifts at different sites that result in bypass of a natural stop codon; these events may and will occur, but counting those in will make the definition of the Neo-ORFeome less well defined. For the magnitude of the numbers these rare events do not matter much.

Visualizing nops—Visualization of the nops was performed using custom perl scripts, which were assembled such that they can accept all the necessary input data structures such as protein sequence, frameshifted protein sequences, somatic mutation data, library definitions, and the peptide products from frameshift translations.

Detection of frameshift resulting neopeptides in colorectal cancer patients with cancer predisposition mutations—Somatic and germline mutation data were downloaded from the supplementary files attached to the manuscript posted here: https://www.biorxiv.org/content/biorxiv/early/2019/01/16/415133.full.pdf. Frameshift mutations were selected from the somatic mutation files and out-of-frame peptides were predicted using custom Perl and Python scripts, based on the human reference genome GRCh37. Out-of-frame peptides were selected based on their length (>=10 amino acids) and mapped against out of frame peptide sequences for each possible alternative transcript for genes present in the human genome, based on Ensembl annotation (ensembl.org).

REFERENCES

1 Schumacher T. N., & Schreiber R. D. Neoantigens in cancer immunotherapy. *Science.* 348, 69-74 (2015).
2 Gubin M. M., Artyomov M. N., Mardis E. R., & Schreiber R. D. Tumor neoantigens: building a framework for personalized cancer immunotherapy. *J Clin Invest.* 125, 3413-21 (2015).
3 Ward J. P., Gubin M. M., & Schreiber R. D. The Role of Neoantigens in Naturally Occurring and Therapeutically Induced Immune Responses to Cancer. *Adv Immunol.* 130, 25-74 (2016).
4 DeWeerdt S. Calling cancer's bluff with neoantigen vaccines. *Nature.* 552, S76-S77 (2017).
5 Guo C., et al. Therapeutic cancer vaccines: past, present, and future. *Adv Cancer Res.* 119, 421-75 (2013).
6 Overwijk W. W., Wang E., Marincola F. M., Rammensee & Restifo N. P. Mining the mutanome: developing highly personalized Immunotherapies based on mutational analysis of tumors. *J Immunother Cancer.* 1, 11 (2013).
7 Yamada A., Sasada T., Noguchi M., & Itoh K. Next-generation peptide vaccines for advanced cancer. *Cancer Sci.* 104, 15-21 (2013).
8 Ott P. A., et al. An immunogenic personal neoantigen vaccine for patients with melanoma. *Nature.* 547, 217-221 (2017).
9 Wirth T. C., & Kuhnel F. Neoantigen Targeting-Dawn of a New Era in Cancer Immunotherapy? *Front Immunol.* 8, 1848 (2017).
10 Yarchoan M., Hopkins A., & Jaffee E. M. Tumor Mutational Burden and Response Rate to PD-1 Inhibition. *N Eng J Med.* 377, 2500-2501 (2017).
11 Sahin U., et al. Personalized RNA mutanome vaccines mobilize poly-specific therapeutic immunity against cancer. *Nature.* 547, 222-226 (2017).
12 Linnebacher M., et al. Frameshift peptide-derived T-cell epitopes: a source of novel tumor-specific antigens. *Int J Cancer.* 93, 6-11 (2001).
13 Sonntag K., et al. Immune monitoring and TCR sequencing of CD4 T cells in a long term responsive patient with metastasized pancreatic ductal carcinoma treated with individualized, neoepitope derived multipeptide vaccines: a case report. *J Transl Med.* 16, 23 (2018).

14 MacArthur D. G., et al. A systematic survey of loss-of-function variants in human protein-coding genes. *Science.* 335, 823-8 (2012).
15 Turajlic S., et al. Insertion-and-deletion-derived tumour-specific neoantigens and the immunogenic phenotype: a pan-cancer analysis. *Lancet Oncol.* 18, 1009-1021 (2017).
16 Rammensee H., Bachmann J., Emmerich N. P., Bachor O. A., & Stevanovic S. SYFPEITHI: database for MHC ligands and peptide motifs. *Immunogenetics.* 50, 213-9 (1999).
17 Alvarez B., Barra C., Nielsen M., & Andreatta M. Computational Tools for the Identification and Interpretation of Sequence Motifs in Immunopeptidomes. *Proteomics.* 18, e1700252 (2018).
18 Andreatta M., et al. Accurate pan-specific prediction of peptide-MHC class II binding affinity with improved binding core identification. *Immunogenetics.* 67, 641-50 (2015).
19 Rizvi N. A., et al. Cancer immunology. Mutational landscape determines sensitivity to PD-1 blockade in non-small cell lung cancer. *Science.* 348, 124-8 (2015).
20 Prickett T. D., et al. Durable Complete Response from Metastatic Melanoma after Transfer of Autologous T Cells Recognizing 10 Mutated Tumor Antigens. *Cancer Immunol Res.* 4, 669-78 (2016).
21 Liu R., et al. H7N9 T-cell epitopes that mimic human sequences are less immunogenic and may induce Treg-mediated tolerance. *Hum Vaccin Immunother.* 11, 2241-52 (2015).
22 Weinstein J. N., et al. The Cancer Genome Atlas Pan-Cancer analysis project. *Nat Genet.* 45, 1113-20 (2013).
23 Lindeboom R. G., Supek F., & Lehner B. The rules and impact of nonsense-mediated mRNA decay in human cancers. *Nat Genet.* 48, 1112-8 (2016).
24 Longman D., Plasterk R. H., Johnstone II., & Caceres J. F. Mechanistic insights and identification of two novel factors in the *C. elegans* NMD pathway. *Genes Dec.* 21, 1075-85 (2007).
25 Nguyen L. S., Wilkinson M. F., & Gecz J. Nonsense-mediated mRNA decay: inter-individual variability and human disease. *Neurosci Biobehav Rec.* 46 Pt 2, 175-86 (2014).
26 Zehir A., et al. Mutational landscape of metastatic cancer revealed from prospective clinical sequencing of 10,000 patients. *Nat Med.* 23, 703-713 (2017).
27 Fest J., et al. Underestimation of pancreatic cancer in the national cancer registry *Eur J Cancer.* 72, 186-191 (2017).
28 Boisguerin V., et al. Translation of genomics-guided RNA-based personalised cancer vaccines: towards the bedside. *Br J Cancer.* 111, 1469-75 (2014).
29 Keenan B. P., et al. A *Listeria* vaccine and depletion of T-regulatory cells activate immunity against early stage pancreatic intraepithelial neoplasms and prolong survival of mice. *Gastroenterology.* 146, 1784-94.e6 (2014).
30 Ramello M. C., Haura E. B., & Abate-Daga D. CAR-T cells and combination therapies: What's next in the immunotherapy revolution? *Pharmacol Res.* 129, 194-203 (2018)
31 Giannakis, Marios, et al. "Genomic Correlates of Immune-Cell Infiltrates in Colorectal Carcinoma." Cell Reports, vol. 17, no. 4, Oct. 2016, p. 1206.
32 Linnebacher, M., et al. "Frameshift Peptide-Derived T-Cell Epitopes: A Source of Novel Tumor-Specific Antigens." International Journal of Cancer. Journal International Du Cancer, vol. 93, no. 1, July 2001, pp. 6-11.
33 Maby, Pauline, et al. "Correlation between Density of CD8+ T-Cell Infiltrate in Microsatellite Unstable Colorectal Cancers and Frameshift Mutations: A Rationale for Personalized Immunotherapy." Cancer Research, vol. 75, no. 17, September 2015, pp. 3446-55.
34 Saeterdal, I., et al. "A TGF betaRII Frameshift-Mutation-Derived CTL Epitope Recognised by HLA-A2-Restricted CD8+ T Cells." Cancer Immunology, Immunotherapy: CII, vol. 50, no. 9, November 2001, pp. 469-76.
35 Turajlic, Samra, et al. "Insertion-and-Deletion-Derived Tumour-Specific Neoantigens and the Immunogenic Phenotype: A Pan-Cancer Analysis." The Lancet Oncology, vol. 18, no. 8, August 2017, pp. 1009-21.
36 Williams, David S., et al. "Nonsense Mediated Decay Resistant Mutations Are a Source of Expressed Mutant Proteins in Colon Cancer Cell Lines with Microsatellite Instability." PloS One, vol. 5, no. 12, December 2010, p. e16012.

The invention claimed is:

1. A therapeutic vaccine or collection of therapeutic vaccines for treating colorectal cancer comprising:
- a peptide, or a collection of tiled peptides, having the amino acid sequence selected from SEQ ID NO:709, an amino acid sequence having 90% identity to SEQ ID NO:709, a fragment comprising at least 10 consecutive amino acids of SEQ ID NO:709, or one or more nucleic acids encoding said peptide or collection of tiled peptides; and
- a peptide, or a collection of tiled peptides, having the amino acid sequence selected from SEQ ID NO:710, an amino acid sequence having 90% identity to SEQ ID NO:710, a fragment comprising at least 10 consecutive amino acids of SEQ ID NO:710, or one or more nucleic acids encoding said peptide or collection of tiled peptides; preferably also comprising
- a peptide, or a collection of tiled peptides, having the amino acid sequence selected from SEQ ID NO:711, an amino acid sequence having 90% identity to SEQ ID NO:711, a fragment comprising at least 10 consecutive amino acids of SEQ ID NO:711, or one or more nucleic acids encoding said peptide or collection of tiled peptides; and/or
- a peptide, or a collection of tiled peptides, having the amino acid sequence selected from SEQ ID NO:712, an amino acid sequence having 90% identity to SEQ ID NO:712, a fragment comprising at least 10 consecutive amino acids of SEQ ID NO:712, or one or more nucleic acids encoding said peptide or collection of tiled peptides.

2. The therapeutic vaccine or collection of therapeutic vaccines of claim 1, wherein at least two of said peptides are linked.

3. The therapeutic vaccine or collection of therapeutic vaccines of 2, wherein said peptides are comprised within the same polypeptide.

4. The therapeutic vaccine or collection of therapeutic vaccines of claim 1, wherein the nucleic acid molecules encoding said peptides are comprised in one or more vectors.

5. The therapeutic vaccine or collection of therapeutic vaccines of claim 4, wherein said vector is a viral vector.

6. The therapeutic vaccine or collection of therapeutic vaccines of claim 1, further comprising a pharmaceutically acceptable excipient, an adjuvant, or a therapeutic agent.

7. The therapeutic vaccine or collection of therapeutic vaccines of claim 6, wherein the therapeutic agent is a checkpoint inhibitor, a chemotherapeutic agent, or an antibody.

8. The therapeutic vaccine or collection of therapeutic vaccines of claim 6, further comprising an immune-effective amount of adjuvant.

9. A method of treating an individual for colorectal cancer, the method comprising administering to the individual in need thereof a therapeutic vaccine selected from the therapeutic vaccine or collection of therapeutic vaccines of claim 1.

* * * * *

SEQUENCE LISTING

<160> NUMBER OF SEQ ID NOS: 725

<210> SEQ ID NO 1
<211> LENGTH: 33
<212> TYPE: PRT
<213> ORGANISM: Artificial Sequence
<220> FEATURE:
<223> OTHER INFORMATION: pNOP255295

<400> SEQUENCE: 1

Met Leu Gln Phe Arg Gly Ser Arg Phe Phe Gln Met Leu Ile Leu Tyr
1               5                   10                  15

Tyr Ile Leu Pro Arg Lys Val Leu Gln Met Asp Phe Leu Val His Pro
            20                  25                  30

Ala

<210> SEQ ID NO 2
<211> LENGTH: 53
<212> TYPE: PRT
<213> ORGANISM: Artificial Sequence
<220> FEATURE:

<223> OTHER INFORMATION: pNOP124349

<400> SEQUENCE: 2

Ala Pro Val Ile Phe Gln Ile Ala Leu Asp Lys Pro Cys His Gln Ala
1               5                   10                  15

Glu Val Lys His Leu His His Leu Leu Lys Gln Leu Lys Pro Ser Glu
            20                  25                  30

Lys Tyr Leu Lys Ile Lys His Leu Leu Leu Lys Arg Glu Arg Val Asp
        35                  40                  45

Leu Ser Lys Leu Gln
    50

<210> SEQ ID NO 3
<211> LENGTH: 26
<212> TYPE: PRT
<213> ORGANISM: Artificial Sequence
<220> FEATURE:
<223> OTHER INFORMATION: pNOP344680

<400> SEQUENCE: 3

Tyr Phe Ile Thr Phe Cys His Gly Lys Tyr Ser Arg Trp Ile Phe Leu
1               5                   10                  15

Phe Ile Gln Pro Glu Cys Ser Glu Pro Arg
            20                  25

<210> SEQ ID NO 4
<211> LENGTH: 93
<212> TYPE: PRT
<213> ORGANISM: Artificial Sequence
<220> FEATURE:
<223> OTHER INFORMATION: pNOP39262

<400> SEQUENCE: 4

Ala Lys Phe Gln Gln Cys His Ser Thr Leu Glu Pro Asn Pro Ala Asp
1               5                   10                  15

Cys Arg Val Leu Val Tyr Leu Gln Asn Gln Pro Gly Thr Lys Leu Leu
            20                  25                  30

Asn Phe Leu Gln Glu Arg Asn Leu Pro Pro Lys Val Val Leu Arg His
        35                  40                  45

Pro Lys Val His Leu Asn Thr Met Phe Arg Arg Pro His Ser Cys Leu
    50                  55                  60

Ala Asp Val Leu Leu Ser Val His Leu Ile Val Leu Arg Val Val Arg
65                  70                  75                  80

Leu Pro Ala Pro Phe Arg Val Asn His Ala Val Glu Trp
                85                  90

<210> SEQ ID NO 5
<211> LENGTH: 39
<212> TYPE: PRT
<213> ORGANISM: Artificial Sequence
<220> FEATURE:
<223> OTHER INFORMATION: pNOP200871

<400> SEQUENCE: 5

Cys Leu Gln Phe Arg Lys Met Thr Met Gly Met Lys Gln Asn Gln Ser
1               5                   10                  15

Ser Leu Lys Asn Gln Met Lys Thr Lys Arg Lys Arg Gln Lys Lys Leu
            20                  25                  30

Leu Ile Leu Lys Arg Thr Tyr
        35

<210> SEQ ID NO 6
<211> LENGTH: 73
<212> TYPE: PRT
<213> ORGANISM: Artificial Sequence
<220> FEATURE:
<223> OTHER INFORMATION: pNOP68492

<400> SEQUENCE: 6

Lys Asn Val Leu Phe Leu Pro Cys Gln Gln Ser His His Val Lys Gln
1               5                   10                  15

Lys Ser Gln Pro Arg Leu Leu Gln Asn Tyr Leu His Leu Trp Gln Gly
            20                  25                  30

Asn Gln Val Ser Cys Leu Cys Thr Asn Phe Tyr His His Lys Thr Gly
        35                  40                  45

Cys Asn Pro Lys Ser Met Leu Val Leu His Arg Gly Met Ile Cys His
    50                  55                  60

Gly Cys Ile Val Leu Lys Gly His Leu
65                  70

<210> SEQ ID NO 7
<211> LENGTH: 20
<212> TYPE: PRT
<213> ORGANISM: Artificial Sequence
<220> FEATURE:
<223> OTHER INFORMATION: pNOP433821

<400> SEQUENCE: 7

Ile Phe Phe Arg Ser Glu Ile Ser Leu Gln Lys Trp Cys Ser Asp Thr
1               5                   10                  15

Gln Lys Ser Thr
            20

<210> SEQ ID NO 8
<211> LENGTH: 82
<212> TYPE: PRT
<213> ORGANISM: Artificial Sequence
<220> FEATURE:
<223> OTHER INFORMATION: pNOP53481

<400> SEQUENCE: 8

Asn Met Pro Gln Ile Phe Leu His His Arg Asn Ser His Phe His Ser
1               5                   10                  15

Gln Arg Val His Leu Asp Lys Ala Val Lys Pro Asn Ile Cys Leu Gln
            20                  25                  30

Ala Val Arg Ile Arg Pro His Leu His Leu Met Pro Arg Gly Arg Ile
        35                  40                  45

Ser Ser Ile Gln Val Leu His Arg Val Glu Val Val Ser Leu Lys Arg
    50                  55                  60

Leu Pro Leu Ala Lys Phe Leu Leu Leu Thr Lys Lys Gln Tyr Arg Leu
65                  70                  75                  80

Ile Val

<210> SEQ ID NO 9
<211> LENGTH: 38
<212> TYPE: PRT
<213> ORGANISM: Artificial Sequence
<220> FEATURE:
<223> OTHER INFORMATION: pNOP212577

<400> SEQUENCE: 9

Gln Met Arg Glu Met His Leu Glu Glu Ala Leu Leu Pro Ile His Ile

-continued

```
                1               5                  10                 15
Gln Thr Leu Thr Ile Ser Leu Ser Arg Lys Ile Gln Ile Gly His Val
            20                  25                 30

Leu Cys Leu Met Pro Asn
            35

<210> SEQ ID NO 10
<211> LENGTH: 18
<212> TYPE: PRT
<213> ORGANISM: Artificial Sequence
<220> FEATURE:
<223> OTHER INFORMATION: pNOP475043

<400> SEQUENCE: 10

Ile Val Leu Val Leu Lys Lys Ile Glu Val Trp Arg Glu Asn Ala Glu
1               5                  10                 15

Leu Val

<210> SEQ ID NO 11
<211> LENGTH: 13
<212> TYPE: PRT
<213> ORGANISM: Artificial Sequence
<220> FEATURE:
<223> OTHER INFORMATION: pNOP620105

<400> SEQUENCE: 11

Tyr Pro Ala Asn Ser Arg Asn Lys Arg Lys Asp Trp Asn
1               5                  10

<210> SEQ ID NO 12
<211> LENGTH: 117
<212> TYPE: PRT
<213> ORGANISM: Artificial Sequence
<220> FEATURE:
<223> OTHER INFORMATION: pNOP22093

<400> SEQUENCE: 12

Leu Cys Leu Ala Pro Lys Thr Ala Val Tyr Pro Cys Asp Ser Leu Asp
1               5                  10                 15

Val Phe Leu Ser Ser Ser Phe Tyr Met Ala Met Thr Lys Thr Leu
            20                  25                 30

Tyr Cys Trp Glu Ile Pro Gly Ala Val Lys Arg Leu Gly Pro Gly Pro
            35                  40                 45

Val Gln His Ser Thr Thr Ser Phe Thr His Ser Leu Met Thr Arg Glu
        50                  55                 60

Ala Gly Val Lys Ser Glu Ser Phe Ile Phe Trp Asn Arg Tyr Ala Leu
65                  70                  75                 80

Thr Val Lys Pro Val Gly Ser Gly Arg Lys Leu Met Asn Gln Ala Trp
            85                  90                 95

Thr Arg Thr Lys Ile Gln Cys Gln Leu Leu Asn Ile Arg Ser Val
            100                 105                110

Leu Leu Cys Val Phe
        115

<210> SEQ ID NO 13
<211> LENGTH: 20
<212> TYPE: PRT
<213> ORGANISM: Artificial Sequence
<220> FEATURE:
<223> OTHER INFORMATION: pNOP441505

<400> SEQUENCE: 13
```

```
Arg Leu Thr Ala Gly Tyr Cys Glu Cys Phe Glu Glu Phe Val Leu Ala
1               5                   10                  15

Ser Arg Cys Lys
            20
```

<210> SEQ ID NO 14
<211> LENGTH: 12
<212> TYPE: PRT
<213> ORGANISM: Artificial Sequence
<220> FEATURE:
<223> OTHER INFORMATION: pNOP632151

<400> SEQUENCE: 14

```
Lys Lys Arg Leu Glu Leu Gly Gln Leu Lys Ile Leu
1               5                   10
```

<210> SEQ ID NO 15
<211> LENGTH: 64
<212> TYPE: PRT
<213> ORGANISM: Artificial Sequence
<220> FEATURE:
<223> OTHER INFORMATION: pNOP89454

<400> SEQUENCE: 15

```
Asn Lys Val Ser Lys Asp Asn Gln Gly Ile Lys Val Gln Leu Ile Leu
1               5                   10                  15

Phe Ile Leu Arg Ala Leu Met Ile Asn Thr Ser Ser Asn His Ile
                20                  25                  30

Leu Asp Ser Arg Asn Val Phe Leu His Thr Gly His Gly Glu Pro Met
            35                  40                  45

Val Gln Lys Gln Ile Glu Trp Val Leu Ile Met Glu Leu Ile Lys Met
    50                  55                  60
```

<210> SEQ ID NO 16
<211> LENGTH: 60
<212> TYPE: PRT
<213> ORGANISM: Artificial Sequence
<220> FEATURE:
<223> OTHER INFORMATION: pNOP100473

<400> SEQUENCE: 16

```
Lys Phe Gly Glu Arg Thr Arg Asn Trp Ser Arg Gln Leu Pro Ser Ser
1               5                   10                  15

Asn Arg Lys Ser Arg Asn Phe Phe Lys Ala Arg Phe Ala Asp Leu His
                20                  25                  30

His Cys Ser Pro Asp Cys Gln Ser His Gly Arg Ser Val Ser His Ser
            35                  40                  45

Tyr Leu Ser Gly Arg Gln Lys Phe Trp Val Tyr His
    50                  55                  60
```

<210> SEQ ID NO 17
<211> LENGTH: 58
<212> TYPE: PRT
<213> ORGANISM: Artificial Sequence
<220> FEATURE:
<223> OTHER INFORMATION: pNOP108458

<400> SEQUENCE: 17

```
Ser Lys Ala Asn Gln Ser Cys Asp Gly Arg Thr Thr Arg Tyr Leu Pro
1               5                   10                  15

Gly Tyr Gly Lys Thr Ser Thr Ala Lys Asn Ser Gln Asn Ser Ala Asn
                20                  25                  30
```

Arg Lys Gly His Thr Ser Tyr Thr Thr Ala Phe Thr Val Pro Ser Asn
          35                  40                  45

Arg Ser Arg Glu Val Ile Ser Glu Gln Ala
    50                  55

<210> SEQ ID NO 18
<211> LENGTH: 54
<212> TYPE: PRT
<213> ORGANISM: Artificial Sequence
<220> FEATURE:
<223> OTHER INFORMATION: pNOP120488

<400> SEQUENCE: 18

Ala Thr Thr Ile Gln Gln Gln Lys Ile Gln Glu Leu Leu Gln Ser Glu
1               5                   10                  15

Val Cys Arg Ser Pro Pro Leu Gln Pro Arg Leu Pro Lys Ser Trp Lys
            20                  25                  30

Lys Cys Gln Pro Phe Ile Pro Leu Arg Lys Thr Glu Val Leu Gly Leu
        35                  40                  45

Pro Leu Asn Tyr Ile Val
    50

<210> SEQ ID NO 19
<211> LENGTH: 29
<212> TYPE: PRT
<213> ORGANISM: Artificial Sequence
<220> FEATURE:
<223> OTHER INFORMATION: pNOP296350

<400> SEQUENCE: 19

His Thr Leu Cys Thr Ser Lys Ala Asp Lys Ser Ser Gly Asn Gln Gly
1               5                   10                  15

Gly Asn Gly Val Phe Ile Val Val Asn Ala Trp Tyr Ser
            20                  25

<210> SEQ ID NO 20
<211> LENGTH: 18
<212> TYPE: PRT
<213> ORGANISM: Artificial Sequence
<220> FEATURE:
<223> OTHER INFORMATION: pNOP471295

<400> SEQUENCE: 20

Glu Thr Lys Ser Pro Arg Ser Arg Ile Arg Cys Ser Ala Leu Ile Arg
1               5                   10                  15

Asn Phe

<210> SEQ ID NO 21
<211> LENGTH: 16
<212> TYPE: PRT
<213> ORGANISM: Artificial Sequence
<220> FEATURE:
<223> OTHER INFORMATION: pNOP515199

<400> SEQUENCE: 21

Asp Val Ile Arg Arg His Arg Lys Gln Ile Leu Leu Ile Pro Cys Lys
1               5                   10                  15

<210> SEQ ID NO 22
<211> LENGTH: 47
<212> TYPE: PRT
<213> ORGANISM: Artificial Sequence
<220> FEATURE:

<223> OTHER INFORMATION: pNOP154897

<400> SEQUENCE: 22

Gln Val Ile Trp Glu Pro Arg Tyr Ala Leu Thr Val Lys Pro Val Gly
1               5                   10                  15

Ser Gly Arg Lys Leu Met Asn Gln Ala Trp Thr Arg Thr Lys Ile Gln
            20                  25                  30

Cys Gln Leu Leu Leu Asn Ile Arg Ser Val Leu Leu Cys Val Phe
        35                  40                  45

<210> SEQ ID NO 23
<211> LENGTH: 33
<212> TYPE: PRT
<213> ORGANISM: Artificial Sequence
<220> FEATURE:
<223> OTHER INFORMATION: pNOP252656

<400> SEQUENCE: 23

Gly Ile Ser Trp Gln Ile Gly Leu Arg Ser Thr Arg Met Pro Ile Leu
1               5                   10                  15

Cys Leu Leu Ala Gln Ala Cys His Leu Phe Met Leu Gly Asn Lys Lys
            20                  25                  30

Pro

<210> SEQ ID NO 24
<211> LENGTH: 27
<212> TYPE: PRT
<213> ORGANISM: Artificial Sequence
<220> FEATURE:
<223> OTHER INFORMATION: pNOP331017

<400> SEQUENCE: 24

Tyr Trp Gln His Asp Cys Pro Phe Thr Ile Phe Glu Tyr Tyr Ser Val
1               5                   10                  15

Thr Gln Leu Leu Phe Ile Lys Arg Lys Leu Arg
            20                  25

<210> SEQ ID NO 25
<211> LENGTH: 26
<212> TYPE: PRT
<213> ORGANISM: Artificial Sequence
<220> FEATURE:
<223> OTHER INFORMATION: pNOP333709

<400> SEQUENCE: 25

Phe Lys Ile Cys His Arg Tyr Ser Phe Ile Thr Glu Thr Val Ile Phe
1               5                   10                  15

Ile Leu Lys Glu Phe Ile Trp Thr Lys Gln
            20                  25

<210> SEQ ID NO 26
<211> LENGTH: 21
<212> TYPE: PRT
<213> ORGANISM: Artificial Sequence
<220> FEATURE:
<223> OTHER INFORMATION: pNOP396063

<400> SEQUENCE: 26

Gly Pro Gln Ala Asn Pro Lys Arg Glu Gln Leu Ser Thr Asn Phe Ile
1               5                   10                  15

Thr Thr Leu Lys Ile
            20

<210> SEQ ID NO 27
<211> LENGTH: 19
<212> TYPE: PRT
<213> ORGANISM: Artificial Sequence
<220> FEATURE:
<223> OTHER INFORMATION: pNOP458837

<400> SEQUENCE: 27

Pro Glu Gly Asn Trp Asn Met Lys Gln Gly Lys Ser Glu Leu Arg Trp
1               5                   10                  15

Lys Asn Asn

<210> SEQ ID NO 28
<211> LENGTH: 16
<212> TYPE: PRT
<213> ORGANISM: Artificial Sequence
<220> FEATURE:
<223> OTHER INFORMATION: pNOP525451

<400> SEQUENCE: 28

Asn Thr Arg Arg Met Tyr Tyr Phe Cys His Ala Asn Lys Val Ile Thr
1               5                   10                  15

<210> SEQ ID NO 29
<211> LENGTH: 73
<212> TYPE: PRT
<213> ORGANISM: Artificial Sequence
<220> FEATURE:
<223> OTHER INFORMATION: pNOP68811

<400> SEQUENCE: 29

Pro Glu Phe Ser Lys Ser Lys Arg Thr Tyr Phe Val Tyr Asp Ser Phe
1               5                   10                  15

Tyr Ser Pro Lys Gln Gln Lys Gln Arg Gly His Leu Arg Thr Ser Met
                20                  25                  30

Lys Pro Ala His Met Met Leu Ser Gly Arg Met Lys Val Lys Glu Trp
            35                  40                  45

Glu Lys Ser Thr Trp Gln Leu Leu Val Met Val Arg Val Gln Leu His
        50                  55                  60

Glu Trp Thr Met Lys Gln Pro Val Phe
65                  70

<210> SEQ ID NO 30
<211> LENGTH: 59
<212> TYPE: PRT
<213> ORGANISM: Artificial Sequence
<220> FEATURE:
<223> OTHER INFORMATION: pNOP105449

<400> SEQUENCE: 30

Val Pro Ala Arg Ile Trp Lys Asn Glu His Arg Gly His Leu Arg Thr
1               5                   10                  15

Ser Met Lys Pro Ala His Met Met Leu Ser Gly Arg Met Lys Val Lys
                20                  25                  30

Glu Trp Glu Lys Ser Thr Trp Gln Leu Leu Val Met Val Arg Val Gln
            35                  40                  45

Leu His Glu Trp Thr Met Lys Gln Pro Val Phe
        50                  55

<210> SEQ ID NO 31
<211> LENGTH: 56
<212> TYPE: PRT

<213> ORGANISM: Artificial Sequence
<220> FEATURE:
<223> OTHER INFORMATION: pNOP113394

<400> SEQUENCE: 31

Phe Pro Trp Ser Lys Thr Ala Val Lys Asn Val Pro Pro Phe Leu Trp
1               5                   10                  15

Lys Pro Gly Arg Ile Cys Ile Lys Pro Phe Trp Arg Val Gln Ser Cys
            20                  25                  30

Ser Tyr Gly Phe Ile Ser Lys Lys Arg Val Cys Lys Trp Lys Gln Arg
        35                  40                  45

Lys Tyr Trp Ile Phe Arg Arg Thr
    50                  55

<210> SEQ ID NO 32
<211> LENGTH: 34
<212> TYPE: PRT
<213> ORGANISM: Artificial Sequence
<220> FEATURE:
<223> OTHER INFORMATION: pNOP244561

<400> SEQUENCE: 32

Lys Asn Leu Arg Lys Arg Gly His Cys Phe Leu Leu Ile Leu Thr Lys
1               5                   10                  15

Lys Lys Arg Lys Lys Thr Gly Ile Thr Leu Asn Phe Arg Ile Ser Leu
            20                  25                  30

Lys Glu

<210> SEQ ID NO 33
<211> LENGTH: 32
<212> TYPE: PRT
<213> ORGANISM: Artificial Sequence
<220> FEATURE:
<223> OTHER INFORMATION: pNOP269190

<400> SEQUENCE: 33

Thr Pro Gln Val Pro Thr Thr Phe Trp Thr Ala Gly Met Cys Phe Ser
1               5                   10                  15

Ile Gln Val Thr Gly Ser Gln Trp Phe Arg Asn Lys Ser Ser Gly Phe
            20                  25                  30

<210> SEQ ID NO 34
<211> LENGTH: 27
<212> TYPE: PRT
<213> ORGANISM: Artificial Sequence
<220> FEATURE:
<223> OTHER INFORMATION: pNOP330901

<400> SEQUENCE: 34

Tyr Met Cys Cys Arg Trp Cys Thr Cys Ile Phe Gly Trp His Ser Tyr
1               5                   10                  15

Leu Pro Glu Pro Asp Lys His Phe Ser His Tyr
            20                  25

<210> SEQ ID NO 35
<211> LENGTH: 24
<212> TYPE: PRT
<213> ORGANISM: Artificial Sequence
<220> FEATURE:
<223> OTHER INFORMATION: pNOP368169

<400> SEQUENCE: 35

Asn Pro Arg Leu Asn Pro Ile Leu Lys Met Met Lys Val Ser Phe Ala

```
1               5                   10                  15
Val Met Val Asn Thr Gln Pro Thr
            20

<210> SEQ ID NO 36
<211> LENGTH: 19
<212> TYPE: PRT
<213> ORGANISM: Artificial Sequence
<220> FEATURE:
<223> OTHER INFORMATION: pNOP459502

<400> SEQUENCE: 36

Pro Arg Asn Asn Thr Asp Leu Leu Cys Arg Arg Tyr Ser Asn Met Phe
1               5                   10                  15

Phe Lys Met

<210> SEQ ID NO 37
<211> LENGTH: 16
<212> TYPE: PRT
<213> ORGANISM: Artificial Sequence
<220> FEATURE:
<223> OTHER INFORMATION: pNOP514964

<400> SEQUENCE: 37

Asp Met Phe Tyr Ala Leu Cys Gln Ile Arg Ile Gln Glu Ile Phe Lys
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: pNOP525461

<400> SEQUENCE: 38

Asn Thr Ser Thr Thr Ser Ser Asn Ser Ser Asn Gln Ala Arg Ser Thr
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: pNOP536966

<400> SEQUENCE: 39

Ala Lys Thr Ile Lys Glu Ser Lys Tyr Asn Leu Ser Cys Leu Tyr
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: pNOP545659

<400> SEQUENCE: 40

Lys Phe Phe Leu Thr Asn Arg Tyr Asp Gln Lys Ala Ile Gly Ile
1               5                   10                  15

<210> SEQ ID NO 41
<211> LENGTH: 13
<212> TYPE: PRT
<213> ORGANISM: Artificial Sequence
<220> FEATURE:
<223> OTHER INFORMATION: pNOP612365
```

-continued

<400> SEQUENCE: 41

Arg Ser Cys Glu Arg Ser Ser Ser Val Thr Ala Pro
1               5                   10

<210> SEQ ID NO 42
<211> LENGTH: 73
<212> TYPE: PRT
<213> ORGANISM: Artificial Sequence
<220> FEATURE:
<223> OTHER INFORMATION: pNOP69534

<400> SEQUENCE: 42

Val Leu Ser Val Thr Leu Thr Lys Lys Thr Thr Ile Lys Lys Met Asn
1               5                   10                  15

Leu Ser Lys Arg Leu Ser Pro Leu Thr His Arg Glu Asn Gln Val Asn
            20                  25                  30

Leu Lys His Gln Ala Met Leu Leu Asn His Phe Met Leu Lys Ile Pro
        35                  40                  45

Gln Phe Val Ser Gln Glu Thr Val Leu Ser Val Leu Leu Val Leu Thr
    50                  55                  60

Leu Lys Met Thr Cys Cys Arg Asn Val
65                  70

<210> SEQ ID NO 43
<211> LENGTH: 50
<212> TYPE: PRT
<213> ORGANISM: Artificial Sequence
<220> FEATURE:
<223> OTHER INFORMATION: pNOP138480

<400> SEQUENCE: 43

Ile Glu Val Ser Leu Asn Pro Tyr Phe Arg Asn Asn Pro Leu Phe Pro
1               5                   10                  15

Ser His Pro Lys Thr Tyr Gln Thr Glu Gly Gln Gln Leu Met Lys Ser
            20                  25                  30

Tyr Arg Ile Leu Leu Leu Lys Ile Leu Arg Phe Ala Phe Leu Ile Ile
        35                  40                  45

Pro Leu
    50

<210> SEQ ID NO 44
<211> LENGTH: 47
<212> TYPE: PRT
<213> ORGANISM: Artificial Sequence
<220> FEATURE:
<223> OTHER INFORMATION: pNOP152447

<400> SEQUENCE: 44

Phe Ile Phe Gln Glu Phe Glu Ile Ala Pro Gln Val Gln Val Leu Phe
1               5                   10                  15

Leu Lys Lys Ala His Pro Leu Arg Leu Gln Pro Lys Ala Leu Val
            20                  25                  30

Lys Val Lys Gln Pro Pro Leu Leu Leu Glu Glu Pro Ser His Leu
        35                  40                  45

<210> SEQ ID NO 45
<211> LENGTH: 40
<212> TYPE: PRT
<213> ORGANISM: Artificial Sequence
<220> FEATURE:
<223> OTHER INFORMATION: pNOP198985

```
<400> SEQUENCE: 45

Ser Val Met His Val Glu Leu Cys Gly Ile Ser Gln Gln Glu Ile Leu
1               5                   10                  15

Lys Thr Arg Lys His Tyr Gly Thr Trp Gly Gln Leu Ala Cys Ser Arg
            20                  25                  30

Thr Ser Phe Ile Gln Ser Thr Lys
        35                  40

<210> SEQ ID NO 46
<211> LENGTH: 39
<212> TYPE: PRT
<213> ORGANISM: Artificial Sequence
<220> FEATURE:
<223> OTHER INFORMATION: pNOP207088

<400> SEQUENCE: 46

Val Pro Arg His Leu Ile Val Val Ser Arg Asp Thr Ser Lys Val Ser
1               5                   10                  15

Met Val Ile Met Phe Leu Thr Pro Ile Asp Met Met Ile Ile Gly Gln
            20                  25                  30

Thr Ile Leu Ile Leu Ala Thr
        35

<210> SEQ ID NO 47
<211> LENGTH: 38
<212> TYPE: PRT
<213> ORGANISM: Artificial Sequence
<220> FEATURE:
<223> OTHER INFORMATION: pNOP208063

<400> SEQUENCE: 47

Ala Ser Leu Cys Val Lys Lys Met Thr Met Lys Met Ile Ser Leu Pro
1               5                   10                  15

Ile Ile Val Asn Val Thr Leu Lys Asn Ser Met Lys Lys Arg
            20                  25                  30

Asp Gln Gln Ile Ile Ala
        35

<210> SEQ ID NO 48
<211> LENGTH: 38
<212> TYPE: PRT
<213> ORGANISM: Artificial Sequence
<220> FEATURE:
<223> OTHER INFORMATION: pNOP211063

<400> SEQUENCE: 48

Leu Leu Glu Lys Glu Leu Glu Glu Gly His Ser Gln Val Asn Leu Lys
1               5                   10                  15

Asn Glu Ile Pro Phe Leu Gln Lys Ala Glu Val Gln Met Arg Leu Lys
            20                  25                  30

Glu Glu Lys Pro His Leu
        35

<210> SEQ ID NO 49
<211> LENGTH: 38
<212> TYPE: PRT
<213> ORGANISM: Artificial Sequence
<220> FEATURE:
<223> OTHER INFORMATION: pNOP211568

<400> SEQUENCE: 49
```

-continued

Asn Cys Gly Gln Lys Cys Pro Ser Val Leu Met Glu Ala Gly Lys Asp
1               5                   10                  15

Leu Tyr Gln Ala Val Leu Glu Ser Ala Val Leu Phe Leu Trp Val His
            20                  25                  30

Phe Gln Glu Glu Gly Leu
        35

<210> SEQ ID NO 50
<211> LENGTH: 22
<212> TYPE: PRT
<213> ORGANISM: Artificial Sequence
<220> FEATURE:
<223> OTHER INFORMATION: pNOP398231

<400> SEQUENCE: 50

Lys Ile Leu Gln Tyr Val Phe Gln Asp Val Val His Tyr His Leu Cys
1               5                   10                  15

His Gln Leu Lys Met Lys
            20

<210> SEQ ID NO 51
<211> LENGTH: 19
<212> TYPE: PRT
<213> ORGANISM: Artificial Sequence
<220> FEATURE:
<223> OTHER INFORMATION: pNOP454649

<400> SEQUENCE: 51

Lys Asp Val Ala Arg Ser Trp Lys Cys Glu Ser Ile Asp Gly Met Cys
1               5                   10                  15

Phe Arg Ser

<210> SEQ ID NO 52
<211> LENGTH: 19
<212> TYPE: PRT
<213> ORGANISM: Artificial Sequence
<220> FEATURE:
<223> OTHER INFORMATION: pNOP466104

<400> SEQUENCE: 52

Val Pro Tyr Gly Ile Cys Gln His Ile Ala Leu Arg Ile Lys Leu Ile
1               5                   10                  15

Tyr Val Leu

<210> SEQ ID NO 53
<211> LENGTH: 18
<212> TYPE: PRT
<213> ORGANISM: Artificial Sequence
<220> FEATURE:
<223> OTHER INFORMATION: pNOP486470

<400> SEQUENCE: 53

Thr Leu Glu Gly Lys Val Leu His Arg Met Lys Asp Gly Gln Asp Pro
1               5                   10                  15

Asn Thr

<210> SEQ ID NO 54
<211> LENGTH: 16
<212> TYPE: PRT
<213> ORGANISM: Artificial Sequence
<220> FEATURE:
<223> OTHER INFORMATION: pNOP524901

<400> SEQUENCE: 54

```
Asn Ile Met Lys Arg Asn Val Met Trp Ile Ser Leu Leu Ile Ile Val
1               5                   10                  15
```

<210> SEQ ID NO 55
<211> LENGTH: 16
<212> TYPE: PRT
<213> ORGANISM: Artificial Sequence
<220> FEATURE:
<223> OTHER INFORMATION: pNOP526125

<400> SEQUENCE: 55

```
Pro Ile Lys Tyr Ile Val Gln Ile Ile Trp Met Ile Met Met Glu Asn
1               5                   10                  15
```

<210> SEQ ID NO 56
<211> LENGTH: 15
<212> TYPE: PRT
<213> ORGANISM: Artificial Sequence
<220> FEATURE:
<223> OTHER INFORMATION: pNOP547138

<400> SEQUENCE: 56

```
Lys Trp Ser Ala Ser Lys Gly Cys His Leu Gln Ser Phe Phe Tyr
1               5                   10                  15
```

<210> SEQ ID NO 57
<211> LENGTH: 15
<212> TYPE: PRT
<213> ORGANISM: Artificial Sequence
<220> FEATURE:
<223> OTHER INFORMATION: pNOP559516

<400> SEQUENCE: 57

```
Thr Ser Asp Leu Ser Cys Cys Val Cys Ser Asn Glu Thr Phe Ile
1               5                   10                  15
```

<210> SEQ ID NO 58
<211> LENGTH: 12
<212> TYPE: PRT
<213> ORGANISM: Artificial Sequence
<220> FEATURE:
<223> OTHER INFORMATION: pNOP640763

<400> SEQUENCE: 58

```
Gln Arg Leu Cys Ile Val Gly Lys Phe Pro Gly Gln
1               5                   10
```

<210> SEQ ID NO 59
<211> LENGTH: 12
<212> TYPE: PRT
<213> ORGANISM: Artificial Sequence
<220> FEATURE:
<223> OTHER INFORMATION: pNOP641160

<400> SEQUENCE: 59

```
Gln Tyr Arg Gln Phe Lys Ser Gln Gly Ile Ser Ser
1               5                   10
```

<210> SEQ ID NO 60
<211> LENGTH: 10
<212> TYPE: PRT
<213> ORGANISM: Artificial Sequence
<220> FEATURE:
<223> OTHER INFORMATION: pNOP717530

<400> SEQUENCE: 60

Thr Leu Cys Ser Gly Asp Pro Thr His Val
1               5                   10

<210> SEQ ID NO 61
<211> LENGTH: 58
<212> TYPE: PRT
<213> ORGANISM: Artificial Sequence
<220> FEATURE:
<223> OTHER INFORMATION: pNOP109202

<400> SEQUENCE: 61

Tyr Val Arg Leu Pro Gly Leu Gly Ser Gly Arg Pro Phe Ala Arg Phe
1               5                   10                  15

Cys Thr Thr Leu Ser Ser Arg Val Leu Glu His Arg Arg Gln Gln Glu
                20                  25                  30

Leu Arg Pro Ala Gly Asp Glu Glu Pro Gly Arg Arg Ser Tyr Phe Trp
            35                  40                  45

Pro Leu Gly Glu Arg Leu Ala Gly Ser Thr
        50                  55

<210> SEQ ID NO 62
<211> LENGTH: 45
<212> TYPE: PRT
<213> ORGANISM: Artificial Sequence
<220> FEATURE:
<223> OTHER INFORMATION: pNOP164140

<400> SEQUENCE: 62

Lys Ile Ile Pro Arg Ser Ser Met Ile Ser Ser Gln Ile Met Lys Ile
1               5                   10                  15

Glu Ser Glu Glu Val Leu Leu Leu Ile His Leu Ile Ile Thr Arg Leu
                20                  25                  30

Leu Lys Glu Leu Leu Thr Val Phe His Glu Met Ile Leu
            35                  40                  45

<210> SEQ ID NO 63
<211> LENGTH: 45
<212> TYPE: PRT
<213> ORGANISM: Artificial Sequence
<220> FEATURE:
<223> OTHER INFORMATION: pNOP166473

<400> SEQUENCE: 63

Ser Ile Met Met Glu Asp Gln Gln Ser Ala Met Ile Leu His Gly Leu
1               5                   10                  15

Ile Leu Lys Val Leu Leu Asp Phe Gln Ser Ile Gly Gln Glu Pro Gly
                20                  25                  30

Asn Val Ser Thr Ala Asn Ile His His Pro Phe Leu Glu
            35                  40                  45

<210> SEQ ID NO 64
<211> LENGTH: 44
<212> TYPE: PRT
<213> ORGANISM: Artificial Sequence
<220> FEATURE:
<223> OTHER INFORMATION: pNOP171017

<400> SEQUENCE: 64

Pro Leu Gln Tyr Tyr Thr Lys Thr Ile Cys Trp Asn Gly Phe Asp Lys
1               5                   10                  15

Leu Asp Phe Trp Arg Cys Ser Gln Gln Gly Tyr Ala Met Leu Tyr Glu
                20                  25                  30

```
Arg Leu His Glu Ser Thr Cys Gly Pro Thr Lys Ile
        35                  40
```

<210> SEQ ID NO 65
<211> LENGTH: 40
<212> TYPE: PRT
<213> ORGANISM: Artificial Sequence
<220> FEATURE:
<223> OTHER INFORMATION: pNOP198614

<400> SEQUENCE: 65

```
Ser Lys Lys Ala Ser Pro Asp Cys Phe Lys Ile Thr Ser Thr Cys Gly
1               5                   10                  15
Lys Glu Thr Lys Ser Ala Ala Cys Val Gln Thr Ser Thr Ile Thr Lys
            20                  25                  30
Gln Val Ala Thr Pro Lys Ala Cys
        35                  40
```

<210> SEQ ID NO 66
<211> LENGTH: 39
<212> TYPE: PRT
<213> ORGANISM: Artificial Sequence
<220> FEATURE:
<223> OTHER INFORMATION: pNOP203842

<400> SEQUENCE: 66

```
Leu Thr Val Phe Gln Lys Arg Gln Ile Gln Thr Leu Lys Ile Gln Lys
1               5                   10                  15
Ile Ile Arg Gln Asn Lys Met Trp Val Met Ala Val Phe Pro Cys Val
            20                  25                  30
Pro Trp Val Trp Lys Ile Ala
        35
```

<210> SEQ ID NO 67
<211> LENGTH: 38
<212> TYPE: PRT
<213> ORGANISM: Artificial Sequence
<220> FEATURE:
<223> OTHER INFORMATION: pNOP209147

<400> SEQUENCE: 67

```
Phe Cys Tyr Ala Gln Arg Glu Lys Ser Gln Ala Phe Pro Cys Glu Lys
1               5                   10                  15
Asp Asn Gly Pro Gly Pro Ala Ser Ile Cys Val Phe Phe Cys Thr Gln
            20                  25                  30
Gln Lys Ser Val Arg Trp
        35
```

<210> SEQ ID NO 68
<211> LENGTH: 37
<212> TYPE: PRT
<213> ORGANISM: Artificial Sequence
<220> FEATURE:
<223> OTHER INFORMATION: pNOP223140

<400> SEQUENCE: 68

```
Trp Lys Glu Leu Leu Gly Met Arg Glu Arg Gly Gly Gly Arg Lys Tyr
1               5                   10                  15
Leu Asn Asn Tyr Lys Glu Val Leu Lys Met Lys Leu Trp Leu Leu Leu
            20                  25                  30
Asp Arg Leu Ile Tyr
        35
```

```
<210> SEQ ID NO 69
<211> LENGTH: 36
<212> TYPE: PRT
<213> ORGANISM: Artificial Sequence
<220> FEATURE:
<223> OTHER INFORMATION: pNOP231193

<400> SEQUENCE: 69
```

Val Leu Leu Thr Asn Tyr Leu Asn Phe Gln Gly His His Pro Leu Val
1               5                   10                  15

Leu Leu Gln Leu Ser Pro Gln Val Leu Glu Lys Cys His Ile His Leu
            20                  25                  30

Gln Val Asp Arg
        35

```
<210> SEQ ID NO 70
<211> LENGTH: 34
<212> TYPE: PRT
<213> ORGANISM: Artificial Sequence
<220> FEATURE:
<223> OTHER INFORMATION: pNOP246740

<400> SEQUENCE: 70
```

Pro Tyr Leu Asn Trp Met Thr Ile Lys Gln Arg Lys Val Ile Phe Leu
1               5                   10                  15

Gln Asn Ala Leu Ile Leu Leu Cys Pro Lys Gly Lys Val Thr Ser Leu
            20                  25                  30

Ser Val

```
<210> SEQ ID NO 71
<211> LENGTH: 32
<212> TYPE: PRT
<213> ORGANISM: Artificial Sequence
<220> FEATURE:
<223> OTHER INFORMATION: pNOP262357

<400> SEQUENCE: 71
```

Phe Arg Asn Phe Arg Pro Asn Glu Thr Ala Pro Ser Ser Lys His Ala
1               5                   10                  15

Phe Asn Leu Ser Arg Gln Asp Asn Asp Ser Tyr Ser Arg Ser Ser Lys
            20                  25                  30

```
<210> SEQ ID NO 72
<211> LENGTH: 32
<212> TYPE: PRT
<213> ORGANISM: Artificial Sequence
<220> FEATURE:
<223> OTHER INFORMATION: pNOP262906

<400> SEQUENCE: 72
```

Gly Arg Gly Phe Gln Gly Asp Tyr Arg Pro Leu Gln Asn Tyr Cys Lys
1               5                   10                  15

Trp Thr Val Lys Cys Met Gly Leu Leu Met Thr Thr Thr Val Leu His
            20                  25                  30

```
<210> SEQ ID NO 73
<211> LENGTH: 31
<212> TYPE: PRT
<213> ORGANISM: Artificial Sequence
<220> FEATURE:
<223> OTHER INFORMATION: pNOP270883

<400> SEQUENCE: 73
```

```
Ala Gln Gln Thr Phe Ile Ile Pro Ser Ser Lys His Leu Glu Lys
1               5                   10                  15

Asn Trp Lys Phe Ile Phe Asn Ser Phe Cys Phe Ile Arg Ile Gln
            20                  25                  30
```

<210> SEQ ID NO 74
<211> LENGTH: 31
<212> TYPE: PRT
<213> ORGANISM: Artificial Sequence
<220> FEATURE:
<223> OTHER INFORMATION: pNOP272083

<400> SEQUENCE: 74

```
Glu Glu Asn Trp Arg Asn Leu Leu His Leu Asn Leu Phe Leu His His
1               5                   10                  15

Leu Asp Gln Leu Leu Pro Leu Gly Pro Arg His Lys Leu Gln Phe
            20                  25                  30
```

<210> SEQ ID NO 75
<211> LENGTH: 31
<212> TYPE: PRT
<213> ORGANISM: Artificial Sequence
<220> FEATURE:
<223> OTHER INFORMATION: pNOP274267

<400> SEQUENCE: 75

```
Ile Arg Lys Thr Cys Ile Ser Thr Pro Val Asn Phe His Gln Arg Ser
1               5                   10                  15

Ser Lys Pro Asn Leu Lys Lys Lys Ile Gly Gly Ile Cys Phe Ile
            20                  25                  30
```

<210> SEQ ID NO 76
<211> LENGTH: 30
<212> TYPE: PRT
<213> ORGANISM: Artificial Sequence
<220> FEATURE:
<223> OTHER INFORMATION: pNOP281689

<400> SEQUENCE: 76

```
Ala Leu Gly Glu Glu Leu Glu Val His Leu Gln Phe Phe Leu Leu His
1               5                   10                  15

Gln Asn Pro Val Lys Lys Gln Lys Val Arg Met Lys Asn Met
            20                  25                  30
```

<210> SEQ ID NO 77
<211> LENGTH: 30
<212> TYPE: PRT
<213> ORGANISM: Artificial Sequence
<220> FEATURE:
<223> OTHER INFORMATION: pNOP283121

<400> SEQUENCE: 77

```
Glu Gly Tyr Pro Gly His Phe Ile Thr Gly Ala Arg Ala Gly Ala Phe
1               5                   10                  15

Arg Gly Thr Thr Gly His Cys Arg Ile Ile Ala Ser Gly Leu
            20                  25                  30
```

<210> SEQ ID NO 78
<211> LENGTH: 30
<212> TYPE: PRT
<213> ORGANISM: Artificial Sequence
<220> FEATURE:
<223> OTHER INFORMATION: pNOP285366

<400> SEQUENCE: 78

```
Ile Thr Thr Gln Arg Ser Glu Ile Pro Lys Leu Thr Ala Gln Asn Pro
1               5                   10                  15

Val Glu Pro Lys Val Leu Ser Ala Ile Leu Gly Leu Thr Leu
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: pNOP285606

<400> SEQUENCE: 79

Lys Ile Tyr Arg Asp Gln Ile Gln Asn Met Val Tyr Pro Leu Ile Gln
1               5                   10                  15

Lys Ile Leu Ile Gly Lys Leu Phe Arg Lys Val Gln Ile Pro
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: pNOP288797

<400> SEQUENCE: 80

Gln Val Ile Trp Glu Pro Arg Trp Lys Trp Cys Ile His Cys Cys Gln
1               5                   10                  15

Cys Leu Val Leu Met Ile Arg Met Ile Cys Arg Glu Leu Cys
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: pNOP290267

<400> SEQUENCE: 81

Ser Lys Ala Asn Gln Ser Cys Asp Gly Arg Thr Thr Arg Tyr Leu Pro
1               5                   10                  15

Gly Tyr Gly Lys Thr Ser Thr Glu Val Ile Ser Glu Gln Ala
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: pNOP291694

<400> SEQUENCE: 82

Val Leu Pro Phe Leu Ile Cys Leu Tyr Pro His Ile Arg Leu Phe Arg
1               5                   10                  15

Leu Val Asp Gly Glu Asn Ser His Leu Ile Ser Val Pro Leu
            20                  25                  30

<210> SEQ ID NO 83
<211> LENGTH: 29
<212> TYPE: PRT
<213> ORGANISM: Artificial Sequence
<220> FEATURE:
<223> OTHER INFORMATION: pNOP299057
```

<400> SEQUENCE: 83

Asn Gln Glu Ser Leu Trp Asp His His Phe Ile Leu His Leu Ile Lys
1               5                   10                  15

Lys Lys Asn Pro Leu Gln Val Ile Lys Ala His Glu Phe
            20                  25

<210> SEQ ID NO 84
<211> LENGTH: 28
<212> TYPE: PRT
<213> ORGANISM: Artificial Sequence
<220> FEATURE:
<223> OTHER INFORMATION: pNOP305102

<400> SEQUENCE: 84

Ala Pro Gln Cys Gln Lys Arg Lys Ser Leu Gln Asp Ser Arg Val Ile
1               5                   10                  15

Met Lys Asn Ile Val Pro Glu Ile Trp Val Ala Tyr
            20                  25

<210> SEQ ID NO 85
<211> LENGTH: 27
<212> TYPE: PRT
<213> ORGANISM: Artificial Sequence
<220> FEATURE:
<223> OTHER INFORMATION: pNOP317504

<400> SEQUENCE: 85

Ala Asn Arg Thr Leu Pro Asn Lys Gln Val Tyr Pro Arg Met Pro Val
1               5                   10                  15

Val Phe Gln Glu Val Ser Leu Pro Pro Lys Asp
            20                  25

<210> SEQ ID NO 86
<211> LENGTH: 27
<212> TYPE: PRT
<213> ORGANISM: Artificial Sequence
<220> FEATURE:
<223> OTHER INFORMATION: pNOP320163

<400> SEQUENCE: 86

Gly Asp Tyr Arg Pro Leu Gln Asn Tyr Cys Lys Trp Thr Val Lys Cys
1               5                   10                  15

Met Gly Leu Leu Met Thr Thr Thr Val Leu His
            20                  25

<210> SEQ ID NO 87
<211> LENGTH: 27
<212> TYPE: PRT
<213> ORGANISM: Artificial Sequence
<220> FEATURE:
<223> OTHER INFORMATION: pNOP321066

<400> SEQUENCE: 87

His Ala Gln Glu Pro His Ser Phe Lys Ala Gln Asn Asp Cys Tyr Gly
1               5                   10                  15

Lys Cys Cys Ser Phe Lys Glu Ser His Gly Lys
            20                  25

<210> SEQ ID NO 88
<211> LENGTH: 27
<212> TYPE: PRT
<213> ORGANISM: Artificial Sequence
<220> FEATURE:
<223> OTHER INFORMATION: pNOP322417

```
<400> SEQUENCE: 88

Lys Lys Met Asn Phe Leu Pro Gln Ile Val Leu Leu Arg Pro Phe Pro
1               5                   10                  15

Gln Val Leu Gln Met Val Leu Asn Gln Arg Leu
            20                  25

<210> SEQ ID NO 89
<211> LENGTH: 27
<212> TYPE: PRT
<213> ORGANISM: Artificial Sequence
<220> FEATURE:
<223> OTHER INFORMATION: pNOP323347

<400> SEQUENCE: 89

Leu Leu Leu Ile Thr Thr Gln Ala Leu Gly Lys Ala Ala Gln Ile Ala
1               5                   10                  15

Leu Gln Leu Gly His Leu Arg Ser Gln Leu Gln
            20                  25

<210> SEQ ID NO 90
<211> LENGTH: 25
<212> TYPE: PRT
<213> ORGANISM: Artificial Sequence
<220> FEATURE:
<223> OTHER INFORMATION: pNOP358839

<400> SEQUENCE: 90

Val Val Tyr Ile Lys Leu Leu Leu His Val Tyr Leu Asp Lys Leu
1               5                   10                  15

Arg Leu Ile Gln Ile Pro Ser Phe Pro
            20                  25

<210> SEQ ID NO 91
<211> LENGTH: 24
<212> TYPE: PRT
<213> ORGANISM: Artificial Sequence
<220> FEATURE:
<223> OTHER INFORMATION: pNOP360210

<400> SEQUENCE: 91

Ala Pro Phe Trp Val Leu Pro Cys Asp Ile Cys Leu Lys Glu Arg Lys
1               5                   10                  15

Asn Glu Thr Lys Lys Ile Leu Cys
            20

<210> SEQ ID NO 92
<211> LENGTH: 24
<212> TYPE: PRT
<213> ORGANISM: Artificial Sequence
<220> FEATURE:
<223> OTHER INFORMATION: pNOP366823

<400> SEQUENCE: 92

Leu Pro Arg Gln Leu Tyr Ile His Ala Thr Val Trp Met Ser Ser Ser
1               5                   10                  15

Pro His Pro Ala Phe Thr Trp Gln
            20

<210> SEQ ID NO 93
<211> LENGTH: 24
<212> TYPE: PRT
<213> ORGANISM: Artificial Sequence
<220> FEATURE:
```

<223> OTHER INFORMATION: pNOP370727

<400> SEQUENCE: 93

Arg Lys Tyr Leu Asn Asn Tyr Lys Glu Val Leu Lys Met Lys Leu Trp
1               5                   10                  15
Leu Leu Leu Asp Arg Leu Ile Tyr
            20

<210> SEQ ID NO 94
<211> LENGTH: 24
<212> TYPE: PRT
<213> ORGANISM: Artificial Sequence
<220> FEATURE:
<223> OTHER INFORMATION: pNOP371340

<400> SEQUENCE: 94

Arg Ser Gln Ala Ile Cys Glu Ile Arg Ile Lys Pro Cys Cys Gln Ala
1               5                   10                  15
Asp Ile Pro Asn Arg Trp Val Lys
            20

<210> SEQ ID NO 95
<211> LENGTH: 24
<212> TYPE: PRT
<213> ORGANISM: Artificial Sequence
<220> FEATURE:
<223> OTHER INFORMATION: pNOP373907

<400> SEQUENCE: 95

Val Gly Gln Val Lys His Leu Leu Asp Gln Asp Leu Glu Ile Arg Pro
1               5                   10                  15
Leu Gln Asp Leu Pro Ser Asn His
            20

<210> SEQ ID NO 96
<211> LENGTH: 24
<212> TYPE: PRT
<213> ORGANISM: Artificial Sequence
<220> FEATURE:
<223> OTHER INFORMATION: pNOP374715

<400> SEQUENCE: 96

Trp Asn Val Pro His Ser Val Leu Ala Ala Gln Ala Asn Thr Val His
1               5                   10                  15
Leu Val Gly Leu Leu Leu Pro Glu
            20

<210> SEQ ID NO 97
<211> LENGTH: 23
<212> TYPE: PRT
<213> ORGANISM: Artificial Sequence
<220> FEATURE:
<223> OTHER INFORMATION: pNOP389496

<400> SEQUENCE: 97

Thr His Thr Ser Glu Thr Ile His Phe Ser Pro Val Ile Gln Arg His
1               5                   10                  15
Thr Arg Gln Arg Gly Ser Asn
            20

<210> SEQ ID NO 98
<211> LENGTH: 23
<212> TYPE: PRT
<213> ORGANISM: Artificial Sequence
<220> FEATURE:
<223> OTHER INFORMATION: pNOP391151

<400> SEQUENCE: 98

Trp Gln Cys Ser His Ala Tyr Arg Gly Phe Gly Lys Ser Pro Glu Leu
1               5                   10                  15

Leu Tyr Ser Gly Gly Cys Pro
            20

<210> SEQ ID NO 99
<211> LENGTH: 22
<212> TYPE: PRT
<213> ORGANISM: Artificial Sequence
<220> FEATURE:
<223> OTHER INFORMATION: pNOP394532

<400> SEQUENCE: 99

Glu Leu Arg Thr Val Pro Leu Thr Ile Leu Asp Leu Glu Asp Leu Pro
1               5                   10                  15

Gln Val Ile Leu Pro Arg
            20

<210> SEQ ID NO 100
<211> LENGTH: 22
<212> TYPE: PRT
<213> ORGANISM: Artificial Sequence
<220> FEATURE:
<223> OTHER INFORMATION: pNOP400812

<400> SEQUENCE: 100

Asn Phe Leu Glu Cys Leu Gln Leu Asn Gln Val Glu Val Asn Leu Ile
1               5                   10                  15

Asp Gln Lys Asp Leu Tyr
            20

<210> SEQ ID NO 101
<211> LENGTH: 22
<212> TYPE: PRT
<213> ORGANISM: Artificial Sequence
<220> FEATURE:
<223> OTHER INFORMATION: pNOP406915

<400> SEQUENCE: 101

Thr Leu Phe Gln Glu Pro Asn Lys Val Lys Thr Lys Tyr Pro Gln
1               5                   10                  15

Lys Glu His Gly Glu Lys
            20

<210> SEQ ID NO 102
<211> LENGTH: 21
<212> TYPE: PRT
<213> ORGANISM: Artificial Sequence
<220> FEATURE:
<223> OTHER INFORMATION: pNOP409301

<400> SEQUENCE: 102

Ala Cys Glu Val Gln Gly Cys Gln Tyr Tyr Val Ser Trp Leu Lys Leu
1               5                   10                  15

Ala Ile Ser Ser Cys
            20

<210> SEQ ID NO 103
<211> LENGTH: 21
<212> TYPE: PRT

```
<213> ORGANISM: Artificial Sequence
<220> FEATURE:
<223> OTHER INFORMATION: pNOP412763

<400> SEQUENCE: 103

Phe Arg Phe His Pro Phe Pro Glu Ile Arg Asn Leu Ser Gly Ile Thr
1               5                   10                  15

Ile Ser Ser Tyr Thr
            20

<210> SEQ ID NO 104
<211> LENGTH: 21
<212> TYPE: PRT
<213> ORGANISM: Artificial Sequence
<220> FEATURE:
<223> OTHER INFORMATION: pNOP420385

<400> SEQUENCE: 104

Pro Val Ala Gly Met Tyr Lys Leu Arg Asn Ala Lys Lys Glu Lys Ala
1               5                   10                  15

Phe Lys Thr Gln Gly
            20

<210> SEQ ID NO 105
<211> LENGTH: 20
<212> TYPE: PRT
<213> ORGANISM: Artificial Sequence
<220> FEATURE:
<223> OTHER INFORMATION: pNOP433641

<400> SEQUENCE: 105

His Thr Leu Cys Thr Ser Lys Ala Asp Lys Ser Ser Gly Asn Gln Asp
1               5                   10                  15

Thr Arg Leu Leu
            20

<210> SEQ ID NO 106
<211> LENGTH: 20
<212> TYPE: PRT
<213> ORGANISM: Artificial Sequence
<220> FEATURE:
<223> OTHER INFORMATION: pNOP434724

<400> SEQUENCE: 106

Lys Gly Ile Asn Pro Gln Lys Arg Ile Glu Cys Leu Met Glu Phe Val
1               5                   10                  15

Ser Thr Leu His
            20

<210> SEQ ID NO 107
<211> LENGTH: 19
<212> TYPE: PRT
<213> ORGANISM: Artificial Sequence
<220> FEATURE:
<223> OTHER INFORMATION: pNOP457669

<400> SEQUENCE: 107

Met Val His Leu His Phe Trp Leu Ala Leu Leu Leu Thr Gly Ala Arg
1               5                   10                  15

Gln Thr Leu

<210> SEQ ID NO 108
<211> LENGTH: 19
<212> TYPE: PRT
```

```
<213> ORGANISM: Artificial Sequence
<220> FEATURE:
<223> OTHER INFORMATION: pNOP467541

<400> SEQUENCE: 108

Tyr Val Ser Ile His Thr Phe Val Cys Ser Gly Trp Trp Met Ala Lys
1               5                   10                  15

Thr Pro Thr

<210> SEQ ID NO 109
<211> LENGTH: 18
<212> TYPE: PRT
<213> ORGANISM: Artificial Sequence
<220> FEATURE:
<223> OTHER INFORMATION: pNOP468037

<400> SEQUENCE: 109

Ala Ile Tyr Thr Glu Arg Cys Gly Ile Lys Asn Asn Ala Ser Ser Ser
1               5                   10                  15

Gly Lys

<210> SEQ ID NO 110
<211> LENGTH: 18
<212> TYPE: PRT
<213> ORGANISM: Artificial Sequence
<220> FEATURE:
<223> OTHER INFORMATION: pNOP471165

<400> SEQUENCE: 110

Glu Arg Gln Lys Lys Ile Arg Asn Gln Arg Leu Lys Leu Pro Ala Thr
1               5                   10                  15

Gln Asn

<210> SEQ ID NO 111
<211> LENGTH: 18
<212> TYPE: PRT
<213> ORGANISM: Artificial Sequence
<220> FEATURE:
<223> OTHER INFORMATION: pNOP482475

<400> SEQUENCE: 111

Arg Gly Ser Gly Gln Gly Gln Cys Ser Thr Pro Gln His His Ser Leu
1               5                   10                  15

Thr Ala

<210> SEQ ID NO 112
<211> LENGTH: 18
<212> TYPE: PRT
<213> ORGANISM: Artificial Sequence
<220> FEATURE:
<223> OTHER INFORMATION: pNOP486128

<400> SEQUENCE: 112

Thr Asp Glu Pro Thr Glu Pro Tyr Gln Thr Asn Arg Phe Ile Gln Glu
1               5                   10                  15

Cys Gln

<210> SEQ ID NO 113
<211> LENGTH: 18
<212> TYPE: PRT
<213> ORGANISM: Artificial Sequence
<220> FEATURE:
<223> OTHER INFORMATION: pNOP487292
```

```
<400> SEQUENCE: 113

Val Asp Leu Tyr Ser Leu Leu Ala Glu Thr Gln Phe Pro Leu Val Glu
1               5                   10                  15

Met Glu

<210> SEQ ID NO 114
<211> LENGTH: 18
<212> TYPE: PRT
<213> ORGANISM: Artificial Sequence
<220> FEATURE:
<223> OTHER INFORMATION: pNOP488775

<400> SEQUENCE: 114

Trp Thr Arg Ser Ser Lys His Leu Arg Leu Leu Leu His Pro Thr Lys
1               5                   10                  15

Ile Ser

<210> SEQ ID NO 115
<211> LENGTH: 17
<212> TYPE: PRT
<213> ORGANISM: Artificial Sequence
<220> FEATURE:
<223> OTHER INFORMATION: pNOP490250

<400> SEQUENCE: 115

Ala Ser Cys Ser Lys Cys Cys Ser Ser Glu Gly Pro Gly Ser Ser Arg
1               5                   10                  15

Cys

<210> SEQ ID NO 116
<211> LENGTH: 17
<212> TYPE: PRT
<213> ORGANISM: Artificial Sequence
<220> FEATURE:
<223> OTHER INFORMATION: pNOP501789

<400> SEQUENCE: 116

Asn Gln Asp Lys Ile Ile Leu Ser Leu Tyr Gln Arg Leu Met Lys Val
1               5                   10                  15

Leu

<210> SEQ ID NO 117
<211> LENGTH: 17
<212> TYPE: PRT
<213> ORGANISM: Artificial Sequence
<220> FEATURE:
<223> OTHER INFORMATION: pNOP502953

<400> SEQUENCE: 117

Pro Pro Thr Asn Asn Gln Leu Ile Arg His Lys Leu Leu Gln Ser Ser
1               5                   10                  15

Gln

<210> SEQ ID NO 118
<211> LENGTH: 17
<212> TYPE: PRT
<213> ORGANISM: Artificial Sequence
<220> FEATURE:
<223> OTHER INFORMATION: pNOP504281

<400> SEQUENCE: 118

Gln Arg Arg Lys Gly Lys Arg Leu Val Leu Arg Ser Thr Ser Glu Ser
1               5                   10                  15
```

His

<210> SEQ ID NO 119
<211> LENGTH: 16
<212> TYPE: PRT
<213> ORGANISM: Artificial Sequence
<220> FEATURE:
<223> OTHER INFORMATION: pNOP516184

<400> SEQUENCE: 119

Glu Ser Phe Leu Arg Gln Gln Arg Phe Lys Glu Thr Glu Phe Glu Lys
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: pNOP521009

<400> SEQUENCE: 120

Lys Ile Ile Pro Ile Ile Leu Gln Asn Trp Lys Leu Arg His Leu Ile
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: pNOP522194

<400> SEQUENCE: 121

Lys Trp Arg Trp Asp Ile Thr Glu Cys Val Gln Leu Asp Ser Tyr Lys
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: pNOP524270

<400> SEQUENCE: 122

Met Leu Arg Glu Phe Ser Gln Thr Thr Lys Ile Gln Arg Asn Arg Ile
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: pNOP525002

<400> SEQUENCE: 123

Asn Leu Lys Val Lys Glu Ser Lys Glu Glu Lys Lys Phe Ile Lys Val
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: pNOP525366

<400> SEQUENCE: 124

Asn Ser Pro Phe Lys Gln Thr Cys Leu Gln Ser Leu Glu Ala Gly Gln

```
<210> SEQ ID NO 125
<211> LENGTH: 16
<212> TYPE: PRT
<213> ORGANISM: Artificial Sequence
<220> FEATURE:
<223> OTHER INFORMATION: pNOP529050

<400> SEQUENCE: 125

Arg Lys Pro Ser Ile Arg Lys Arg Asn Met Glu Lys Asn Lys Arg Lys
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: pNOP540192

<400> SEQUENCE: 126

Glu Lys Glu Thr Asn Phe Thr Ser Lys Thr Tyr Thr Thr Lys Tyr
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: pNOP541018

<400> SEQUENCE: 127

Phe Glu Arg Tyr Thr Glu Thr Arg Phe Arg Thr Trp Ser Ile Pro
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: pNOP541108

<400> SEQUENCE: 128

Phe Ile Lys Trp His Leu Leu Phe Leu Lys Gln Arg Met Phe Gly
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: pNOP543049

<400> SEQUENCE: 129

Gly Thr Glu Asp Gly Glu Leu Lys Ser Ser Thr Arg Ala Arg Arg
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: ILMMMMLTFPGKRLN

<400> SEQUENCE: 130

Ile Leu Met Met Met Met Leu Thr Phe Pro Gly Lys Arg Leu Asn
1               5                   10                  15
```

-continued

```
<210> SEQ ID NO 131
<211> LENGTH: 15
<212> TYPE: PRT
<213> ORGANISM: Artificial Sequence
<220> FEATURE:
<223> OTHER INFORMATION: pNOP546033

<400> SEQUENCE: 131

Lys Lys Leu Cys Cys Pro Tyr Thr Phe Lys His Leu Gln Phe His
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: pNOP551509

<400> SEQUENCE: 132

Pro Leu Leu Lys Val Glu Val Gly Tyr Tyr Gly Met Cys Pro Ala
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: pNOP555084

<400> SEQUENCE: 133

Arg Pro Thr Asn Ser Lys Thr Arg Gly Glu Lys Tyr Ile Gly Asn
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: pNOP556098

<400> SEQUENCE: 134

Arg Tyr Pro Ser Leu Phe Leu Lys Lys Gln Phe Ser Gln Phe Ser
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: pNOP559222

<400> SEQUENCE: 135

Thr Pro Leu Phe Arg Trp Met Pro Leu Thr Lys Lys Glu Leu Arg
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: pNOP559389

<400> SEQUENCE: 136

Thr Arg Gly Thr Thr Gly His Cys Arg Ile Ile Ala Ser Gly Leu
1               5                   10                  15
```

<210> SEQ ID NO 137
<211> LENGTH: 14
<212> TYPE: PRT
<213> ORGANISM: Artificial Sequence
<220> FEATURE:
<223> OTHER INFORMATION: pNOP564648

<400> SEQUENCE: 137

Cys Gln Glu Ala Glu Ser Ala Pro Ser Lys Phe Cys Thr Glu
1               5                   10

<210> SEQ ID NO 138
<211> LENGTH: 14
<212> TYPE: PRT
<213> ORGANISM: Artificial Sequence
<220> FEATURE:
<223> OTHER INFORMATION: pNOP565904

<400> SEQUENCE: 138

Asp Thr Ser Tyr Cys Lys Ala Ala Asn Lys Ser Arg Ser Ala
1               5                   10

<210> SEQ ID NO 139
<211> LENGTH: 14
<212> TYPE: PRT
<213> ORGANISM: Artificial Sequence
<220> FEATURE:
<223> OTHER INFORMATION: pNOP571486

<400> SEQUENCE: 139

Ile Leu Gln Cys Tyr Pro Ala Pro Leu His Gln Glu Glu Ala
1               5                   10

<210> SEQ ID NO 140
<211> LENGTH: 14
<212> TYPE: PRT
<213> ORGANISM: Artificial Sequence
<220> FEATURE:
<223> OTHER INFORMATION: pNOP571991

<400> SEQUENCE: 140

Ile Val Ser Val Val Val Met Val Met Val Lys Glu Val Lys
1               5                   10

<210> SEQ ID NO 141
<211> LENGTH: 14
<212> TYPE: PRT
<213> ORGANISM: Artificial Sequence
<220> FEATURE:
<223> OTHER INFORMATION: pNOP574858

<400> SEQUENCE: 141

Leu Leu Glu Lys Phe Asp Leu Ile Gln Lys Phe Gln Ala Lys
1               5                   10

<210> SEQ ID NO 142
<211> LENGTH: 14
<212> TYPE: PRT
<213> ORGANISM: Artificial Sequence
<220> FEATURE:
<223> OTHER INFORMATION: pNOP577317

<400> SEQUENCE: 142

Asn Leu Lys Val Lys Thr Tyr Ser Arg Leu Leu Arg Val Phe
1               5                   10

```
<210> SEQ ID NO 143
<211> LENGTH: 14
<212> TYPE: PRT
<213> ORGANISM: Artificial Sequence
<220> FEATURE:
<223> OTHER INFORMATION: pNOP577487

<400> SEQUENCE: 143

Asn Pro Ser Pro Ser Ser Phe Gly Thr Asp Thr Arg Leu Leu
1               5                   10

<210> SEQ ID NO 144
<211> LENGTH: 14
<212> TYPE: PRT
<213> ORGANISM: Artificial Sequence
<220> FEATURE:
<223> OTHER INFORMATION: pNOP586031

<400> SEQUENCE: 144

Ser Tyr Gln Pro His Arg Thr Asn Leu Gln Pro Thr Ile Ser
1               5                   10

<210> SEQ ID NO 145
<211> LENGTH: 14
<212> TYPE: PRT
<213> ORGANISM: Artificial Sequence
<220> FEATURE:
<223> OTHER INFORMATION: pNOP587088

<400> SEQUENCE: 145

Thr Arg His Gly Pro Gly Gln Lys Ser Asn Ala Ser Ser Cys
1               5                   10

<210> SEQ ID NO 146
<211> LENGTH: 14
<212> TYPE: PRT
<213> ORGANISM: Artificial Sequence
<220> FEATURE:
<223> OTHER INFORMATION: pNOP589723

<400> SEQUENCE: 146

Tyr Ala Ser Gln Leu Ser Ser Lys Lys Leu Gln Ala Gln Pro
1               5                   10

<210> SEQ ID NO 147
<211> LENGTH: 78
<212> TYPE: PRT
<213> ORGANISM: Artificial Sequence
<220> FEATURE:
<223> OTHER INFORMATION: pNOP59141

<400> SEQUENCE: 147

Cys Thr Pro Pro Trp Ala Arg Val Arg Ser Pro Leu Cys Pro Leu Leu
1               5                   10                  15

Tyr His Pro Gln Phe Ser Gly Pro Gly Ala Pro Ala Ala Ala Gly Ala
            20                  25                  30

Ala Ser Gly Arg Arg Arg Arg Ala Ala Ala Leu Val Leu Leu Ala
        35                  40                  45

Thr Gly Arg Ala Ser Gly Arg Lys Tyr Leu Asn Asn Tyr Lys Glu Val
    50                  55                  60

Leu Lys Met Lys Leu Trp Leu Leu Leu Asp Arg Leu Ile Tyr
65                  70                  75

<210> SEQ ID NO 148
<211> LENGTH: 13
```

```
<212> TYPE: PRT
<213> ORGANISM: Artificial Sequence
<220> FEATURE:
<223> OTHER INFORMATION: pNOP592613

<400> SEQUENCE: 148

Cys Met Trp Asn Phe Val Glu Ser Leu Ser Lys Lys Ser
1               5                   10

<210> SEQ ID NO 149
<211> LENGTH: 13
<212> TYPE: PRT
<213> ORGANISM: Artificial Sequence
<220> FEATURE:
<223> OTHER INFORMATION: pNOP598578

<400> SEQUENCE: 149

His Phe Ser Ser Ala Ile Ser Asp Pro Asn Ser Ser Glu
1               5                   10

<210> SEQ ID NO 150
<211> LENGTH: 13
<212> TYPE: PRT
<213> ORGANISM: Artificial Sequence
<220> FEATURE:
<223> OTHER INFORMATION: pNOP599868

<400> SEQUENCE: 150

Ile Lys Asp Ser Asn Leu Ser Asn Gly Thr Cys Cys Phe
1               5                   10

<210> SEQ ID NO 151
<211> LENGTH: 13
<212> TYPE: PRT
<213> ORGANISM: Artificial Sequence
<220> FEATURE:
<223> OTHER INFORMATION: pNOP602641

<400> SEQUENCE: 151

Lys Thr Arg Tyr His Ser Tyr Arg Arg Gln Lys Tyr Arg
1               5                   10

<210> SEQ ID NO 152
<211> LENGTH: 13
<212> TYPE: PRT
<213> ORGANISM: Artificial Sequence
<220> FEATURE:
<223> OTHER INFORMATION: pNOP603193

<400> SEQUENCE: 152

Leu Glu Ser Tyr Ser Gly Arg Cys Lys Phe His Ser Lys
1               5                   10

<210> SEQ ID NO 153
<211> LENGTH: 13
<212> TYPE: PRT
<213> ORGANISM: Artificial Sequence
<220> FEATURE:
<223> OTHER INFORMATION: pNOP610345

<400> SEQUENCE: 153

Arg Asp Thr Tyr Lys Leu Phe His Ser Tyr Ile Ser Lys
1               5                   10

<210> SEQ ID NO 154
<211> LENGTH: 13
<212> TYPE: PRT
```

```
<213> ORGANISM: Artificial Sequence
<220> FEATURE:
<223> OTHER INFORMATION: pNOP610470

<400> SEQUENCE: 154

Arg Phe Asp Pro Phe Lys Thr Cys Pro Ala Thr Ile Lys
1               5                   10

<210> SEQ ID NO 155
<211> LENGTH: 13
<212> TYPE: PRT
<213> ORGANISM: Artificial Sequence
<220> FEATURE:
<223> OTHER INFORMATION: pNOP612555

<400> SEQUENCE: 155

Arg Ser Arg Ser Gly Arg Asn Gln His Gly Asn Phe Trp
1               5                   10

<210> SEQ ID NO 156
<211> LENGTH: 13
<212> TYPE: PRT
<213> ORGANISM: Artificial Sequence
<220> FEATURE:
<223> OTHER INFORMATION: pNOP616618

<400> SEQUENCE: 156

Thr Met Gln Trp Asn Gly Lys Trp His Tyr Lys Pro Gln
1               5                   10

<210> SEQ ID NO 157
<211> LENGTH: 13
<212> TYPE: PRT
<213> ORGANISM: Artificial Sequence
<220> FEATURE:
<223> OTHER INFORMATION: pNOP617519

<400> SEQUENCE: 157

Thr Tyr Thr Val Ser Trp Pro Lys Leu Asn Phe Pro Trp
1               5                   10

<210> SEQ ID NO 158
<211> LENGTH: 13
<212> TYPE: PRT
<213> ORGANISM: Artificial Sequence
<220> FEATURE:
<223> OTHER INFORMATION: pNOP618023

<400> SEQUENCE: 158

Val Leu Gln Leu Trp Ser Ile Pro Ser Arg Pro Ser Pro
1               5                   10

<210> SEQ ID NO 159
<211> LENGTH: 13
<212> TYPE: PRT
<213> ORGANISM: Artificial Sequence
<220> FEATURE:
<223> OTHER INFORMATION: pNOP618027

<400> SEQUENCE: 159

Val Leu Arg Phe Trp Lys Asn Val Ile Tyr Ile Ser Arg
1               5                   10

<210> SEQ ID NO 160
<211> LENGTH: 13
<212> TYPE: PRT
<213> ORGANISM: Artificial Sequence
```

```
<220> FEATURE:
<223> OTHER INFORMATION: pNOP618122

<400> SEQUENCE: 160

Val Pro Ala Arg Ile Trp Lys Asn Glu His Ser Glu Glu
1               5                   10

<210> SEQ ID NO 161
<211> LENGTH: 13
<212> TYPE: PRT
<213> ORGANISM: Artificial Sequence
<220> FEATURE:
<223> OTHER INFORMATION: pNOP618153

<400> SEQUENCE: 161

Val Pro Gly Thr Asn Ser Ser Phe Lys Ser Phe Pro Ser
1               5                   10

<210> SEQ ID NO 162
<211> LENGTH: 13
<212> TYPE: PRT
<213> ORGANISM: Artificial Sequence
<220> FEATURE:
<223> OTHER INFORMATION: pNOP619854

<400> SEQUENCE: 162

Tyr Phe Ser Asp Arg Phe Leu Arg Cys Tyr Lys Trp Cys
1               5                   10

<210> SEQ ID NO 163
<211> LENGTH: 12
<212> TYPE: PRT
<213> ORGANISM: Artificial Sequence
<220> FEATURE:
<223> OTHER INFORMATION: pNOP621732

<400> SEQUENCE: 163

Ala Ser Met Ser His Leu Tyr Arg Lys Met Trp Asn
1               5                   10

<210> SEQ ID NO 164
<211> LENGTH: 12
<212> TYPE: PRT
<213> ORGANISM: Artificial Sequence
<220> FEATURE:
<223> OTHER INFORMATION: pNOP621939

<400> SEQUENCE: 164

Ala Val Glu Leu Trp Lys Ala Lys Ser Phe Thr Glu
1               5                   10

<210> SEQ ID NO 165
<211> LENGTH: 12
<212> TYPE: PRT
<213> ORGANISM: Artificial Sequence
<220> FEATURE:
<223> OTHER INFORMATION: pNOP625526

<400> SEQUENCE: 165

Glu Arg Thr Thr Val Tyr Lys Leu Tyr Tyr Asn Thr
1               5                   10

<210> SEQ ID NO 166
<211> LENGTH: 12
<212> TYPE: PRT
<213> ORGANISM: Artificial Sequence
<220> FEATURE:
```

<223> OTHER INFORMATION: pNOP628448

<400> SEQUENCE: 166

Gly Ser Arg Arg Lys Asn Leu Ile Cys Asn His Thr
1               5                   10

<210> SEQ ID NO 167
<211> LENGTH: 12
<212> TYPE: PRT
<213> ORGANISM: Artificial Sequence
<220> FEATURE:
<223> OTHER INFORMATION: pNOP633163

<400> SEQUENCE: 167

Lys Thr Cys Glu Leu Tyr Phe Arg Asn Gln Thr Lys
1               5                   10

<210> SEQ ID NO 168
<211> LENGTH: 12
<212> TYPE: PRT
<213> ORGANISM: Artificial Sequence
<220> FEATURE:
<223> OTHER INFORMATION: pNOP637232

<400> SEQUENCE: 168

Asn Leu Tyr His Lys Ile Leu Asn Ile Gly His Val
1               5                   10

<210> SEQ ID NO 169
<211> LENGTH: 12
<212> TYPE: PRT
<213> ORGANISM: Artificial Sequence
<220> FEATURE:
<223> OTHER INFORMATION: pNOP637386

<400> SEQUENCE: 169

Asn Gln Gly Arg Lys Val His Trp Lys Leu Lys Arg
1               5                   10

<210> SEQ ID NO 170
<211> LENGTH: 12
<212> TYPE: PRT
<213> ORGANISM: Artificial Sequence
<220> FEATURE:
<223> OTHER INFORMATION: pNOP649061

<400> SEQUENCE: 170

Val Gly Arg Leu Pro Gly Ala Phe His His Arg Ser
1               5                   10

<210> SEQ ID NO 171
<211> LENGTH: 11
<212> TYPE: PRT
<213> ORGANISM: Artificial Sequence
<220> FEATURE:
<223> OTHER INFORMATION: pNOP655968

<400> SEQUENCE: 171

Asp Thr Cys Lys Lys Lys Cys Arg Leu Lys Lys
1               5                   10

<210> SEQ ID NO 172
<211> LENGTH: 11
<212> TYPE: PRT
<213> ORGANISM: Artificial Sequence
<220> FEATURE:
<223> OTHER INFORMATION: pNOP658090

<400> SEQUENCE: 172

Phe Ile Phe Arg Ile Ser Gln Ala Gln Ser Cys
1               5                   10

<210> SEQ ID NO 173
<211> LENGTH: 11
<212> TYPE: PRT
<213> ORGANISM: Artificial Sequence
<220> FEATURE:
<223> OTHER INFORMATION: pNOP658639

<400> SEQUENCE: 173

Phe Thr Ser Ser Cys Cys Cys Cys Met Phe Ile
1               5                   10

<210> SEQ ID NO 174
<211> LENGTH: 11
<212> TYPE: PRT
<213> ORGANISM: Artificial Sequence
<220> FEATURE:
<223> OTHER INFORMATION: pNOP663444

<400> SEQUENCE: 174

Ile Val Lys Arg Arg Cys Glu Lys Leu Glu Val
1               5                   10

<210> SEQ ID NO 175
<211> LENGTH: 11
<212> TYPE: PRT
<213> ORGANISM: Artificial Sequence
<220> FEATURE:
<223> OTHER INFORMATION: pNOP664052

<400> SEQUENCE: 175

Lys Phe Tyr Ser Gly Thr Tyr Pro Ile Gln Phe
1               5                   10

<210> SEQ ID NO 176
<211> LENGTH: 11
<212> TYPE: PRT
<213> ORGANISM: Artificial Sequence
<220> FEATURE:
<223> OTHER INFORMATION: pNOP664687

<400> SEQUENCE: 176

Lys Leu Lys Arg Asn Gln Pro Ser Lys Ala Tyr
1               5                   10

<210> SEQ ID NO 177
<211> LENGTH: 11
<212> TYPE: PRT
<213> ORGANISM: Artificial Sequence
<220> FEATURE:
<223> OTHER INFORMATION: pNOP664820

<400> SEQUENCE: 177

Lys Met Gly Lys Thr Gln Thr His Asn Arg Arg
1               5                   10

<210> SEQ ID NO 178
<211> LENGTH: 11
<212> TYPE: PRT
<213> ORGANISM: Artificial Sequence
<220> FEATURE:
<223> OTHER INFORMATION: pNOP668825

```
<400> SEQUENCE: 178

Met Leu Ser Thr Tyr Gln Lys Leu Leu Thr Ile
1               5                   10

<210> SEQ ID NO 179
<211> LENGTH: 11
<212> TYPE: PRT
<213> ORGANISM: Artificial Sequence
<220> FEATURE:
<223> OTHER INFORMATION: pNOP669525

<400> SEQUENCE: 179

Asn Phe His Leu Met Lys Ser Ile Asp Met Gln
1               5                   10

<210> SEQ ID NO 180
<211> LENGTH: 11
<212> TYPE: PRT
<213> ORGANISM: Artificial Sequence
<220> FEATURE:
<223> OTHER INFORMATION: pNOP673249

<400> SEQUENCE: 180

Gln Ile Ile Ser Thr Ser Lys Asp Ile Ile Pro
1               5                   10

<210> SEQ ID NO 181
<211> LENGTH: 11
<212> TYPE: PRT
<213> ORGANISM: Artificial Sequence
<220> FEATURE:
<223> OTHER INFORMATION: pNOP676143

<400> SEQUENCE: 181

Arg Pro Gly Ser Ile Met Gly His Gly Gly Ser
1               5                   10

<210> SEQ ID NO 182
<211> LENGTH: 11
<212> TYPE: PRT
<213> ORGANISM: Artificial Sequence
<220> FEATURE:
<223> OTHER INFORMATION: pNOP678565

<400> SEQUENCE: 182

Ser Lys Cys Lys Pro Val Phe Val Ser Arg Arg
1               5                   10

<210> SEQ ID NO 183
<211> LENGTH: 11
<212> TYPE: PRT
<213> ORGANISM: Artificial Sequence
<220> FEATURE:
<223> OTHER INFORMATION: pNOP683285

<400> SEQUENCE: 183

Val Leu Val Ala His Thr Leu His Leu Glu Gly
1               5                   10

<210> SEQ ID NO 184
<211> LENGTH: 10
<212> TYPE: PRT
<213> ORGANISM: Artificial Sequence
<220> FEATURE:
<223> OTHER INFORMATION: pNOP687997

<400> SEQUENCE: 184
```

```
Cys Glu Ser Ser Gly Lys Ser Tyr Trp Gly
1               5                   10

<210> SEQ ID NO 185
<211> LENGTH: 10
<212> TYPE: PRT
<213> ORGANISM: Artificial Sequence
<220> FEATURE:
<223> OTHER INFORMATION: pNOP691856

<400> SEQUENCE: 185

Glu Ser Phe Asp Cys Gln Leu Arg Ser Glu
1               5                   10

<210> SEQ ID NO 186
<211> LENGTH: 10
<212> TYPE: PRT
<213> ORGANISM: Artificial Sequence
<220> FEATURE:
<223> OTHER INFORMATION: pNOP697423

<400> SEQUENCE: 186

Ile Ile Val Leu Asn Ile Gln Met Ser Ser
1               5                   10

<210> SEQ ID NO 187
<211> LENGTH: 10
<212> TYPE: PRT
<213> ORGANISM: Artificial Sequence
<220> FEATURE:
<223> OTHER INFORMATION: pNOP700014

<400> SEQUENCE: 187

Lys Pro Arg Glu Arg Gly Arg Lys Asn Tyr
1               5                   10

<210> SEQ ID NO 188
<211> LENGTH: 10
<212> TYPE: PRT
<213> ORGANISM: Artificial Sequence
<220> FEATURE:
<223> OTHER INFORMATION: pNOP703850

<400> SEQUENCE: 188

Met Ile Gln Met Met Met Ile Leu Lys Tyr
1               5                   10

<210> SEQ ID NO 189
<211> LENGTH: 10
<212> TYPE: PRT
<213> ORGANISM: Artificial Sequence
<220> FEATURE:
<223> OTHER INFORMATION: pNOP704337

<400> SEQUENCE: 189

Met Val Arg Lys Arg Asn Gln Leu His Gln
1               5                   10

<210> SEQ ID NO 190
<211> LENGTH: 10
<212> TYPE: PRT
<213> ORGANISM: Artificial Sequence
<220> FEATURE:
<223> OTHER INFORMATION: pNOP708330

<400> SEQUENCE: 190
```

```
Pro Trp Thr Asn His Ala Thr Lys Gln Lys
1               5                   10

<210> SEQ ID NO 191
<211> LENGTH: 10
<212> TYPE: PRT
<213> ORGANISM: Artificial Sequence
<220> FEATURE:
<223> OTHER INFORMATION: pNOP708440

<400> SEQUENCE: 191

Gln Cys Phe Arg Lys Gly Lys Ser Lys His
1               5                   10

<210> SEQ ID NO 192
<211> LENGTH: 10
<212> TYPE: PRT
<213> ORGANISM: Artificial Sequence
<220> FEATURE:
<223> OTHER INFORMATION: pNOP708789

<400> SEQUENCE: 192

Gln His Arg Ile Gln Trp Asn Pro Lys Ser
1               5                   10

<210> SEQ ID NO 193
<211> LENGTH: 10
<212> TYPE: PRT
<213> ORGANISM: Artificial Sequence
<220> FEATURE:
<223> OTHER INFORMATION: pNOP713466

<400> SEQUENCE: 193

Arg Trp Arg Thr Gln Ile Phe Asp Lys Ser
1               5                   10

<210> SEQ ID NO 194
<211> LENGTH: 10
<212> TYPE: PRT
<213> ORGANISM: Artificial Sequence
<220> FEATURE:
<223> OTHER INFORMATION: pNOP718963

<400> SEQUENCE: 194

Val Cys Leu Gln Arg Thr Lys Ser Asp Glu
1               5                   10

<210> SEQ ID NO 195
<211> LENGTH: 10
<212> TYPE: PRT
<213> ORGANISM: Artificial Sequence
<220> FEATURE:
<223> OTHER INFORMATION: pNOP720338

<400> SEQUENCE: 195

Trp Asp Cys Cys Cys Gln Ser Asp Ser Phe
1               5                   10

<210> SEQ ID NO 196
<211> LENGTH: 10
<212> TYPE: PRT
<213> ORGANISM: Artificial Sequence
<220> FEATURE:
<223> OTHER INFORMATION: pNOP721298

<400> SEQUENCE: 196

Trp Ser Gly Phe Asn Tyr Thr Asn Gly Pro
```

```
<210> SEQ ID NO 197
<211> LENGTH: 67
<212> TYPE: PRT
<213> ORGANISM: Artificial Sequence
<220> FEATURE:
<223> OTHER INFORMATION: pNOP82315

<400> SEQUENCE: 197

Arg Ser Tyr Arg Arg Met Ile His Leu Trp Trp Thr Ala Gln Ile Ser
1               5                   10                  15

Leu Gly Val Cys Arg Ser Leu Thr Val Ala Cys Cys Thr Gly Gly Leu
            20                  25                  30

Val Gly Gly Thr Pro Leu Ser Ile Ser Arg Pro Thr Ser Arg Ala Arg
        35                  40                  45

Gln Ser Cys Cys Leu Pro Gly Leu Thr His Pro Ala His Gln Pro Leu
    50                  55                  60

Gly Ser Met
65

<210> SEQ ID NO 198
<211> LENGTH: 179
<212> TYPE: PRT
<213> ORGANISM: Artificial Sequence
<220> FEATURE:
<223> OTHER INFORMATION: pNOP6110

<400> SEQUENCE: 198

Ala Leu Gly Pro His Ser Arg Ile Ser Cys Leu Pro Thr Gln Thr Arg
1               5                   10                  15

Gly Cys Ile Leu Leu Ala Ala Thr Pro Arg Ser Ser Ser Ser Ser Ser
            20                  25                  30

Ser Asn Asp Met Ile Pro Met Ala Ile Ser Ser Pro Pro Lys Ala Pro
        35                  40                  45

Leu Leu Ala Ala Pro Ser Pro Ala Ser Arg Leu Gln Cys Ile Asn Ser
    50                  55                  60

Asn Ser Arg Ile Thr Ser Gly Gln Trp Met Ala His Met Ala Leu Leu
65                  70                  75                  80

Pro Ser Gly Thr Lys Gly Arg Cys Thr Ala Cys His Thr Ala Leu Gly
                85                  90                  95

Arg Gly Ser Leu Ser Ser Ser Cys Pro Gln Pro Ser Pro Ser Leu
            100                 105                 110

Pro Ala Ser Asn Lys Leu Pro Ser Leu Pro Leu Ser Lys Met Tyr Thr
        115                 120                 125

Thr Ser Met Ala Met Pro Ile Leu Pro Leu Pro Gln Leu Leu Leu Ser
    130                 135                 140

Ala Asp Gln Gln Ala Ala Pro Arg Thr Asn Phe His Ser Ser Leu Ala
145                 150                 155                 160

Glu Thr Val Ser Leu His Pro Leu Ala Pro Met Pro Ser Lys Thr Cys
                165                 170                 175

His His Lys

<210> SEQ ID NO 199
<211> LENGTH: 130
<212> TYPE: PRT
<213> ORGANISM: Artificial Sequence
<220> FEATURE:
<223> OTHER INFORMATION: pNOP16341
```

<400> SEQUENCE: 199

Ala Pro Arg Glu Val Ala Leu Arg Ala Pro Arg Arg Arg Leu Pro
1               5                   10                  15

Ala Pro Ser Arg Leu Pro Pro Ala Pro Pro Pro Arg Arg Leu
            20                  25                  30

Arg Pro Ser Leu Ser Ser Ala Ser Gly Pro Trp Gly Glu Ala Ala Pro
            35                  40                  45

Pro Arg Pro Ala Gly Glu Leu Pro Ser Pro Pro Pro Pro Pro Ser
    50                  55                  60

Thr Asn Cys Ser Arg Arg Pro Ala Arg Pro Gly Ala Thr Arg Ala Thr
65                  70                  75                  80

Pro Gly Ala Thr Thr Val Ala Gly Pro Arg Thr Gly Ala Pro Ala Arg
                85                  90                  95

Ala Arg Arg Thr Trp Pro Arg Ser Val Gly Gly Leu Arg Arg Gln
                100                 105                 110

Leu Arg Arg Arg Pro Pro Arg Glu Gly Pro Asn Lys Gly Ala Thr Thr
                115                 120                 125

Arg Pro
    130

<210> SEQ ID NO 200
<211> LENGTH: 64
<212> TYPE: PRT
<213> ORGANISM: Artificial Sequence
<220> FEATURE:
<223> OTHER INFORMATION: pNOP88606

<400> SEQUENCE: 200

Phe Trp Pro His Pro Pro Ser Ala Ala Trp Arg Ser Cys Ile Ala Leu
1               5                   10                  15

Trp Cys Ala Ser Ser Val Thr Glu Arg Thr Arg Cys Ala Gly Arg Trp
                20                  25                  30

Leu Trp Tyr Cys Trp Pro Thr Trp Leu Arg Gly Thr Ala Trp Gln Leu
                35                  40                  45

Val Pro Leu Gln Cys Arg Arg Ala Val Ser Ala Thr Ser Trp Ala Ser
    50                  55                  60

<210> SEQ ID NO 201
<211> LENGTH: 282
<212> TYPE: PRT
<213> ORGANISM: Artificial Sequence
<220> FEATURE:
<223> OTHER INFORMATION: pNOP1299

<400> SEQUENCE: 201

Pro His Gly Ala Ala Arg Arg Arg Trp Arg Gln Gln Arg Trp Gly
1               5                   10                  15

Gly Gly Ala Ser Ser Leu Ser Arg Gly Arg Leu Ala Ala Pro Ser Leu
                20                  25                  30

Arg Leu Arg Ala Thr Leu Arg Pro Glu Pro Val Cys Arg Arg Arg
                35                  40                  45

Arg Gly Arg Arg Leu Pro Pro Thr Thr Trp Arg Thr Thr Lys Pro Trp
    50                  55                  60

Pro Gly Ser Ala Ala Glu Arg Arg Arg Gly Pro Gly Ala Leu Arg
65                  70                  75                  80

Gly Ala Pro Ala Glu Leu Ser Arg Pro Arg Leu Pro Gln Pro Pro Val
                85                  90                  95

```
Gln Leu Leu Leu Pro Gln Pro Gln Arg Leu Pro Pro Ala Arg Pro Gly
                100                 105                 110

Leu Arg Ala Glu Leu Pro Glu Arg Trp His Ser Gly Leu Arg Arg Gly
            115                 120                 125

Gly Gly Cys Arg Leu Gln Ala Ala Ser Leu Leu Gln Arg Leu Arg Leu
        130                 135                 140

Leu Val Val Phe Val Leu Arg Ser Ala Ala Leu Arg Gly His Gly Gly
145                 150                 155                 160

Arg Arg Pro Leu Arg Gly Arg Gly Asn Ser Pro Ala His Arg His
                165                 170                 175

Pro His Pro Gln Pro Thr Ala His Val Ala Gln Leu Gly Pro Gly Leu
                180                 185                 190

Pro Gly Leu Pro Arg Gly Arg Leu Gln Trp Arg Ala Pro Gly Arg Gly
            195                 200                 205

Arg Arg Gln Gly Pro Gly Gly His Gly Leu Ala Val Leu Gly Gly Cys
        210                 215                 220

Gly Gly Gly Ser Cys Gly Gly Gly Arg Leu Gly Arg Gly Pro Thr Lys
225                 230                 235                 240

Glu Pro Pro Arg Ala His Glu Pro Arg Glu Gln Arg Arg Gly Ala
                245                 250                 255

Ala Ala Arg Pro Asp Pro Ser Ala Ile Gln Ser Asn Gly Ser Asp Gly
                260                 265                 270

Gln Asp Glu Thr Ser Ala Ile Trp Arg Asp
                275                 280

<210> SEQ ID NO 202
<211> LENGTH: 185
<212> TYPE: PRT
<213> ORGANISM: Artificial Sequence
<220> FEATURE:
<223> OTHER INFORMATION: pNOP5538

<400> SEQUENCE: 202

Pro Cys Arg Ala Gly Arg Arg Val Pro Trp Ala Ala Ser Leu Ile His
1               5                   10                  15

Ser Arg Phe Leu Leu Met Asp Asn Lys Ala Pro Ala Gly Met Val Asn
            20                  25                  30

Arg Ala Arg Leu His Ile Thr Thr Ser Lys Val Leu Thr Leu Ser Ser
        35                  40                  45

Ser Ser His Pro Thr Pro Ser Asn His Arg Pro Arg Pro Leu Met Pro
    50                  55                  60

Asn Leu Arg Ile Ser Ser Ser His Ser Leu Asn His Ser Ser Ser
65                  70                  75                  80

Pro Leu Ser Leu His Thr Pro Ser Ser His Pro Ser Leu His Ile Ser
                85                  90                  95

Ser Pro Arg Leu His Thr Pro Pro Ser Ser Arg Arg His Ser Ser Thr
            100                 105                 110

Pro Arg Ala Ser Pro Pro Thr His Ser His Arg Leu Ser Leu Leu Thr
        115                 120                 125

Ser Ser Ser Asn Leu Ser Ser Gln His Pro Arg Arg Ser Pro Ser Arg
    130                 135                 140

Leu Arg Ile Leu Ser Pro Ser Leu Ser Ser Pro Ser Lys Leu Pro Ile
145                 150                 155                 160

Pro Ser Ser Ala Ser Leu His Arg Arg Ser Tyr Leu Lys Ile His Leu
                165                 170                 175
```

```
Gly Leu Arg His Pro Gln Pro Pro Gln
            180             185

<210> SEQ ID NO 203
<211> LENGTH: 27
<212> TYPE: PRT
<213> ORGANISM: Artificial Sequence
<220> FEATURE:
<223> OTHER INFORMATION: pNOP323677

<400> SEQUENCE: 203

Leu Arg Ser Thr Arg Thr Lys Asn Gly Gly Asn Leu Gln Pro Thr Ser
1               5                   10                  15

Met Trp Ala His Gln Ala Val Leu Pro Ala Pro
            20                  25

<210> SEQ ID NO 204
<211> LENGTH: 90
<212> TYPE: PRT
<213> ORGANISM: Artificial Sequence
<220> FEATURE:
<223> OTHER INFORMATION: pNOP43369

<400> SEQUENCE: 204

Thr Asn Gln Ala Leu Pro Lys Ile Glu Val Ile Cys Arg Gly Thr Pro
1               5                   10                  15

Arg Cys Pro Ser Thr Val Pro Pro Ser Pro Ala Gln Pro Tyr Leu Arg
            20                  25                  30

Val Ser Leu Pro Glu Asp Arg Tyr Thr Gln Ala Trp Ala Pro Thr Ser
        35                  40                  45

Arg Thr Pro Trp Gly Ala Met Val Pro Arg Gly Val Ser Met Ala His
    50                  55                  60

Lys Val Ala Thr Pro Gly Ser Gln Thr Ile Met Pro Cys Pro Met Pro
65                  70                  75                  80

Thr Thr Pro Val Gln Ala Trp Leu Glu Ala
            85                  90

<210> SEQ ID NO 205
<211> LENGTH: 46
<212> TYPE: PRT
<213> ORGANISM: Artificial Sequence
<220> FEATURE:
<223> OTHER INFORMATION: pNOP160041

<400> SEQUENCE: 205

Gln Gly Pro Leu His Leu Thr Thr Ser Pro His Gln Ala Cys Arg Ile
1               5                   10                  15

Thr Phe Leu Arg Tyr Pro Ala Leu Leu Pro Cys Pro Gly Gln Trp Arg
            20                  25                  30

Thr Ala Pro Leu Leu Ala Ser Leu His Ser Cys Thr Leu Gly
        35                  40                  45

<210> SEQ ID NO 206
<211> LENGTH: 67
<212> TYPE: PRT
<213> ORGANISM: Artificial Sequence
<220> FEATURE:
<223> OTHER INFORMATION: pNOP81513

<400> SEQUENCE: 206

Lys Ser Ser Ile Ser Ser Val Ser Met Pro Leu Asn Ala Arg Leu Asn
1               5                   10                  15
```

```
Gly Glu Lys Thr Leu Pro Gln Thr Ser Leu Gln Leu Ile Pro Arg
            20                  25                  30

Ser Pro Ser Pro Arg Ser Ser Leu Pro Leu Leu Arg Asp Gln Asp Leu
        35                  40                  45

Cys Arg Gly Pro Arg Leu Pro Ser Gln Pro Ala Val Pro Trp Gln Lys
50                  55                  60

Glu Glu Thr
65

<210> SEQ ID NO 207
<211> LENGTH: 140
<212> TYPE: PRT
<213> ORGANISM: Artificial Sequence
<220> FEATURE:
<223> OTHER INFORMATION: pNOP13360

<400> SEQUENCE: 207

Ser Ser Ser Val Ser Phe Leu Ser Ser Tyr Leu Pro Ser Pro Ala Trp
1               5                   10                  15

His Pro Arg Pro Phe Pro Val Pro Cys Trp Leu Ser Arg Gln Cys Cys
            20                  25                  30

Ser Val Ser Leu Arg Thr Thr Leu Ala Cys Cys Ser Ala Arg Gln Pro
        35                  40                  45

Asp Ala Thr Ser Ala Thr Gln Trp Pro Val Gly Gln His His Ala Ser
50                  55                  60

Phe His Glu Pro Ile Lys His Cys Pro Arg Ser Arg Leu Tyr Ala Glu
65                  70                  75                  80

Glu Pro Pro Asp Ala Pro Val Gln Phe Pro Pro Ala Arg Leu Ser Leu
                85                  90                  95

Ile Ser Ala Ser Ala Phe Arg Arg Thr Asp Thr His Arg His Gly Leu
            100                 105                 110

Leu Pro Ala Glu Leu His Gly Glu Leu Trp Ser Pro Gly Gly Ser Val
        115                 120                 125

Trp Pro Thr Arg Trp Leu Pro Gln Ala Ala Lys Leu
    130                 135                 140

<210> SEQ ID NO 208
<211> LENGTH: 57
<212> TYPE: PRT
<213> ORGANISM: Artificial Sequence
<220> FEATURE:
<223> OTHER INFORMATION: pNOP109934

<400> SEQUENCE: 208

Glu Thr Ser Gly Pro Leu Ser Pro Leu Cys Val Cys Glu Gly Asp Trp
1               5                   10                  15

Trp Ile Asp Ser Gly Gln Gln Glu Gln Lys Met Ala Gly Thr Cys Asn
            20                  25                  30

Gln Pro Gln Cys Gly His Ile Lys Gln Cys Cys Gln Leu Leu Glu Lys
        35                  40                  45

Ala Val Tyr Pro Val Ser Leu Cys Leu
50                  55

<210> SEQ ID NO 209
<211> LENGTH: 39
<212> TYPE: PRT
<213> ORGANISM: Artificial Sequence
<220> FEATURE:
<223> OTHER INFORMATION: pNOP205126
```

<400> SEQUENCE: 209

Gln Gln Gln Arg Val His Gln Gly Gln Gln Thr Arg Arg Gly Pro His
1               5                   10                  15

Leu Met Asp Leu Gln Lys Asn Gly Ser Gln Pro Leu Trp Met Thr Cys
                20                  25                  30

Cys Leu Leu Gly Leu Ala Pro
            35

<210> SEQ ID NO 210
<211> LENGTH: 222
<212> TYPE: PRT
<213> ORGANISM: Artificial Sequence
<220> FEATURE:
<223> OTHER INFORMATION: pNOP3000

<400> SEQUENCE: 210

Pro Ile Leu Ala Ala Thr Gly Thr Ser Val Arg Thr Ala Ala Arg Thr
1               5                   10                  15

Trp Val Pro Arg Ala Ala Ile Arg Val Pro Asp Pro Ala Ala Val Pro
                20                  25                  30

Asp Asp His Ala Gly Pro Gly Ala Glu Cys His Gly Arg Pro Leu Leu
                35                  40                  45

Tyr Thr Ala Asp Ser Ser Leu Trp Thr Thr Arg Pro Gln Arg Val Trp
    50                  55                  60

Ser Thr Gly Pro Asp Ser Ile Leu Gln Pro Ala Lys Ser Ser Pro Ser
65                  70                  75                  80

Ala Ala Ala Thr Leu Leu Pro Ala Thr Thr Val Pro Asp Pro Ser
                85                  90                  95

Cys Pro Thr Phe Val Ser Ala Ala Thr Val Ser Thr Thr Thr Ala
                100                 105                 110

Pro Val Leu Ser Ala Ser Ile Leu Pro Ala Ile Pro Ala Ser Thr
                115                 120                 125

Ser Ala Val Pro Gly Ser Ile Pro Leu Pro Ala Val Asp Asp Thr Ala
    130                 135                 140

Ala Pro Pro Glu Pro Ala Pro Leu Leu Thr Ala Thr Gly Ser Val Ser
145                 150                 155                 160

Leu Pro Ala Ala Ala Thr Ser Ala Ala Ser Thr Leu Asp Ala Leu Pro
                165                 170                 175

Ala Gly Cys Val Ser Ser Ala Pro Val Ser Ala Val Pro Ala Asn Cys
                180                 185                 190

Leu Phe Pro Ala Ala Leu Pro Ser Thr Ala Gly Ala Ile Ser Arg Phe
                195                 200                 205

Ile Trp Val Ser Gly Ile Leu Ser Pro Leu Asn Asp Leu Gln
    210                 215                 220

<210> SEQ ID NO 211
<211> LENGTH: 27
<212> TYPE: PRT
<213> ORGANISM: Artificial Sequence
<220> FEATURE:
<223> OTHER INFORMATION: pNOP317526

<400> SEQUENCE: 211

Ala Pro Gly Ala Ala Ala Ala Gly Gly Ser Arg Ser Pro Gly Pro Leu
1               5                   10                  15

Ser His Pro Val Gln Trp Ile Arg Trp Ala Arg
                20                  25

<210> SEQ ID NO 212
<211> LENGTH: 92
<212> TYPE: PRT
<213> ORGANISM: Artificial Sequence
<220> FEATURE:
<223> OTHER INFORMATION: pNOP40276

<400> SEQUENCE: 212

Ala Ala Thr Lys Trp Ser Gly Gly Gly Thr Ala Trp Arg Cys Ser Gly
1               5                   10                  15

Lys Thr Pro Trp Leu His Ser Pro Thr Ser Arg Gly Ser Trp Thr Tyr
            20                  25                  30

Leu His Thr Pro Arg Ala Phe Ala Cys Leu Ser Trp Thr Asp Ser Tyr
        35                  40                  45

Thr Gly Gln Phe Ala Leu Gln Leu Lys Pro Arg Thr Pro Phe Pro Pro
    50                  55                  60

Trp Ala Pro Met Pro Ser Phe Pro Arg Arg Asp Trp Ser Trp Lys Pro
65                  70                  75                  80

Ser Ala Asn Ser Ala Ser Arg Thr Thr Met Trp Thr
                85                  90

<210> SEQ ID NO 213
<211> LENGTH: 54
<212> TYPE: PRT
<213> ORGANISM: Artificial Sequence
<220> FEATURE:
<223> OTHER INFORMATION: pNOP120573

<400> SEQUENCE: 213

Cys Leu Ala Gln Cys Gln Leu Pro Gln Cys Arg His Gly Trp Arg His
1               5                   10                  15

Lys Pro His Gly Cys Arg Arg Ser Asn Ala Trp Thr Ala Trp His Pro
            20                  25                  30

Thr Leu Trp His Thr Pro Ser Arg Glu Asp Glu Ser Arg Leu His Gly
        35                  40                  45

Gln Pro Ala Leu Trp Pro
    50

<210> SEQ ID NO 214
<211> LENGTH: 50
<212> TYPE: PRT
<213> ORGANISM: Artificial Sequence
<220> FEATURE:
<223> OTHER INFORMATION: pNOP140600

<400> SEQUENCE: 214

Ser Pro Gly Pro Leu Phe His Pro Gly Pro Gln Cys Arg Pro Phe Pro
1               5                   10                  15

Ala Glu Thr Gly Leu Gly Asn Pro Gln Gln Thr Gln His Pro Gly Gln
            20                  25                  30

Gln Cys Gly Pro Asp Ser Gly His Thr Pro Leu Gln Pro Pro Gly Glu
        35                  40                  45

Val Val
    50

<210> SEQ ID NO 215
<211> LENGTH: 49
<212> TYPE: PRT
<213> ORGANISM: Artificial Sequence
<220> FEATURE:

<223> OTHER INFORMATION: pNOP141882

<400> SEQUENCE: 215

Cys Gly His Asp Ala Ala Gly Cys Pro Arg Ala Ala Cys Leu Gly Gln
1               5                   10                  15

Gly Gly Arg Glu Pro Leu Arg Val Tyr Ser Val Arg Ile Thr Ala Val
            20                  25                  30

Gly His Leu Gly Ile Thr Val Asp Glu Leu Ile Gly Phe Thr Ser His
        35                  40                  45

Leu

<210> SEQ ID NO 216
<211> LENGTH: 45
<212> TYPE: PRT
<213> ORGANISM: Artificial Sequence
<220> FEATURE:
<223> OTHER INFORMATION: pNOP162214

<400> SEQUENCE: 216

Ala Pro Thr Ser Arg Arg Pro Pro Glu Pro Ile Ser Ile Pro Val Trp
1               5                   10                  15

Pro Arg Pro Cys Leu Cys Thr Pro Trp His Gln Cys Pro Ala Lys His
            20                  25                  30

Ala Thr Thr Asn Asp Gly Arg Pro His Thr Gly Ile Ser
        35                  40                  45

<210> SEQ ID NO 217
<211> LENGTH: 39
<212> TYPE: PRT
<213> ORGANISM: Artificial Sequence
<220> FEATURE:
<223> OTHER INFORMATION: pNOP204073

<400> SEQUENCE: 217

Asn Ala Ala His Arg Ser Glu Gly Gln Pro Arg Arg Leu Val Ala Phe
1               5                   10                  15

Pro Trp His Thr Pro Ala Pro Ile Trp Ser Leu Cys Pro Cys Ala Pro
            20                  25                  30

His Asp Lys Ala Pro Ser Ile
        35

<210> SEQ ID NO 218
<211> LENGTH: 37
<212> TYPE: PRT
<213> ORGANISM: Artificial Sequence
<220> FEATURE:
<223> OTHER INFORMATION: pNOP221454

<400> SEQUENCE: 218

Arg Ser Met Arg Trp Val Thr Gln Asp Arg Glu Arg Tyr Trp Ile Leu
1               5                   10                  15

Gly Gly Ser Ala Arg Cys Leu Val Gln Leu Pro Trp Arg Val Gly Lys
            20                  25                  30

Lys Lys Lys Asn Phe
        35

<210> SEQ ID NO 219
<211> LENGTH: 117
<212> TYPE: PRT
<213> ORGANISM: Artificial Sequence
<220> FEATURE:
<223> OTHER INFORMATION: pNOP22341

-continued

<400> SEQUENCE: 219

Thr Ile Thr Ser Arg Ser Arg Pro Ala Ala Val Ala Ala Ala Ala
1               5                   10                  15

Met Gly Trp Gly Arg Leu Leu Thr Gln Pro Arg Pro Cys Arg Pro
            20                  25                  30

Gln Pro Thr Ala Ser Gly Asn Pro Thr Ala Gly Ala Arg Leu Pro Ser
        35                  40                  45

Pro Pro Arg Pro Pro Ser Ser Thr Asn Asn Met Ala Asp Asn Lys
    50                  55                  60

Ala Leu Ala Trp Gln Arg Cys Arg Ala Ala Ala Gly Ala Trp Ser
65                  70                  75                  80

Pro Thr Arg Gly Pro Ser Arg Thr Leu Thr Thr Thr Ala Ser Pro Thr
                85                  90                  95

Thr Ser Thr Thr Pro Thr Thr Pro Thr Ala Ala Pro Thr Pro Arg Pro
                100                 105                 110

Pro Arg Pro Thr Arg
            115

<210> SEQ ID NO 220
<211> LENGTH: 109
<212> TYPE: PRT
<213> ORGANISM: Artificial Sequence
<220> FEATURE:
<223> OTHER INFORMATION: pNOP26533

<400> SEQUENCE: 220

His Gly Arg Ala Gly Arg Pro Arg Arg Gln Gln Pro Gly Gln Pro
1               5                   10                  15

Ala Ala Ala Ala Ala Leu Gly Ala Glu Glu Ser Arg Ala Ala Ala
            20                  25                  30

Gly Gly Gly Gly Gly Arg Gly Gly Gly Gly Ser Gly Arg Ala Arg
        35                  40                  45

Gly Asn Glu Gly Ser Arg Arg Ala Gly Lys Arg Gly Pro Arg Arg Gly
    50                  55                  60

Ala Ala Ala Ala Ala Gly Lys Gly Ala Ala Gly Arg Gly Arg Glu Gln
65                  70                  75                  80

Trp Gly Trp Arg Arg Arg Ser Arg Gln Arg Arg Ala Arg Arg
                85                  90                  95

Gly Ala Gly Pro Glu Glu Leu Glu Arg Glu Arg Gly Pro
            100                 105

<210> SEQ ID NO 221
<211> LENGTH: 31
<212> TYPE: PRT
<213> ORGANISM: Artificial Sequence
<220> FEATURE:
<223> OTHER INFORMATION: pNOP271959

<400> SEQUENCE: 221

Asp Val Gln Thr Pro Arg Ala Ala Ala His Pro Gly Gln Ala Asp Pro
1               5                   10                  15

Ala Ala Pro Gln Ala Pro Arg Thr Glu Ala Gly Thr Thr Asn Leu
            20                  25                  30

<210> SEQ ID NO 222
<211> LENGTH: 106
<212> TYPE: PRT
<213> ORGANISM: Artificial Sequence

```
<220> FEATURE:
<223> OTHER INFORMATION: pNOP28543

<400> SEQUENCE: 222

Phe Leu Trp Gln Ser Val Leu His Pro Arg His Pro Phe Trp Gln Pro
1               5                   10                  15

Leu Pro Gln Pro Ala Asp Tyr Asn Val Ser Thr Ala Thr Ala Glu Leu
            20                  25                  30

Gln Ala Ala Asn Gly Trp His Ile Trp Pro Ser Cys Gln Ala Ala Arg
        35                  40                  45

Arg Gly Asp Val Gln Arg Ala Ile Gln His Trp Ala Gly Ala Ala Ser
    50                  55                  60

Ala Ala Ala Val Ala Pro Ser Pro Ala Pro Cys Gln Pro Ala Thr
65                  70                  75                  80

Ser Cys Pro Ala Phe Pro Ser Ala Arg Cys Ile Gln Pro Val Trp Gln
                85                  90                  95

Cys Leu Ser Cys His Cys His Ser Cys Tyr
            100                 105

<210> SEQ ID NO 223
<211> LENGTH: 26
<212> TYPE: PRT
<213> ORGANISM: Artificial Sequence
<220> FEATURE:
<223> OTHER INFORMATION: pNOP339133

<400> SEQUENCE: 223

Pro Pro His Gly Asp Arg Arg Ser Ser Glu Ser Trp Ser Glu His Ile
1               5                   10                  15

Arg Asp Phe Gln Gln Pro Arg Arg Ala Glu
            20                  25

<210> SEQ ID NO 224
<211> LENGTH: 25
<212> TYPE: PRT
<213> ORGANISM: Artificial Sequence
<220> FEATURE:
<223> OTHER INFORMATION: pNOP355250

<400> SEQUENCE: 224

Arg Lys Pro Ser Ser Ser Gly Arg Arg Gly Ala Arg Arg
1               5                   10                  15

Arg Arg Gln Arg Pro Ser Ala Gly Lys
            20                  25

<210> SEQ ID NO 225
<211> LENGTH: 23
<212> TYPE: PRT
<213> ORGANISM: Artificial Sequence
<220> FEATURE:
<223> OTHER INFORMATION: pNOP390796

<400> SEQUENCE: 225

Trp Ala Ala Pro Tyr Arg His Gln Leu Arg Leu Ser Lys Ala Pro
1               5                   10                  15

Cys Gly Arg Gly Val Met Thr
            20

<210> SEQ ID NO 226
<211> LENGTH: 21
<212> TYPE: PRT
<213> ORGANISM: Artificial Sequence
```

```
<220> FEATURE:
<223> OTHER INFORMATION: pNOP419746

<400> SEQUENCE: 226

Pro Ile Ile Met Pro Thr Gly Arg Ala Arg Ala Leu Pro Pro Arg Ala
1               5                   10                  15

Pro Pro Ile Met Ala
            20

<210> SEQ ID NO 227
<211> LENGTH: 19
<212> TYPE: PRT
<213> ORGANISM: Artificial Sequence
<220> FEATURE:
<223> OTHER INFORMATION: pNOP450666

<400> SEQUENCE: 227

Glu Met Trp Arg Trp Asp His Asp Ser Thr Ile Pro Met Glu Val Leu
1               5                   10                  15

Met Thr Glu

<210> SEQ ID NO 228
<211> LENGTH: 18
<212> TYPE: PRT
<213> ORGANISM: Artificial Sequence
<220> FEATURE:
<223> OTHER INFORMATION: pNOP484623

<400> SEQUENCE: 228

Ser His Gln Leu Gln His Pro His His Thr Val Arg Ser Pro His Cys
1               5                   10                  15

Gln Ala

<210> SEQ ID NO 229
<211> LENGTH: 10
<212> TYPE: PRT
<213> ORGANISM: Artificial Sequence
<220> FEATURE:
<223> OTHER INFORMATION: pNOP709605

<400> SEQUENCE: 229

Gln Ser Glu Asp Gly Ala Trp Asn Arg Ala
1               5                   10

<210> SEQ ID NO 230
<211> LENGTH: 69
<212> TYPE: PRT
<213> ORGANISM: Artificial Sequence
<220> FEATURE:
<223> OTHER INFORMATION: pNOP78127

<400> SEQUENCE: 230

Tyr Gly Trp His Asp Gln Pro Ser Gly Thr Pro Ile Phe His Gly Trp
1               5                   10                  15

Asn His Gly Gln Gln Phe Cys Arg Asp Gly Ser Gln Pro Arg Asp Asp
            20                  25                  30

Gly Pro Trp Gly Cys Lys Val Asn Ser Ser His Gln Asn Glu Gln Gln
        35                  40                  45

Gly Arg Trp Asp Thr Gln Asp Arg Ile Gln Ile Gln Glu Ile Gln Phe
    50                  55                  60

Phe Tyr Tyr Asn Gln
65
```

<210> SEQ ID NO 231
<211> LENGTH: 66
<212> TYPE: PRT
<213> ORGANISM: Artificial Sequence
<220> FEATURE:
<223> OTHER INFORMATION: pNOP84384

<400> SEQUENCE: 231

Pro Lys Glu Pro Gly Val Pro Gly Asp Gly Cys Gly Thr Ala Gly Gln
1               5                   10                  15

Pro Gly Ser Gly Gly Gln Pro Gly Ser Ser Cys His Cys Ser Ala Glu
            20                  25                  30

Gly Gln Tyr Arg Gln Pro Pro Gly Leu Pro Arg Gly Gln Pro Cys Arg
        35                  40                  45

His Thr Val Pro Ala Glu Pro Gly Gln Pro Pro His Ala Glu Pro
    50                  55                  60

Thr Leu
65

<210> SEQ ID NO 232
<211> LENGTH: 65
<212> TYPE: PRT
<213> ORGANISM: Artificial Sequence
<220> FEATURE:
<223> OTHER INFORMATION: pNOP86506

<400> SEQUENCE: 232

Lys Gly Gly Thr Gly Pro Arg Gly Glu Leu Gln Gln Ser Gly Val
1               5                   10                  15

Val Val Gly Leu Leu Gly Asp Ala Pro Gly Lys His Leu Gly Tyr Thr
            20                  25                  30

Arg Gln His Leu Gly Ala Val Gly Pro Ile Ser Ile Pro Arg Glu His
        35                  40                  45

Leu Pro Ala Cys Pro Gly Arg Thr Pro Thr Leu Gly Ser Leu Pro Phe
    50                  55                  60

Ser
65

<210> SEQ ID NO 233
<211> LENGTH: 58
<212> TYPE: PRT
<213> ORGANISM: Artificial Sequence
<220> FEATURE:
<223> OTHER INFORMATION: pNOP108335

<400> SEQUENCE: 233

Arg Thr Asn Pro Thr Val Arg Met Arg Pro His Cys Val Pro Phe Trp
1               5                   10                  15

Thr Gly Arg Ile Leu Leu Pro Ser Ala Ala Ser Val Cys Pro Ile Pro
            20                  25                  30

Phe Glu Ala Cys His Leu Cys Gln Ala Met Thr Leu Arg Cys Pro Asn
        35                  40                  45

Thr Gln Gly Cys Cys Ser Ser Trp Ala Ser
    50                  55

<210> SEQ ID NO 234
<211> LENGTH: 56
<212> TYPE: PRT
<213> ORGANISM: Artificial Sequence
<220> FEATURE:
<223> OTHER INFORMATION: pNOP115908

<400> SEQUENCE: 234

Thr Thr Arg Gln Met Gly His Pro Arg Gln Asn Pro Asn Pro Arg Asn
1               5                   10                  15

Pro Val Leu Leu Leu Gln Pro Met Arg Arg Ser Pro Ser Cys Met Ser
            20                  25                  30

Trp Val Val Ser Leu Arg Gly Arg Cys Gly Trp Thr Val Ile Trp Pro
        35                  40                  45

Ser Leu Arg Arg Arg Pro Trp Ala
        50                  55

<210> SEQ ID NO 235
<211> LENGTH: 49
<212> TYPE: PRT
<213> ORGANISM: Artificial Sequence
<220> FEATURE:
<223> OTHER INFORMATION: pNOP144966

<400> SEQUENCE: 235

Arg Gln Pro Pro Gly Arg Lys Ala Arg Ala Pro Pro Trp Gly Arg Arg
1               5                   10                  15

Ser Arg Trp Glu Arg Ser Cys Arg Thr Gly Pro Arg Ala Met Gly Val
            20                  25                  30

Ala Ala Ala Ala Glu Pro Ala Ala Ala Gly Pro Ala Arg Ser Arg
        35                  40                  45

Thr

<210> SEQ ID NO 236
<211> LENGTH: 49
<212> TYPE: PRT
<213> ORGANISM: Artificial Sequence
<220> FEATURE:
<223> OTHER INFORMATION: pNOP145255

<400> SEQUENCE: 236

Ser His Thr Ala Cys Val Glu Ala Glu Ala Ala His Asn Glu Arg
1               5                   10                  15

His Trp Asn Pro Gly Gly Met Ala Gly Asn Asp Val Pro Gln Val Trp
            20                  25                  30

Ser Pro Gly Arg Glu His Met Gly Ile Arg Tyr His Gln His Pro Ala
        35                  40                  45

Val

<210> SEQ ID NO 237
<211> LENGTH: 47
<212> TYPE: PRT
<213> ORGANISM: Artificial Sequence
<220> FEATURE:
<223> OTHER INFORMATION: pNOP152466

<400> SEQUENCE: 237

Phe Leu Trp Gln Ser Val Leu His Pro Arg His Pro Phe Trp Gln Pro
1               5                   10                  15

Leu Pro Gln Pro Ala Asp Tyr Asn Val Ser Thr Ala Thr Ala Gly Ile
            20                  25                  30

Gln Pro Cys Ser Pro Ala Pro Ala Asn Gly Glu Pro His Leu Ser
        35                  40                  45

<210> SEQ ID NO 238
<211> LENGTH: 46

<212> TYPE: PRT
<213> ORGANISM: Artificial Sequence
<220> FEATURE:
<223> OTHER INFORMATION: pNOP157058

<400> SEQUENCE: 238

Ala Tyr Pro Asp Pro Leu Arg Glu Gln Asp Arg Ala Ala Ala Phe Pro
1               5                   10                  15

Ala Ser Arg Thr Leu Pro Thr Ser Pro Ser Glu Ala Cys Asp Asn Ser
            20                  25                  30

Arg Gly Tyr Thr Arg Asp Asn Arg Pro Gly Gly Ala Pro Thr
        35                  40                  45

<210> SEQ ID NO 239
<211> LENGTH: 44
<212> TYPE: PRT
<213> ORGANISM: Artificial Sequence
<220> FEATURE:
<223> OTHER INFORMATION: pNOP171474

<400> SEQUENCE: 239

Gln Val Ser Ile Pro Ala Leu Trp Asp Glu Asn Ala Glu Gly Arg Ser
1               5                   10                  15

Pro Ser Thr Cys Leu Ala His Ser Thr Cys Pro Cys Ala Ala Pro His
            20                  25                  30

Asp Ser Ala Gly Tyr His Leu Pro Thr Trp Leu Cys
        35                  40

<210> SEQ ID NO 240
<211> LENGTH: 41
<212> TYPE: PRT
<213> ORGANISM: Artificial Sequence
<220> FEATURE:
<223> OTHER INFORMATION: pNOP187097

<400> SEQUENCE: 240

Asp Leu Ser His Met Ala Gly Leu Thr His Thr Arg Ser Asn Arg Asp
1               5                   10                  15

Leu Arg Gln Asp Arg Ser Lys Asp Met Gly Thr Gln Gly Ser His Thr
            20                  25                  30

Gly Pro Arg Pro Arg Ser Gly Thr Arg
        35                  40

<210> SEQ ID NO 241
<211> LENGTH: 37
<212> TYPE: PRT
<213> ORGANISM: Artificial Sequence
<220> FEATURE:
<223> OTHER INFORMATION: pNOP222331

<400> SEQUENCE: 241

Thr Glu Gln Met Lys Cys Cys Thr Gln Ile Arg Gly Pro Thr Thr Lys
1               5                   10                  15

Ala Arg Gly Leu Pro Met Ala His Ala Ser Pro His Met Val Pro Leu
            20                  25                  30

Pro Leu Cys Pro Pro
        35

<210> SEQ ID NO 242
<211> LENGTH: 35
<212> TYPE: PRT
<213> ORGANISM: Artificial Sequence
<220> FEATURE:

```
<223> OTHER INFORMATION: pNOP232518

<400> SEQUENCE: 242

Cys Gly Gly Leu Pro Ala Arg Cys Leu Pro Trp Pro Arg Trp Thr Arg
1               5                   10                  15

Thr Thr Gln Ser Leu Leu Cys Thr Asn His Gly Cys Trp Thr Ser Arg
            20                  25                  30

Tyr His Arg
        35

<210> SEQ ID NO 243
<211> LENGTH: 33
<212> TYPE: PRT
<213> ORGANISM: Artificial Sequence
<220> FEATURE:
<223> OTHER INFORMATION: pNOP251638

<400> SEQUENCE: 243

Asp Pro Thr Val Tyr Pro Ser Gly Leu Ala Gly Phe Ser Cys Gln Ala
1               5                   10                  15

Leu Arg Leu Cys Val Gln Tyr His Ser Lys Pro Val Ile Cys Ala Arg
            20                  25                  30

Gln

<210> SEQ ID NO 244
<211> LENGTH: 32
<212> TYPE: PRT
<213> ORGANISM: Artificial Sequence
<220> FEATURE:
<223> OTHER INFORMATION: pNOP266437

<400> SEQUENCE: 244

Pro Arg Met Glu Leu Arg Val Gln Arg Pro Ser Arg Arg Ala Ala Ser
1               5                   10                  15

Phe His Leu Ala Leu Ala Gln His Arg Ala Thr Gly Thr Ser Arg Ser
            20                  25                  30

<210> SEQ ID NO 245
<211> LENGTH: 31
<212> TYPE: PRT
<213> ORGANISM: Artificial Sequence
<220> FEATURE:
<223> OTHER INFORMATION: pNOP272985

<400> SEQUENCE: 245

Gly Lys Leu Gln Gly Val Ile Pro Ser Cys Pro Gln Gly Arg Ala Pro
1               5                   10                  15

Thr Ala Gly Trp Val Thr Pro Thr Val Val Leu Pro Ala Leu Gly
            20                  25                  30

<210> SEQ ID NO 246
<211> LENGTH: 31
<212> TYPE: PRT
<213> ORGANISM: Artificial Sequence
<220> FEATURE:
<223> OTHER INFORMATION: pNOP280686

<400> SEQUENCE: 246

Val Thr Pro Pro Trp Ala Thr Gly Leu Met Ala Leu Thr Trp Pro Ile
1               5                   10                  15

Cys His Leu Arg Leu Gly Gln Gly Cys Val Pro His Gln Gly Ala
            20                  25                  30
```

<210> SEQ ID NO 247
<211> LENGTH: 106
<212> TYPE: PRT
<213> ORGANISM: Artificial Sequence
<220> FEATURE:
<223> OTHER INFORMATION: pNOP28463

<400> SEQUENCE: 247

Cys Thr Val Phe Asp Trp Pro Val Met Thr Ala Val Gly His Leu Pro
1               5                   10                  15

Pro Pro Cys Val Cys Ala Cys Val Glu Asn Leu Glu Thr Asp Cys Cys
                20                  25                  30

Pro Leu Phe Met Gln Asn His Leu Arg Ile Gln Phe Thr Leu Cys Cys
            35                  40                  45

Pro Ala Ser Pro Leu Gly Lys Ser Leu Ser Cys Phe Ser Leu Leu Leu
        50                  55                  60

Pro Pro Pro Leu Pro Pro Ser Pro His Ala Phe Leu Phe Leu Val Leu
65                  70                  75                  80

Thr Leu Leu Pro Ser Gly Pro Tyr Pro Thr Leu Phe Glu Lys Thr Lys
                85                  90                  95

Leu Cys Leu His Arg Arg Leu Phe Leu Phe
            100                 105

<210> SEQ ID NO 248
<211> LENGTH: 30
<212> TYPE: PRT
<213> ORGANISM: Artificial Sequence
<220> FEATURE:
<223> OTHER INFORMATION: pNOP286473

<400> SEQUENCE: 248

Leu Pro Ala Pro Thr Lys His Ala Glu Ser His Ser Ser Gly Ile Gln
1               5                   10                  15

Pro Cys Ser Pro Ala Pro Ala Asn Gly Glu Pro His Leu Ser
                20                  25                  30

<210> SEQ ID NO 249
<211> LENGTH: 30
<212> TYPE: PRT
<213> ORGANISM: Artificial Sequence
<220> FEATURE:
<223> OTHER INFORMATION: pNOP289760

<400> SEQUENCE: 249

Arg Thr Ala Leu Pro Pro His Ser Ser Ser Ala Arg Pro Ala Ser
1               5                   10                  15

Ser Thr Cys Arg Thr His Pro Leu Ser Gln Leu Val Trp Thr
                20                  25                  30

<210> SEQ ID NO 250
<211> LENGTH: 27
<212> TYPE: PRT
<213> ORGANISM: Artificial Sequence
<220> FEATURE:
<223> OTHER INFORMATION: pNOP325333

<400> SEQUENCE: 250

Pro Leu Gln Ser Cys Cys Arg Pro Trp Ala Arg Lys Cys Gly Asp Gly
1               5                   10                  15

Thr Thr Thr Ala Leu Ser Leu Trp Arg Ser Leu
            20                  25

<210> SEQ ID NO 251
<211> LENGTH: 27
<212> TYPE: PRT
<213> ORGANISM: Artificial Sequence
<220> FEATURE:
<223> OTHER INFORMATION: pNOP326245

<400> SEQUENCE: 251

Gln Gln His His Asp Leu Gln Pro Gln Ser Ala Pro Arg Val Ala Arg
1               5                   10                  15

Ala Pro Cys Arg Ile Phe Pro Thr Met Pro Asp
            20                  25

<210> SEQ ID NO 252
<211> LENGTH: 27
<212> TYPE: PRT
<213> ORGANISM: Artificial Sequence
<220> FEATURE:
<223> OTHER INFORMATION: pNOP329083

<400> SEQUENCE: 252

Thr Gly Lys Pro Lys Lys Leu Leu Ser Pro Cys Met Leu Leu Pro Thr
1               5                   10                  15

Leu Ser Lys Thr Gly Arg Gln Ala Thr Pro Ile
            20                  25

<210> SEQ ID NO 253
<211> LENGTH: 26
<212> TYPE: PRT
<213> ORGANISM: Artificial Sequence
<220> FEATURE:
<223> OTHER INFORMATION: pNOP342491

<400> SEQUENCE: 253

Ser Thr Leu Arg Asp Pro His Ile Pro Trp Val Glu Pro Trp Pro Thr
1               5                   10                  15

Ile Leu Gln Gly Trp Gln Pro Ala Gln Arg
            20                  25

<210> SEQ ID NO 254
<211> LENGTH: 25
<212> TYPE: PRT
<213> ORGANISM: Artificial Sequence
<220> FEATURE:
<223> OTHER INFORMATION: pNOP345053

<400> SEQUENCE: 254

Ala Gly Ala Ile Gln Leu Gly Ser Arg Met Pro Leu Met Met Glu Val
1               5                   10                  15

Thr Pro His Ser Arg Ser Gly Ile Pro
            20                  25

<210> SEQ ID NO 255
<211> LENGTH: 25
<212> TYPE: PRT
<213> ORGANISM: Artificial Sequence
<220> FEATURE:
<223> OTHER INFORMATION: pNOP357957

<400> SEQUENCE: 255

Thr Pro Trp Val Pro Glu Val Lys Cys Met Asp Ser Leu Ala Ser His
1               5                   10                  15

Leu Met Ala His Ser Leu Gln Gly Gly
            20                  25

<210> SEQ ID NO 256
<211> LENGTH: 24
<212> TYPE: PRT
<213> ORGANISM: Artificial Sequence
<220> FEATURE:
<223> OTHER INFORMATION: pNOP363287

<400> SEQUENCE: 256

Gly Lys His Glu His Trp Gly Pro Thr Ala Glu Ser His Ala Phe Gln
1               5                   10                  15

Pro Arg Leu Gly Asp Val Phe Ser
            20

<210> SEQ ID NO 257
<211> LENGTH: 24
<212> TYPE: PRT
<213> ORGANISM: Artificial Sequence
<220> FEATURE:
<223> OTHER INFORMATION: pNOP366177

<400> SEQUENCE: 257

Leu Ala Ser His Asp Ser Arg Gly Thr Pro Pro Pro Val Cys Val
1               5                   10                  15

Cys Val Cys Gly Glu Leu Arg Asn
            20

<210> SEQ ID NO 258
<211> LENGTH: 23
<212> TYPE: PRT
<213> ORGANISM: Artificial Sequence
<220> FEATURE:
<223> OTHER INFORMATION: pNOP382230

<400> SEQUENCE: 258

Leu Cys Gln Gln Ala Glu His Gly Leu Cys Pro Pro Gly Pro Arg Leu
1               5                   10                  15

Ser Trp Arg Glu Pro Asn Arg
            20

<210> SEQ ID NO 259
<211> LENGTH: 23
<212> TYPE: PRT
<213> ORGANISM: Artificial Sequence
<220> FEATURE:
<223> OTHER INFORMATION: pNOP391130

<400> SEQUENCE: 259

Trp Pro Arg Arg Ser Pro Pro Pro Pro Ala Ala Trp Ala Thr Arg
1               5                   10                  15

Arg Arg Arg Arg Pro Arg Ser
            20

<210> SEQ ID NO 260
<211> LENGTH: 93
<212> TYPE: PRT
<213> ORGANISM: Artificial Sequence
<220> FEATURE:
<223> OTHER INFORMATION: pNOP39264

<400> SEQUENCE: 260

Ala Leu Gly Pro His Ser Arg Ile Ser Cys Leu Pro Thr Gln Thr Arg
1               5                   10                  15

Gly Cys Ile Leu Leu Ala Ala Thr Pro Arg Ser Ser Ser Ser Ser Ser

```
                    20                  25                  30
Ser Asn Asp Met Ile Pro Met Ala Ile Ser Ser Pro Pro Lys Ala Pro
                35                  40                  45

Leu Leu Ala Ala Pro Ser Pro Ala Ser Arg Leu Gln Cys Ile Asn Ser
            50                  55                  60

Asn Ser Arg Tyr Pro Ala Leu Leu Pro Cys Pro Gly Gln Trp Arg Thr
65                  70                  75                  80

Ala Pro Leu Leu Ala Ser Leu His Ser Cys Thr Leu Gly
                85                  90
```

<210> SEQ ID NO 261
<211> LENGTH: 22
<212> TYPE: PRT
<213> ORGANISM: Artificial Sequence
<220> FEATURE:
<223> OTHER INFORMATION: pNOP399373

<400> SEQUENCE: 261

```
Leu His Ile Pro Glu Ala Glu Phe His Asp Ser Lys Pro Trp Val Ser
1               5                   10                  15

Ala Gln Tyr Glu Tyr Leu
            20
```

<210> SEQ ID NO 262
<211> LENGTH: 19
<212> TYPE: PRT
<213> ORGANISM: Artificial Sequence
<220> FEATURE:
<223> OTHER INFORMATION: pNOP460168

<400> SEQUENCE: 262

```
Gln Ile Cys Leu Leu Trp Val Gly Asn Leu Trp Thr Ser Ile Ala Ser
1               5                   10                  15

Met Cys Leu
```

<210> SEQ ID NO 263
<211> LENGTH: 18
<212> TYPE: PRT
<213> ORGANISM: Artificial Sequence
<220> FEATURE:
<223> OTHER INFORMATION: pNOP471545

<400> SEQUENCE: 263

```
Phe Gly Gly Ile Ser Pro Ser His Leu Ala Leu Leu Lys Pro His Ser
1               5                   10                  15

Leu Cys
```

<210> SEQ ID NO 264
<211> LENGTH: 18
<212> TYPE: PRT
<213> ORGANISM: Artificial Sequence
<220> FEATURE:
<223> OTHER INFORMATION: pNOP472965

<400> SEQUENCE: 264

```
Gly Arg Ala Arg Arg Tyr Glu Pro Glu Pro Ser Val Lys Thr Leu Gln
1               5                   10                  15

Leu Ala
```

<210> SEQ ID NO 265
<211> LENGTH: 17
<212> TYPE: PRT

```
<213> ORGANISM: Artificial Sequence
<220> FEATURE:
<223> OTHER INFORMATION: pNOP503306

<400> SEQUENCE: 265

Pro Ser Thr Glu Pro Pro Glu His Gln Asp Pro Arg Gly Arg Thr Pro
1               5                   10                  15
Gln

<210> SEQ ID NO 266
<211> LENGTH: 16
<212> TYPE: PRT
<213> ORGANISM: Artificial Sequence
<220> FEATURE:
<223> OTHER INFORMATION: pNOP525902

<400> SEQUENCE: 266

Pro Phe Gln Ala Arg Thr Ser Gln Leu Gln Arg Ile Val Arg Arg Ser
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: pNOP526697

<400> SEQUENCE: 267

Pro Arg Thr Glu Asn Ala Thr Gly Ser Trp Glu Val Gln Gln Gly Val
1               5                   10                  15

<210> SEQ ID NO 268
<211> LENGTH: 16
<212> TYPE: PRT
<213> ORGANISM: Artificial Sequence
<220> FEATURE:
<223> OTHER INFORMATION: pNOP532250

<400> SEQUENCE: 268

Ser Ser Ser His Gly Gly Trp Gly Arg Arg Arg Arg Thr Ser Arg Ser
1               5                   10                  15

<210> SEQ ID NO 269
<211> LENGTH: 16
<212> TYPE: PRT
<213> ORGANISM: Artificial Sequence
<220> FEATURE:
<223> OTHER INFORMATION: pNOP535077

<400> SEQUENCE: 269

Trp Glu Leu Asp Leu Leu Met Asp Lys Gly Leu Ile Val Trp Leu Ala
1               5                   10                  15

<210> SEQ ID NO 270
<211> LENGTH: 15
<212> TYPE: PRT
<213> ORGANISM: Artificial Sequence
<220> FEATURE:
<223> OTHER INFORMATION: pNOP536697

<400> SEQUENCE: 270

Ala Phe Ser Gln Asp Pro Pro Ala Cys Leu Ile Tyr Leu Val Gln
1               5                   10                  15

<210> SEQ ID NO 271
<211> LENGTH: 15
```

```
<212> TYPE: PRT
<213> ORGANISM: Artificial Sequence
<220> FEATURE:
<223> OTHER INFORMATION: pNOP539995

<400> SEQUENCE: 271

Glu Phe Arg Gly His Gln Gly Glu Gln Gln Val Ser Ile Trp His
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: pNOP561120

<400> SEQUENCE: 272

Trp Gly Ala Cys Pro Met Ser Gln Ile Arg Ile Leu Met Ala Ala
1               5                   10                  15

<210> SEQ ID NO 273
<211> LENGTH: 14
<212> TYPE: PRT
<213> ORGANISM: Artificial Sequence
<220> FEATURE:
<223> OTHER INFORMATION: pNOP564630

<400> SEQUENCE: 273

Cys Pro Ser Ser Leu Val Ser Trp Gln Arg Ala His Gly His
1               5                   10

<210> SEQ ID NO 274
<211> LENGTH: 14
<212> TYPE: PRT
<213> ORGANISM: Artificial Sequence
<220> FEATURE:
<223> OTHER INFORMATION: pNOP568326

<400> SEQUENCE: 274

Gly Asp Ser Leu Phe Arg Gln Gly Gln Ala Ser Phe Arg Glu
1               5                   10

<210> SEQ ID NO 275
<211> LENGTH: 79
<212> TYPE: PRT
<213> ORGANISM: Artificial Sequence
<220> FEATURE:
<223> OTHER INFORMATION: pNOP57388

<400> SEQUENCE: 275

Ala His Gln Gly Phe Pro Ala Ala Lys Glu Ser Arg Val Ile Gln Leu
1               5                   10                  15

Ser Leu Leu Ser Leu Leu Ile Pro Pro Leu Thr Cys Leu Ala Ser Glu
            20                  25                  30

Ala Leu Pro Arg Pro Leu Leu Ala Leu Pro Pro Val Leu Leu Ser Leu
        35                  40                  45

Ala Gln Asp His Ser Arg Leu Leu Gln Cys Gln Ala Thr Arg Cys His
    50                  55                  60

Leu Gly His Pro Val Ala Ser Arg Thr Ala Ser Cys Ile Leu Pro
65                  70                  75

<210> SEQ ID NO 276
<211> LENGTH: 14
<212> TYPE: PRT
<213> ORGANISM: Artificial Sequence
```

```
<220> FEATURE:
<223> OTHER INFORMATION: pNOP578746

<400> SEQUENCE: 276

Pro Leu Pro Pro Ala Ala Ala Ala Ala Ala Ala Thr Thr
1               5                   10

<210> SEQ ID NO 277
<211> LENGTH: 14
<212> TYPE: PRT
<213> ORGANISM: Artificial Sequence
<220> FEATURE:
<223> OTHER INFORMATION: pNOP580855

<400> SEQUENCE: 277

Gln Trp Pro Ala Ala Leu Ala Asp Trp Trp Gly Gly His His
1               5                   10

<210> SEQ ID NO 278
<211> LENGTH: 14
<212> TYPE: PRT
<213> ORGANISM: Artificial Sequence
<220> FEATURE:
<223> OTHER INFORMATION: pNOP583798

<400> SEQUENCE: 278

Ser Cys Cys Thr Thr Ser Thr Gln Asn Gly Ser Arg His His
1               5                   10

<210> SEQ ID NO 279
<211> LENGTH: 14
<212> TYPE: PRT
<213> ORGANISM: Artificial Sequence
<220> FEATURE:
<223> OTHER INFORMATION: pNOP584557

<400> SEQUENCE: 279

Ser Leu His Val Leu Arg Ala Gly Pro Gln Arg Arg Asp Gly
1               5                   10

<210> SEQ ID NO 280
<211> LENGTH: 13
<212> TYPE: PRT
<213> ORGANISM: Artificial Sequence
<220> FEATURE:
<223> OTHER INFORMATION: pNOP596649

<400> SEQUENCE: 280

Gly Glu Gly His Gly His Asp Lys Ser Ala Cys Cys Gly
1               5                   10

<210> SEQ ID NO 281
<211> LENGTH: 13
<212> TYPE: PRT
<213> ORGANISM: Artificial Sequence
<220> FEATURE:
<223> OTHER INFORMATION: pNOP600191

<400> SEQUENCE: 281

Ile Pro Ser Thr Ser Cys Cys Met Met Thr Thr Ala Ser
1               5                   10

<210> SEQ ID NO 282
<211> LENGTH: 13
<212> TYPE: PRT
<213> ORGANISM: Artificial Sequence
<220> FEATURE:
```

```
<223> OTHER INFORMATION: pNOP600818

<400> SEQUENCE: 282

Lys Cys Arg Arg Gln Val Pro Gln Tyr Leu Pro Arg Thr
1               5                   10

<210> SEQ ID NO 283
<211> LENGTH: 13
<212> TYPE: PRT
<213> ORGANISM: Artificial Sequence
<220> FEATURE:
<223> OTHER INFORMATION: pNOP616167

<400> SEQUENCE: 283

Thr Gly Arg Arg Pro Ser Pro Arg His Leu Cys Ser Cys
1               5                   10

<210> SEQ ID NO 284
<211> LENGTH: 13
<212> TYPE: PRT
<213> ORGANISM: Artificial Sequence
<220> FEATURE:
<223> OTHER INFORMATION: pNOP616285

<400> SEQUENCE: 284

Thr His Trp Phe His Lys Ser Phe Val Met Tyr Cys Phe
1               5                   10

<210> SEQ ID NO 285
<211> LENGTH: 12
<212> TYPE: PRT
<213> ORGANISM: Artificial Sequence
<220> FEATURE:
<223> OTHER INFORMATION: pNOP624639

<400> SEQUENCE: 285

Glu Glu Asp Val Gly Gly Pro Leu Ser Gly Leu His
1               5                   10

<210> SEQ ID NO 286
<211> LENGTH: 12
<212> TYPE: PRT
<213> ORGANISM: Artificial Sequence
<220> FEATURE:
<223> OTHER INFORMATION: pNOP628397

<400> SEQUENCE: 286

Gly Ser Leu Trp Gln His Glu Glu Ser Ser Arg Glu
1               5                   10

<210> SEQ ID NO 287
<211> LENGTH: 12
<212> TYPE: PRT
<213> ORGANISM: Artificial Sequence
<220> FEATURE:
<223> OTHER INFORMATION: pNOP643975

<400> SEQUENCE: 287

Arg Thr Arg Thr Gly Thr Arg Ala Leu Gly Pro Pro
1               5                   10

<210> SEQ ID NO 288
<211> LENGTH: 12
<212> TYPE: PRT
<213> ORGANISM: Artificial Sequence
<220> FEATURE:
<223> OTHER INFORMATION: pNOP650952
```

```
<400> SEQUENCE: 288

Trp Thr Ser Arg Lys Thr Asp His Ser His Tyr Gly
1               5                   10

<210> SEQ ID NO 289
<211> LENGTH: 11
<212> TYPE: PRT
<213> ORGANISM: Artificial Sequence
<220> FEATURE:
<223> OTHER INFORMATION: pNOP658966

<400> SEQUENCE: 289

Gly Cys Ser Ala Arg His His Val Ala Gly Ala
1               5                   10

<210> SEQ ID NO 290
<211> LENGTH: 11
<212> TYPE: PRT
<213> ORGANISM: Artificial Sequence
<220> FEATURE:
<223> OTHER INFORMATION: pNOP667279

<400> SEQUENCE: 290

Leu Met Lys Arg Arg Arg Asn Arg Thr Lys Gly
1               5                   10

<210> SEQ ID NO 291
<211> LENGTH: 10
<212> TYPE: PRT
<213> ORGANISM: Artificial Sequence
<220> FEATURE:
<223> OTHER INFORMATION: pNOP700714

<400> SEQUENCE: 291

Lys Thr Leu Glu Pro Arg Arg His Gly Gly
1               5                   10

<210> SEQ ID NO 292
<211> LENGTH: 10
<212> TYPE: PRT
<213> ORGANISM: Artificial Sequence
<220> FEATURE:
<223> OTHER INFORMATION: pNOP704301

<400> SEQUENCE: 292

Met Thr Ser Pro Trp Gly Gln Lys Glu Leu
1               5                   10

<210> SEQ ID NO 293
<211> LENGTH: 10
<212> TYPE: PRT
<213> ORGANISM: Artificial Sequence
<220> FEATURE:
<223> OTHER INFORMATION: pNOP708028

<400> SEQUENCE: 293

Pro Ser Thr Ser Val Ser Ser Gln Gly Cys
1               5                   10

<210> SEQ ID NO 294
<211> LENGTH: 10
<212> TYPE: PRT
<213> ORGANISM: Artificial Sequence
<220> FEATURE:
<223> OTHER INFORMATION: pNOP708425
```

<400> SEQUENCE: 294

Gln Ala Ser Ser Lys Asp Arg Thr Glu Glu
1               5                   10

<210> SEQ ID NO 295
<211> LENGTH: 10
<212> TYPE: PRT
<213> ORGANISM: Artificial Sequence
<220> FEATURE:
<223> OTHER INFORMATION: pNOP718154

<400> SEQUENCE: 295

Thr Arg Arg Gly Arg Arg Arg Gly Ser Ser
1               5                   10

<210> SEQ ID NO 296
<211> LENGTH: 69
<212> TYPE: PRT
<213> ORGANISM: Artificial Sequence
<220> FEATURE:
<223> OTHER INFORMATION: pNOP76377

<400> SEQUENCE: 296

Phe Gln Glu Val Pro Ala Gln Asp Pro Ala Ser Leu Ser Cys Gly Ile
1               5                   10                  15

Arg Ile Tyr Ala Gly Ala Pro Asp Ser Pro Val Asn Gln Gln Phe His
            20                  25                  30

Gly Arg Arg Arg Leu Lys Ala Thr Asn Ser Ser Ile His Thr Thr
        35                  40                  45

Gln Ser Asp Pro Pro Ile Ala Arg His Glu Gln Glu Gln Phe Ser Trp
    50                  55                  60

Asp Pro Gly Cys Leu
65

<210> SEQ ID NO 297
<211> LENGTH: 63
<212> TYPE: PRT
<213> ORGANISM: Artificial Sequence
<220> FEATURE:
<223> OTHER INFORMATION: pNOP91542

<400> SEQUENCE: 297

His Gly Gln Tyr Ala Thr Ser Gly Trp Val Arg Asp Val Ser Pro Thr
1               5                   10                  15

Arg Gly His Glu Pro Glu Asn Pro Arg Asn Cys Cys Arg His Ala Cys
            20                  25                  30

Cys Cys Gln Leu Tyr Pro Lys Gln Ala Ala Arg Leu Pro Gln Tyr Glu
        35                  40                  45

Ser Arg Gly His Asp Gly Asn Trp Thr Ser Leu Trp Thr Arg Asp
    50                  55                  60

<210> SEQ ID NO 298
<211> LENGTH: 35
<212> TYPE: PRT
<213> ORGANISM: Artificial Sequence
<220> FEATURE:
<223> OTHER INFORMATION: pNOP234091

<400> SEQUENCE: 298

Gly Pro Arg Ser His Pro Leu Pro Arg Leu Trp His Leu Leu Leu Gln
1               5                   10                  15

Val Thr Gln Thr Ser Phe Ala Leu Ala Pro Thr Leu Thr His Met Leu

Ser Pro His
        35

<210> SEQ ID NO 299
<211> LENGTH: 494
<212> TYPE: PRT
<213> ORGANISM: Artificial Sequence
<220> FEATURE:
<223> OTHER INFORMATION: pNOP134

<400> SEQUENCE: 299

Thr Arg Arg Cys His Cys Cys Pro His Leu Arg Ser His Pro Cys Pro
1               5                   10                  15

His His Leu Arg Asn His Pro Arg Pro His His Leu Arg His His Ala
            20                  25                  30

Cys His His His Leu Arg Asn Cys Pro His Pro His Phe Leu Arg His
        35                  40                  45

Cys Thr Cys Pro Gly Arg Trp Arg Asn Arg Pro Ser Leu Arg Arg Leu
    50                  55                  60

Arg Ser Leu Leu Cys Leu Pro His Leu Asn His His Leu Phe Leu His
65                  70                  75                  80

Trp Arg Ser Arg Pro Cys Leu His Arg Lys Ser His Pro His Leu Leu
                85                  90                  95

His Leu Arg Arg Leu Tyr Pro His His Leu Lys His Arg Pro Cys Pro
            100                 105                 110

His His Leu Lys Asn Leu Leu Cys Pro Arg His Leu Arg Asn Cys Pro
        115                 120                 125

Leu Pro Arg His Leu Lys His Leu Ala Cys Leu His His Leu Arg Ser
    130                 135                 140

His Pro Cys Pro Leu His Leu Lys Ser His Pro Cys Leu His His Arg
145                 150                 155                 160

Arg His Leu Val Cys Ser His His Leu Lys Ser Leu Leu Cys Pro Leu
                165                 170                 175

His Leu Arg Ser Leu Pro Phe Pro His His Leu Arg His His Ala Cys
            180                 185                 190

Pro His His Leu Arg Thr Arg Leu Cys Pro His His Leu Lys Asn His
        195                 200                 205

Leu Cys Pro Pro His Leu Arg Tyr Arg Ala Tyr Pro Pro Cys Leu Trp
    210                 215                 220

Cys His Ala Cys Leu His Arg Leu Arg Asn Leu Pro Cys Pro His Arg
225                 230                 235                 240

Leu Arg Ser Leu Pro Arg Pro Leu His Leu Arg Leu His Ala Ser Pro
                245                 250                 255

His His Leu Arg Thr Pro Pro His Pro His His Leu Arg Thr His Leu
            260                 265                 270

Leu Pro His His Arg Arg Thr Arg Ser Cys Pro Cys Arg Trp Arg Ser
        275                 280                 285

His Pro Cys Cys His Tyr Leu Arg Ser Arg Asn Ser Ala Pro Gly Pro
    290                 295                 300

Arg Gly Arg Thr Cys His Pro Gly Leu Arg Ser Arg Thr Cys Pro Pro
305                 310                 315                 320

Gly Leu Arg Ser His Thr Tyr Leu Arg Arg Leu Arg Ser His Thr Cys
                325                 330                 335

Pro Pro Ser Leu Arg Ser His Ala Tyr Ala Leu Cys Leu Arg Ser His

```
                340                 345                 350
Thr Cys Pro Pro Arg Leu Arg Asp His Ile Cys Pro Leu Ser Leu Arg
            355                 360                 365

Asn Cys Thr Cys Pro Pro Arg Leu Arg Ser Arg Thr Cys Leu Leu Cys
            370                 375                 380

Leu Arg Ser His Ala Cys Pro Pro Asn Leu Arg Asn His Thr Cys Pro
385                 390                 395                 400

Pro Ser Leu Arg Ser His Ala Cys Pro Pro Gly Leu Arg Asn Arg Ile
                405                 410                 415

Cys Pro Leu Ser Leu Arg Ser His Pro Cys Pro Leu Gly Leu Lys Ser
            420                 425                 430

Pro Leu Arg Ser Gln Ala Asn Ala Leu His Leu Arg Ser Cys Pro Cys
            435                 440                 445

Ser Leu Pro Leu Gly Asn His Pro Tyr Leu Pro Cys Leu Glu Ser Gln
            450                 455                 460

Pro Cys Leu Ser Leu Gly Asn His Leu Cys Pro Leu Cys Pro Arg Ser
465                 470                 475                 480

Cys Arg Cys Pro His Leu Gly Ser His Pro Cys Arg Leu Ser
                485                 490

<210> SEQ ID NO 300
<211> LENGTH: 117
<212> TYPE: PRT
<213> ORGANISM: Artificial Sequence
<220> FEATURE:
<223> OTHER INFORMATION: pNOP21934

<400> SEQUENCE: 300

Ala Arg Val Met Pro Val Pro Val Phe Leu Ala Gln Ser Pro Ser Trp
1               5                   10                  15

Ala Leu Gln Thr Arg Arg Gly Val Ala Pro Cys Pro Trp Ser Trp Gly
            20                  25                  30

Ser Leu Arg Met Leu Val Gln Pro Glu Met Arg Ala Pro Tyr Gly Ser
        35                  40                  45

Val Leu Thr His Cys Gln Arg Leu Met Thr His Tyr Cys Ala Met Leu
    50                  55                  60

Gly Gln Leu Ser Ala Glu Ala Lys Leu Arg Gly Arg Gly Gly
65                  70                  75                  80

Ala Ala Pro Gln Pro Val Pro Ala Ser Asn Arg Val Ala Ala Val
            85                  90                  95

Ser Gln Glu Asp Ala Gly Leu Val Glu Glu Pro Met Gly Asp Val Val
            100                 105                 110

Glu Asp Gly Pro Gly
        115

<210> SEQ ID NO 301
<211> LENGTH: 57
<212> TYPE: PRT
<213> ORGANISM: Artificial Sequence
<220> FEATURE:
<223> OTHER INFORMATION: pNOP111349

<400> SEQUENCE: 301

Pro Thr Leu Arg Trp Gly Leu Gly Gly Ser Gln Gln Pro Cys Pro Arg
1               5                   10                  15

Gly Gln Gln Val Ser Ser Met Pro Arg Ser Gln Val Gly Ser Pro Pro
            20                  25                  30
```

```
Ile Leu Ser Gly Pro Leu Gly Arg Val His Leu Trp Ala Pro Pro Leu
        35                  40                  45

Pro Cys Val Ser Leu Ser Leu Arg Gln
    50                  55

<210> SEQ ID NO 302
<211> LENGTH: 44
<212> TYPE: PRT
<213> ORGANISM: Artificial Sequence
<220> FEATURE:
<223> OTHER INFORMATION: pNOP170800

<400> SEQUENCE: 302

Asn Arg Leu Met Arg Arg Leu Asn Gly Arg Pro Cys Cys Gly Gly Trp
1               5                   10                  15

Ser Gln Asp Pro Trp Ala Leu Arg Ser Ala Leu Pro Leu Leu Leu Met
            20                  25                  30

Pro Leu Asn Pro Ala Trp His Leu Cys Ser Leu Arg
        35                  40

<210> SEQ ID NO 303
<211> LENGTH: 79
<212> TYPE: PRT
<213> ORGANISM: Artificial Sequence
<220> FEATURE:
<223> OTHER INFORMATION: pNOP58594

<400> SEQUENCE: 303

Ser Lys Ser Leu Ala Ser Phe Ser Gly Glu Asn Gly Cys Thr Cys Ser
1               5                   10                  15

Val Trp Gly Ala Leu Cys Ser Thr Pro Ser Asp Ser Cys Cys Leu Thr
            20                  25                  30

Arg Trp Leu Thr Phe Ile Val Pro Leu Pro Ser Ile Pro Trp Ala Thr
        35                  40                  45

Arg Pro Arg Ala Ser Ile Gly Ala Ser Ala Pro Thr Ile Val Ala Ala
    50                  55                  60

Ala Ile Ala Val Leu Leu Val Arg Thr Thr Gly Gly Arg Ser Leu
65                  70                  75

<210> SEQ ID NO 304
<211> LENGTH: 128
<212> TYPE: PRT
<213> ORGANISM: Artificial Sequence
<220> FEATURE:
<223> OTHER INFORMATION: pNOP17440

<400> SEQUENCE: 304

Trp Thr Ala Arg Ser Trp Leu Val Arg Ile Lys Ile Gln Asn Arg Gln
1               5                   10                  15

Leu Met Asp Leu Gln Leu Leu Arg Thr Gln Val Pro Leu Ser Gln Thr
            20                  25                  30

Cys Pro Thr His Met Trp Glu Arg Ser Leu Ser Leu Val Leu Gly Val
        35                  40                  45

Pro Gly Phe Arg Arg Leu Leu Arg Thr Ala Val Gly Val Arg Cys Gly
    50                  55                  60

Val Val Leu Ser Val Thr Ala Gly Ser Pro Val Tyr Thr Gly Ser Gly
65                  70                  75                  80

Ser Tyr Gly Ala Leu Ser Cys His Leu Ile Gly Pro Gly Val Gln Trp
                85                  90                  95

Cys Pro Leu Gly Gly Ala Gln Gly Pro Met Arg Gln Cys Cys Pro Val
```

```
                    100                 105                 110
Arg Thr Tyr His Arg Leu Val Ser Leu Arg Ala Leu His Leu Pro Thr
        115                 120                 125
```

<210> SEQ ID NO 305
<211> LENGTH: 55
<212> TYPE: PRT
<213> ORGANISM: Artificial Sequence
<220> FEATURE:
<223> OTHER INFORMATION: pNOP118816

<400> SEQUENCE: 305

```
Pro Thr Gly Pro Thr Ser Pro His Ser Pro Ala Ala Arg Gly Thr Gly
1               5                   10                  15
Gln Pro Ala Pro Arg Cys Cys Pro His His Phe His Trp Gln Pro His
            20                  25                  30
Tyr Pro Arg Arg Leu Val Tyr Leu Cys Gly Arg Val Pro Glu Ala Ala
        35                  40                  45
Gly Gly Leu Gly Ala Trp Pro
    50                  55
```

<210> SEQ ID NO 306
<211> LENGTH: 49
<212> TYPE: PRT
<213> ORGANISM: Artificial Sequence
<220> FEATURE:
<223> OTHER INFORMATION: pNOP144483

<400> SEQUENCE: 306

```
Pro Val Arg Leu Thr Asp Arg Pro Tyr Ile Ser Ala Phe Pro Arg Ser
1               5                   10                  15
Gln Gly His Trp Ala Ala Arg Pro Pro Leu Leu Pro Pro Pro Phe Ser
            20                  25                  30
Leu Ala Ala Pro Leu Pro Pro Ala Cys Leu Pro Leu Arg Thr Gly
        35                  40                  45
Ser
```

<210> SEQ ID NO 307
<211> LENGTH: 41
<212> TYPE: PRT
<213> ORGANISM: Artificial Sequence
<220> FEATURE:
<223> OTHER INFORMATION: pNOP189145

<400> SEQUENCE: 307

```
Leu Leu Gly Pro Asn Leu Arg Pro Leu Arg Ala Ala Val Leu Cys Pro
1               5                   10                  15
Leu Ala His Cys Pro Pro Thr Leu Ser Pro Glu Cys Leu Pro Val Leu
            20                  25                  30
Ser Pro Ser Pro Ala Pro Ser Leu His
        35                  40
```

<210> SEQ ID NO 308
<211> LENGTH: 22
<212> TYPE: PRT
<213> ORGANISM: Artificial Sequence
<220> FEATURE:
<223> OTHER INFORMATION: pNOP408074

<400> SEQUENCE: 308

```
Val Thr Arg Arg His His Pro Arg Arg Cys Pro Pro Pro His Pro His
1               5                   10                  15
```

Arg Cys Ser Arg Arg Trp
            20

<210> SEQ ID NO 309
<211> LENGTH: 21
<212> TYPE: PRT
<213> ORGANISM: Artificial Sequence
<220> FEATURE:
<223> OTHER INFORMATION: pNOP413106

<400> SEQUENCE: 309

Gly Glu Ala Lys Leu Pro Ser Pro Cys Ser Arg Pro His Leu Leu Gly
1               5                   10                  15

Ser Pro Gly Arg Pro
            20

<210> SEQ ID NO 310
<211> LENGTH: 148
<212> TYPE: PRT
<213> ORGANISM: Artificial Sequence
<220> FEATURE:
<223> OTHER INFORMATION: pNOP11179

<400> SEQUENCE: 310

Ala Pro Cys Gln Gly Pro Lys Trp Ala Pro Gln Phe Cys Pro Val
1               5                   10                  15

Pro Trp Asp Gly Cys Ile Cys Gly His Pro Leu Ser His Ala Phe His
            20                  25                  30

Phe Pro Ser Gly Ser Arg Gly Ala Phe Pro Lys Ala Pro Cys Pro Ser
        35                  40                  45

Ala Trp Ser Pro Ala Thr Pro Trp Asp Gln Gln Pro Phe Trp Ala Arg
    50                  55                  60

Pro His Leu Gly Gln Ala Ser Lys His Lys Leu His Ser Ser His Arg
65                  70                  75                  80

Glu Leu Pro Pro Ile Gly Gln Pro Pro Gly Ala Gln Gln Arg Val His
                85                  90                  95

Arg Gly Glu Leu Trp Ala Val Pro Thr Thr Pro Ser Val Gly Ser Ala
            100                 105                 110

Thr Thr Cys Thr Arg Arg Ile Pro Pro Leu Pro Val Pro Trp Ser Leu
        115                 120                 125

Thr Ala Ile Arg His His Leu Ser Cys Arg Lys Ala Arg Pro Arg
    130                 135                 140

Asp Trp Asn Gly
145

<210> SEQ ID NO 311
<211> LENGTH: 52
<212> TYPE: PRT
<213> ORGANISM: Artificial Sequence
<220> FEATURE:
<223> OTHER INFORMATION: pNOP129784

<400> SEQUENCE: 311

Lys His Cys Ser Cys Tyr Ala Gln Ser Thr Val Arg Gly Leu His Ile
1               5                   10                  15

Trp Arg Arg Leu Ala Val Gln Cys Val Arg Gly Gln Gly Ser Cys Val
            20                  25                  30

Thr Cys Ser Ser Val Pro Ala Val Gly Ile Thr Ile Thr Gly Pro Ala
        35                  40                  45

```
Trp Thr Leu Leu
    50

<210> SEQ ID NO 312
<211> LENGTH: 50
<212> TYPE: PRT
<213> ORGANISM: Artificial Sequence
<220> FEATURE:
<223> OTHER INFORMATION: pNOP139704

<400> SEQUENCE: 312

Pro Ser Pro Gly Cys Ser Val Pro Ser Trp His Ser Arg Val Arg
1               5                   10                  15

Ala Leu Trp Asp Thr Gly Trp Ser Gln Pro Ser Ser Ser Ser Asn
            20                  25                  30

Asn Ser Thr Asn Ser Lys Gly Pro Trp Gln Gly Cys Pro Ile Phe Ser
        35                  40                  45

Arg Val
    50

<210> SEQ ID NO 313
<211> LENGTH: 49
<212> TYPE: PRT
<213> ORGANISM: Artificial Sequence
<220> FEATURE:
<223> OTHER INFORMATION: pNOP143520

<400> SEQUENCE: 313

Leu Cys Leu Leu Pro Ala Leu Arg Gly Lys Ala Cys Gly Ala Cys Cys
1               5                   10                  15

Thr Ser Arg Ala Gly Ala His Glu Gly Glu Arg Ala Arg Ala Pro Val
            20                  25                  30

Leu Ser Leu Arg Arg Cys Val Ala Asp Arg Asn Trp His Gly Leu Ala
        35                  40                  45

Ala

<210> SEQ ID NO 314
<211> LENGTH: 131
<212> TYPE: PRT
<213> ORGANISM: Artificial Sequence
<220> FEATURE:
<223> OTHER INFORMATION: pNOP16127

<400> SEQUENCE: 314

Lys Ala Ala Val Arg His Cys Arg Gly Pro Phe Phe Lys Val Asp Ser
1               5                   10                  15

Leu Trp Ala Ile Cys Pro Pro Ala Ala Gln Trp Thr Pro Thr Gln Ala
            20                  25                  30

Ser Ala Ser Pro Arg Ser Trp Ile Leu Gly Ser Ala Gly Ala Ser Leu
        35                  40                  45

Ala Arg Asn Pro Val Ser Pro Thr Ala Pro Gly Arg Ala Gln Val Ala
    50                  55                  60

Pro Arg Pro Pro Pro Gln Pro Pro Arg Arg Val Arg Ala Thr
65                  70                  75                  80

Asp Ser Pro Ile Thr Ser Gly Val Phe Ser Ala Gly Arg Arg Met Arg
                85                  90                  95

Ser Trp Ala Ser Cys Pro Pro Ser His Leu Cys Ser Met Pro Thr Leu
            100                 105                 110

Ile Phe Leu Ile Ser Ser Lys Thr Thr Gln Thr Gly Gln Ala Val Ala
        115                 120                 125
```

Asn Lys Ser
    130

<210> SEQ ID NO 315
<211> LENGTH: 42
<212> TYPE: PRT
<213> ORGANISM: Artificial Sequence
<220> FEATURE:
<223> OTHER INFORMATION: pNOP179906

<400> SEQUENCE: 315

Ala Leu Pro Gln Ala Pro Thr Pro Gly Ala Arg Pro Ser Ala Phe Ala
1               5                   10                  15

Gly Pro Leu Trp Thr Gly Pro Cys Leu Ser Pro Gly Ala Pro Leu Pro
            20                  25                  30

His Gly Thr Ala His Leu Ser Pro Leu Ser
        35                  40

<210> SEQ ID NO 316
<211> LENGTH: 41
<212> TYPE: PRT
<213> ORGANISM: Artificial Sequence
<220> FEATURE:
<223> OTHER INFORMATION: pNOP187538

<400> SEQUENCE: 316

Phe Gly Ser Arg Ser Ser Ala Thr Pro Cys Gly Arg Arg Lys Gln
1               5                   10                  15

Leu Gln Gln Leu Gln Glu Gln Trp Gly Leu Gln Ala Ala Gly Val Leu
            20                  25                  30

Ser Pro Ala Ala Leu Pro Leu Ser Ser
        35                  40

<210> SEQ ID NO 317
<211> LENGTH: 121
<212> TYPE: PRT
<213> ORGANISM: Artificial Sequence
<220> FEATURE:
<223> OTHER INFORMATION: pNOP20115

<400> SEQUENCE: 317

Gly Leu Phe Ser Gln Phe Gly Trp Val Pro Thr Ala Ala Phe Pro Gly
1               5                   10                  15

Ser Cys Arg Cys Pro Thr Ala Arg Phe Ala Pro Ala Thr Asp Ala His
            20                  25                  30

Pro Ala Thr Ser Ser Cys Pro Pro Ala Thr Pro Gly Ser Ile His Gly
        35                  40                  45

Tyr Gly Val Gln Ser Arg Ala Tyr Ala Lys Trp Ala Trp Arg Ala
    50                  55                  60

Gly Arg Leu Gly Thr Pro Ala Glu Leu Thr Ala Ser Ala Ile Thr Glu
65                  70                  75                  80

Ala His Gly His His Ala Thr Phe His Val His Glu Ala Ala Ile
                85                  90                  95

Gly Asn Ala Ala Ala Ala Gly Lys Gln Leu Leu Pro Arg Tyr Arg Pro
            100                 105                 110

Gly Gln Ile Cys Cys Arg Arg Tyr His
        115                 120

<210> SEQ ID NO 318
<211> LENGTH: 38

-continued

```
<212> TYPE: PRT
<213> ORGANISM: Artificial Sequence
<220> FEATURE:
<223> OTHER INFORMATION: pNOP209010

<400> SEQUENCE: 318

Glu Pro Trp Gly Arg Gly Arg Gln Ser Phe Arg Ala Pro Ala Leu Ala
1               5                   10                  15

Pro Thr Phe Trp Gly Val Pro Glu Gly Pro Arg Gly Glu Glu Gly Arg
            20                  25                  30

Ala Trp Gly Ile Leu Ser
            35

<210> SEQ ID NO 319
<211> LENGTH: 117
<212> TYPE: PRT
<213> ORGANISM: Artificial Sequence
<220> FEATURE:
<223> OTHER INFORMATION: pNOP22159

<400> SEQUENCE: 319

Pro Cys His His Cys Thr Ser Gly Ala Asn Gly Glu Asp Gly Leu Ala
1               5                   10                  15

Ser Gln Ala Arg Gln Asp Trp Arg Val Leu Ser Pro Gln Met Pro Leu
            20                  25                  30

Ala Leu Met Thr Arg Arg Met Gly Thr Trp Thr Pro Met Ser Cys Ser
            35                  40                  45

Arg Val Lys Val Val Trp Ser Thr Trp Ser Ala Lys Leu Asn Trp Arg
        50                  55                  60

Ala Pro Ser Ala Leu Met Trp Ser Leu Ala Lys Arg Pro Arg Lys
65                  70                  75                  80

Ala Lys Asn Ala Ser Val Asn His Ile Gly Leu Ala Leu Val Val Ser
                85                  90                  95

Trp Cys Asp Ser Gly Asn Pro Thr His Ala Arg Lys Gly Leu Leu
            100                 105                 110

His Arg Arg Arg Cys
        115

<210> SEQ ID NO 320
<211> LENGTH: 34
<212> TYPE: PRT
<213> ORGANISM: Artificial Sequence
<220> FEATURE:
<223> OTHER INFORMATION: pNOP248474

<400> SEQUENCE: 320

Ser Pro Leu Ser Leu Ser Leu Val Ser Arg His Pro Met Gly Ser Thr
1               5                   10                  15

Ala Ile Leu Gly Pro Ala Pro Trp Ala Ser Leu Lys Ala Gln Thr
            20                  25                  30

Thr Gln

<210> SEQ ID NO 321
<211> LENGTH: 33
<212> TYPE: PRT
<213> ORGANISM: Artificial Sequence
<220> FEATURE:
<223> OTHER INFORMATION: pNOP251217

<400> SEQUENCE: 321

Cys Gln Cys Gln Phe Ser Trp Leu Arg Ala Pro Pro Gly Leu Ser Arg
```

```
                1               5                  10                 15
Pro Gly Gly Gly Trp Leu Pro Val His Gly Val Gly Gly Leu Tyr Gly
                20                 25                 30

Cys

<210> SEQ ID NO 322
<211> LENGTH: 32
<212> TYPE: PRT
<213> ORGANISM: Artificial Sequence
<220> FEATURE:
<223> OTHER INFORMATION: pNOP264714

<400> SEQUENCE: 322

Leu His Thr Leu Trp Ala Leu Cys Gln Pro Gly Asp Leu Pro Tyr Leu
1               5                   10                  15
Ser Cys Ser Leu Arg Arg Arg Gly Pro Thr Asn Pro Val Pro Pro Leu
                20                  25                  30

<210> SEQ ID NO 323
<211> LENGTH: 107
<212> TYPE: PRT
<213> ORGANISM: Artificial Sequence
<220> FEATURE:
<223> OTHER INFORMATION: pNOP28077

<400> SEQUENCE: 323

Pro Gln Gly Thr Ser Thr His Arg Ala Ala Pro Trp Gly Pro Ala Ala
1               5                   10                  15
Gly Pro Gln Gly Arg Ala Met Gly Cys Pro His Tyr Ala Leu Arg Arg
                20                  25                  30
Phe Cys His His Leu His Pro Thr Asp Pro Ser Pro Thr Cys Pro Met
            35                  40                  45
Glu Pro His Ser Asp Gln Ala Ser Pro Leu Leu Ser Lys Ser Glu Lys
        50                  55                  60
Thr Gln Gly Leu Glu Trp Val Ala Leu Trp Arg Gln Leu Asn Ser Gln
65                  70                  75                  80
Val Pro Arg Thr Gln Ala Cys Pro Ala Leu Ala Lys Gln Ser Trp Arg
                85                  90                  95
Ser Asn Gly Ser Ala Ser Asp Tyr Glu Ser Cys
            100                 105

<210> SEQ ID NO 324
<211> LENGTH: 105
<212> TYPE: PRT
<213> ORGANISM: Artificial Sequence
<220> FEATURE:
<223> OTHER INFORMATION: pNOP29324

<400> SEQUENCE: 324

Gly Gln Gly Leu Asp Leu Arg Ala His Pro Gly Ser Leu Pro His Gln
1               5                   10                  15
Glu Pro Tyr Leu Gln Asp Gln Ser Leu Ala Leu Ser Ile Pro His Leu
                20                  25                  30
His His Pro Ala Leu Lys Ser Gln Arg Asp Leu His Asn Tyr Leu Pro
            35                  40                  45
Pro Ala Pro Ser Phe Pro Leu Arg Pro Ser Ser Leu Pro Pro Ile Gln
        50                  55                  60
Gly Pro Pro Asn Leu Arg Gly Gln Pro Trp Ser Arg Leu Leu Gly Gly
65                  70                  75                  80
```

-continued

```
Ser His Leu Leu Leu Pro Ser Leu Gln Ile Pro Cys Leu Ala Arg Val
             85                  90                  95

Trp Asp Leu Gly Ile Pro Gln Thr Thr
            100                 105

<210> SEQ ID NO 325
<211> LENGTH: 27
<212> TYPE: PRT
<213> ORGANISM: Artificial Sequence
<220> FEATURE:
<223> OTHER INFORMATION: pNOP324899

<400> SEQUENCE: 325

Pro Ala Asp Thr Thr Leu Val Ala Ala Pro His Pro Thr Pro Ile Gly
1               5                   10                  15

Ala Ala Glu Asp Gly Glu Trp Arg His Pro Ile
            20                  25

<210> SEQ ID NO 326
<211> LENGTH: 24
<212> TYPE: PRT
<213> ORGANISM: Artificial Sequence
<220> FEATURE:
<223> OTHER INFORMATION: pNOP363170

<400> SEQUENCE: 326

Gly Gly Pro Leu Glu Val Gly Arg Cys Pro Leu Ala Leu Thr Thr Ile
1               5                   10                  15

Pro Ser Cys Leu Pro Arg Ile Thr
            20

<210> SEQ ID NO 327
<211> LENGTH: 96
<212> TYPE: PRT
<213> ORGANISM: Artificial Sequence
<220> FEATURE:
<223> OTHER INFORMATION: pNOP36658

<400> SEQUENCE: 327

Gly Pro Tyr Thr Cys Pro Pro Arg Arg Thr Trp Arg Val Leu Leu Gly
1               5                   10                  15

Ser Pro Leu Val Cys Cys Met Val Gly Arg Arg Met Gly Ala Gly Gly
            20                  25                  30

Pro Arg Thr Met Trp Cys Gly Gln Gly His Leu Leu Arg Asp Leu Thr
            35                  40                  45

Ala Leu Leu Pro Leu His Gln Ala Arg Cys Leu His Pro Leu Pro Leu
        50                  55                  60

Thr Trp Met Ser Thr Ala Leu Pro Leu Pro Leu Arg Asp Cys Gln Arg
65                  70                  75                  80

Phe Leu Pro Ile His Glu Asn Thr Ala Ala Met Pro Arg Ala Gln
            85                  90                  95

<210> SEQ ID NO 328
<211> LENGTH: 21
<212> TYPE: PRT
<213> ORGANISM: Artificial Sequence
<220> FEATURE:
<223> OTHER INFORMATION: pNOP412059

<400> SEQUENCE: 328

Glu Leu Leu Ser Leu Ser Pro Leu Ser Gln Ser Pro Gly Arg Ser Asp
1               5                   10                  15
```

```
Tyr Pro Leu Arg Cys
            20

<210> SEQ ID NO 329
<211> LENGTH: 21
<212> TYPE: PRT
<213> ORGANISM: Artificial Sequence
<220> FEATURE:
<223> OTHER INFORMATION: pNOP421083

<400> SEQUENCE: 329

Gln Arg Gly Gln Asn His His Leu Gln Pro Ala Asn Pro Gln Arg
1               5                   10                  15

Arg Gly Ala Asn Leu
            20

<210> SEQ ID NO 330
<211> LENGTH: 90
<212> TYPE: PRT
<213> ORGANISM: Artificial Sequence
<220> FEATURE:
<223> OTHER INFORMATION: pNOP43053

<400> SEQUENCE: 330

Pro Leu Gly Val Trp His Tyr Leu Asp Ser Leu Val Ala Pro Ser Leu
1               5                   10                  15

Ile Gln Leu Trp Pro Asn Ser Ser Asn Ser Asn Ile Leu Val Gly Leu
            20                  25                  30

Asp Pro Trp Leu Ala Leu Gln Gly Ala Ser Ser Leu Ala Thr Leu Leu
        35                  40                  45

Phe Glu Ala Ser Asp Leu Ile Gln Gly Phe Tyr Arg Lys Gly Ser Cys
    50                  55                  60

Ser Cys Ser Ser Asn Val Cys Ser Trp Pro Arg Asn Cys Ser Ser Ser
65                  70                  75                  80

Ser Ser Ser Asn Ser Ser Ser Ser Thr Phe
                85                  90

<210> SEQ ID NO 331
<211> LENGTH: 88
<212> TYPE: PRT
<213> ORGANISM: Artificial Sequence
<220> FEATURE:
<223> OTHER INFORMATION: pNOP44838

<400> SEQUENCE: 331

Cys Cys Ser Arg Ala Gly Val Val Trp Ser Val Leu Cys Val Arg Cys
1               5                   10                  15

Val Ala Arg Pro Pro Thr Pro His Ala Cys Cys Ser Val Met Thr Val
            20                  25                  30

Ile Leu Ala Thr Thr His Thr Ala Trp Thr Pro His Cys Ser Pro Ser
        35                  40                  45

Pro Arg Ala Ala Gly Ser Ala Ser Gly Val Cys Pro Val Cys Ser Val
    50                  55                  60

Gly Leu Leu Pro Leu Ala Ser Thr Val Asn Gly Arg Ile Val Thr His
65                  70                  75                  80

Thr Val Gly Pro Val Pro Ala Trp
                85

<210> SEQ ID NO 332
<211> LENGTH: 18
<212> TYPE: PRT
```

```
<213> ORGANISM: Artificial Sequence
<220> FEATURE:
<223> OTHER INFORMATION: pNOP483870

<400> SEQUENCE: 332

Arg Thr Leu Pro Ala Pro Phe Pro Leu Gly Thr Phe Ser Cys Gln Ser
1               5                   10                  15

Pro Tyr

<210> SEQ ID NO 333
<211> LENGTH: 14
<212> TYPE: PRT
<213> ORGANISM: Artificial Sequence
<220> FEATURE:
<223> OTHER INFORMATION: pNOP580931

<400> SEQUENCE: 333

Arg Ala Gly Gly Ala Pro Gln Gly Cys Cys Leu Cys Pro Gly
1               5                   10

<210> SEQ ID NO 334
<211> LENGTH: 13
<212> TYPE: PRT
<213> ORGANISM: Artificial Sequence
<220> FEATURE:
<223> OTHER INFORMATION: pNOP596763

<400> SEQUENCE: 334

Gly Gly Cys Ile Ser Gly Gly Gly Ser Leu Cys Ser Val
1               5                   10

<210> SEQ ID NO 335
<211> LENGTH: 73
<212> TYPE: PRT
<213> ORGANISM: Artificial Sequence
<220> FEATURE:
<223> OTHER INFORMATION: pNOP68935

<400> SEQUENCE: 335

Pro Thr Leu Pro Ala Thr Ser Thr Ser His Ala Phe Leu Tyr Gly Cys
1               5                   10                  15

Glu Gln Pro Ala Thr Gly Arg Arg Leu Pro Ser Phe Leu Ser Ala Ser
                20                  25                  30

Thr Leu Ser Trp Val Pro Ala Leu Thr Ala Ala Thr Ala Thr Thr Val
            35                  40                  45

Ala Ala Thr Thr Gly Asn Ser Ser Asn Leu His Ala Ile Cys His Val
        50                  55                  60

Ser Ser Leu Ser Ile Asn Ser Trp Thr
65                  70

<210> SEQ ID NO 336
<211> LENGTH: 72
<212> TYPE: PRT
<213> ORGANISM: Artificial Sequence
<220> FEATURE:
<223> OTHER INFORMATION: pNOP69709

<400> SEQUENCE: 336

Ala Cys Pro Pro Tyr Asp Pro Ser Pro Ile Ser Arg Leu Pro Ser Gly
1               5                   10                  15

Ala Gly Phe Ser His Pro Asp Gly Ala Pro Ser Ser Val Phe Ala
                20                  25                  30

Thr Pro Ser Ala Phe Pro Gly Ser Pro Lys Leu Pro Ser Phe Pro Val
```

```
              35                  40                  45
Leu Ser Ser Cys Pro Thr Thr Val Arg Ser Leu Pro Val Glu Ser His
 50                  55                  60

Arg Glu Gly Ser Gly Gly Leu Arg
 65                  70
```

<210> SEQ ID NO 337
<211> LENGTH: 165
<212> TYPE: PRT
<213> ORGANISM: Artificial Sequence
<220> FEATURE:
<223> OTHER INFORMATION: pNOP8118

<400> SEQUENCE: 337

```
Tyr Arg Ala Thr Thr Ser Gln Thr Arg Thr Cys Pro Pro Val Trp Ala
 1               5                  10                  15

Gly Ser Ala Trp Gly Trp Asn His Ala Tyr Gly Ser Ala Ser Ser
              20                  25                  30

Thr Ala Pro Arg Ser Pro Gly Gln Lys Pro Thr Ala Ala Ala Leu Lys
              35                  40                  45

Ser Ser Ala Ala Ala Ala Thr Gly Thr Pro His Ala Ala Ala Ala
 50                  55                  60

Ala Ala Glu Ser Gly Ser Thr Pro Asp Pro Thr Leu Pro Gly Ala Trp
 65                  70                  75                  80

Asp Pro Asp Leu Ser Pro Pro Gly Pro Pro Gly Leu Pro Thr Ser Thr
                  85                  90                  95

Trp Gly Leu Pro Trp Thr Thr Asp Arg Pro Pro Gly Ala Arg Gly
             100                 105                 110

Arg Ala Ser Thr Ser Gly Pro Thr Pro Ala Pro Cys Pro Thr Arg Ser
             115                 120                 125

Leu Ile Tyr Arg Thr Ser Pro Trp Pro Cys Pro Ser His Thr Ser Thr
130                 135                 140

Ile Gln Pro Ser Arg Ala Lys Glu Thr Phe Thr Ile Thr Phe Pro Gln
145                 150                 155                 160

Leu Pro Ala Ser His
            165
```

<210> SEQ ID NO 338
<211> LENGTH: 60
<212> TYPE: PRT
<213> ORGANISM: Artificial Sequence
<220> FEATURE:
<223> OTHER INFORMATION: pNOP102126

<400> SEQUENCE: 338

```
Thr Thr Val Phe Ile Gln His Pro Thr Pro Arg Val Leu Pro Cys Gln
 1               5                  10                  15

Leu Val Trp Ser Trp Ser Thr Gly Pro Arg Arg Ala Leu Ser Leu Ala
              20                  25                  30

Ala Pro Ile Leu Trp Pro Trp Lys Leu Gly Ser Cys Pro Val Arg Ile
              35                  40                  45

Pro Ser Trp Met Thr Ile Leu Met Pro Thr Arg Pro
 50                  55                  60
```

<210> SEQ ID NO 339
<211> LENGTH: 58
<212> TYPE: PRT
<213> ORGANISM: Artificial Sequence
<220> FEATURE:

<223> OTHER INFORMATION: pNOP106859

<400> SEQUENCE: 339

His Pro Gly Leu Cys Leu Leu Lys Leu Phe Ala His His Pro Leu Pro
1               5                   10                  15

Leu Ala Ser Ser Pro Leu Thr Leu Ile Leu Ala His Pro His Ala Leu
            20                  25                  30

Ser Pro Val Thr His Leu Pro His Cys Ile Ser His Pro Asp Pro Ser
        35                  40                  45

Pro Leu Lys Leu Pro Leu Arg Leu Gly Leu
    50                  55

<210> SEQ ID NO 340
<211> LENGTH: 298
<212> TYPE: PRT
<213> ORGANISM: Artificial Sequence
<220> FEATURE:
<223> OTHER INFORMATION: pNOP1069

<400> SEQUENCE: 340

Phe Lys Ala Phe Thr Gly Lys Ala Ala Ala Ala Ala Ala Thr Tyr
1               5                   10                  15

Ala Ala Gly Pro Glu Thr Ala Ala Ala Ala Ala Thr Ala Ala
            20                  25                  30

Ala Ala Pro Ser Arg Thr Gly Gly Asn Pro Ala Ala Thr Ala Ala Gly
        35                  40                  45

Ser Trp Ser Thr Asp Lys Pro Ser Ser Gly Ser Gln Ala Pro Gly Pro
    50                  55                  60

Tyr Ala Ser Gln Gln Pro Pro Arg Pro Pro Gly Pro Ala Ala Val Pro
65                  70                  75                  80

Ser Thr Thr Pro Gly Ala Pro Gly His Ala Gly Pro Cys Pro Gly Gly
                85                  90                  95

Cys Val Ala Ala Ala Pro Trp Ser Phe Gly Pro Pro Gly Pro Ser
            100                 105                 110

Gln Thr Gly Ala Tyr Asp Pro Val Pro Gly Ala Gln Phe Pro Pro Ala
        115                 120                 125

Gly Thr Ala Gly Ser Gly Pro Tyr Gly Thr Gln Ala Gly His Ser Pro
    130                 135                 140

Ala Ala Ala Ala Ala Thr Thr Ala Pro Thr Ala Arg Val His Gly Arg
145                 150                 155                 160

Ala Val Pro Ser Ser Ala Glu Ser Asp Val Thr Gln Trp Ala Ala Gln
                165                 170                 175

Thr Glu Arg Ser Ala His Gly Leu Phe Thr Ala Ala Ser Ala Ala Ala
            180                 185                 190

Ala Ala Ala Thr Ala Thr Ala Thr Ser Ala Ala Ala Ala Ala Ala
        195                 200                 205

Thr Thr Ala Thr Ala Thr Ser Ala Ala Thr Ala Ser Thr Ala Ala Thr
    210                 215                 220

Ala Ala Ala Ala Ser Thr Thr Ala Ala Thr Ala Ser Thr Ala Ala
225                 230                 235                 240

Thr Ala Ala Thr Thr Ala Thr Ala Thr Thr Ala Ala Val Ser Thr
                245                 250                 255

Ala Ala Ala Thr Ala Ala Asp Gly Pro Phe Lys Pro Glu Ser Asn Phe
            260                 265                 270

Thr Val Ser Ser Ala Thr Thr Ala Ala Ala Ser Gly Thr Trp Pro Trp
        275                 280                 285

His Ala Ser Lys Ala Ser Ser Thr Leu Phe
    290                 295

<210> SEQ ID NO 341
<211> LENGTH: 58
<212> TYPE: PRT
<213> ORGANISM: Artificial Sequence
<220> FEATURE:
<223> OTHER INFORMATION: pNOP108932

<400> SEQUENCE: 341

Val Pro Arg Trp Arg Glu Phe Pro Pro Val Cys Gln Ala Leu Val Ser
1               5                   10                  15

Gln Cys Leu Val Gln Leu Val Leu Pro Ser Ser Leu Ser Cys Gly Thr
            20                  25                  30

Met Tyr Arg Lys Asp Trp Asp Leu Gly Ala Leu Arg Phe Leu Val Arg
        35                  40                  45

Ala His Leu Arg Asp Pro Val Phe Thr Leu
    50                  55

<210> SEQ ID NO 342
<211> LENGTH: 57
<212> TYPE: PRT
<213> ORGANISM: Artificial Sequence
<220> FEATURE:
<223> OTHER INFORMATION: pNOP109806

<400> SEQUENCE: 342

Glu Ala Pro Lys Leu Ser Ile Ser Glu His Pro Ile Leu Gly Pro Cys
1               5                   10                  15

Pro Tyr Ser Ser Asn Ser Asn Asn Cys Gly Ser Asn Asn Arg Gln Gln
            20                  25                  30

Gln Gln Pro Pro Cys Asp Leu Pro Cys Gln Leu Ala Phe His Gln Leu
        35                  40                  45

Leu Asp Leu Asn Leu Ala Ala Lys Pro
    50                  55

<210> SEQ ID NO 343
<211> LENGTH: 57
<212> TYPE: PRT
<213> ORGANISM: Artificial Sequence
<220> FEATURE:
<223> OTHER INFORMATION: pNOP110054

<400> SEQUENCE: 343

Gly Glu Ala Gln Gly Gly Gly Trp Thr Pro Pro Phe Ser Leu Pro
1               5                   10                  15

Ile His His Cys Tyr Pro Gln Gly Arg Ala Arg Thr Cys Cys Gln Phe
            20                  25                  30

Pro Trp Pro Gly Ala Lys Ala Arg Thr Glu His Asp Gly Gln Pro Gly
        35                  40                  45

Tyr Pro Asp Gly His Arg Ala Ile Phe
    50                  55

<210> SEQ ID NO 344
<211> LENGTH: 56
<212> TYPE: PRT
<213> ORGANISM: Artificial Sequence
<220> FEATURE:
<223> OTHER INFORMATION: pNOP114830

<400> SEQUENCE: 344

```
Pro Ser Ala Pro Cys Ala Ser Glu Leu Val Pro Ala Ala Ile
1               5                   10                  15

Ala Cys Val Ala Pro Met Ser Thr Ile Leu Leu Val Pro Ser Val Pro
                20                  25                  30

Ser Ala Cys Ser Ser Arg Thr Arg Pro Cys Cys Val Gln Cys Ile Arg
            35                  40                  45

Ser Arg Gly Pro Val Ser Lys Ser
        50                  55
```

<210> SEQ ID NO 345
<211> LENGTH: 56
<212> TYPE: PRT
<213> ORGANISM: Artificial Sequence
<220> FEATURE:
<223> OTHER INFORMATION: pNOP116135

<400> SEQUENCE: 345

```
Trp Gly Ser Gln Met Arg Leu Ser Cys Thr Arg Trp Arg Leu Arg Lys
1               5                   10                  15

Phe Gln Asn Leu Asn Ala Gln Pro Trp Asn Pro Val Pro Pro Val Leu
                20                  25                  30

Ser Leu Pro Gln Trp Gly Thr Phe Pro Ala Pro Pro Ala Leu Pro
            35                  40                  45

Gln Pro Trp Met Thr Ser Leu Ala
        50                  55
```

<210> SEQ ID NO 346
<211> LENGTH: 55
<212> TYPE: PRT
<213> ORGANISM: Artificial Sequence
<220> FEATURE:
<223> OTHER INFORMATION: pNOP118654

<400> SEQUENCE: 346

```
Pro Gly Ser Ser Pro His Gln Gln Gly Ala Glu Ala Arg Gly Thr Gly
1               5                   10                  15

Gln Pro Ala Pro Arg Cys Cys Pro His His Phe His Trp Gln Pro His
                20                  25                  30

Tyr Pro Arg Arg Leu Val Tyr Leu Cys Gly Arg Val Pro Glu Ala Ala
            35                  40                  45

Gly Gly Leu Gly Ala Trp Pro
        50                  55
```

<210> SEQ ID NO 347
<211> LENGTH: 55
<212> TYPE: PRT
<213> ORGANISM: Artificial Sequence
<220> FEATURE:
<223> OTHER INFORMATION: pNOP118804

<400> SEQUENCE: 347

```
Pro Ser Arg Arg Ala Val Gly Gly Arg Arg Met Ser Gly Lys Trp Gln
1               5                   10                  15

Ser Leu Trp Ser Ser Leu Ala Gln Pro Cys Asp Leu Thr Arg Tyr Arg
                20                  25                  30

Glu Thr Cys Val Ala Ala Val Ser Val Met Arg Arg Val Thr Gly Pro
            35                  40                  45

Leu Met Gly Leu Pro Val Cys
        50                  55
```

<210> SEQ ID NO 348
<211> LENGTH: 53
<212> TYPE: PRT
<213> ORGANISM: Artificial Sequence
<220> FEATURE:
<223> OTHER INFORMATION: pNOP127343

<400> SEQUENCE: 348

```
Ser Gly Pro Cys Lys Ile Ile Gln Gly His Asn Leu Pro Asn Gln Asp
1               5                   10                  15

Leu Ser Ser Ser Leu Gly Arg Val Cys Leu Gly Leu Glu Ser Cys Leu
            20                  25                  30

Arg Trp Val Ser Phe Glu His Ser Ser Lys Glu Ser Trp Pro Lys Thr
        35                  40                  45

His Ser Cys Gly Thr
    50
```

<210> SEQ ID NO 349
<211> LENGTH: 53
<212> TYPE: PRT
<213> ORGANISM: Artificial Sequence
<220> FEATURE:
<223> OTHER INFORMATION: pNOP127724

<400> SEQUENCE: 349

```
Thr Arg Thr Ala Ser Gly Leu Trp Asn Pro Trp Pro Arg Arg Gln Pro
1               5                   10                  15

Tyr Ala Thr Ala Glu Ala Leu Ser Ser Arg Trp Thr Pro Phe Gly Gln
            20                  25                  30

Ser Ala Leu Gln Gln Pro Asn Gly Leu Leu Pro Arg Pro Leu Pro Val
        35                  40                  45

Pro Val Pro Gly Phe
    50
```

<210> SEQ ID NO 350
<211> LENGTH: 50
<212> TYPE: PRT
<213> ORGANISM: Artificial Sequence
<220> FEATURE:
<223> OTHER INFORMATION: pNOP137298

<400> SEQUENCE: 350

```
Cys Leu Gln Ser Pro Pro Asp Pro Ser Gly Ile Ser Gly Arg Ala Pro
1               5                   10                  15

Glu Pro Gly Leu Gly Pro Lys Ala Pro Gly Ala Thr Pro Cys Pro Gly
            20                  25                  30

Phe Gly Thr Phe Ser Ser Lys Ser Pro Arg His Leu Ser Pro Trp Leu
        35                  40                  45

Leu His
    50
```

<210> SEQ ID NO 351
<211> LENGTH: 50
<212> TYPE: PRT
<213> ORGANISM: Artificial Sequence
<220> FEATURE:
<223> OTHER INFORMATION: pNOP137386

<400> SEQUENCE: 351

```
Cys Ser Val Ala Trp Leu Tyr Pro Glu Glu Pro Thr Arg His Leu Glu
1               5                   10                  15
```

-continued

```
Pro Pro Glu Thr Gly Glu Pro Arg Pro Arg Ala Thr His Ser Ala Gln
            20                  25                  30

Leu Tyr Leu Gln Cys Leu Gln Ser Gly Cys Ala Thr Ala Leu Gly Pro
        35                  40                  45

Thr Ser
    50

<210> SEQ ID NO 352
<211> LENGTH: 49
<212> TYPE: PRT
<213> ORGANISM: Artificial Sequence
<220> FEATURE:
<223> OTHER INFORMATION: pNOP142770

<400> SEQUENCE: 352

Gly Pro Gln Lys Pro Arg Glu Met Glu Ala Gln Lys Gly Arg Asn Ser
1               5                   10                  15

Pro His Arg Arg Lys Glu Met Met Val Gln Ile Leu Gln Met Lys Asn
            20                  25                  30

Pro Val Ala Ser Arg Ala Lys Pro Ile His Gln Asp Leu Arg Met Gly
        35                  40                  45

Ala

<210> SEQ ID NO 353
<211> LENGTH: 49
<212> TYPE: PRT
<213> ORGANISM: Artificial Sequence
<220> FEATURE:
<223> OTHER INFORMATION: pNOP144316

<400> SEQUENCE: 353

Pro Asn Arg Ala Gly Glu Ala Thr Ala Ala Pro Ala Thr Thr Arg Ala
1               5                   10                  15

Ala Asp Ser Ala Ala Asp Pro Ala Gln His Pro Ala Ala Gly Glu Gly
            20                  25                  30

Asn Ser Cys Ser Ser Cys Arg Ser Ser Gly Ala Ser Arg Gln Leu Gly
        35                  40                  45

Cys

<210> SEQ ID NO 354
<211> LENGTH: 47
<212> TYPE: PRT
<213> ORGANISM: Artificial Sequence
<220> FEATURE:
<223> OTHER INFORMATION: pNOP152835

<400> SEQUENCE: 354

Gly Arg Ser Ala Gln Asp Pro Leu Pro Leu Trp Ser Leu Glu Leu Ser
1               5                   10                  15

Glu Met Asp Glu Leu Arg Ser Phe Glu Ala Thr Arg Gln Gly Ser Pro
            20                  25                  30

Pro Thr His Asn Leu Phe Pro Glu Arg Asp Glu Gly Glu Glu Arg
        35                  40                  45

<210> SEQ ID NO 355
<211> LENGTH: 47
<212> TYPE: PRT
<213> ORGANISM: Artificial Sequence
<220> FEATURE:
<223> OTHER INFORMATION: pNOP154481

<400> SEQUENCE: 355
```

```
Pro Leu Trp Arg Ser Thr Pro Asn Ala Ser Arg Gln Gln Gly Arg Ala
1               5                   10                  15

His His Val Lys Asn Arg Lys Ser His Val His Arg Trp Pro Pro His
            20                  25                  30

His Pro Leu Ser Ser Asn Pro Thr Ser Leu Thr Arg Ser Leu Ile
        35                  40                  45
```

<210> SEQ ID NO 356
<211> LENGTH: 47
<212> TYPE: PRT
<213> ORGANISM: Artificial Sequence
<220> FEATURE:
<223> OTHER INFORMATION: pNOP155302

<400> SEQUENCE: 356

```
Arg Ser Pro Thr Pro Met Arg Cys Cys Ser Gln Arg Ala Pro Pro Gly
1               5                   10                  15

Gln Ala Leu Ser Gln Arg Arg Gly Lys Leu Arg Val Leu Val Gly Arg
            20                  25                  30

Lys Arg Val Trp Lys Ala Arg Ala Gln Thr Leu Ala Leu Ile Gly
        35                  40                  45
```

<210> SEQ ID NO 357
<211> LENGTH: 46
<212> TYPE: PRT
<213> ORGANISM: Artificial Sequence
<220> FEATURE:
<223> OTHER INFORMATION: pNOP161094

<400> SEQUENCE: 357

```
Ser Ser Gly Glu Arg Phe Gln Gln Leu Thr Lys Pro Pro Thr Cys Lys
1               5                   10                  15

Arg Pro Lys Ile Thr Gly Gln Leu Thr Ala Ser Thr Arg Cys Arg Ser
            20                  25                  30

Arg Leu Arg Ala Arg Ser Thr Ser Arg Pro Arg Trp Ala Thr
        35                  40                  45
```

<210> SEQ ID NO 358
<211> LENGTH: 45
<212> TYPE: PRT
<213> ORGANISM: Artificial Sequence
<220> FEATURE:
<223> OTHER INFORMATION: pNOP165656

<400> SEQUENCE: 358

```
Gln Arg Ile Pro Tyr Phe Leu Pro Lys Thr Thr His Gly Gly Thr Ala
1               5                   10                  15

Cys Ser Leu Leu Glu Val Gln Gly Val Pro Gly Val Pro Gly Leu Trp
            20                  25                  30

Gly Gly Leu Ser Arg Thr Glu Ser Gln Leu Gly Val Val
        35                  40                  45
```

<210> SEQ ID NO 359
<211> LENGTH: 44
<212> TYPE: PRT
<213> ORGANISM: Artificial Sequence
<220> FEATURE:
<223> OTHER INFORMATION: pNOP169094

<400> SEQUENCE: 359

```
Gly Lys Thr Gln Pro Leu Trp Met Gly Leu Met Leu Arg Val His Ser
1               5                   10                  15
```

```
Gln Ser Leu Asp Arg Pro Leu Ala Val Trp Leu Val Asn Leu Lys Ala
        20                  25                  30

Pro Leu Cys Ser Trp Thr Pro Arg Ser Trp Pro Leu
        35                  40

<210> SEQ ID NO 360
<211> LENGTH: 44
<212> TYPE: PRT
<213> ORGANISM: Artificial Sequence
<220> FEATURE:
<223> OTHER INFORMATION: pNOP172213

<400> SEQUENCE: 360

Ser His Cys Lys Gly Gln Asp Gly Gly Phe Glu Arg His Gln Glu Ser
1               5                   10                  15

Asp Gly Ser Gly Gln His Trp Gly Gly Thr Trp Tyr Glu Gln Thr Ala
        20                  25                  30

Ser Val Ser Ala Ser Pro Glu Ala Leu Gly Gly Thr
        35                  40

<210> SEQ ID NO 361
<211> LENGTH: 44
<212> TYPE: PRT
<213> ORGANISM: Artificial Sequence
<220> FEATURE:
<223> OTHER INFORMATION: pNOP172370

<400> SEQUENCE: 361

Ser Gln Leu Leu Leu Pro Leu Arg Leu Trp Leu Leu Thr Leu Ile Ala
1               5                   10                  15

Leu Pro Val Arg Arg Arg Arg Lys Lys Met Met Thr Pro Cys Arg Ile
        20                  25                  30

Pro Trp Phe Ser Ser Pro Thr Gln Thr Asn Leu Ser
        35                  40

<210> SEQ ID NO 362
<211> LENGTH: 44
<212> TYPE: PRT
<213> ORGANISM: Artificial Sequence
<220> FEATURE:
<223> OTHER INFORMATION: pNOP172794

<400> SEQUENCE: 362

Thr Arg Arg Gly Lys Ala Leu Thr Leu Trp Gly Leu Thr Thr Pro Ala
1               5                   10                  15

Cys Pro Thr Pro Ala Pro Ala Ser Ala Gln Leu Ser Ala Ala Ala Ala
        20                  25                  30

Thr Ser Glu Ala Ser Arg Thr Thr Ala Ala Ala Ser
        35                  40

<210> SEQ ID NO 363
<211> LENGTH: 128
<212> TYPE: PRT
<213> ORGANISM: Artificial Sequence
<220> FEATURE:
<223> OTHER INFORMATION: pNOP17361

<400> SEQUENCE: 363

Arg Ser Arg Leu Val Tyr Thr Ala Ser Pro Gly Arg Leu Cys Val Pro
1               5                   10                  15

Ser Ser Ala Leu Pro Lys Lys Leu Ala Val Ser Ser Gln Lys Leu Met
        20                  25                  30
```

-continued

Leu Arg Ser Ser Ser Trp Leu Gln Ser Ser Arg Ala Arg Ser Arg Asn
        35                  40                  45

Asn Trp Ile Arg Ser Gly Asn Ser Arg Arg Ser Thr Leu Ile Ser Trp
 50                  55                  60

Gln Asn Ile Gly Thr Ser Ser Asn Asn Ser Ser Ser Ser Ser Ser Asn
 65                  70                  75                  80

Asn Ser Asn Ser Thr Gln Leu Cys Trp Leu Ser Ala Leu Pro Arg Val
                85                  90                  95

Pro Gly Cys Ser Pro Ser Ser Leu Val Ser Cys Ser Leu Ala Met Gly
            100                 105                 110

Cys Ser His His Arg Gly Leu Arg Val Gly Lys Pro Glu Val Phe Ala
            115                 120                 125

<210> SEQ ID NO 364
<211> LENGTH: 43
<212> TYPE: PRT
<213> ORGANISM: Artificial Sequence
<220> FEATURE:
<223> OTHER INFORMATION: pNOP174645

<400> SEQUENCE: 364

Glu Glu Gly Ala Ala Glu Ala Ala Ala Phe Ser Thr Val Ala Ala
 1               5                  10                  15

Cys Pro Ala Ala Ala Thr Ala Ala Ala Phe Pro Thr Val Cys
                20                  25                  30

Thr Arg Pro Cys Pro Gly His Val Phe Ala Thr
            35                  40

<210> SEQ ID NO 365
<211> LENGTH: 43
<212> TYPE: PRT
<213> ORGANISM: Artificial Sequence
<220> FEATURE:
<223> OTHER INFORMATION: pNOP175361

<400> SEQUENCE: 365

Gly Val Ala Val Pro Tyr Pro Ala Ala Pro Thr Asp Ala Ala Glu Gly
 1               5                  10                  15

Ala Arg Gly Ala Asp Trp Cys Thr Pro Gln Val Pro Glu Gly Ser Val
                20                  25                  30

Cys Gln Ala Ala His Cys Gln Lys Ser Trp Pro
            35                  40

<210> SEQ ID NO 366
<211> LENGTH: 43
<212> TYPE: PRT
<213> ORGANISM: Artificial Sequence
<220> FEATURE:
<223> OTHER INFORMATION: pNOP178870

<400> SEQUENCE: 366

Thr Ile Ser Ala Trp His Trp Trp Phe His Gly Ala Thr Ala Glu Ile
 1               5                  10                  15

Pro His Thr His Glu Lys Gly Ala Cys Cys Thr Gly Gly Val Glu
                20                  25                  30

Trp Gly Trp Ala Ala Arg Arg Gly Asp Thr Cys
            35                  40

<210> SEQ ID NO 367
<211> LENGTH: 42

```
<212> TYPE: PRT
<213> ORGANISM: Artificial Sequence
<220> FEATURE:
<223> OTHER INFORMATION: pNOP182619

<400> SEQUENCE: 367

Leu Pro Ala Asn Val Leu Ala Gly Ser Ala Leu Asn Ala Lys Cys Ala
1               5                   10                  15

Lys Pro Ala Gly Asn Leu Gly Met Thr Leu Arg Cys Trp Phe Val Arg
            20                  25                  30

Arg Val Thr Lys Asp Thr Ile Leu Ser Ala
        35                  40

<210> SEQ ID NO 368
<211> LENGTH: 42
<212> TYPE: PRT
<213> ORGANISM: Artificial Sequence
<220> FEATURE:
<223> OTHER INFORMATION: pNOP183568

<400> SEQUENCE: 368

Pro Arg Gly Ser Arg Gly Asp Leu Ala Val Ile Cys Arg Thr Met Trp
1               5                   10                  15

Gln Leu Gly Val Ala Arg Ser Gly Val Leu Val Ile Pro Pro Ser Leu
            20                  25                  30

Val Pro Thr Arg Pro Leu Leu Leu Arg Glu
        35                  40

<210> SEQ ID NO 369
<211> LENGTH: 42
<212> TYPE: PRT
<213> ORGANISM: Artificial Sequence
<220> FEATURE:
<223> OTHER INFORMATION: pNOP185368

<400> SEQUENCE: 369

Thr Arg Val Glu Leu Tyr Cys Leu Leu Ser Asn Asn Ser Ser Ser Lys
1               5                   10                  15

Trp His Leu Ala Leu Ala Cys Gln Gln Ser Leu Phe Asn Thr Phe Leu
            20                  25                  30

Ala Leu Glu Pro Trp Val Gln Pro Ser Ser
        35                  40

<210> SEQ ID NO 370
<211> LENGTH: 124
<212> TYPE: PRT
<213> ORGANISM: Artificial Sequence
<220> FEATURE:
<223> OTHER INFORMATION: pNOP18835

<400> SEQUENCE: 370

Lys Ala Ala Val Arg His Cys Arg Gly Pro Phe Phe Lys Val Asp Ser
1               5                   10                  15

Leu Trp Ala Ile Cys Pro Pro Ala Ala Gln Trp Thr Pro Thr Gln Ala
            20                  25                  30

Ser Ala Ser Pro Arg Ser Trp Ile Leu Ala Arg Asn Pro Val Ser Pro
        35                  40                  45

Thr Ala Pro Gly Arg Ala Gln Val Ala Arg Pro Pro Pro Gln
    50                  55                  60

Pro Pro Pro Arg Arg Val Arg Ala Thr Asp Ser Pro Ile Thr Ser Gly
65                  70                  75                  80
```

Val Phe Ser Ala Gly Arg Arg Met Arg Ser Trp Ala Ser Cys Pro Pro
            85                  90                  95

Ser His Leu Cys Ser Met Pro Thr Leu Ile Phe Leu Ile Ser Ser Lys
        100                 105                 110

Thr Thr Gln Thr Gly Gln Ala Val Ala Asn Lys Ser
        115                 120

<210> SEQ ID NO 371
<211> LENGTH: 41
<212> TYPE: PRT
<213> ORGANISM: Artificial Sequence
<220> FEATURE:
<223> OTHER INFORMATION: pNOP188940

<400> SEQUENCE: 371

Lys Thr Trp Arg Pro Met Thr Pro Thr Trp Met Thr Cys Ser Met Glu
1               5                   10                  15

Thr Ser Leu Thr Cys Trp His Ile Leu Ile Leu Ser Trp Thr Leu Gly
            20                  25                  30

Thr Arg Arg Ile Ser Ser Met Ser Thr
        35                  40

<210> SEQ ID NO 372
<211> LENGTH: 41
<212> TYPE: PRT
<213> ORGANISM: Artificial Sequence
<220> FEATURE:
<223> OTHER INFORMATION: pNOP191904

<400> SEQUENCE: 372

Ser Thr Pro Leu Val Pro Lys Gly Thr Val Thr Leu Ser His Arg Trp
1               5                   10                  15

Leu Pro Pro Ser Trp Arg His Pro Ser Ala Leu His Gln Lys Leu Thr
            20                  25                  30

Ala Leu Thr Leu Ser Leu Ser Pro Leu
        35                  40

<210> SEQ ID NO 373
<211> LENGTH: 40
<212> TYPE: PRT
<213> ORGANISM: Artificial Sequence
<220> FEATURE:
<223> OTHER INFORMATION: pNOP193752

<400> SEQUENCE: 373

Cys Arg Thr Cys Val Trp Tyr Val Ala Ala Leu Ala Gly Gly Gln Arg
1               5                   10                  15

Ala Thr Ser Leu Pro Val Arg Ser Ala Leu Ser Ala Ile Thr Leu Thr
            20                  25                  30

Val Ser Thr Ala Arg Ser Pro Arg
        35                  40

<210> SEQ ID NO 374
<211> LENGTH: 40
<212> TYPE: PRT
<213> ORGANISM: Artificial Sequence
<220> FEATURE:
<223> OTHER INFORMATION: pNOP194798

<400> SEQUENCE: 374

Gly Leu Ile Cys Ala Pro Pro Ala Gly Ser Ala Leu Cys Phe Leu Arg
1               5                   10                  15

Gly Ser Ala Trp Val His Asp Pro Glu Pro Ser Gly Pro Thr Ala
            20                  25                  30

His Ala Arg Ala Ala His Ala Lys
            35                  40

<210> SEQ ID NO 375
<211> LENGTH: 40
<212> TYPE: PRT
<213> ORGANISM: Artificial Sequence
<220> FEATURE:
<223> OTHER INFORMATION: pNOP198849

<400> SEQUENCE: 375

Ser Arg Ser Asn Trp Gln Cys Ser Ser Ser Trp Gln Thr Ala Ser Ser
1               5                   10                  15

Gln Ile Gln Thr Trp Thr Asn Leu Leu Gln Lys Ile Ser Leu Ile Pro
            20                  25                  30

Leu Gln Arg Pro Arg Trp Trp Leu
            35                  40

<210> SEQ ID NO 376
<211> LENGTH: 40
<212> TYPE: PRT
<213> ORGANISM: Artificial Sequence
<220> FEATURE:
<223> OTHER INFORMATION: pNOP198864

<400> SEQUENCE: 376

Ser Ser Ala Ala Thr Val Asn Gly Gly Cys Met Gln Ala Val Arg Ala
1               5                   10                  15

Ser Ser Gln Arg Thr Met Trp Ser Arg Gln Pro Met Lys Ala Leu Thr
            20                  25                  30

Val Ser Pro Ala Ser Pro Thr Trp
            35                  40

<210> SEQ ID NO 377
<211> LENGTH: 40
<212> TYPE: PRT
<213> ORGANISM: Artificial Sequence
<220> FEATURE:
<223> OTHER INFORMATION: pNOP199023

<400> SEQUENCE: 377

Ser Tyr Gly Gly Pro Cys Ala Ala Pro Asp Ala Gly Arg Leu Ile Ser
1               5                   10                  15

Ser Trp Gly Trp Pro Ala Arg Gly Ile Pro His Tyr Pro Thr Trp His
            20                  25                  30

Pro Gln Thr Pro Ala Leu His Thr
            35                  40

<210> SEQ ID NO 378
<211> LENGTH: 40
<212> TYPE: PRT
<213> ORGANISM: Artificial Sequence
<220> FEATURE:
<223> OTHER INFORMATION: pNOP199159

<400> SEQUENCE: 378

Thr Ile Ser Ala Trp His Trp Trp Phe His Gly Ala Thr Ala Glu Ile
1               5                   10                  15

Pro His Thr His Glu Lys Gly Ala Cys Cys Thr Gly Gly Gly Val Glu
            20                  25                  30

-continued

```
Trp Gly Trp Ala Ala Arg Arg Gly
        35                  40
```

<210> SEQ ID NO 379
<211> LENGTH: 39
<212> TYPE: PRT
<213> ORGANISM: Artificial Sequence
<220> FEATURE:
<223> OTHER INFORMATION: pNOP201536

<400> SEQUENCE: 379

```
Glu Leu Leu Cys Ser Ala Pro Ser Leu Thr Ala Leu Arg Pro Phe Leu
1               5                   10                  15

Pro Ser Ala Cys Gln Ser Ser Val Pro Val Gln Leu Pro Val Ser Thr
            20                  25                  30

Asp Thr Pro Ala Ser Val Cys
        35
```

<210> SEQ ID NO 380
<211> LENGTH: 121
<212> TYPE: PRT
<213> ORGANISM: Artificial Sequence
<220> FEATURE:
<223> OTHER INFORMATION: pNOP20393

<400> SEQUENCE: 380

```
Thr Cys Trp Leu Pro Cys Leu His Pro Leu Thr Ile Arg Leu Arg Met
1               5                   10                  15

Ser Gly Trp Arg Val Met Arg Ile Ala Ile Leu Leu Thr Ala Leu Cys
            20                  25                  30

Gln Leu His Pro Leu Arg Ala Ser Trp Gly Arg Arg Pro Leu Val Ser
        35                  40                  45

Leu Ile Trp Ala Gln Ala Gly Gly Ser Lys Arg Thr Gly Pro Ser Pro
    50                  55                  60

Leu Ser Ser Pro Ser Phe Leu Gly Pro Ala Ser Gln Ser Ser Gln Ile
65                  70                  75                  80

Pro Asn Leu Met Gly Pro Leu Ala Trp Arg Ser Leu Glu Ser Cys Leu
                85                  90                  95

Ser Gln Leu Gly Lys Arg Ala Lys Glu Val Arg Cys Gln Ser Cys Ser
            100                 105                 110

Gln Ser Leu Leu Leu Gln Pro Arg Thr
        115                 120
```

<210> SEQ ID NO 381
<211> LENGTH: 38
<212> TYPE: PRT
<213> ORGANISM: Artificial Sequence
<220> FEATURE:
<223> OTHER INFORMATION: pNOP209424

<400> SEQUENCE: 381

```
Gly Gly Glu Gly Ala Ala Ala Gln Leu Pro Ser Pro Phe Pro His Gln
1               5                   10                  15

Thr Gly Ser Gln Gln Gln Phe Pro Arg Lys Thr Pro Ala Ser Trp Arg
            20                  25                  30

Ser Pro Trp Arg Thr Trp
        35
```

<210> SEQ ID NO 382
<211> LENGTH: 38
<212> TYPE: PRT

```
<213> ORGANISM: Artificial Sequence
<220> FEATURE:
<223> OTHER INFORMATION: pNOP211037

<400> SEQUENCE: 382

Leu Lys Gly Met Arg Arg Ser Asn Ser Gly Glu Gly Ala Arg Arg
1               5                   10                  15

Ala Asn Trp Arg Thr Cys Ser Leu Leu Thr Cys Arg Lys Pro Ser Leu
            20                  25                  30

Gly Arg Ser Cys Trp Thr
            35

<210> SEQ ID NO 383
<211> LENGTH: 38
<212> TYPE: PRT
<213> ORGANISM: Artificial Sequence
<220> FEATURE:
<223> OTHER INFORMATION: pNOP211152

<400> SEQUENCE: 383

Leu Pro His Ile Leu Pro Gly Pro Pro Thr Ala His Arg Pro Gln Gly
1               5                   10                  15

Arg Leu Glu Val Gln Val Val Cys Val Leu Tyr Ala Val Trp Gly Cys
            20                  25                  30

Phe Pro Trp Leu Pro Leu
            35

<210> SEQ ID NO 384
<211> LENGTH: 119
<212> TYPE: PRT
<213> ORGANISM: Artificial Sequence
<220> FEATURE:
<223> OTHER INFORMATION: pNOP21288

<400> SEQUENCE: 384

Ser Arg Arg Arg Ala Arg Cys Leu Ala Leu Thr Arg Leu Val Ser Ser
1               5                   10                  15

Ser Ser Ser His Pro Arg Cys Pro Pro Lys Cys Leu Arg Arg Thr
            20                  25                  30

Pro Leu Asp Trp Pro Leu Pro Ile Pro Trp Ser Pro Ala Ser Pro Arg
            35                  40                  45

His Arg Pro Pro Ile Pro Ile Leu Val Leu Arg Gly Pro Leu Arg
    50                  55                  60

Ser Pro Arg Cys Trp Ala Pro His Leu Val Leu Gly Leu Ala Ser Gln
65                  70                  75                  80

Gly Asn Ser Thr Leu Pro His Leu Ala Pro Pro Asp Thr Ser Pro Pro
                85                  90                  95

His Leu Thr His Ser Ser Asn Pro Ala Ala Pro Arg Trp Ile Thr Trp
            100                 105                 110

Leu Cys Leu Arg Ala Leu Gly
            115

<210> SEQ ID NO 385
<211> LENGTH: 38
<212> TYPE: PRT
<213> ORGANISM: Artificial Sequence
<220> FEATURE:
<223> OTHER INFORMATION: pNOP214330

<400> SEQUENCE: 385

Thr Gly Phe Pro Gln Lys Asn Cys Pro Arg Trp Asn Pro Arg Thr Cys
```

```
                1               5                  10                 15
Ser Ser Ser Ser Arg Met Phe Trp Ala Leu Asn Glu Asn Ser Ile Trp
                20                 25                 30
Val Val Glu Pro Leu Ala
                35
```

<210> SEQ ID NO 386
<211> LENGTH: 38
<212> TYPE: PRT
<213> ORGANISM: Artificial Sequence
<220> FEATURE:
<223> OTHER INFORMATION: pNOP215253

<400> SEQUENCE: 386

```
Trp Ser Pro Phe Leu Leu Ser Val Arg His Ser Phe Ser Ile Pro Trp
1               5                  10                 15
Phe Pro Lys Thr Pro Leu Leu Pro Ser Ala Leu Leu Pro Tyr His
                20                 25                 30
Cys Pro Phe Pro Pro Arg
                35
```

<210> SEQ ID NO 387
<211> LENGTH: 37
<212> TYPE: PRT
<213> ORGANISM: Artificial Sequence
<220> FEATURE:
<223> OTHER INFORMATION: pNOP215460

<400> SEQUENCE: 387

```
Ala Ala Glu Ser Arg Pro Asp Pro Leu Cys Trp Asp Thr Gly Gln Glu
1               5                  10                 15
Gln Pro Cys Gly Val Ala Pro Lys Gln Ala Glu Trp Pro His Pro Gly
                20                 25                 30
Ala Arg Val Leu Pro
                35
```

<210> SEQ ID NO 388
<211> LENGTH: 37
<212> TYPE: PRT
<213> ORGANISM: Artificial Sequence
<220> FEATURE:
<223> OTHER INFORMATION: pNOP217529

<400> SEQUENCE: 388

```
Gly Pro Ala Pro Ser His Pro Ser Arg Asp Pro Gln Thr Ser Gly Ala
1               5                  10                 15
Asn Leu Gly Ala Ala Ser Trp Glu Gly Leu Thr Cys Cys Cys Pro Ala
                20                 25                 30
Cys Arg Tyr Leu Val
                35
```

<210> SEQ ID NO 389
<211> LENGTH: 37
<212> TYPE: PRT
<213> ORGANISM: Artificial Sequence
<220> FEATURE:
<223> OTHER INFORMATION: pNOP217538

<400> SEQUENCE: 389

```
Gly Pro Phe Cys Ser Trp Gly Gly Pro Ala Lys Leu Trp Thr Arg Asp
1               5                  10                 15
Pro Lys Ser Gln Gly Arg Trp Arg Leu Arg Lys Glu Gly Thr Pro His
```

Ile Ala Glu Arg Arg
            35

<210> SEQ ID NO 390
<211> LENGTH: 37
<212> TYPE: PRT
<213> ORGANISM: Artificial Sequence
<220> FEATURE:
<223> OTHER INFORMATION: pNOP218359

<400> SEQUENCE: 390

Ile Thr Ala Arg Gly Gly Glu Leu Ser Lys Leu Phe Ile Pro Leu Trp
1               5                   10                  15

Ala Pro Pro Tyr Gly Ala Ala Thr His Asp Gln Pro His Trp Leu
            20                  25                  30

Cys Pro Ile Arg Ala
            35

<210> SEQ ID NO 391
<211> LENGTH: 37
<212> TYPE: PRT
<213> ORGANISM: Artificial Sequence
<220> FEATURE:
<223> OTHER INFORMATION: pNOP218743

<400> SEQUENCE: 391

Lys Ser Thr Gln Trp Leu Ser Ser Thr Leu Ala Pro Ser Phe Gly Thr
1               5                   10                  15

Arg Trp Pro Thr Gly Gly Arg Lys Ser Thr Lys Ser Arg Ile Glu Ala
            20                  25                  30

Ser Thr Cys Ser Glu
            35

<210> SEQ ID NO 392
<211> LENGTH: 37
<212> TYPE: PRT
<213> ORGANISM: Artificial Sequence
<220> FEATURE:
<223> OTHER INFORMATION: pNOP220563

<400> SEQUENCE: 392

Gln Gly Ser Gly Thr Leu Gly Ser Pro Arg Gln Pro Ser Arg Asn Pro
1               5                   10                  15

Glu Ala Arg Ala Glu Gln Pro Gly Thr Trp Ala Ser Gly Pro Gly Glu
            20                  25                  30

Trp Thr Gly Gly Ala
            35

<210> SEQ ID NO 393
<211> LENGTH: 37
<212> TYPE: PRT
<213> ORGANISM: Artificial Sequence
<220> FEATURE:
<223> OTHER INFORMATION: pNOP223482

<400> SEQUENCE: 393

Tyr Ser Ser Gly Pro Thr Ala Ala Thr Ala Thr Phe Trp Trp Gly Trp
1               5                   10                  15

Ile Pro Gly Trp Pro Phe Arg Gly Leu Leu Pro Trp Gln Pro Cys Ser
            20                  25                  30

Ser Lys Pro Arg Thr

-continued

```
                35

<210> SEQ ID NO 394
<211> LENGTH: 36
<212> TYPE: PRT
<213> ORGANISM: Artificial Sequence
<220> FEATURE:
<223> OTHER INFORMATION: pNOP224854

<400> SEQUENCE: 394

Glu Glu Glu Ala Thr Ala Ala Arg Ala Gln Glu Glu Gln Thr Gly Gly
1               5                   10                  15

His Val Pro Cys Leu Leu Ala Gly Ser Leu Leu Trp Glu Gly Ala Ala
            20                  25                  30

Gly Pro Glu Pro
        35

<210> SEQ ID NO 395
<211> LENGTH: 114
<212> TYPE: PRT
<213> ORGANISM: Artificial Sequence
<220> FEATURE:
<223> OTHER INFORMATION: pNOP23772

<400> SEQUENCE: 395

Asn Arg Arg Ala Pro Pro Gln Ser His Pro Leu Ser Thr Ala Ile Pro
1               5                   10                  15

Thr Met Ser Pro Ile Trp Met Cys Asp Ser Ser Arg Pro His Leu Leu
            20                  25                  30

Lys Asn Pro Pro Arg Pro Leu Pro Pro Trp His Leu Leu Leu Pro Val
        35                  40                  45

Pro Leu Leu Ser Pro Trp Leu Asn Phe Pro Pro Asn Pro Trp Leu Ser
    50                  55                  60

His Pro Ser Pro His Leu Cys His Trp Pro His Pro Leu Asn Gln Pro
65                  70                  75                  80

Asp Pro Ser Pro Val Pro Gly Pro Leu Lys Lys Val Lys Ile Pro Val
                85                  90                  95

Leu Leu Ala Ser Arg Asn Gly Lys Glu Cys Ala Gly Ser Gly Phe Gly
            100                 105                 110

Cys Cys

<210> SEQ ID NO 396
<211> LENGTH: 35
<212> TYPE: PRT
<213> ORGANISM: Artificial Sequence
<220> FEATURE:
<223> OTHER INFORMATION: pNOP240334

<400> SEQUENCE: 396

Trp Ala Ala Gly Ile Pro Gly Trp Ala Gln Gly His Phe Leu Ala Val
1               5                   10                  15

Gly Thr Gln Leu Arg Arg Pro Pro Leu Gly Pro Arg Glu Asp His Gln
            20                  25                  30

Leu Thr Cys
        35

<210> SEQ ID NO 397
<211> LENGTH: 34
<212> TYPE: PRT
<213> ORGANISM: Artificial Sequence
<220> FEATURE:
```

<223> OTHER INFORMATION: pNOP243509

<400> SEQUENCE: 397

Gly Val Ser His Ala His Ser Leu Cys Cys Ser Gln Glu Pro Glu
1               5                   10                  15

Trp Arg Asp Gly Gly Ser Gly Gly Ala Ala Glu His Gly Asp Pro Gln
            20                  25                  30

Leu Leu

<210> SEQ ID NO 398
<211> LENGTH: 34
<212> TYPE: PRT
<213> ORGANISM: Artificial Sequence
<220> FEATURE:
<223> OTHER INFORMATION: pNOP245157

<400> SEQUENCE: 398

Leu Leu Thr Leu Ile Ala Leu Pro Val Arg Arg Arg Lys Lys Met
1               5                   10                  15

Met Thr Pro Cys Arg Ile Pro Trp Phe Ser Ser Pro Thr Gln Thr Asn
            20                  25                  30

Leu Ser

<210> SEQ ID NO 399
<211> LENGTH: 33
<212> TYPE: PRT
<213> ORGANISM: Artificial Sequence
<220> FEATURE:
<223> OTHER INFORMATION: pNOP257143

<400> SEQUENCE: 399

Arg Phe Pro Ser Ser Ser Pro Gln Glu Met Glu Arg Ser Ala Leu Glu
1               5                   10                  15

Ala Ala Ser Ala Ala Ala Asp His Pro Glu Gly Gln Trp Ala Ala Gly
            20                  25                  30

Gly

<210> SEQ ID NO 400
<211> LENGTH: 33
<212> TYPE: PRT
<213> ORGANISM: Artificial Sequence
<220> FEATURE:
<223> OTHER INFORMATION: pNOP257396

<400> SEQUENCE: 400

Arg Leu Pro Cys Ala Pro Gly Pro Arg Gly Ala Gly Pro Cys Asp Pro
1               5                   10                  15

Tyr Gly Gly Leu Pro Arg Met Gln Ala Asp Ser Arg Ala Gly Leu Thr
            20                  25                  30

Met

<210> SEQ ID NO 401
<211> LENGTH: 33
<212> TYPE: PRT
<213> ORGANISM: Artificial Sequence
<220> FEATURE:
<223> OTHER INFORMATION: pNOP257632

<400> SEQUENCE: 401

Arg Arg Lys Ser Leu Gly His Pro Leu Leu Ala Met Gly Pro Gln Thr
1               5                   10                  15

-continued

Trp Ala Leu Leu Thr His Pro Pro Gln Ala Pro Thr Trp Val Ala Trp
            20                  25                  30
Ser

<210> SEQ ID NO 402
<211> LENGTH: 33
<212> TYPE: PRT
<213> ORGANISM: Artificial Sequence
<220> FEATURE:
<223> OTHER INFORMATION: pNOP258695

<400> SEQUENCE: 402

Ser Thr Pro Leu Ala Val Pro Asp Gln Ser Leu Lys Ser Ser His Thr
1               5                   10                  15

Thr Asn Ala Phe Ser His Pro Leu Ser His Leu Ile Leu Thr Thr Thr
            20                  25                  30
Leu

<210> SEQ ID NO 403
<211> LENGTH: 33
<212> TYPE: PRT
<213> ORGANISM: Artificial Sequence
<220> FEATURE:
<223> OTHER INFORMATION: pNOP259446

<400> SEQUENCE: 403

Val Gly Ser Met Glu Gly Arg Gln Ala Trp Tyr Pro Ser Arg Ala His
1               5                   10                  15

Ser Gln Cys Tyr His Arg Ser Pro Trp Ala Pro Cys His Leu Pro Cys
            20                  25                  30
Ala

<210> SEQ ID NO 404
<211> LENGTH: 32
<212> TYPE: PRT
<213> ORGANISM: Artificial Sequence
<220> FEATURE:
<223> OTHER INFORMATION: pNOP261027

<400> SEQUENCE: 404

Cys His Cys Pro Leu Ser Arg Gly Leu Arg Gly His Ala His Leu Leu
1               5                   10                  15

Glu Pro Pro His Gln Gln Ser Ser Leu Leu Ser Leu Phe Tyr Trp
            20                  25                  30

<210> SEQ ID NO 405
<211> LENGTH: 32
<212> TYPE: PRT
<213> ORGANISM: Artificial Sequence
<220> FEATURE:
<223> OTHER INFORMATION: pNOP261872

<400> SEQUENCE: 405

Glu Gly Leu Leu Trp Gly His Gly Arg Thr Thr Ser Ser Pro Ala Asp
1               5                   10                  15

Pro Gln Pro Thr Glu Trp Pro Arg Arg Ile Leu Pro Ala Gly Lys Val
            20                  25                  30

<210> SEQ ID NO 406
<211> LENGTH: 32
<212> TYPE: PRT
<213> ORGANISM: Artificial Sequence
<220> FEATURE:

<223> OTHER INFORMATION: pNOP269687

<400> SEQUENCE: 406

Val Arg Thr Pro Thr Asp Trp Leu Leu Lys Gly Phe Gly Ala Trp Arg
1               5                   10                  15

Tyr Gln Val Phe Pro His Arg Asn Pro Gln Pro His Arg Pro Leu Asn
            20                  25                  30

<210> SEQ ID NO 407
<211> LENGTH: 31
<212> TYPE: PRT
<213> ORGANISM: Artificial Sequence
<220> FEATURE:
<223> OTHER INFORMATION: pNOP270434

<400> SEQUENCE: 407

Ala Ala Ala Gln Cys Thr Glu Arg Thr Gly Thr Trp Gly His Ser Val
1               5                   10                  15

Ser Trp Ser Gly Pro Thr Ser Glu Thr Pro Phe Leu Pro Cys Lys
            20                  25                  30

<210> SEQ ID NO 408
<211> LENGTH: 31
<212> TYPE: PRT
<213> ORGANISM: Artificial Sequence
<220> FEATURE:
<223> OTHER INFORMATION: pNOP276046

<400> SEQUENCE: 408

Met Pro Ser Leu Gly Thr Gln Cys His Gln Ser Ser Pro Phe Pro Asn
1               5                   10                  15

Gly Gly Pro Phe Leu Pro Arg Pro Gln Pro Cys Pro Ser Pro Gly
            20                  25                  30

<210> SEQ ID NO 409
<211> LENGTH: 31
<212> TYPE: PRT
<213> ORGANISM: Artificial Sequence
<220> FEATURE:
<223> OTHER INFORMATION: pNOP277209

<400> SEQUENCE: 409

Pro Val Leu Leu Tyr Gln Leu Trp Ala Ser Leu Ser Arg Gly Leu Pro
1               5                   10                  15

Gly His Cys Ser Asp Cys Pro Gln Thr Cys Trp Leu Ala Val Pro
            20                  25                  30

<210> SEQ ID NO 410
<211> LENGTH: 31
<212> TYPE: PRT
<213> ORGANISM: Artificial Sequence
<220> FEATURE:
<223> OTHER INFORMATION: pNOP277754

<400> SEQUENCE: 410

Arg Ala Arg Cys Ser Val Arg Cys Met Pro Arg Ala Ala Lys Gly Trp
1               5                   10                  15

Ala Arg Asp Leu Tyr Ala Thr Gln Gly Thr Arg Ala Pro Ala Met
            20                  25                  30

<210> SEQ ID NO 411
<211> LENGTH: 31
<212> TYPE: PRT
<213> ORGANISM: Artificial Sequence
<220> FEATURE:
<223> OTHER INFORMATION: pNOP279143

<400> SEQUENCE: 411

Ser Lys Ser Ser Ser Arg Ala Trp Arg Thr Trp Ser Ser Leu Thr Pro
1               5                   10                  15

Leu Pro Arg Pro Cys Gly Ile Ala Ser Leu Ser Leu Trp Leu Pro
            20                  25                  30

<210> SEQ ID NO 412
<211> LENGTH: 30
<212> TYPE: PRT
<213> ORGANISM: Artificial Sequence
<220> FEATURE:
<223> OTHER INFORMATION: pNOP284778

<400> SEQUENCE: 412

His His Ser Ala Gly Arg Thr Ala Ala His Val Pro Cys Gly Gly Pro
1               5                   10                  15

Cys Val Pro Arg His Arg Thr Ala Ala Ser Pro Asp Gly
            20                  25                  30

<210> SEQ ID NO 413
<211> LENGTH: 30
<212> TYPE: PRT
<213> ORGANISM: Artificial Sequence
<220> FEATURE:
<223> OTHER INFORMATION: pNOP285042

<400> SEQUENCE: 413

Ile Glu Gln Gln Ser Ser Ser Asn Thr Pro His Gln Gly Ser Tyr Pro
1               5                   10                  15

Ala Asn Trp Phe Gly Ala Gly Gln Pro Ala Pro Val Glu His
            20                  25                  30

<210> SEQ ID NO 414
<211> LENGTH: 30
<212> TYPE: PRT
<213> ORGANISM: Artificial Sequence
<220> FEATURE:
<223> OTHER INFORMATION: pNOP287872

<400> SEQUENCE: 414

Pro Leu Cys Pro Leu Trp Gln Trp Leu Pro Ser Gln Trp Ala Glu Pro
1               5                   10                  15

Ala Glu Gly Gly Leu Trp Lys Trp Gly Ala Ala His Trp Pro
            20                  25                  30

<210> SEQ ID NO 415
<211> LENGTH: 29
<212> TYPE: PRT
<213> ORGANISM: Artificial Sequence
<220> FEATURE:
<223> OTHER INFORMATION: pNOP298931

<400> SEQUENCE: 415

Asn His Pro Trp Arg Asn Cys Leu Leu Thr Leu Gly Ser Ala Arg Arg
1               5                   10                  15

Ala Gly Cys Ala Gly Pro Val Gly Arg Ala Gln Gln Asn
            20                  25

<210> SEQ ID NO 416
<211> LENGTH: 29
<212> TYPE: PRT

```
<213> ORGANISM: Artificial Sequence
<220> FEATURE:
<223> OTHER INFORMATION: pNOP302234

<400> SEQUENCE: 416

Ser Pro His Ser Leu Gly Thr His Asn Ser Cys Leu Ser Asn Pro Ser
1               5                   10                  15

Pro Ser Leu Ser Pro Ala Leu Cys Ser Cys Ser His Leu
            20                  25

<210> SEQ ID NO 417
<211> LENGTH: 29
<212> TYPE: PRT
<213> ORGANISM: Artificial Sequence
<220> FEATURE:
<223> OTHER INFORMATION: pNOP303477

<400> SEQUENCE: 417

Val Ala Pro Ser Trp Gly Gln Gly Pro Ser Leu Ala Met Thr Asp Ser
1               5                   10                  15

Pro Gly His Leu His Gln Pro Arg Leu Pro Leu Trp Met
            20                  25

<210> SEQ ID NO 418
<211> LENGTH: 28
<212> TYPE: PRT
<213> ORGANISM: Artificial Sequence
<220> FEATURE:
<223> OTHER INFORMATION: pNOP310713

<400> SEQUENCE: 418

Met Asp Arg Trp Cys Leu Arg His Pro Asn Ser Ala Ser Ser Arg Asn
1               5                   10                  15

Leu Gly Lys Ser His Val Pro Trp Glu Pro Ser Gln
            20                  25

<210> SEQ ID NO 419
<211> LENGTH: 27
<212> TYPE: PRT
<213> ORGANISM: Artificial Sequence
<220> FEATURE:
<223> OTHER INFORMATION: pNOP318057

<400> SEQUENCE: 419

Cys His Gln Ile Pro Phe Leu Leu His Ser His Pro Ser Ser Gln Leu
1               5                   10                  15

Arg Pro His Arg Pro Cys Leu Leu Trp Gly Ser
            20                  25

<210> SEQ ID NO 420
<211> LENGTH: 27
<212> TYPE: PRT
<213> ORGANISM: Artificial Sequence
<220> FEATURE:
<223> OTHER INFORMATION: pNOP318220

<400> SEQUENCE: 420

Cys Pro Pro Ser His Gln Leu Met Pro Ser Ser Asn Ala Trp Leu His
1               5                   10                  15

Pro Trp Leu Trp Cys Pro Ile Lys Gly Ile Cys
            20                  25

<210> SEQ ID NO 421
<211> LENGTH: 27
```

```
<212> TYPE: PRT
<213> ORGANISM: Artificial Sequence
<220> FEATURE:
<223> OTHER INFORMATION: pNOP318964

<400> SEQUENCE: 421

Glu Ala Gln Ala Gly Tyr Arg Ala Ala Glu Gln Asp Pro Glu Thr Thr
1               5                   10                  15

Gly Ser Gly Pro Glu Thr Ala Glu Gly Ala His
            20                  25

<210> SEQ ID NO 422
<211> LENGTH: 27
<212> TYPE: PRT
<213> ORGANISM: Artificial Sequence
<220> FEATURE:
<223> OTHER INFORMATION: pNOP323435

<400> SEQUENCE: 422

Leu Asn His Cys Pro Gly Trp Arg Ala Val Lys Thr Ile Tyr Ser Ala
1               5                   10                  15

Met Gly Ala Thr Pro Leu Trp Ser Cys His Ser
            20                  25

<210> SEQ ID NO 423
<211> LENGTH: 27
<212> TYPE: PRT
<213> ORGANISM: Artificial Sequence
<220> FEATURE:
<223> OTHER INFORMATION: pNOP323658

<400> SEQUENCE: 423

Leu Arg Gln Asp Phe His Arg Arg Thr Ala Gln Asp Gly Ile Gln Gly
1               5                   10                  15

Pro Ala Ala Ala Leu Gln Gly Cys Ser Gly Leu
            20                  25

<210> SEQ ID NO 424
<211> LENGTH: 27
<212> TYPE: PRT
<213> ORGANISM: Artificial Sequence
<220> FEATURE:
<223> OTHER INFORMATION: pNOP325001

<400> SEQUENCE: 424

Pro Asp His Val Thr Thr Ala Gln Ala Ala Pro Thr Ala Arg Thr Ala
1               5                   10                  15

Trp Pro Pro Arg Arg Gly Arg Ile Gly Gly Phe
            20                  25

<210> SEQ ID NO 425
<211> LENGTH: 27
<212> TYPE: PRT
<213> ORGANISM: Artificial Sequence
<220> FEATURE:
<223> OTHER INFORMATION: pNOP325387

<400> SEQUENCE: 425

Pro Met Thr Ile Ser Leu Ile Leu Arg Thr Ile Ser Thr Arg Ser Pro
1               5                   10                  15

Ala Thr Val Glu Pro Gly Ile Val Gly Asn Gly
            20                  25

<210> SEQ ID NO 426
```

```
-continued

<211> LENGTH: 27
<212> TYPE: PRT
<213> ORGANISM: Artificial Sequence
<220> FEATURE:
<223> OTHER INFORMATION: pNOP325875

<400> SEQUENCE: 426

Pro Trp Ser Pro Gly Ser Asn Pro Pro Asp Gly Gln Gly Thr Lys
1               5                   10                  15

His Arg Arg Pro Ser Arg Phe Phe Arg Gly His
            20                  25

<210> SEQ ID NO 427
<211> LENGTH: 26
<212> TYPE: PRT
<213> ORGANISM: Artificial Sequence
<220> FEATURE:
<223> OTHER INFORMATION: pNOP334374

<400> SEQUENCE: 427

Gly Leu Thr Cys Phe Pro Thr Thr Gly Gly Leu Ala His Val Pro Ala
1               5                   10                  15

Ala Gly Gly Val Thr Pro Val Ala Thr Thr
            20                  25

<210> SEQ ID NO 428
<211> LENGTH: 26
<212> TYPE: PRT
<213> ORGANISM: Artificial Sequence
<220> FEATURE:
<223> OTHER INFORMATION: pNOP336175

<400> SEQUENCE: 428

Lys Gly Thr Glu Gly Tyr Phe Arg Gly Glu Glu Ser Arg Pro Ala Gly
1               5                   10                  15

Cys Leu Ala Tyr Thr Pro Ser Gln Ser Asp
            20                  25

<210> SEQ ID NO 429
<211> LENGTH: 26
<212> TYPE: PRT
<213> ORGANISM: Artificial Sequence
<220> FEATURE:
<223> OTHER INFORMATION: pNOP341158

<400> SEQUENCE: 429

Arg Ser Leu Leu Ser Pro Pro Ile Leu Ala Ser Leu Pro Pro Leu Ala
1               5                   10                  15

Val Ala Ala Gln Ser Met Gly Arg Ala Ser
            20                  25

<210> SEQ ID NO 430
<211> LENGTH: 26
<212> TYPE: PRT
<213> ORGANISM: Artificial Sequence
<220> FEATURE:
<223> OTHER INFORMATION: pNOP343442

<400> SEQUENCE: 430

Thr Trp Thr Trp Thr Cys Gly Cys Thr Ser Thr Val Pro Phe Gly Pro
1               5                   10                  15

Arg Arg Cys Met Arg Pro Arg Ala Gly His
            20                  25
```

```
<210> SEQ ID NO 431
<211> LENGTH: 26
<212> TYPE: PRT
<213> ORGANISM: Artificial Sequence
<220> FEATURE:
<223> OTHER INFORMATION: pNOP344075

<400> SEQUENCE: 431

Trp Ala Cys Pro Ser Ala Glu Pro Gly Pro Val Gly Ala Pro
1               5                   10                  15

Gln Leu Cys Pro Leu Val His Gly Gly Val
            20                  25

<210> SEQ ID NO 432
<211> LENGTH: 25
<212> TYPE: PRT
<213> ORGANISM: Artificial Sequence
<220> FEATURE:
<223> OTHER INFORMATION: pNOP352206

<400> SEQUENCE: 432

Met Ala Ser Pro His Leu Lys Ser Trp Gly Ser Thr Pro Arg Met Leu
1               5                   10                  15

Pro Leu Pro Gly Ile Val Lys Gly His
            20                  25

<210> SEQ ID NO 433
<211> LENGTH: 25
<212> TYPE: PRT
<213> ORGANISM: Artificial Sequence
<220> FEATURE:
<223> OTHER INFORMATION: pNOP356926

<400> SEQUENCE: 433

Ser Gln Ala Arg Leu Pro Arg Leu Val Lys Pro Leu Gln Thr Asn His
1               5                   10                  15

Glu Ala Leu Glu Lys Gly Ser Ser Ser
            20                  25

<210> SEQ ID NO 434
<211> LENGTH: 24
<212> TYPE: PRT
<213> ORGANISM: Artificial Sequence
<220> FEATURE:
<223> OTHER INFORMATION: pNOP362881

<400> SEQUENCE: 434

Phe Trp Glu Ser Gln Ala Ser Gly Asp Ser Ser Gly Leu Gln Trp Gly
1               5                   10                  15

Ser Gly Ala Ala Leu Cys Ser Leu
            20

<210> SEQ ID NO 435
<211> LENGTH: 24
<212> TYPE: PRT
<213> ORGANISM: Artificial Sequence
<220> FEATURE:
<223> OTHER INFORMATION: pNOP363905

<400> SEQUENCE: 435

Gly Trp Val Ser Ser Pro His Phe Ala Gly Gly Trp Gly Val Pro Ser
1               5                   10                  15

Ser Pro Ala Arg Gly Ala Ser Arg
            20
```

<210> SEQ ID NO 436
<211> LENGTH: 24
<212> TYPE: PRT
<213> ORGANISM: Artificial Sequence
<220> FEATURE:
<223> OTHER INFORMATION: pNOP364735

<400> SEQUENCE: 436

Ile Ile Thr Phe Phe Ser Thr Gly Gly Val Ala Leu Val Ser Thr Gly
1               5                   10                  15

Arg Val Thr Pro Ile Ser Cys Thr
            20

<210> SEQ ID NO 437
<211> LENGTH: 24
<212> TYPE: PRT
<213> ORGANISM: Artificial Sequence
<220> FEATURE:
<223> OTHER INFORMATION: pNOP370861

<400> SEQUENCE: 437

Arg Met Met Lys Ser Leu Leu Thr Trp Val Trp Val Trp Met Trp Pro
1               5                   10                  15

Arg Val Met Met Asn Leu Ala Pro
            20

<210> SEQ ID NO 438
<211> LENGTH: 95
<212> TYPE: PRT
<213> ORGANISM: Artificial Sequence
<220> FEATURE:
<223> OTHER INFORMATION: pNOP37587

<400> SEQUENCE: 438

Gly Ile Ser Glu His Leu His Arg Arg Asp Gln His Pro Leu Gln Gln
1               5                   10                  15

Ala Val Cys Ala Leu Gln Val Ile Ser Val Pro Ala Ala Ala His Arg
            20                  25                  30

Met Glu Glu Gln Arg Val Pro Gly Ser Leu Pro Tyr Pro Gly Pro Gly
        35                  40                  45

Ala Leu Cys Ser Gln Gly Pro Arg Lys Ala His Asn Gly Tyr Arg Val
    50                  55                  60

His Trp His His His Ser Glu Arg Gly Gly Gln Pro Ala Gly Glu Asn
65                  70                  75                  80

Leu Arg Arg Ala Glu Ser Arg His Leu His Val Pro Asn Lys Gln
                85                  90                  95

<210> SEQ ID NO 439
<211> LENGTH: 23
<212> TYPE: PRT
<213> ORGANISM: Artificial Sequence
<220> FEATURE:
<223> OTHER INFORMATION: pNOP376012

<400> SEQUENCE: 439

Ala Arg Gln Pro Leu Asp Gly Leu Arg Trp His His Ala Leu His Pro
1               5                   10                  15

His Asn Pro His His Gly Gly
            20

<210> SEQ ID NO 440
<211> LENGTH: 23

```
<212> TYPE: PRT
<213> ORGANISM: Artificial Sequence
<220> FEATURE:
<223> OTHER INFORMATION: pNOP378675

<400> SEQUENCE: 440

Gly Ala Ala Leu Val Pro Ser Pro Trp Gly Thr Ile Leu Ile Ser Leu
1               5                   10                  15

Ala Trp Arg Ala Ser Pro Val
            20

<210> SEQ ID NO 441
<211> LENGTH: 23
<212> TYPE: PRT
<213> ORGANISM: Artificial Sequence
<220> FEATURE:
<223> OTHER INFORMATION: pNOP378896

<400> SEQUENCE: 441

Gly Phe Gln Asp Asn Ser Ser Ser Lys Leu Ala Cys Ser Thr Gln Gln
1               5                   10                  15

Val Glu Glu Ala Met Gly Ser
            20

<210> SEQ ID NO 442
<211> LENGTH: 23
<212> TYPE: PRT
<213> ORGANISM: Artificial Sequence
<220> FEATURE:
<223> OTHER INFORMATION: pNOP386633

<400> SEQUENCE: 442

Arg His Pro Gln Cys Pro Val Thr Leu Arg Ser Gln Ala Pro Gln Val
1               5                   10                  15

Lys Gly Cys Leu Ala Leu Thr
            20

<210> SEQ ID NO 443
<211> LENGTH: 23
<212> TYPE: PRT
<213> ORGANISM: Artificial Sequence
<220> FEATURE:
<223> OTHER INFORMATION: pNOP388467

<400> SEQUENCE: 443

Ser Met Lys Leu Thr Ser Gly Ser Met Arg Ser Gly Cys Ser Ile Pro
1               5                   10                  15

Ser Ser Ser Tyr Arg Cys Ser
            20

<210> SEQ ID NO 444
<211> LENGTH: 23
<212> TYPE: PRT
<213> ORGANISM: Artificial Sequence
<220> FEATURE:
<223> OTHER INFORMATION: pNOP390234

<400> SEQUENCE: 444

Val Glu Ala Arg Pro Pro Leu Leu Gly His Arg Thr Arg Ala Ala Leu
1               5                   10                  15

Trp Gly Cys Pro Gln Ala Ser
            20

<210> SEQ ID NO 445
```

```
<211> LENGTH: 22
<212> TYPE: PRT
<213> ORGANISM: Artificial Sequence
<220> FEATURE:
<223> OTHER INFORMATION: pNOP394670

<400> SEQUENCE: 445

Glu Gln Arg Ala Ala Gly Val Cys Asn Gln Ser His Arg Ala Gly Pro
1               5                   10                  15

Gly Gly Pro Gly Leu His
            20

<210> SEQ ID NO 446
<211> LENGTH: 22
<212> TYPE: PRT
<213> ORGANISM: Artificial Sequence
<220> FEATURE:
<223> OTHER INFORMATION: pNOP404863

<400> SEQUENCE: 446

Arg Thr Gly Arg Ala Thr Cys Thr Gly Gly Pro His Thr His Thr Ser
1               5                   10                  15

His Gln Ile Arg His Arg
            20

<210> SEQ ID NO 447
<211> LENGTH: 22
<212> TYPE: PRT
<213> ORGANISM: Artificial Sequence
<220> FEATURE:
<223> OTHER INFORMATION: pNOP405923

<400> SEQUENCE: 447

Ser Pro Arg Trp Arg Arg Val Asp Ala Thr Leu Leu Leu Ala Asn Ser
1               5                   10                  15

Pro Leu Leu Pro Pro Arg
            20

<210> SEQ ID NO 448
<211> LENGTH: 22
<212> TYPE: PRT
<213> ORGANISM: Artificial Sequence
<220> FEATURE:
<223> OTHER INFORMATION: pNOP406378

<400> SEQUENCE: 448

Ser Thr Pro Leu Ala Val Pro Asp Gln Ser Leu Lys Ser Ser His Thr
1               5                   10                  15

Thr Asn Gly Pro Ile Pro
            20

<210> SEQ ID NO 449
<211> LENGTH: 21
<212> TYPE: PRT
<213> ORGANISM: Artificial Sequence
<220> FEATURE:
<223> OTHER INFORMATION: pNOP410165

<400> SEQUENCE: 449

Ala Val Asp His Leu Leu Arg Pro His Leu Cys Pro Thr Cys Trp Leu
1               5                   10                  15

Ser Pro Leu Phe Pro
            20
```

```
<210> SEQ ID NO 450
<211> LENGTH: 21
<212> TYPE: PRT
<213> ORGANISM: Artificial Sequence
<220> FEATURE:
<223> OTHER INFORMATION: pNOP414691

<400> SEQUENCE: 450

His Leu Thr Lys Arg Thr Lys Ser Ser Ser Pro Ala Gly Glu Ser
1               5                   10                  15

Pro Lys Glu Arg Ser
            20

<210> SEQ ID NO 451
<211> LENGTH: 21
<212> TYPE: PRT
<213> ORGANISM: Artificial Sequence
<220> FEATURE:
<223> OTHER INFORMATION: pNOP421373

<400> SEQUENCE: 451

Arg Ala Ser Gly Pro Gly Gly Ile Arg Ser Pro Thr Glu Thr Leu
1               5                   10                  15

Ser Pro Thr Gly Pro
            20

<210> SEQ ID NO 452
<211> LENGTH: 21
<212> TYPE: PRT
<213> ORGANISM: Artificial Sequence
<220> FEATURE:
<223> OTHER INFORMATION: pNOP425823

<400> SEQUENCE: 452

Thr Trp Pro Pro Ser Pro Arg Phe Pro Val Gly Gly Asn Phe His Pro
1               5                   10                  15

Ser Ala Arg Pro Trp
            20

<210> SEQ ID NO 453
<211> LENGTH: 20
<212> TYPE: PRT
<213> ORGANISM: Artificial Sequence
<220> FEATURE:
<223> OTHER INFORMATION: pNOP438522

<400> SEQUENCE: 453

Pro Ala Ala Leu Pro Gly Thr Leu Thr Ile Pro Val Pro Leu Thr Val
1               5                   10                  15

Trp Pro Lys Ser
            20

<210> SEQ ID NO 454
<211> LENGTH: 88
<212> TYPE: PRT
<213> ORGANISM: Artificial Sequence
<220> FEATURE:
<223> OTHER INFORMATION: pNOP44778

<400> SEQUENCE: 454

Ala Leu Ser Pro Trp Ala Leu Tyr Ser Ser Phe Ser Ser Ser Ser
1               5                   10                  15

Cys Asn Ser Asn Ser Asn Phe Ser Ser Ser Ser Ser Tyr Asn
        20                  25                  30
```

Ser Asn Ser Asn Phe Ser Ser Asn Ser Phe Asn Ser Ser Asn Ser Ser
            35                  40                  45

Ser Ser Phe Asn Asn Ser Ser Ser Asn Ser Phe Asn Ser Ser Asn Ser
    50                  55                  60

Ser Tyr Asn Ser Asn Ser Asn Asn Asn Ser Ser Ser Phe Asn Ser Ser
65                  70                  75                  80

Ser Asn Ser Ser Arg Trp Ala Phe
                85

<210> SEQ ID NO 455
<211> LENGTH: 19
<212> TYPE: PRT
<213> ORGANISM: Artificial Sequence
<220> FEATURE:
<223> OTHER INFORMATION: pNOP458695

<400> SEQUENCE: 455

Pro Ala Pro His Ser Arg Trp Arg Lys Pro Trp Ala Arg Gln Trp
1               5                   10                  15

Ile Ile Phe

<210> SEQ ID NO 456
<211> LENGTH: 19
<212> TYPE: PRT
<213> ORGANISM: Artificial Sequence
<220> FEATURE:
<223> OTHER INFORMATION: pNOP465144

<400> SEQUENCE: 456

Thr Gln Pro Phe Leu Gln Arg Pro Leu Arg Gly Pro Leu His Ile Arg
1               5                   10                  15

Glu Gly Arg

<210> SEQ ID NO 457
<211> LENGTH: 19
<212> TYPE: PRT
<213> ORGANISM: Artificial Sequence
<220> FEATURE:
<223> OTHER INFORMATION: pNOP466225

<400> SEQUENCE: 457

Val Ser Glu Gly Arg Gly Ala Leu Trp Ala Asp Gly Ala Cys Arg Ala
1               5                   10                  15

Ser His Ser

<210> SEQ ID NO 458
<211> LENGTH: 87
<212> TYPE: PRT
<213> ORGANISM: Artificial Sequence
<220> FEATURE:
<223> OTHER INFORMATION: pNOP46646

<400> SEQUENCE: 458

Pro Ala Ser Tyr Pro Cys Ser Leu Arg Thr Cys Trp Ser Met Arg Arg
1               5                   10                  15

Arg Ser Cys Arg Arg Ser Ser Ser Phe Gln His Ser Cys Ser Leu Pro
                20                  25                  30

Ser Ser Ser Ser Asn Ser Ser Ser Ile Pro Tyr Cys Leu His Gln
            35                  40                  45

Ala Leu Pro Arg Pro Cys Leu Cys His Met Arg Ala Leu Leu Pro Val
        50                  55                  60

```
Trp Leu Gly Pro Asn Ser Ser Phe Pro Trp Val Leu Gln Val Pro Asp
 65                  70                  75                  80

Ser Gln Val Cys Pro Ser His
                 85

<210> SEQ ID NO 459
<211> LENGTH: 18
<212> TYPE: PRT
<213> ORGANISM: Artificial Sequence
<220> FEATURE:
<223> OTHER INFORMATION: pNOP468251

<400> SEQUENCE: 459

Ala Pro Glu Arg Ser Cys Gly Arg Arg Thr Gly Ser Gly Pro Ala Arg
 1               5                  10                  15

Pro Cys

<210> SEQ ID NO 460
<211> LENGTH: 18
<212> TYPE: PRT
<213> ORGANISM: Artificial Sequence
<220> FEATURE:
<223> OTHER INFORMATION: pNOP473253

<400> SEQUENCE: 460

Gly Ser Trp Trp Glu Gly Lys Gly Ser Gly Arg Gln Glu Pro Arg His
 1               5                  10                  15

Trp Pro

<210> SEQ ID NO 461
<211> LENGTH: 18
<212> TYPE: PRT
<213> ORGANISM: Artificial Sequence
<220> FEATURE:
<223> OTHER INFORMATION: pNOP481442

<400> SEQUENCE: 461

Gln Lys Pro Arg Ser Gln Ser Arg Ala Ala Trp Tyr Leu Gly Ile Trp
 1               5                  10                  15

Thr Arg

<210> SEQ ID NO 462
<211> LENGTH: 18
<212> TYPE: PRT
<213> ORGANISM: Artificial Sequence
<220> FEATURE:
<223> OTHER INFORMATION: pNOP487229

<400> SEQUENCE: 462

Val Ala Gln Glu Asp Pro Pro Cys Trp Lys Ser Leu Ser Ser Arg Val
 1               5                  10                  15

Gly Leu

<210> SEQ ID NO 463
<211> LENGTH: 18
<212> TYPE: PRT
<213> ORGANISM: Artificial Sequence
<220> FEATURE:
<223> OTHER INFORMATION: pNOP487911

<400> SEQUENCE: 463

Val Thr Val Gly Cys Pro His Pro Gly Asp Thr His Gln Pro Ser Thr
 1               5                  10                  15
```

Arg Ser

<210> SEQ ID NO 464
<211> LENGTH: 17
<212> TYPE: PRT
<213> ORGANISM: Artificial Sequence
<220> FEATURE:
<223> OTHER INFORMATION: pNOP490058

<400> SEQUENCE: 464

Ala Pro Val Gly Gly Pro Pro Lys Arg Gly Asp Ala Thr Ala Ala Pro
1               5                   10                  15

Thr

<210> SEQ ID NO 465
<211> LENGTH: 17
<212> TYPE: PRT
<213> ORGANISM: Artificial Sequence
<220> FEATURE:
<223> OTHER INFORMATION: pNOP490152

<400> SEQUENCE: 465

Ala Arg Glu Trp Gly Phe Asp Leu Ala Trp Trp Thr Cys Ser Ile Trp
1               5                   10                  15

Gly

<210> SEQ ID NO 466
<211> LENGTH: 17
<212> TYPE: PRT
<213> ORGANISM: Artificial Sequence
<220> FEATURE:
<223> OTHER INFORMATION: pNOP490194

<400> SEQUENCE: 466

Ala Arg Gln Asp Gly Glu Leu Thr Gly Ser Gln Arg Val Thr Pro Ala
1               5                   10                  15

His

<210> SEQ ID NO 467
<211> LENGTH: 17
<212> TYPE: PRT
<213> ORGANISM: Artificial Sequence
<220> FEATURE:
<223> OTHER INFORMATION: pNOP493996

<400> SEQUENCE: 467

Gly Ala Ala Thr Leu Pro Pro Val Arg Gly Ala Ala Pro Val Thr Pro
1               5                   10                  15

Ala

<210> SEQ ID NO 468
<211> LENGTH: 17
<212> TYPE: PRT
<213> ORGANISM: Artificial Sequence
<220> FEATURE:
<223> OTHER INFORMATION: pNOP494542

<400> SEQUENCE: 468

Gly Ile Ala Pro Ile Pro Pro Ala Cys Gly Val Thr Pro Val Ser Thr
1               5                   10                  15

Ala

<210> SEQ ID NO 469

```
<211> LENGTH: 17
<212> TYPE: PRT
<213> ORGANISM: Artificial Sequence
<220> FEATURE:
<223> OTHER INFORMATION: pNOP494543

<400> SEQUENCE: 469

Gly Ile Ala Pro Val Pro Ala Ala Gly Gly Ile Ala Pro Leu Ser Ala
1               5                   10                  15
Ala

<210> SEQ ID NO 470
<211> LENGTH: 17
<212> TYPE: PRT
<213> ORGANISM: Artificial Sequence
<220> FEATURE:
<223> OTHER INFORMATION: pNOP501743

<400> SEQUENCE: 470

Asn Pro His Thr Leu Gln Thr Ala Pro Tyr Pro Glu Gln His Gln His
1               5                   10                  15
Val

<210> SEQ ID NO 471
<211> LENGTH: 17
<212> TYPE: PRT
<213> ORGANISM: Artificial Sequence
<220> FEATURE:
<223> OTHER INFORMATION: pNOP502714

<400> SEQUENCE: 471

Pro Leu Cys Asn Pro Arg Asn Gln Gly Pro Cys Asn Val Lys Pro Asn
1               5                   10                  15
His

<210> SEQ ID NO 472
<211> LENGTH: 17
<212> TYPE: PRT
<213> ORGANISM: Artificial Sequence
<220> FEATURE:
<223> OTHER INFORMATION: pNOP506673

<400> SEQUENCE: 472

Arg Val Thr His Val Ser Thr Thr Gly Gly Ile Ser Ser Val Pro Thr
1               5                   10                  15
Ile

<210> SEQ ID NO 473
<211> LENGTH: 17
<212> TYPE: PRT
<213> ORGANISM: Artificial Sequence
<220> FEATURE:
<223> OTHER INFORMATION: pNOP507548

<400> SEQUENCE: 473

Ser Leu Pro Ala Ser Ser Gln Pro Ala His Phe Cys Ser Gly Ser Asp
1               5                   10                  15
Gln

<210> SEQ ID NO 474
<211> LENGTH: 17
<212> TYPE: PRT
<213> ORGANISM: Artificial Sequence
<220> FEATURE:
```

<223> OTHER INFORMATION: pNOP508277

<400> SEQUENCE: 474

Ser Ser Gln Gln Pro Tyr Glu Ala Pro Tyr Pro Glu Gln His Gln His
1               5                   10                  15

Val

<210> SEQ ID NO 475
<211> LENGTH: 16
<212> TYPE: PRT
<213> ORGANISM: Artificial Sequence
<220> FEATURE:
<223> OTHER INFORMATION: pNOP512482

<400> SEQUENCE: 475

Ala Gly Ser Gly Arg Val Tyr Gly Ala Ala Trp His Ser Leu Ala Thr
1               5                   10                  15

<210> SEQ ID NO 476
<211> LENGTH: 16
<212> TYPE: PRT
<213> ORGANISM: Artificial Sequence
<220> FEATURE:
<223> OTHER INFORMATION: pNOP513338

<400> SEQUENCE: 476

Ala Val Arg Pro Phe Leu Gln Leu Gly Trp Ala Gly Gln Ala Leu Asp
1               5                   10                  15

<210> SEQ ID NO 477
<211> LENGTH: 16
<212> TYPE: PRT
<213> ORGANISM: Artificial Sequence
<220> FEATURE:
<223> OTHER INFORMATION: pNOP513379

<400> SEQUENCE: 477

Ala Trp Pro Pro Gln Ser Ser Gly Pro Gly Ser Trp Glu Val Ala Leu
1               5                   10                  15

<210> SEQ ID NO 478
<211> LENGTH: 16
<212> TYPE: PRT
<213> ORGANISM: Artificial Sequence
<220> FEATURE:
<223> OTHER INFORMATION: pNOP513605

<400> SEQUENCE: 478

Cys Gly Ala Trp Gln Arg Gly Asp Arg Gly Lys Gln Lys Thr Gln Ala
1               5                   10                  15

<210> SEQ ID NO 479
<211> LENGTH: 16
<212> TYPE: PRT
<213> ORGANISM: Artificial Sequence
<220> FEATURE:
<223> OTHER INFORMATION: pNOP514247

<400> SEQUENCE: 479

Cys Ser Gly Phe Thr Ala Arg Ala Trp Thr Asp Pro Trp Gln Phe Gly
1               5                   10                  15

<210> SEQ ID NO 480
<211> LENGTH: 16
<212> TYPE: PRT
<213> ORGANISM: Artificial Sequence

```
<220> FEATURE:
<223> OTHER INFORMATION: pNOP517078

<400> SEQUENCE: 480

Gly Ala Leu Tyr Thr Ser Gly Arg Ala Val Ser Asn Arg Asn Tyr Pro
1               5                   10                  15

<210> SEQ ID NO 481
<211> LENGTH: 16
<212> TYPE: PRT
<213> ORGANISM: Artificial Sequence
<220> FEATURE:
<223> OTHER INFORMATION: pNOP518512

<400> SEQUENCE: 481

Gly Val Gly Pro Ala Val His His Leu Thr Cys Ala Leu Cys Gln His
1               5                   10                  15

<210> SEQ ID NO 482
<211> LENGTH: 16
<212> TYPE: PRT
<213> ORGANISM: Artificial Sequence
<220> FEATURE:
<223> OTHER INFORMATION: pNOP522295

<400> SEQUENCE: 482

Leu Ala Pro Val Ser Ser Gly Val Pro Trp Gly Glu Pro Arg Ala Gln
1               5                   10                  15

<210> SEQ ID NO 483
<211> LENGTH: 16
<212> TYPE: PRT
<213> ORGANISM: Artificial Sequence
<220> FEATURE:
<223> OTHER INFORMATION: pNOP523824

<400> SEQUENCE: 483

Leu Thr Leu Leu Arg His Pro Pro Gly Trp Pro Gly Val Lys Asp Thr
1               5                   10                  15

<210> SEQ ID NO 484
<211> LENGTH: 83
<212> TYPE: PRT
<213> ORGANISM: Artificial Sequence
<220> FEATURE:
<223> OTHER INFORMATION: pNOP52423

<400> SEQUENCE: 484

Ser His Gly Arg Ile Ser Glu Gln Ala Ala Thr Thr Ala Ala Ala
1               5                   10                  15

Ala Ala Thr Thr Ala Thr Ala Leu Ser Cys Ala Gly Ser Gln Pro Phe
                20                  25                  30

Pro Glu Ser Pro Ala Ala His Gln Ala Pro Trp Ser Ala Ala Pro Trp
            35                  40                  45

Pro Trp Ala Ala Ala Thr Thr Gly Ala Ser Gly Trp Ala Ser Arg Arg
        50                  55                  60

Ser Ser Pro Asp Pro Trp Gly Tyr Gly Thr Thr Trp Thr Ala Trp Trp
65                  70                  75                  80

Pro Leu Pro

<210> SEQ ID NO 485
<211> LENGTH: 16
<212> TYPE: PRT
<213> ORGANISM: Artificial Sequence
```

-continued

```
<220> FEATURE:
<223> OTHER INFORMATION: pNOP526117

<400> SEQUENCE: 485

Pro Ile Cys Ser Ala Pro Ile Asp Ser Ser Ala Pro Thr Ser Ala Pro
1               5                   10                  15

<210> SEQ ID NO 486
<211> LENGTH: 16
<212> TYPE: PRT
<213> ORGANISM: Artificial Sequence
<220> FEATURE:
<223> OTHER INFORMATION: pNOP530549

<400> SEQUENCE: 486

Ser Ala Glu Pro Cys Gly Ser Trp Glu Trp Pro Gly Ala Glu Cys Trp
1               5                   10                  15

<210> SEQ ID NO 487
<211> LENGTH: 16
<212> TYPE: PRT
<213> ORGANISM: Artificial Sequence
<220> FEATURE:
<223> OTHER INFORMATION: pNOP530881

<400> SEQUENCE: 487

Ser Phe Pro His Leu Gln Ala Pro Gln Trp Gly Arg Leu Leu Pro Ser
1               5                   10                  15

<210> SEQ ID NO 488
<211> LENGTH: 15
<212> TYPE: PRT
<213> ORGANISM: Artificial Sequence
<220> FEATURE:
<223> OTHER INFORMATION: pNOP537026

<400> SEQUENCE: 488

Ala Leu Leu Leu Ser Ser Gly Gly Ser Thr Leu Ser Gly Thr Arg
1               5                   10                  15

<210> SEQ ID NO 489
<211> LENGTH: 15
<212> TYPE: PRT
<213> ORGANISM: Artificial Sequence
<220> FEATURE:
<223> OTHER INFORMATION: pNOP548556

<400> SEQUENCE: 489

Leu Arg Gly Ala Gln Ser Thr Arg Ala Ala Gly Ala Thr Ala Leu
1               5                   10                  15

<210> SEQ ID NO 490
<211> LENGTH: 15
<212> TYPE: PRT
<213> ORGANISM: Artificial Sequence
<220> FEATURE:
<223> OTHER INFORMATION: pNOP548811

<400> SEQUENCE: 490

Leu Thr Ile Val Arg Cys Trp Asp Ser Tyr Gln Arg Arg Gln Ser
1               5                   10                  15

<210> SEQ ID NO 491
<211> LENGTH: 15
<212> TYPE: PRT
<213> ORGANISM: Artificial Sequence
<220> FEATURE:
```

<223> OTHER INFORMATION: pNOP550374

<400> SEQUENCE: 491

Asn Pro His Thr Leu Gln Thr Arg Phe His Ile His Tyr Leu Ile
1               5                   10                  15

<210> SEQ ID NO 492
<211> LENGTH: 81
<212> TYPE: PRT
<213> ORGANISM: Artificial Sequence
<220> FEATURE:
<223> OTHER INFORMATION: pNOP55230

<400> SEQUENCE: 492

Gln Gln Ala Gly Trp Ala Gly Ala Glu Thr Gly Tyr Pro Gln Gln
1               5                   10                  15

Gln Gly Gly Cys Ser Ser Lys Glu Ala Phe Asp Thr Glu Ala Gln Ala
            20                  25                  30

Gly Thr Glu Gly Lys Arg Gln Val Gly Glu Leu Pro Lys Glu Ala Ala
        35                  40                  45

Glu Gly Gly Arg Gly Gln Gly Gln Arg Gly Leu Ala Glu Thr Ala Glu
    50                  55                  60

Thr Gly Ala Val Pro Ala Ala Pro Asn Gly Ala Cys Tyr His Arg Gln
65                  70                  75                  80

Phe

<210> SEQ ID NO 493
<211> LENGTH: 15
<212> TYPE: PRT
<213> ORGANISM: Artificial Sequence
<220> FEATURE:
<223> OTHER INFORMATION: pNOP558727

<400> SEQUENCE: 493

Thr Gly Gly Pro Ala Ala Gly Gly Gly Ala Arg Thr Leu Gly Pro
1               5                   10                  15

<210> SEQ ID NO 494
<211> LENGTH: 80
<212> TYPE: PRT
<213> ORGANISM: Artificial Sequence
<220> FEATURE:
<223> OTHER INFORMATION: pNOP56040

<400> SEQUENCE: 494

Asp Arg Trp Gln Ser Ser Asn Ser Ser Arg Val Leu Glu Tyr Arg
1               5                   10                  15

Gln Thr Lys Leu Trp Val Pro Ser Pro Arg Ala Leu Cys Leu Pro Ala
            20                  25                  30

Ala Thr Lys Ala Ser Trp Ser Ser Ser Cys Pro Leu Asn His Pro Arg
        35                  40                  45

Gly Pro Arg Ala Cys Trp Ala Leu Pro Arg Trp Leu Cys Cys Ser Ser
    50                  55                  60

Ser Thr Leu Glu Leu Trp Ala Pro Arg Ala Leu Thr Asp Arg Cys Leu
65                  70                  75                  80

<210> SEQ ID NO 495
<211> LENGTH: 14
<212> TYPE: PRT
<213> ORGANISM: Artificial Sequence
<220> FEATURE:
<223> OTHER INFORMATION: pNOP563434

<400> SEQUENCE: 495

Ala Arg Ala Glu Leu Phe Cys Cys Leu Pro Ala Gly Leu His
1               5                   10

<210> SEQ ID NO 496
<211> LENGTH: 14
<212> TYPE: PRT
<213> ORGANISM: Artificial Sequence
<220> FEATURE:
<223> OTHER INFORMATION: pNOP566785

<400> SEQUENCE: 496

Glu Pro Asp Gln Gln Ala Asp Gln Gly Gly Arg His Ser Pro
1               5                   10

<210> SEQ ID NO 497
<211> LENGTH: 14
<212> TYPE: PRT
<213> ORGANISM: Artificial Sequence
<220> FEATURE:
<223> OTHER INFORMATION: pNOP568806

<400> SEQUENCE: 497

Gly Lys Gln Gly Ser Asn Leu Ser Pro Ser Trp Arg Pro Pro
1               5                   10

<210> SEQ ID NO 498
<211> LENGTH: 14
<212> TYPE: PRT
<213> ORGANISM: Artificial Sequence
<220> FEATURE:
<223> OTHER INFORMATION: pNOP569843

<400> SEQUENCE: 498

Gly Val Trp Pro Gly Leu Arg Pro Leu Thr Pro Ala Ala Leu
1               5                   10

<210> SEQ ID NO 499
<211> LENGTH: 14
<212> TYPE: PRT
<213> ORGANISM: Artificial Sequence
<220> FEATURE:
<223> OTHER INFORMATION: pNOP570795

<400> SEQUENCE: 499

His Arg Ser Pro Ser Gly Tyr Arg Arg Gln Ala Thr Gly Trp
1               5                   10

<210> SEQ ID NO 500
<211> LENGTH: 14
<212> TYPE: PRT
<213> ORGANISM: Artificial Sequence
<220> FEATURE:
<223> OTHER INFORMATION: pNOP573651

<400> SEQUENCE: 500

Lys Ser Gln Ser Pro Ser Thr Phe Ala Ser Lys Val Cys Gly
1               5                   10

<210> SEQ ID NO 501
<211> LENGTH: 14
<212> TYPE: PRT
<213> ORGANISM: Artificial Sequence
<220> FEATURE:
<223> OTHER INFORMATION: pNOP575068

<400> SEQUENCE: 501

Leu Leu Trp Pro Arg Gly Arg His Ser Pro Ser Gly Trp Asp
1               5                   10

<210> SEQ ID NO 502
<211> LENGTH: 14
<212> TYPE: PRT
<213> ORGANISM: Artificial Sequence
<220> FEATURE:
<223> OTHER INFORMATION: pNOP580906

<400> SEQUENCE: 502

Arg Ala Cys Ser Pro Gly Ser Gly Cys Gly Cys Gly Gln Gly
1               5                   10

<210> SEQ ID NO 503
<211> LENGTH: 14
<212> TYPE: PRT
<213> ORGANISM: Artificial Sequence
<220> FEATURE:
<223> OTHER INFORMATION: pNOP581766

<400> SEQUENCE: 503

Arg Ile Pro Trp Pro Arg Gly Gln Ser Arg Tyr Thr Arg Thr
1               5                   10

<210> SEQ ID NO 504
<211> LENGTH: 14
<212> TYPE: PRT
<213> ORGANISM: Artificial Sequence
<220> FEATURE:
<223> OTHER INFORMATION: pNOP584053

<400> SEQUENCE: 504

Ser Phe Leu Pro Ile Thr Arg Tyr Pro Ser Leu Pro Val Pro
1               5                   10

<210> SEQ ID NO 505
<211> LENGTH: 14
<212> TYPE: PRT
<213> ORGANISM: Artificial Sequence
<220> FEATURE:
<223> OTHER INFORMATION: pNOP588394

<400> SEQUENCE: 505

Val Arg Pro Ala Gln Pro Thr Cys Gly Arg Gly Leu Cys Pro
1               5                   10

<210> SEQ ID NO 506
<211> LENGTH: 14
<212> TYPE: PRT
<213> ORGANISM: Artificial Sequence
<220> FEATURE:
<223> OTHER INFORMATION: pNOP589969

<400> SEQUENCE: 506

Tyr Leu Leu Thr Cys Leu Gln Arg Ala Pro Trp Ser Arg Ala
1               5                   10

<210> SEQ ID NO 507
<211> LENGTH: 13
<212> TYPE: PRT
<213> ORGANISM: Artificial Sequence
<220> FEATURE:
<223> OTHER INFORMATION: pNOP591792

<400> SEQUENCE: 507

```
Ala Thr Arg Pro Leu Thr Ser Ala Thr Gly Leu Ile Pro
1               5                   10

<210> SEQ ID NO 508
<211> LENGTH: 13
<212> TYPE: PRT
<213> ORGANISM: Artificial Sequence
<220> FEATURE:
<223> OTHER INFORMATION: pNOP594808

<400> SEQUENCE: 508

Glu Lys Arg Leu Thr Cys Cys Asp Ser Ser Leu Ser Ile
1               5                   10

<210> SEQ ID NO 509
<211> LENGTH: 13
<212> TYPE: PRT
<213> ORGANISM: Artificial Sequence
<220> FEATURE:
<223> OTHER INFORMATION: pNOP594895

<400> SEQUENCE: 509

Glu Leu Pro Leu Ser Gln Trp Pro Leu Asn Gln Glu Arg
1               5                   10

<210> SEQ ID NO 510
<211> LENGTH: 13
<212> TYPE: PRT
<213> ORGANISM: Artificial Sequence
<220> FEATURE:
<223> OTHER INFORMATION: pNOP595078

<400> SEQUENCE: 510

Glu Pro Leu His Arg Gly Arg Cys Gly Ala Gly Ser Arg
1               5                   10

<210> SEQ ID NO 511
<211> LENGTH: 13
<212> TYPE: PRT
<213> ORGANISM: Artificial Sequence
<220> FEATURE:
<223> OTHER INFORMATION: pNOP607374

<400> SEQUENCE: 511

Pro Gly Ser Ser Pro His Gln Gln Gly Ala Glu Ala Gly
1               5                   10

<210> SEQ ID NO 512
<211> LENGTH: 13
<212> TYPE: PRT
<213> ORGANISM: Artificial Sequence
<220> FEATURE:
<223> OTHER INFORMATION: pNOP608986

<400> SEQUENCE: 512

Gln Gly Thr Ala Arg His Ala Ser Leu Leu Phe Leu Ser
1               5                   10

<210> SEQ ID NO 513
<211> LENGTH: 77
<212> TYPE: PRT
<213> ORGANISM: Artificial Sequence
<220> FEATURE:
<223> OTHER INFORMATION: pNOP60941

<400> SEQUENCE: 513
```

Glu Asn Leu Glu Gly Pro Ala Gly Leu Thr Ile Val Leu His Gly
1               5                   10                  15

Arg Gln Ala Tyr Gly Gly Arg Ala Gln Asn Tyr Val Val Trp Thr
            20                  25                  30

Arg Pro Ser Ser Gln Gly Ser His Ser Ala Ala Pro Thr Ala Pro Gly
        35                  40                  45

Ser Val Pro Pro Ser Leu Ala Ala His Leu Asp Val His Gly Phe Thr
    50                  55                  60

Thr Ser Pro Ala Arg Leu Pro Ala Val Pro Ser Tyr Pro
65                  70                  75

<210> SEQ ID NO 514
<211> LENGTH: 77
<212> TYPE: PRT
<213> ORGANISM: Artificial Sequence
<220> FEATURE:
<223> OTHER INFORMATION: pNOP61039

<400> SEQUENCE: 514

Gly His Gln Glu Pro Ala Thr Thr Ser Cys Trp Gln Ala Leu Ala Gln
1               5                   10                  15

Lys Leu Gly Ile Cys Ser Cys Arg Ser Tyr Ser Gly Gln Arg Met Cys
            20                  25                  30

Asn Ser Ala Leu Gly Gly Gly Pro Arg Gly Cys Glu Leu Arg Ser Thr
        35                  40                  45

Gly Thr Leu Thr Ala Ser Trp Leu Gly Trp Ser Arg Asn Tyr Arg Val
    50                  55                  60

Pro Pro Ala Thr Arg Arg Met Gln Gln Gln Gly Ser Leu
65                  70                  75

<210> SEQ ID NO 515
<211> LENGTH: 13
<212> TYPE: PRT
<213> ORGANISM: Artificial Sequence
<220> FEATURE:
<223> OTHER INFORMATION: pNOP614310

<400> SEQUENCE: 515

Ser Leu Trp Arg Leu Leu His Leu Gln Ser Trp Cys Pro
1               5                   10

<210> SEQ ID NO 516
<211> LENGTH: 12
<212> TYPE: PRT
<213> ORGANISM: Artificial Sequence
<220> FEATURE:
<223> OTHER INFORMATION: pNOP621656

<400> SEQUENCE: 516

Ala Ser Ala Trp Ser Ser Trp Ser Cys Pro Val His
1               5                   10

<210> SEQ ID NO 517
<211> LENGTH: 12
<212> TYPE: PRT
<213> ORGANISM: Artificial Sequence
<220> FEATURE:
<223> OTHER INFORMATION: pNOP626830

<400> SEQUENCE: 517

Gly Ala Val Pro Arg Glu Pro Arg Pro Gly Arg His
1               5                   10

<210> SEQ ID NO 518
<211> LENGTH: 76
<212> TYPE: PRT
<213> ORGANISM: Artificial Sequence
<220> FEATURE:
<223> OTHER INFORMATION: pNOP62730

<400> SEQUENCE: 518

```
Gly Ile Pro Thr Gln His Gln Ala Gly Thr Ser Gly Arg Ala Met Cys
1               5                   10                  15

Pro Gly Ser Pro Val Ser Glu Glu Gly Gln Trp Gly Ala Asn Arg
            20                  25                  30

Gly Thr Arg Asn Gln Gln Pro Pro Ala Gly Arg Pro Ser Leu Arg
        35                  40                  45

Ser Trp Ala Ser Ala Leu Ala Glu Ala Thr Pro Gly Lys Glu Cys Ala
    50                  55                  60

Thr Gln His Trp Ala Gly Val Arg Gly Ala Ala Ser
65                  70                  75
```

<210> SEQ ID NO 519
<211> LENGTH: 12
<212> TYPE: PRT
<213> ORGANISM: Artificial Sequence
<220> FEATURE:
<223> OTHER INFORMATION: pNOP636166

<400> SEQUENCE: 519

```
Met Gln Ser Val Pro Ser Leu Gln Glu Thr Trp Glu
1               5                   10
```

<210> SEQ ID NO 520
<211> LENGTH: 12
<212> TYPE: PRT
<213> ORGANISM: Artificial Sequence
<220> FEATURE:
<223> OTHER INFORMATION: pNOP637952

<400> SEQUENCE: 520

```
Pro Ala Cys Arg Gly Arg Arg Gly Ala Glu Leu Ser
1               5                   10
```

<210> SEQ ID NO 521
<211> LENGTH: 12
<212> TYPE: PRT
<213> ORGANISM: Artificial Sequence
<220> FEATURE:
<223> OTHER INFORMATION: pNOP638098

<400> SEQUENCE: 521

```
Pro Cys Leu Val Asp Leu Gln His Leu Gly Met Ser
1               5                   10
```

<210> SEQ ID NO 522
<211> LENGTH: 12
<212> TYPE: PRT
<213> ORGANISM: Artificial Sequence
<220> FEATURE:
<223> OTHER INFORMATION: pNOP638632

<400> SEQUENCE: 522

```
Pro Leu Phe Ser Pro Thr Leu Thr Pro Ser Val Pro
1               5                   10
```

<210> SEQ ID NO 523

```
<211> LENGTH: 12
<212> TYPE: PRT
<213> ORGANISM: Artificial Sequence
<220> FEATURE:
<223> OTHER INFORMATION: pNOP640173

<400> SEQUENCE: 523

Gln Ile Phe Thr Pro Arg Ala Trp Arg Tyr Pro His
1               5                   10

<210> SEQ ID NO 524
<211> LENGTH: 12
<212> TYPE: PRT
<213> ORGANISM: Artificial Sequence
<220> FEATURE:
<223> OTHER INFORMATION: pNOP643882

<400> SEQUENCE: 524

Arg Thr Gly Pro Ala Lys Val Asn Cys Phe Phe His
1               5                   10

<210> SEQ ID NO 525
<211> LENGTH: 12
<212> TYPE: PRT
<213> ORGANISM: Artificial Sequence
<220> FEATURE:
<223> OTHER INFORMATION: pNOP645741

<400> SEQUENCE: 525

Ser Pro His Leu Leu Pro Ile Pro Leu Ala Trp Gly
1               5                   10

<210> SEQ ID NO 526
<211> LENGTH: 12
<212> TYPE: PRT
<213> ORGANISM: Artificial Sequence
<220> FEATURE:
<223> OTHER INFORMATION: pNOP648045

<400> SEQUENCE: 526

Thr Pro Arg Tyr Pro Gly Pro Arg His Val Arg Pro
1               5                   10

<210> SEQ ID NO 527
<211> LENGTH: 11
<212> TYPE: PRT
<213> ORGANISM: Artificial Sequence
<220> FEATURE:
<223> OTHER INFORMATION: pNOP652166

<400> SEQUENCE: 527

Ala Gly His Trp Gly Gln Glu Gly Tyr Leu Gln
1               5                   10

<210> SEQ ID NO 528
<211> LENGTH: 11
<212> TYPE: PRT
<213> ORGANISM: Artificial Sequence
<220> FEATURE:
<223> OTHER INFORMATION: pNOP654960

<400> SEQUENCE: 528

Cys Tyr Val Asp Arg Arg Pro Cys Gln Val His
1               5                   10

<210> SEQ ID NO 529
<211> LENGTH: 11
```

<212> TYPE: PRT
<213> ORGANISM: Artificial Sequence
<220> FEATURE:
<223> OTHER INFORMATION: pNOP660899

<400> SEQUENCE: 529

Gly Trp Gly Arg Glu Gly Ile Pro Ser Ala Gln
1               5                   10

<210> SEQ ID NO 530
<211> LENGTH: 11
<212> TYPE: PRT
<213> ORGANISM: Artificial Sequence
<220> FEATURE:
<223> OTHER INFORMATION: pNOP663294

<400> SEQUENCE: 530

Ile Ser Pro Thr Gln Ala Pro Cys Pro Ala Pro
1               5                   10

<210> SEQ ID NO 531
<211> LENGTH: 11
<212> TYPE: PRT
<213> ORGANISM: Artificial Sequence
<220> FEATURE:
<223> OTHER INFORMATION: pNOP671528

<400> SEQUENCE: 531

Pro Ile Pro Gln Thr Pro Leu Pro Leu Ala Gly
1               5                   10

<210> SEQ ID NO 532
<211> LENGTH: 11
<212> TYPE: PRT
<213> ORGANISM: Artificial Sequence
<220> FEATURE:
<223> OTHER INFORMATION: pNOP672236

<400> SEQUENCE: 532

Pro Arg Thr Phe Trp Ala Pro Asn Ser Pro Cys
1               5                   10

<210> SEQ ID NO 533
<211> LENGTH: 11
<212> TYPE: PRT
<213> ORGANISM: Artificial Sequence
<220> FEATURE:
<223> OTHER INFORMATION: pNOP675830

<400> SEQUENCE: 533

Arg Leu Ser Pro Gly Arg Val Glu Ser His His
1               5                   10

<210> SEQ ID NO 534
<211> LENGTH: 11
<212> TYPE: PRT
<213> ORGANISM: Artificial Sequence
<220> FEATURE:
<223> OTHER INFORMATION: pNOP679479

<400> SEQUENCE: 534

Ser Gln Thr Thr Arg Glu Ser Arg Gly Pro Thr
1               5                   10

<210> SEQ ID NO 535
<211> LENGTH: 11
<212> TYPE: PRT

```
<213> ORGANISM: Artificial Sequence
<220> FEATURE:
<223> OTHER INFORMATION: pNOP679892

<400> SEQUENCE: 535

Ser Ser Leu Met Gln Cys Cys Leu Ala Ile Pro
1               5                   10

<210> SEQ ID NO 536
<211> LENGTH: 11
<212> TYPE: PRT
<213> ORGANISM: Artificial Sequence
<220> FEATURE:
<223> OTHER INFORMATION: pNOP682972

<400> SEQUENCE: 536

Val Gly Met Gly Ser Pro Thr Arg Val Arg Arg
1               5                   10

<210> SEQ ID NO 537
<211> LENGTH: 11
<212> TYPE: PRT
<213> ORGANISM: Artificial Sequence
<220> FEATURE:
<223> OTHER INFORMATION: pNOP684498

<400> SEQUENCE: 537

Trp Leu Arg Ala Ala Leu Gly Trp His Leu Val
1               5                   10

<210> SEQ ID NO 538
<211> LENGTH: 72
<212> TYPE: PRT
<213> ORGANISM: Artificial Sequence
<220> FEATURE:
<223> OTHER INFORMATION: pNOP70346

<400> SEQUENCE: 538

His His Ala Glu Tyr Arg Gly Ser Leu Leu Gln His Arg Gln Ile Cys
1               5                   10                  15

Pro Asn Ala Gly His Val Cys Gly Met Trp Gln Leu Trp Pro Gly Gly
            20                  25                  30

Arg Gly Pro Pro Pro Cys Leu Phe Ala Val Leu Ser Val Leu Ser Pro
        35                  40                  45

Leu Leu Cys Gln Gln Gln Asp His Gln Gly Asp Ala Gln Gly Leu
    50                  55                  60

Ala Leu Cys Gly Val Tyr Cys Val
65                  70

<210> SEQ ID NO 539
<211> LENGTH: 10
<212> TYPE: PRT
<213> ORGANISM: Artificial Sequence
<220> FEATURE:
<223> OTHER INFORMATION: pNOP704364

<400> SEQUENCE: 539

Met Trp Arg Leu Pro Cys Thr Glu Asp Cys
1               5                   10

<210> SEQ ID NO 540
<211> LENGTH: 10
<212> TYPE: PRT
<213> ORGANISM: Artificial Sequence
<220> FEATURE:
```

```
<223> OTHER INFORMATION: pNOP706242

<400> SEQUENCE: 540

Pro Ala Glu Ser Ser Ala Leu Gly Glu Gly
1               5                   10

<210> SEQ ID NO 541
<211> LENGTH: 10
<212> TYPE: PRT
<213> ORGANISM: Artificial Sequence
<220> FEATURE:
<223> OTHER INFORMATION: pNOP708910

<400> SEQUENCE: 541

Gln Lys Leu Ala Trp Pro Cys Cys Val Thr
1               5                   10

<210> SEQ ID NO 542
<211> LENGTH: 10
<212> TYPE: PRT
<213> ORGANISM: Artificial Sequence
<220> FEATURE:
<223> OTHER INFORMATION: pNOP709657

<400> SEQUENCE: 542

Gln Ser Pro Leu Pro Ala Lys Gly Gln Arg
1               5                   10

<210> SEQ ID NO 543
<211> LENGTH: 10
<212> TYPE: PRT
<213> ORGANISM: Artificial Sequence
<220> FEATURE:
<223> OTHER INFORMATION: pNOP713389

<400> SEQUENCE: 543

Arg Trp Cys Gly Ala His Gly Val Arg Asn
1               5                   10

<210> SEQ ID NO 544
<211> LENGTH: 10
<212> TYPE: PRT
<213> ORGANISM: Artificial Sequence
<220> FEATURE:
<223> OTHER INFORMATION: pNOP715424

<400> SEQUENCE: 544

Ser Gln Leu Leu Leu Pro Leu Arg Leu Trp
1               5                   10

<210> SEQ ID NO 545
<211> LENGTH: 10
<212> TYPE: PRT
<213> ORGANISM: Artificial Sequence
<220> FEATURE:
<223> OTHER INFORMATION: pNOP718753

<400> SEQUENCE: 545

Thr Trp His Leu Arg Lys Pro Gly Asp Gln
1               5                   10

<210> SEQ ID NO 546
<211> LENGTH: 68
<212> TYPE: PRT
<213> ORGANISM: Artificial Sequence
<220> FEATURE:
<223> OTHER INFORMATION: pNOP78569
```

<400> SEQUENCE: 546

Glu His Leu Gly Gly Gly Pro Ser Phe Pro Ser Ser Gly Leu Arg
1               5                   10                  15

Pro Val Gly Ala Arg Gly Pro Gly Leu Pro Cys His Pro Pro His
                20                  25                  30

Ser Ser Gly Gln His Pro Ser Leu Pro Arg Tyr Gln Thr Leu Trp Gly
            35                  40                  45

Pro Trp Pro Gly Gly Pro Trp Lys Ala Ala Cys His Asn Leu Gly Lys
        50                  55                  60

Gly Gln Arg Lys
65

<210> SEQ ID NO 547
<211> LENGTH: 67
<212> TYPE: PRT
<213> ORGANISM: Artificial Sequence
<220> FEATURE:
<223> OTHER INFORMATION: pNOP81414

<400> SEQUENCE: 547

Ile Pro Thr Arg Ser Gly Leu Arg Thr Thr Leu Ser Val Thr Ala Val
1               5                   10                  15

Thr Lys Pro Arg Glu Val Arg Leu Ser Ala Pro Leu Leu Ser Ser Ile
                20                  25                  30

Pro Arg Cys Val Ala Asp Phe His Pro Gln Ser Leu Ala Ile Pro Pro
            35                  40                  45

Leu Thr Ser Pro Met Leu Cys Thr Leu His Ala Lys Gly Ser Gln Arg
        50                  55                  60

Val Gly Thr
65

<210> SEQ ID NO 548
<211> LENGTH: 65
<212> TYPE: PRT
<213> ORGANISM: Artificial Sequence
<220> FEATURE:
<223> OTHER INFORMATION: pNOP85659

<400> SEQUENCE: 548

Ala Trp Gly Thr Thr Ser Val Pro Ser Ala Arg Gly Ala Ala Val Val
1               5                   10                  15

Pro Ile Trp Gly Ala Ile Leu Val Ala Ser Ala Asp Ala Thr Arg Ser
                20                  25                  30

Pro Ser Ser Ser Thr Leu Thr His His His Ser Cys Gly Pro Thr Gly
            35                  40                  45

Pro Val Ser Phe Gly Gly Val Arg Val Pro Leu Trp Cys Gln Arg Gly
        50                  55                  60

Gln
65

<210> SEQ ID NO 549
<211> LENGTH: 65
<212> TYPE: PRT
<213> ORGANISM: Artificial Sequence
<220> FEATURE:
<223> OTHER INFORMATION: pNOP85855

<400> SEQUENCE: 549

Asp Pro Gly Arg Gly Thr Asp Glu Cys Gly Gly Cys Pro Ala Pro Arg

```
                1               5                  10                 15
Thr Ala Asn Gln Val Leu Pro Val Pro Ala Asn Trp Cys His Gln Gln
                               20                 25                 30

Leu Gln Ser His Ala Leu Pro Gln Cys Leu Pro Phe Cys Leu Cys His
                35                 40                 45

Pro Cys Gln Val His Val Leu Gln Gly Gln Asp His Ala Val Ser Asn
        50                 55                 60

Ala
65

<210> SEQ ID NO 550
<211> LENGTH: 65
<212> TYPE: PRT
<213> ORGANISM: Artificial Sequence
<220> FEATURE:
<223> OTHER INFORMATION: pNOP87579

<400> SEQUENCE: 550

Ser Ser Gly Glu Arg Phe Gln Gln Leu Thr Lys Pro Pro Thr Cys Lys
1               5                  10                 15

Arg Pro Lys Ile Thr Gly Gln Leu Thr Ala Ser Thr Arg Cys Arg Ser
                20                 25                 30

Gln Gly His Trp Ala Ala Arg Pro Pro Leu Leu Pro Pro Pro Phe Ser
                35                 40                 45

Leu Ala Ala Pro Leu Pro Pro Pro Ala Cys Leu Pro Leu Arg Thr Gly
        50                 55                 60

Ser
65

<210> SEQ ID NO 551
<211> LENGTH: 62
<212> TYPE: PRT
<213> ORGANISM: Artificial Sequence
<220> FEATURE:
<223> OTHER INFORMATION: pNOP96015

<400> SEQUENCE: 551

Val Leu Ser Ser Ser Ser Ser Tyr Arg His Ser Ser Cys Ser Gly Ser
1               5                  10                 15

Cys Ser Arg Val Arg Gln Tyr Ala Arg Pro His Pro Thr Arg Ser Leu
                20                 25                 30

Gly Pro Arg Pro Leu Pro Ser Arg Ala Ser Trp Ala Ala Asn Leu Asn
                35                 40                 45

Leu Gly Ala Ser Leu Asp His Arg Gln Ala Pro Ser Arg Ser
        50                 55                 60

<210> SEQ ID NO 552
<211> LENGTH: 61
<212> TYPE: PRT
<213> ORGANISM: Artificial Sequence
<220> FEATURE:
<223> OTHER INFORMATION: pNOP98767

<400> SEQUENCE: 552

Thr Ala Pro Ala Cys Leu Arg His Ile Arg Ala Pro Ser Gln Ala Arg
1               5                  10                 15

Pro Thr Pro Pro Thr Ala Ser Ser Leu Cys Thr Pro Ser His Leu Ser
                20                 25                 30

Thr Gly Gly Cys Ala Pro Asn Gly Arg Thr Thr Cys Thr Trp Leu Ala
                35                 40                 45
```

Pro Val Ser Arg Ala Trp Gly Ser Met Gln Pro Arg Thr
    50                  55                  60

<210> SEQ ID NO 553
<211> LENGTH: 172
<212> TYPE: PRT
<213> ORGANISM: Artificial Sequence
<220> FEATURE:
<223> OTHER INFORMATION: pNOP6995

<400> SEQUENCE: 553

Pro Leu Gly Leu Val Pro Trp Thr Arg Trp Cys Pro Gln Gly Lys Pro
1               5                   10                  15

Arg Phe Pro Ala Met Ser Thr Thr Ala Thr Gly Thr Thr Thr Thr
                20                  25                  30

Lys Ser Gly Ser Ser Gly Met Ala Gly Ser Leu Ala Gln Lys Pro Glu
            35                  40                  45

Ser Pro Ser Pro Gly Leu Leu Phe Leu Gly His Ser Pro Ser Gln Ser
    50                  55                  60

His Leu Leu Leu Ile Ser Lys Ser Pro Asp Pro Thr Gln Gln Pro Leu
65                  70                  75                  80

Arg Gly Gly Ser Leu Thr His Ser Ala Pro Gly Pro Ser Leu Ser Gln
                85                  90                  95

Pro Leu Ala Gln Leu Thr Pro Pro Ala Ser Ala Pro Val Pro Ala Val
            100                 105                 110

Cys Ser Thr Cys Lys Asn Pro Ala Ser Leu Pro Asp Thr His Arg Gly
        115                 120                 125

Lys Gly Gly Val Pro Pro Ser Pro Pro Leu Ala Leu Gly Pro Arg
    130                 135                 140

Met Gln Leu Cys Thr Gln Leu Ala Arg Phe Phe Pro Ile Thr Pro Pro
145                 150                 155                 160

Val Trp His Ile Leu Gly Pro Gln Arg His Thr Pro
                165                 170

<210> SEQ ID NO 554
<211> LENGTH: 206
<212> TYPE: PRT
<213> ORGANISM: Artificial Sequence
<220> FEATURE:
<223> OTHER INFORMATION: pNOP3856

<400> SEQUENCE: 554

Ser Ser Trp Leu Arg Cys Cys Ala Ser Gly Ala Ala Pro Ala Thr Ala
1               5                   10                  15

Gly Arg Ile Arg Phe Ser Arg Glu Gln Pro Gly Pro Ser Ala Ser Trp
                20                  25                  30

Pro Pro Gly Gly Thr Arg Pro Ala Ala Gly Arg Pro Gly Val Ser Gly
            35                  40                  45

Gln Thr Gln Gly Ala Ala Ala Gln Pro Leu Cys Val Pro Ser Val
    50                  55                  60

Trp Arg Ser Ser Leu Arg Gly Arg Ser Tyr Gly Ser Phe Pro Ala Ser
65                  70                  75                  80

Met Ser Ser Ile Val Thr Val Trp Thr Pro Gly Tyr Ile Ser Ile Gly
                85                  90                  95

Leu Ala Pro Ser Ala Cys Ser Thr Ser Gln Arg Glu Ile His Phe Pro
            100                 105                 110

Ser Pro Trp Asp Pro Leu Asp Leu Thr Lys Asn Gln Val Glu Asp Ser

```
            115                 120                 125
Thr Ser Phe Ala Ser Ile Pro Ala Met Pro Thr Thr Thr Ser Leu Leu
        130                 135                 140

Pro Thr Cys Trp Ala Leu Pro Gly Val Gln Trp Leu Gly Pro His Asp
145                 150                 155                 160

Leu Val Pro Ser Cys His Pro Arg Ser Gln Ala Trp Ala Leu Gly Ile
                165                 170                 175

Thr Ala Ser Pro Glu Leu His Ile Pro Gly Leu Gln Glu Ser Ser Ser
            180                 185                 190

Ala Trp Gln Glu Pro Ser Thr Pro Met His Lys Ala Gly Asp
        195                 200                 205

<210> SEQ ID NO 555
<211> LENGTH: 74
<212> TYPE: PRT
<213> ORGANISM: Artificial Sequence
<220> FEATURE:
<223> OTHER INFORMATION: pNOP66044

<400> SEQUENCE: 555

Cys Ser Pro Thr Arg Cys Thr Cys Ala Met Pro Val Met Thr Thr Ile
1               5                   10                  15

Trp Ser Leu Asp Ser Ser Ala Ser Ser Ser Trp Arg Val Leu Asp Gly
            20                  25                  30

Pro Pro Ala Pro Ala Cys His Trp Leu Ala Arg Leu Gly Trp Arg Val
        35                  40                  45

Ser Glu Glu Pro Val Leu Ser Ser Leu Thr Ser Leu Arg Ile Glu Leu
    50                  55                  60

Leu Leu Ser Ser Cys Ser Ser Arg Trp Gly
65                  70

<210> SEQ ID NO 556
<211> LENGTH: 117
<212> TYPE: PRT
<213> ORGANISM: Artificial Sequence
<220> FEATURE:
<223> OTHER INFORMATION: pNOP22244

<400> SEQUENCE: 556

Arg Leu Gln His Leu Pro Gln Tyr Gln Gln Ser Val Gln Leu Ala Lys
1               5                   10                  15

Ile Gln Pro Leu Cys Pro Thr Pro Thr Glu Glu Lys Ala Gly Gly Ser
            20                  25                  30

Leu Arg Ala His Pro Trp Leu Ser Ala Pro Gly Cys Asn Cys Ala Pro
        35                  40                  45

Ser Leu Pro Asp Phe Ser Pro Leu His Pro Gln Cys Gly Ile Ser Leu
    50                  55                  60

Val Pro Arg Gly Thr Pro Leu Asp Leu Trp Thr Ser Arg Pro Gly Gln
65                  70                  75                  80

Glu Ala Ala Thr Arg Asn Pro Arg Pro Leu Leu Lys Phe Thr Ala
                85                  90                  95

Ser Val Val Pro Asp Ser Ser Pro Ala Pro Gly Thr Thr Ser Thr
            100                 105                 110

Trp Gly Gly Ala Phe
        115

<210> SEQ ID NO 557
<211> LENGTH: 82
```

<212> TYPE: PRT
<213> ORGANISM: Artificial Sequence
<220> FEATURE:
<223> OTHER INFORMATION: pNOP52830

<400> SEQUENCE: 557

Ala Thr Ser Asn Pro Pro His Ser Thr Leu Leu Leu Ala Gln Cys Pro
1               5                   10                  15

Tyr Ala Gly Pro Gly Pro Leu Thr Ala Val Asp Leu Glu Lys Ala Ile
            20                  25                  30

Ala Gln Asn Ala Val Gly Thr Trp Gln Met Gly Gln Pro Val Thr Pro
        35                  40                  45

Ala Gln Gly Pro Val Met Ala Leu Pro Val Thr Leu Trp Ser Thr Ala
    50                  55                  60

Arg Thr Ser Ala Tyr Arg Gly Ser Met Ala Ala Val Leu Leu Ser Ala
65                  70                  75                  80

Ala Pro

<210> SEQ ID NO 558
<211> LENGTH: 144
<212> TYPE: PRT
<213> ORGANISM: Artificial Sequence
<220> FEATURE:
<223> OTHER INFORMATION: pNOP12229

<400> SEQUENCE: 558

Leu Cys Gly Pro Leu Val Thr Ser Ala Ser Asp Leu Pro Pro Leu His
1               5                   10                  15

Val Gln His His Arg Gly Arg Phe Ile Phe Pro Val Pro Gly Thr Leu
            20                  25                  30

Ser Ile Leu Pro Arg Thr Arg Ser Lys Thr Pro His Ser Pro Ala
        35                  40                  45

Ser Arg Pro Cys Pro Leu Pro Pro Cys Cys Leu Pro Val Gly Pro
    50                  55                  60

Phe Pro Glu Cys Ser Gly Ser Ala Pro Thr Thr Trp Ser Leu Pro Ala
65                  70                  75                  80

Ile Pro Gly Ala Arg His Gly Pro Ser Ala Ser Pro Leu Pro Gln Ser
            85                  90                  95

Cys Thr Ser Pro Gly Ser Arg Arg Ala Ala Pro Gly Arg Ser Pro
            100                 105                 110

Ala Pro Leu Cys Thr Arg Leu Gly Thr Glu Pro Pro Ile His Leu
        115                 120                 125

Thr Ala Pro Cys Cys Leu Pro Ser Ala Pro Thr Pro Gly Gln Ala Pro
    130                 135                 140

<210> SEQ ID NO 559
<211> LENGTH: 34
<212> TYPE: PRT
<213> ORGANISM: Artificial Sequence
<220> FEATURE:
<223> OTHER INFORMATION: pNOP244428

<400> SEQUENCE: 559

Lys Ile Ser Arg Thr Glu Ser Tyr Tyr Gln Ser Asp Pro Leu Glu Asn
1               5                   10                  15

Gly Pro His Arg Lys Thr Glu Ser His Phe Gly Arg Cys Val Cys Trp
            20                  25                  30

Cys Cys

<210> SEQ ID NO 560
<211> LENGTH: 59
<212> TYPE: PRT
<213> ORGANISM: Artificial Sequence
<220> FEATURE:
<223> OTHER INFORMATION: pNOP102838

<400> SEQUENCE: 560

Cys Val Asp Pro Asn Asp Ser Gly Gly His His Leu Cys Asp His Pro
1               5                   10                  15

Gly Phe Gly Ala Ala His Pro Val Pro Pro Pro Gln Gln Ala Gly
            20                  25                  30

Ser Ala Ser Ala Glu Asn Ser Leu Gly His Gln Pro Ala Gly His Gln
        35                  40                  45

Glu Val Pro Gly Gln Leu Gln Ala Gly Pro Gly
    50                  55

<210> SEQ ID NO 561
<211> LENGTH: 27
<212> TYPE: PRT
<213> ORGANISM: Artificial Sequence
<220> FEATURE:
<223> OTHER INFORMATION: pNOP327324

<400> SEQUENCE: 561

Arg Gln Ser Gly Ala Trp Ile His Gln His Arg Gln Ala Gly Glu Ser
1               5                   10                  15

Ser Thr Gly Pro Pro Pro Leu Pro Val Thr Gly
            20                  25

<210> SEQ ID NO 562
<211> LENGTH: 38
<212> TYPE: PRT
<213> ORGANISM: Artificial Sequence
<220> FEATURE:
<223> OTHER INFORMATION: pNOP209936

<400> SEQUENCE: 562

His Glu Trp Trp Pro Pro Ala Ala Ala Gly Cys Pro Leu Ala Leu Ala
1               5                   10                  15

Ala Asp Gly Tyr Pro Ala Gly Arg Leu Trp Thr His Arg Thr Gly Thr
            20                  25                  30

Gly Ser Ser Gly Gly Val
        35

<210> SEQ ID NO 563
<211> LENGTH: 32
<212> TYPE: PRT
<213> ORGANISM: Artificial Sequence
<220> FEATURE:
<223> OTHER INFORMATION: pNOP269967

<400> SEQUENCE: 563

Trp Leu Pro Cys Arg Gln Ala Leu Asp Ala Gln Asp Trp Tyr Trp Gln
1               5                   10                  15

Gln Arg Trp Ser Leu Lys Asp Gln Gln Asn Arg Lys Leu Leu Ser Glu
            20                  25                  30

<210> SEQ ID NO 564
<211> LENGTH: 26
<212> TYPE: PRT
<213> ORGANISM: Artificial Sequence
<220> FEATURE:

<223> OTHER INFORMATION: pNOP336828

<400> SEQUENCE: 564

Leu Cys Gly Gln Leu His Gly His Gln Pro Thr Gly Gly Pro Trp Gln
1               5                   10                  15

Gln Phe Tyr Phe Leu Gln Leu Pro Lys Gln
            20                  25

<210> SEQ ID NO 565
<211> LENGTH: 22
<212> TYPE: PRT
<213> ORGANISM: Artificial Sequence
<220> FEATURE:
<223> OTHER INFORMATION: pNOP407540

<400> SEQUENCE: 565

Val Ala Arg Leu Arg Glu Gln Leu Gln Leu Ser Pro Cys Val Cys His
1               5                   10                  15

Leu Ser Gly Gly Val Leu
            20

<210> SEQ ID NO 566
<211> LENGTH: 13
<212> TYPE: PRT
<213> ORGANISM: Artificial Sequence
<220> FEATURE:
<223> OTHER INFORMATION: pNOP612507

<400> SEQUENCE: 566

Arg Ser Pro Arg Pro Gly Gln Ile Met Met Cys Gly Ser
1               5                   10

<210> SEQ ID NO 567
<211> LENGTH: 56
<212> TYPE: PRT
<213> ORGANISM: Artificial Sequence
<220> FEATURE:
<223> OTHER INFORMATION: pNOP114240

<400> SEQUENCE: 567

Leu Leu Ala Ser Pro Trp Asn His Ile His Leu Gly Arg Gly Leu Leu
1               5                   10                  15

Asn Gly Val Leu Thr Pro Gln Arg Ala Gly His Ala Leu Ile Arg Thr
            20                  25                  30

Ala Arg Cys Cys Arg Pro Ser Leu Val Ser Phe Gln Arg Glu Val Gly
        35                  40                  45

Val Val Gly Arg Gly Asp Tyr Ser
    50                  55

<210> SEQ ID NO 568
<211> LENGTH: 49
<212> TYPE: PRT
<213> ORGANISM: Artificial Sequence
<220> FEATURE:
<223> OTHER INFORMATION: pNOP144417

<400> SEQUENCE: 568

Pro Ser Gly Gln Arg Ile Met Leu Ala Arg Val Gln Glu His Pro Thr
1               5                   10                  15

Ser Ala Arg Cys Tyr Pro Phe Ser Trp Gln Ile Thr Gly Arg Ser Gln
            20                  25                  30

Gly Gly Ala Gly Val Ala Glu Ser Glu Arg His Leu Glu Gly Arg
        35                  40                  45

Val

<210> SEQ ID NO 569
<211> LENGTH: 29
<212> TYPE: PRT
<213> ORGANISM: Artificial Sequence
<220> FEATURE:
<223> OTHER INFORMATION: pNOP295346

<400> SEQUENCE: 569

Gly Ile Arg Lys Ala Leu Gly Arg Pro Gly Val Met Ala His Ala Cys
1               5                   10                  15

Asn Pro Arg Thr Leu Gly Gly Leu Gly Gly Trp Ile Pro
            20                  25

<210> SEQ ID NO 570
<211> LENGTH: 29
<212> TYPE: PRT
<213> ORGANISM: Artificial Sequence
<220> FEATURE:
<223> OTHER INFORMATION: pNOP296302

<400> SEQUENCE: 570

His Arg Arg Gly Gln Ala Met Pro Leu Ser Ala Leu Pro Gly Ala Val
1               5                   10                  15

Gly Pro Ala Trp Leu Arg Gly Gly Thr Arg Gly Ala Val
            20                  25

<210> SEQ ID NO 571
<211> LENGTH: 29
<212> TYPE: PRT
<213> ORGANISM: Artificial Sequence
<220> FEATURE:
<223> OTHER INFORMATION: pNOP302630

<400> SEQUENCE: 571

Ser Val Asp Leu Gln Ala Trp Thr Arg Gly Cys Tyr Gln Lys Pro Gln
1               5                   10                  15

Ala Pro Val Thr Gln Ile His Ser Gln Cys Gly Cys Ala
            20                  25

<210> SEQ ID NO 572
<211> LENGTH: 29
<212> TYPE: PRT
<213> ORGANISM: Artificial Sequence
<220> FEATURE:
<223> OTHER INFORMATION: pNOP304307

<400> SEQUENCE: 572

Trp Arg Val Ser Glu Glu Pro Val Leu Ser Ser Leu Thr Ser Leu Arg
1               5                   10                  15

Ile Glu Leu Leu Leu Ser Ser Cys Ser Ser Arg Trp Gly
            20                  25

<210> SEQ ID NO 573
<211> LENGTH: 101
<212> TYPE: PRT
<213> ORGANISM: Artificial Sequence
<220> FEATURE:
<223> OTHER INFORMATION: pNOP32819

<400> SEQUENCE: 573

Thr Gly Cys Val Arg Cys Ser Gly Leu Ala Pro Thr Lys Ser Val Leu
1               5                   10                  15

```
Gln Met Cys Leu Gly Pro Thr Trp His Arg Val Leu Leu Gly Lys
         20                  25                  30

Glu Arg Thr Thr Ala Asn Thr Ile Leu Phe Ala Val Leu Pro Arg Ser
 35                      40                  45

Thr Gly Arg Gly Leu Val Met Val Gly Glu Arg Val Pro Phe Pro
 50                  55                  60

Ala Pro Ala Pro Asp Leu Val Cys Arg Lys His Leu Gln Cys Ser Lys
65                   70                  75                  80

Ser Met Ser Ser Gln Ala Thr Ser Cys Cys Leu Trp Arg Val Trp Ala
                 85                  90                  95

Gly Ser Leu Glu Gly
            100

<210> SEQ ID NO 574
<211> LENGTH: 96
<212> TYPE: PRT
<213> ORGANISM: Artificial Sequence
<220> FEATURE:
<223> OTHER INFORMATION: pNOP36815

<400> SEQUENCE: 574

Leu Leu Ala Ser Pro Trp Asn His Ile His Leu Gly Arg Gly Leu Leu
1               5                   10                  15

Asn Gly Val Leu Thr Pro Gln Arg Ala Gly His Ala Leu Ile Arg Thr
             20                  25                  30

Ala Arg Cys Cys Arg Pro Ser Leu Ala Gln Arg Arg Asn Ser Arg Ser
         35                  40                  45

Cys Val Asn Arg Leu Cys Glu Met Phe Arg Pro Ser Ser Asn Gln Glu
     50                  55                  60

Cys Ala Pro Asp Val Phe Gly Pro Tyr Leu Ala Gln Ser Pro Ala Pro
65                   70                  75                  80

Gly Lys Gly Lys Asp His Ser Lys His His Ser Phe Cys Arg Thr Ser
                 85                  90                  95

<210> SEQ ID NO 575
<211> LENGTH: 22
<212> TYPE: PRT
<213> ORGANISM: Artificial Sequence
<220> FEATURE:
<223> OTHER INFORMATION: pNOP395545

<400> SEQUENCE: 575

Gly Glu Glu Thr Thr Ala Glu Tyr Phe Arg Thr Gly Glu Val Ser Gln
1               5                   10                  15

Gln Arg Val Asp Gly Ser
            20

<210> SEQ ID NO 576
<211> LENGTH: 22
<212> TYPE: PRT
<213> ORGANISM: Artificial Sequence
<220> FEATURE:
<223> OTHER INFORMATION: pNOP403129

<400> SEQUENCE: 576

Gln Gln Trp Ile Trp Arg Lys Leu Leu His Arg Thr Gln Trp Val Pro
1               5                   10                  15

Gly Arg Trp Ala Ser Gln
            20
```

```
<210> SEQ ID NO 577
<211> LENGTH: 20
<212> TYPE: PRT
<213> ORGANISM: Artificial Sequence
<220> FEATURE:
<223> OTHER INFORMATION: pNOP433557

<400> SEQUENCE: 577

His Arg Arg Gly Gln Ala Met Pro Leu Ser Ala Leu Pro Gly Ala Val
1               5                   10                  15

Gly Pro Ala Trp
            20

<210> SEQ ID NO 578
<211> LENGTH: 20
<212> TYPE: PRT
<213> ORGANISM: Artificial Sequence
<220> FEATURE:
<223> OTHER INFORMATION: pNOP438085

<400> SEQUENCE: 578

Asn Asn Ser Ser Arg Arg Lys Ile Asn Ala Val Pro Pro Ala Val Pro
1               5                   10                  15

Val Gln Cys Gln
            20

<210> SEQ ID NO 579
<211> LENGTH: 17
<212> TYPE: PRT
<213> ORGANISM: Artificial Sequence
<220> FEATURE:
<223> OTHER INFORMATION: pNOP489283

<400> SEQUENCE: 579

Ala Ala Ala Ala Ala Ala Gly Ala Asp Leu Ala Ser Gly Val Asp Leu
1               5                   10                  15

Gly

<210> SEQ ID NO 580
<211> LENGTH: 17
<212> TYPE: PRT
<213> ORGANISM: Artificial Sequence
<220> FEATURE:
<223> OTHER INFORMATION: pNOP491380

<400> SEQUENCE: 580

Cys Thr Ala Ala Leu Lys Gly Ile Pro Ser Glu Trp Thr Cys Ser Leu
1               5                   10                  15

Val

<210> SEQ ID NO 581
<211> LENGTH: 16
<212> TYPE: PRT
<213> ORGANISM: Artificial Sequence
<220> FEATURE:
<223> OTHER INFORMATION: pNOP515288

<400> SEQUENCE: 581

Glu Ala Asp Gly Val Cys Val Gln Glu Pro Lys Gly Pro Cys Glu Asp
1               5                   10                  15

<210> SEQ ID NO 582
<211> LENGTH: 16
<212> TYPE: PRT
```

```
<213> ORGANISM: Artificial Sequence
<220> FEATURE:
<223> OTHER INFORMATION: pNOP530623

<400> SEQUENCE: 582

Ser Ala Ser His Gln Ile Gln Leu Ser Ser Pro Phe Gly Ala Ala Leu
1               5                   10                  15

<210> SEQ ID NO 583
<211> LENGTH: 15
<212> TYPE: PRT
<213> ORGANISM: Artificial Sequence
<220> FEATURE:
<223> OTHER INFORMATION: pNOP560805

<400> SEQUENCE: 583

Val Val Ala Thr Ser Cys Ser Trp Leu Pro Ser Gly Pro Gly Cys
1               5                   10                  15

<210> SEQ ID NO 584
<211> LENGTH: 14
<212> TYPE: PRT
<213> ORGANISM: Artificial Sequence
<220> FEATURE:
<223> OTHER INFORMATION: pNOP574079

<400> SEQUENCE: 584

Leu Ala Asp His Arg Glu Val Pro Gly Arg Cys Trp Cys Gly
1               5                   10

<210> SEQ ID NO 585
<211> LENGTH: 14
<212> TYPE: PRT
<213> ORGANISM: Artificial Sequence
<220> FEATURE:
<223> OTHER INFORMATION: pNOP580384

<400> SEQUENCE: 585

Gln Pro Lys Tyr Leu Thr Ile Gly Thr Ala Tyr His Ala Gly
1               5                   10

<210> SEQ ID NO 586
<211> LENGTH: 13
<212> TYPE: PRT
<213> ORGANISM: Artificial Sequence
<220> FEATURE:
<223> OTHER INFORMATION: pNOP600409

<400> SEQUENCE: 586

Ile Ser Leu Trp Lys Val Cys Leu Leu Val Leu Leu Lys
1               5                   10

<210> SEQ ID NO 587
<211> LENGTH: 13
<212> TYPE: PRT
<213> ORGANISM: Artificial Sequence
<220> FEATURE:
<223> OTHER INFORMATION: pNOP613170

<400> SEQUENCE: 587

Ser Ala Gly Thr Pro His Leu Cys Gln Val Leu Pro Leu
1               5                   10

<210> SEQ ID NO 588
<211> LENGTH: 12
<212> TYPE: PRT
<213> ORGANISM: Artificial Sequence
```

```
<220> FEATURE:
<223> OTHER INFORMATION: pNOP650386

<400> SEQUENCE: 588

Trp Leu Met Pro Val Ile Pro Glu Leu Trp Glu Ala
 1               5                  10

<210> SEQ ID NO 589
<211> LENGTH: 11
<212> TYPE: PRT
<213> ORGANISM: Artificial Sequence
<220> FEATURE:
<223> OTHER INFORMATION: pNOP656602

<400> SEQUENCE: 589

Glu Gly Tyr Ser Arg Asp Asp Asn Gln Asn Thr
 1               5                  10

<210> SEQ ID NO 590
<211> LENGTH: 11
<212> TYPE: PRT
<213> ORGANISM: Artificial Sequence
<220> FEATURE:
<223> OTHER INFORMATION: pNOP658785

<400> SEQUENCE: 590

Gly Ala Gly Ala Thr Gly His Phe Leu Pro Pro
 1               5                  10

<210> SEQ ID NO 591
<211> LENGTH: 11
<212> TYPE: PRT
<213> ORGANISM: Artificial Sequence
<220> FEATURE:
<223> OTHER INFORMATION: pNOP667654

<400> SEQUENCE: 591

Leu Gln Leu Arg Ala Leu Ser Trp Leu Phe Gln
 1               5                  10

<210> SEQ ID NO 592
<211> LENGTH: 11
<212> TYPE: PRT
<213> ORGANISM: Artificial Sequence
<220> FEATURE:
<223> OTHER INFORMATION: pNOP684894

<400> SEQUENCE: 592

Trp Ser Leu Cys Thr Arg Thr Lys Arg Pro Met
 1               5                  10

<210> SEQ ID NO 593
<211> LENGTH: 10
<212> TYPE: PRT
<213> ORGANISM: Artificial Sequence
<220> FEATURE:
<223> OTHER INFORMATION: pNOP686213

<400> SEQUENCE: 593

Ala Glu Gly Ala Pro Gly Leu Ala Arg Leu
 1               5                  10

<210> SEQ ID NO 594
<211> LENGTH: 10
<212> TYPE: PRT
<213> ORGANISM: Artificial Sequence
<220> FEATURE:
```

<223> OTHER INFORMATION: pNOP710735

<400> SEQUENCE: 594

Arg Gly Ser Pro Ala Ser Gly His Ala Ala
1               5                   10

<210> SEQ ID NO 595
<211> LENGTH: 69
<212> TYPE: PRT
<213> ORGANISM: Artificial Sequence
<220> FEATURE:
<223> OTHER INFORMATION: pNOP76090

<400> SEQUENCE: 595

Cys Asp Leu Ser Ala Ser Phe Leu Gly Leu Gly Ala His Arg Gly
1               5                   10                  15

Asn Pro Gly Phe Gln Pro Cys Pro Leu Pro Pro Ala Pro Pro
                20                  25                  30

Leu Gln Lys Ala Val Pro Val Ala Trp Gln Glu Ala Trp Pro Arg Asn
            35                  40                  45

Arg Ser Pro Pro Val Gln Ala Ser Tyr Ser Ser Asp Thr Ala Pro Ala
        50                  55                  60

Arg Ala Thr Phe Ser
65

<210> SEQ ID NO 596
<211> LENGTH: 281
<212> TYPE: PRT
<213> ORGANISM: Artificial Sequence
<220> FEATURE:
<223> OTHER INFORMATION: pNOP1314

<400> SEQUENCE: 596

Pro Val Pro Ala Ala Gln Arg Pro Gly Gly Ala Gly His Ala Arg
1               5                   10                  15

Pro Gly His Leu His Gly Gln Leu Arg His Gln His Arg Gly His
                20                  25                  30

Pro Gly Glu Arg Gly Pro Arg Val Asp Val Gln Ala Ala Gly Ala Ala
            35                  40                  45

Ala Thr Pro Ala Ala Ala Pro Thr Gly Pro Ala Gly Pro Ala Gly Ala
        50                  55                  60

Pro Ala Ala Ala Gly Gly Ala Pro Thr Ala Ala Gly Gly Thr Pro Ala
65                  70                  75                  80

Ala Ala Thr Gly Ala His Ala Asp His Ala Glu Gln Arg Ala Gly Pro
                85                  90                  95

Val Pro Ala Asn Ala His Gln Asp Gly Ala Ala Glu Pro Gln Pro Leu
                100                 105                 110

Gln Arg Ala Ala Ala Ala Leu Ala Pro Thr Asp Arg Leu Gln Pro Leu
            115                 120                 125

Gln Pro Pro Thr Leu Gln Pro Leu Pro Ala His Pro Leu Thr
        130                 135                 140

Val Arg Leu His Arg Pro Pro Glu Leu Gln Leu Leu Leu Gln Pro Arg
145                 150                 155                 160

Gly Arg Pro Gly His Arg Pro Leu Leu His Leu His Leu His Glu Pro
                165                 170                 175

Arg Ser Ala Pro His Val His Pro His Arg Arg His Leu Trp Gly Pro
                180                 185                 190

Phe His Pro Ala Asp Pro Gln Pro Pro Ala Leu Gly Thr Thr Arg Leu

```
                195                 200                 205
His Thr Ala His Ser Thr Leu Arg Arg Pro Pro Thr Lys Gly Glu Asp
    210                 215                 220

Gly Arg Asp Asp Pro Lys Asn Asn Arg Arg Lys Arg Gly Pro Thr Arg
225                 230                 235                 240

Ile Pro Phe Gly His Leu Cys Phe Phe Val Phe Leu Phe Cys Phe Val
                245                 250                 255

Phe Ser Ser Ser Ser Ser Leu Lys Thr Phe Lys Leu Lys Ala Thr
                260                 265                 270

Arg Thr Gln Ile Ser Lys Thr Gln Thr
                275                 280

<210> SEQ ID NO 597
<211> LENGTH: 103
<212> TYPE: PRT
<213> ORGANISM: Artificial Sequence
<220> FEATURE:
<223> OTHER INFORMATION: pNOP30584

<400> SEQUENCE: 597

Ala Ala Thr Ser Ser Pro Thr Ser Arg Pro Ser Met Ser Thr Ser Leu
1               5                   10                  15

Thr Ser Thr Cys Arg Pro Thr Ala Thr Arg Gly Cys Arg Pro Arg Thr
                20                  25                  30

Ala Arg Ser Pro Thr Arg Ala Ala Thr Ala Ser Ala Ala Pro Arg Pro
            35                  40                  45

Pro Arg Arg Ala Arg Ala Thr Cys Gly Cys Pro Ser Ser Arg Arg Arg
        50                  55                  60

Arg His Pro Arg Ser Ser Pro His Arg Pro Arg Pro Arg Arg Pro Arg
65                  70                  75                  80

Pro Arg Ser Arg Arg Arg Pro His Ser Ser Arg Arg His Pro Arg
                85                  90                  95

Ser Ser His Arg Arg Thr Arg
                100

<210> SEQ ID NO 598
<211> LENGTH: 250
<212> TYPE: PRT
<213> ORGANISM: Artificial Sequence
<220> FEATURE:
<223> OTHER INFORMATION: pNOP1997

<400> SEQUENCE: 598

Tyr Glu Ser Pro Gly Pro Leu His Glu Asp Asp Arg Arg Ala Gly Glu
1               5                   10                  15

Gly Pro Val Arg Arg Pro Gln Pro His His Val Arg Gly Leu Arg Gly
                20                  25                  30

Leu Ala Leu Pro Val Gly Leu Arg Leu Gly His Arg Glu His Ala Ala
            35                  40                  45

Pro Gly Glu His Val Pro Gln Gly Arg Ala Arg Ser Glu Glu Gly Glu
        50                  55                  60

Arg Gly Gly Gln Val Pro Arg Val His Pro Arg Gly Gln Pro Gly
65                  70                  75                  80

Ala Gln Arg Leu Arg Leu Asp Ala Gly Ala His Ala Gly Ala Arg Gln
                85                  90                  95

Arg Leu Gln Gln Glu Gln Ala Ala Arg Gln Ala Ala His Glu Arg Leu
            100                 105                 110
```

-continued

```
His Gly Val Gly Ala Gly Gly Ala Gln Glu Ala Arg Gly Pro Val Pro
            115                 120                 125

Ala Leu Ala Gln Arg Arg Ala Gln Gln Asp Ala Gly Gln Ala Leu Glu
        130                 135                 140

Thr Ser Glu Arg Glu Arg Glu Ala Ala Leu Arg Gly Gly Gly Gly Ala
145                 150                 155                 160

Ala Ala Arg Ala Ala Gln Gly Pro Pro Gly Leu Gln Val Pro Ala
                165                 170                 175

Ala Ala Glu Glu Val Gly Glu Glu Arg Ala Gly Gly Arg Gly Gly
            180                 185                 190

His Gly Ala Asp Ala His Leu Pro Gln Arg His Leu Gln Gly Ala Ala
        195                 200                 205

Gly Arg Leu Ala Thr Leu Leu Leu Arg His Glu Arg Gly Ala Leu Pro
    210                 215                 220

Arg Arg Ala Leu Gly Ala Ile Pro Gly Pro Thr Asp Pro Thr His His
225                 230                 235                 240

Pro Gln Asn Arg Arg Ala Ala Gly Gln Gly
                245                 250

<210> SEQ ID NO 599
<211> LENGTH: 25
<212> TYPE: PRT
<213> ORGANISM: Artificial Sequence
<220> FEATURE:
<223> OTHER INFORMATION: pNOP356358

<400> SEQUENCE: 599

Ser Glu Arg Gly Ala Pro Cys Gln Arg Gly Ala Asp Ser Pro Leu Ser
1               5                   10                  15

Thr Ser Ala Thr Trp Thr Ser Ala Ser
            20                  25

<210> SEQ ID NO 600
<211> LENGTH: 66
<212> TYPE: PRT
<213> ORGANISM: Artificial Sequence
<220> FEATURE:
<223> OTHER INFORMATION: pNOP83048

<400> SEQUENCE: 600

Ala Pro Ala Thr Thr Ala Ser Ser Ser Thr Arg Pro Asn Arg Ser
1               5                   10                  15

Pro Thr Ala Pro Ser Thr Ser His Thr Thr Ala Pro Thr Arg Pro
            20                  25                  30

Ser Pro Ala His Ser Thr Thr Thr Pro Thr Arg Thr Pro Ala Pro
        35                  40                  45

Thr Thr Ala Thr Arg Gln Ala Arg Ala Pro Ala Ser Thr Pro Pro Ser
    50                  55                  60

Pro Thr
65

<210> SEQ ID NO 601
<211> LENGTH: 43
<212> TYPE: PRT
<213> ORGANISM: Artificial Sequence
<220> FEATURE:
<223> OTHER INFORMATION: pNOP177083

<400> SEQUENCE: 601

Pro Glu Ala Arg Gly Ala Pro Leu Ala Arg Gly Gly Gln Thr Ala Pro
```

```
                1               5                   10                  15
Tyr Arg Leu Pro Arg Arg Gly His Arg Ala Glu Gln Arg His
                20                  25                  30
Leu Gln His Arg Asp Leu Arg Cys Gln Arg Val
        35                  40
```

<210> SEQ ID NO 602
<211> LENGTH: 49
<212> TYPE: PRT
<213> ORGANISM: Artificial Sequence
<220> FEATURE:
<223> OTHER INFORMATION: pNOP144465

<400> SEQUENCE: 602

```
Pro Thr Ser Arg Arg Arg Ala Cys Pro Ala Pro Pro Ala Pro Cys
1               5                   10                  15
Pro Arg Thr Pro Arg Ala Arg Pro Ala Arg Arg Ala Pro Ala Arg Thr
                20                  25                  30
Pro Arg Thr Arg Gly Pro Arg Arg Thr Arg Ser Pro Ala Ser Pro
        35                  40                  45
Ile
```

<210> SEQ ID NO 603
<211> LENGTH: 33
<212> TYPE: PRT
<213> ORGANISM: Artificial Sequence
<220> FEATURE:
<223> OTHER INFORMATION: pNOP250754

<400> SEQUENCE: 603

```
Ala Arg Cys Thr Pro Pro Ala Ser Thr Arg Gly Asn Pro Arg Ala His
1               5                   10                  15
Arg Pro His Pro Pro Pro Lys Pro Thr Cys Ser Arg Ala Arg Leu
                20                  25                  30
Thr
```

<210> SEQ ID NO 604
<211> LENGTH: 16
<212> TYPE: PRT
<213> ORGANISM: Artificial Sequence
<220> FEATURE:
<223> OTHER INFORMATION: pNOP512212

<400> SEQUENCE: 604

```
Ala Ala Ser Arg Ala Ser Pro Ser Glu Arg Thr Ser Arg Arg Ser Ser
1               5                   10                  15
```

<210> SEQ ID NO 605
<211> LENGTH: 52
<212> TYPE: PRT
<213> ORGANISM: Artificial Sequence
<220> FEATURE:
<223> OTHER INFORMATION: pNOP131867

<400> SEQUENCE: 605

```
Thr Pro Leu Ser Ala Pro Cys Thr Pro Ser Pro Thr Pro Leu Gly
1               5                   10                  15
Ser Leu Pro Ser Arg Arg Pro Thr Ala Pro Ser Thr Gly Asn Asn Pro
                20                  25                  30
Ser Thr His Ser Ser Leu Asp Leu Glu Glu Ala Ser His Glu Gly Arg
        35                  40                  45
```

```
Arg Trp Pro Arg
        50

<210> SEQ ID NO 606
<211> LENGTH: 48
<212> TYPE: PRT
<213> ORGANISM: Artificial Sequence
<220> FEATURE:
<223> OTHER INFORMATION: pNOP150040

<400> SEQUENCE: 606

Arg Arg Arg Ala Arg Thr Ser Ser Pro Cys Ala Ser Ala Arg Arg
1               5                   10                  15

Ser Ala Arg Cys Ser Lys Ala Thr Thr Gly Arg Trp Cys Pro Cys Arg
                20                  25                  30

Cys Ala Ser Thr Ala Pro Ala Arg Thr Ser Arg Thr Ser Ser Gly Pro
            35                  40                  45

<210> SEQ ID NO 607
<211> LENGTH: 36
<212> TYPE: PRT
<213> ORGANISM: Artificial Sequence
<220> FEATURE:
<223> OTHER INFORMATION: pNOP230868

<400> SEQUENCE: 607

Thr Pro Ser Trp Cys Gly Arg Arg Arg Ala Gly Ser Ser Arg Thr
1               5                   10                  15

Ser Thr Arg Thr Cys Thr Thr Pro Ser Ser Ala Arg Trp Ala Ser
                20                  25                  30

Ser Gly Asp Phe
            35

<210> SEQ ID NO 608
<211> LENGTH: 35
<212> TYPE: PRT
<213> ORGANISM: Artificial Sequence
<220> FEATURE:
<223> OTHER INFORMATION: pNOP238602

<400> SEQUENCE: 608

Arg Thr Gly Arg Arg Gln Arg Arg Pro Arg Ser Arg Arg Thr Ser
1               5                   10                  15

Pro Pro Thr Pro Ser Ser Arg Arg Cys Arg Pro Thr Arg His Thr Pro
                20                  25                  30

Pro Pro Ala
        35

<210> SEQ ID NO 609
<211> LENGTH: 35
<212> TYPE: PRT
<213> ORGANISM: Artificial Sequence
<220> FEATURE:
<223> OTHER INFORMATION: pNOP239820

<400> SEQUENCE: 609

Thr Arg Ala Arg Ser Gly Pro Ser Trp Arg Arg Ser Gly Cys Ala
1               5                   10                  15

Cys Ser Thr Arg Arg Thr Thr Arg Ile Thr Ser Thr Ser Arg Gly Gly
                20                  25                  30

Gly Ser Arg
        35
```

<210> SEQ ID NO 610
<211> LENGTH: 115
<212> TYPE: PRT
<213> ORGANISM: Artificial Sequence
<220> FEATURE:
<223> OTHER INFORMATION: pNOP23162

<400> SEQUENCE: 610

```
Lys Lys Ala Arg Pro Ser Thr Arg Ser Leu Gly Gly Gly Met His
1               5                   10                  15

Cys Pro Glu Lys Ser Lys Arg Asn Thr Thr Ser Trp Pro Gly Arg Ser
            20                  25                  30

Asp Ser Phe Ile Cys Asn Cys Thr Pro Ala Gly Pro Arg Gly Ile Thr
                35                  40                  45

Met Glu Arg Arg Arg Arg Gly Lys Gly Thr Ser Ser Arg Glu Arg Pro
        50                  55                  60

Met Met Gln Ile Leu Gln Arg Ser Val Gly His Cys Ser Gly Leu Thr
65                  70                  75                  80

Asp Arg Leu Tyr Gly Ala Asn Arg Ala Gly Glu Lys Lys Ser Ala Phe
                85                  90                  95

Ala Thr Tyr Lys Val Lys Ala Ala Ser Ala His Pro Leu Gln Met
            100                 105                 110

Glu Ala Tyr
        115
```

<210> SEQ ID NO 611
<211> LENGTH: 48
<212> TYPE: PRT
<213> ORGANISM: Artificial Sequence
<220> FEATURE:
<223> OTHER INFORMATION: pNOP146451

<400> SEQUENCE: 611

```
Ala Leu Leu Arg Asn Ala Glu Arg Ala Leu Ala Leu Ile Asn Arg Ile
1               5                   10                  15

Thr Gly Ala Ala Leu Ala Gly Glu Lys Lys Ser Ala Phe Ala Thr Tyr
            20                  25                  30

Lys Val Lys Ala Ala Ala Ser Ala His Pro Leu Gln Met Glu Ala Tyr
                35                  40                  45
```

<210> SEQ ID NO 612
<211> LENGTH: 156
<212> TYPE: PRT
<213> ORGANISM: Artificial Sequence
<220> FEATURE:
<223> OTHER INFORMATION: pNOP9620

<400> SEQUENCE: 612

```
Leu Trp Lys Glu Glu Glu Glu Lys Gly Gln Ala Ala Gly Arg Asp
1               5                   10                  15

Gln Trp Arg Lys Lys Cys Val Arg Tyr Ile Gln Gly Glu Gly Ser
            20                  25                  30

Cys Leu Ser Pro Pro Ser Ser Asp Gly Ser Leu Leu Asp Ser Pro Pro
        35                  40                  45

Pro Ser Pro Asn Leu Leu Gly Ser Pro Arg Asp Ala Lys Ser Gln
        50                  55                  60

Thr Glu Gln Thr Gln Pro Leu Ser Leu Ser Leu Lys Pro Asp Pro Leu
65                  70                  75                  80

Ala His Leu Ser Met Met Pro Pro Pro Pro Ala Leu Leu Leu Ala Glu
```

```
                    85                  90                  95
Ala Thr His Lys Ala Ser Ala Leu Cys Pro Asn Gly Ala Leu Asp Leu
            100                 105                 110

Pro Pro Ala Ala Leu Gln Pro Ala Ala Pro Ser Ser Ser Ile Ala Gln
            115                 120                 125

Pro Ser Thr Ser Ser Leu His Ser His Ser Ser Leu Ala Gly Thr Gln
            130                 135                 140

Pro Gln Pro Leu Ser Leu Val Thr Lys Ser Leu Glu
145                 150                 155

<210> SEQ ID NO 613
<211> LENGTH: 155
<212> TYPE: PRT
<213> ORGANISM: Artificial Sequence
<220> FEATURE:
<223> OTHER INFORMATION: pNOP9889

<400> SEQUENCE: 613

Thr Gln Arg Met Phe Pro Lys Ser Leu Pro Phe Thr Ser Ser Asp Tyr
1               5                   10                  15

Arg Arg Lys Lys Lys Cys Val Arg Tyr Ile Gln Gly Glu Gly Ser Cys
            20                  25                  30

Leu Ser Pro Pro Ser Ser Asp Gly Ser Leu Leu Asp Ser Pro Pro Pro
        35                  40                  45

Ser Pro Asn Leu Leu Gly Ser Pro Pro Arg Asp Ala Lys Ser Gln Thr
50                  55                  60

Glu Gln Thr Gln Pro Leu Ser Leu Ser Leu Lys Pro Asp Pro Leu Ala
65                  70                  75                  80

His Leu Ser Met Met Pro Pro Pro Ala Leu Leu Leu Ala Glu Ala
                85                  90                  95

Thr His Lys Ala Ser Ala Leu Cys Pro Asn Gly Ala Leu Asp Leu Pro
            100                 105                 110

Pro Ala Ala Leu Gln Pro Ala Ala Pro Ser Ser Ser Ile Ala Gln Pro
            115                 120                 125

Ser Thr Ser Ser Leu His Ser His Ser Ser Leu Ala Gly Thr Gln Pro
130                 135                 140

Gln Pro Leu Ser Leu Val Thr Lys Ser Leu Glu
145                 150                 155

<210> SEQ ID NO 614
<211> LENGTH: 55
<212> TYPE: PRT
<213> ORGANISM: Artificial Sequence
<220> FEATURE:
<223> OTHER INFORMATION: pNOP119014

<400> SEQUENCE: 614

Arg Ala Pro Thr Ser Pro Thr Asp Arg Ser Arg Pro Pro Glu Pro
1               5                   10                  15

Leu Thr Lys Cys Gln Trp Cys Ser Thr Leu Thr Met Ser Thr Pro Ser
            20                  25                  30

Arg Leu Leu Ser Arg Thr Ala Met Asn Thr Ser Arg Arg Glu Thr His
        35                  40                  45

Leu His Thr Tyr Gln Pro Thr
50                  55

<210> SEQ ID NO 615
<211> LENGTH: 69
```

```
<212> TYPE: PRT
<213> ORGANISM: Artificial Sequence
<220> FEATURE:
<223> OTHER INFORMATION: pNOP77071

<400> SEQUENCE: 615

Asn Gly His Cys Leu Met Ser Arg Gln Gly Ala Ser Arg Val Asp Lys
1               5                   10                  15

Pro Ser Arg Met Pro Gly Pro His His Arg His Thr Leu Ser Leu Thr
                20                  25                  30

Lys Cys Gln Trp Cys Ser Thr Leu Thr Met Ser Thr Pro Ser Arg Leu
            35                  40                  45

Leu Ser Arg Thr Ala Met Asn Thr Ser Arg Arg Glu Thr His Leu His
        50                  55                  60

Thr Tyr Gln Pro Thr
65

<210> SEQ ID NO 616
<211> LENGTH: 55
<212> TYPE: PRT
<213> ORGANISM: Artificial Sequence
<220> FEATURE:
<223> OTHER INFORMATION: pNOP117898

<400> SEQUENCE: 616

Lys Gly Ala Thr Pro Tyr Lys Lys Leu Gly Ser Pro Gly Val Leu Ser
1               5                   10                  15

Leu Thr Lys Cys Gln Trp Cys Ser Thr Leu Thr Met Ser Thr Pro Ser
                20                  25                  30

Arg Leu Leu Ser Arg Thr Ala Met Asn Thr Ser Arg Arg Glu Thr His
            35                  40                  45

Leu His Thr Tyr Gln Pro Thr
        50                  55

<210> SEQ ID NO 617
<211> LENGTH: 42
<212> TYPE: PRT
<213> ORGANISM: Artificial Sequence
<220> FEATURE:
<223> OTHER INFORMATION: pNOP181832

<400> SEQUENCE: 617

Ile Ala Gly Leu Thr Lys Cys Gln Trp Cys Ser Thr Leu Thr Met Ser
1               5                   10                  15

Thr Pro Ser Arg Leu Leu Ser Arg Thr Ala Met Asn Thr Ser Arg Arg
                20                  25                  30

Glu Thr His Leu His Thr Tyr Gln Pro Thr
            35                  40

<210> SEQ ID NO 618
<211> LENGTH: 40
<212> TYPE: PRT
<213> ORGANISM: Artificial Sequence
<220> FEATURE:
<223> OTHER INFORMATION: pNOP193656

<400> SEQUENCE: 618

Cys Leu Thr Lys Cys Gln Trp Cys Ser Thr Leu Thr Met Ser Thr Pro
1               5                   10                  15

Ser Arg Leu Leu Ser Arg Thr Ala Met Asn Thr Ser Arg Arg Glu Thr
                20                  25                  30
```

His Leu His Thr Tyr Gln Pro Thr
            35                  40

<210> SEQ ID NO 619
<211> LENGTH: 117
<212> TYPE: PRT
<213> ORGANISM: Artificial Sequence
<220> FEATURE:
<223> OTHER INFORMATION: pNOP22344

<400> SEQUENCE: 619

Thr Leu His Ala Gly Lys Pro Thr Ser Thr Leu Thr Ser Arg Arg Arg
1               5                   10                  15

Pro Gln Asn Arg Asn Pro Thr Ala Ser Ala Pro Ser Arg Tyr Ile Pro
            20                  25                  30

Val Leu Pro Thr Ile Ala Trp His Arg Arg Thr Asn Pro Pro Ser Ala
        35                  40                  45

Arg Met Val Ser Thr Thr Ala Arg Ser Thr Ser Val Pro Asn His Asp
    50                  55                  60

Arg Arg Ile Gln Thr Pro Leu Pro His Ser Ser Asp Arg Gln Cys Phe
65                  70                  75                  80

His Val Gln Val Pro Ser Pro Tyr Gly Pro Thr Thr Ser Tyr Ala Thr
                85                  90                  95

His Asp Gly His Ser Ala Ser Gly His Ser His Thr Asn Ser Gln Thr
            100                 105                 110

Gly Ile Val Pro Glu
        115

<210> SEQ ID NO 620
<211> LENGTH: 44
<212> TYPE: PRT
<213> ORGANISM: Artificial Sequence
<220> FEATURE:
<223> OTHER INFORMATION: pNOP169706

<400> SEQUENCE: 620

Ile Arg Asn Glu Ser Lys Gln Leu Leu Arg Phe Arg Gly Gly Lys Thr
1               5                   10                  15

Ala Ser Ala Ser Leu Arg Lys Phe Pro Arg Gln Ile Pro Gly Lys Phe
            20                  25                  30

Gly Arg Ser Gly Gln Glu Ala Arg Trp Arg Ala Leu
        35                  40

<210> SEQ ID NO 621
<211> LENGTH: 35
<212> TYPE: PRT
<213> ORGANISM: Artificial Sequence
<220> FEATURE:
<223> OTHER INFORMATION: pNOP238936

<400> SEQUENCE: 621

Ser His Gln Gln Ser Asn Arg Asn Arg Pro Arg Val Met Ser Ala His
1               5                   10                  15

Ser Ile Val Gln Ser Ile Arg Thr Pro Lys Arg Lys Lys Arg Arg
            20                  25                  30

Ser Pro Thr
        35

<210> SEQ ID NO 622
<211> LENGTH: 113
<212> TYPE: PRT

```
<213> ORGANISM: Artificial Sequence
<220> FEATURE:
<223> OTHER INFORMATION: pNOP24554

<400> SEQUENCE: 622

Thr Leu His Ala Gly Lys Pro Thr Ser Thr Leu Thr Ser Arg Arg Arg
1               5                   10                  15

Pro Gln Asn Arg Asn Pro Thr Ala Ser Ala Pro Ser Arg Tyr Ile Pro
            20                  25                  30

Val Leu Pro Thr Ile Ala Trp His Arg Arg Thr Asn Pro Pro Ser Ala
        35                  40                  45

Arg Met Ala Arg Ser Thr Ser Val Pro Asn His Asp Arg Arg Ile Gln
50                  55                  60

Thr Pro Leu Pro His Ser Ser Asp Arg Gln Cys Phe His Val Gln Val
65                  70                  75                  80

Pro Ser Pro Tyr Gly Pro Thr Thr Ser Tyr Ala Thr His Asp Gly His
                85                  90                  95

Ser Ala Ser Gly His Ser His Thr Asn Ser Gln Thr Gly Ile Val Pro
            100                 105                 110

Glu

<210> SEQ ID NO 623
<211> LENGTH: 22
<212> TYPE: PRT
<213> ORGANISM: Artificial Sequence
<220> FEATURE:
<223> OTHER INFORMATION: pNOP395162

<400> SEQUENCE: 623

Phe Pro Ser Lys Thr Arg Ala Asn Arg Arg Arg Ala Pro Lys Thr
1               5                   10                  15

Pro Arg Gln Arg Gly Ile
            20

<210> SEQ ID NO 624
<211> LENGTH: 69
<212> TYPE: PRT
<213> ORGANISM: Artificial Sequence
<220> FEATURE:
<223> OTHER INFORMATION: pNOP76119

<400> SEQUENCE: 624

Cys Leu Arg His Pro Pro Ser Cys Ser Leu Arg Pro Pro Thr Arg Pro
1               5                   10                  15

Pro Pro Ser Val Pro Thr Gly Pro Trp Thr Cys Pro Gln Pro Leu Cys
            20                  25                  30

Ser Leu Pro Pro Pro His Gln Leu His Ser Arg Arg Leu Leu Pro
        35                  40                  45

Tyr Ile Pro Thr Ala Pro Trp Pro Gly Pro Ser Pro Ser Arg Cys Arg
    50                  55                  60

Ser Ser Pro Ser Leu
65

<210> SEQ ID NO 625
<211> LENGTH: 58
<212> TYPE: PRT
<213> ORGANISM: Artificial Sequence
<220> FEATURE:
<223> OTHER INFORMATION: pNOP108508

<400> SEQUENCE: 625
```

-continued

Ser Met Asn Gln Lys Arg Ile Lys Thr Ala Pro Pro Ile Pro Arg Arg
1               5                   10                  15

Lys Asp Gly Leu Arg Leu Ala Pro Lys Val Ser Glu Thr Asn Pro Gly
            20                  25                  30

Lys Val Trp Lys Lys Arg Pro Arg Gly Lys Met Glu Gly Ser Leu Arg
        35                  40                  45

Gly His Arg Ile Pro Ala Thr Pro Ser Ser
        50                  55

<210> SEQ ID NO 626
<211> LENGTH: 34
<212> TYPE: PRT
<213> ORGANISM: Artificial Sequence
<220> FEATURE:
<223> OTHER INFORMATION: pNOP246621

<400> SEQUENCE: 626

Pro Ser Met Leu Pro Cys Pro Ala Phe Cys Leu Leu Gly Ser Leu Pro
1               5                   10                  15

Ile Trp Ser His His Ile Ile Arg Tyr Thr Arg Arg Ala Phe Arg Ile
            20                  25                  30

Arg Pro

<210> SEQ ID NO 627
<211> LENGTH: 34
<212> TYPE: PRT
<213> ORGANISM: Artificial Sequence
<220> FEATURE:
<223> OTHER INFORMATION: pNOP249601

<400> SEQUENCE: 627

Val Pro Ser Pro Tyr Gly Pro Thr Thr Ser Tyr Ala Thr His Asp Gly
1               5                   10                  15

His Ser Ala Ser Gly His Ser Thr Asn Ser Gln Thr Gly Ile Val
            20                  25                  30

Pro Glu

<210> SEQ ID NO 628
<211> LENGTH: 23
<212> TYPE: PRT
<213> ORGANISM: Artificial Sequence
<220> FEATURE:
<223> OTHER INFORMATION: pNOP391533

<400> SEQUENCE: 628

Tyr His Ser Lys Val Asn Gln Cys Thr Gln Ser Arg Gln Glu Asp Ser
1               5                   10                  15

Asp Thr Pro Thr Pro Gln Leu
            20

<210> SEQ ID NO 629
<211> LENGTH: 22
<212> TYPE: PRT
<213> ORGANISM: Artificial Sequence
<220> FEATURE:
<223> OTHER INFORMATION: pNOP403210

<400> SEQUENCE: 629

Gln Ser Ala Ser Gly Ala Ala Pro Ser Pro Cys Pro Pro His Ala
1               5                   10                  15

Ser Tyr His Val Gln Gln

-continued

```
                    20

<210> SEQ ID NO 630
<211> LENGTH: 65
<212> TYPE: PRT
<213> ORGANISM: Artificial Sequence
<220> FEATURE:
<223> OTHER INFORMATION: pNOP86123

<400> SEQUENCE: 630

Gly His Pro Gln Gly Leu Arg Pro Leu Ser Gln Arg Gly Pro Gly Pro
1               5                   10                  15

Ala Pro Ser Arg Phe Ala Ala Cys Arg Pro Leu Leu Ile Asn Cys Thr
            20                  25                  30

Ala Val Asp Phe Phe Leu Thr Phe Pro Gln Leu Pro Gly Arg Asp Pro
        35                  40                  45

Ala Pro Ala Ala Val Ala Arg His Gln Val Phe Arg Ile Ala Leu Ala
    50                  55                  60

Ser
65

<210> SEQ ID NO 631
<211> LENGTH: 60
<212> TYPE: PRT
<213> ORGANISM: Artificial Sequence
<220> FEATURE:
<223> OTHER INFORMATION: pNOP100389

<400> SEQUENCE: 631

Ile Leu Ala Phe His Phe Leu Arg Leu Gln Met Gln Ile Leu Gln Arg
1               5                   10                  15

Ser Val Gly His Cys Ser Gly Leu Thr Asp Arg Leu Tyr Gly Ala Asn
            20                  25                  30

Arg Ala Gly Glu Lys Lys Ser Ala Phe Ala Thr Tyr Lys Val Lys Ala
        35                  40                  45

Ala Ala Ser Ala His Pro Leu Gln Met Glu Ala Tyr
    50                  55                  60

<210> SEQ ID NO 632
<211> LENGTH: 60
<212> TYPE: PRT
<213> ORGANISM: Artificial Sequence
<220> FEATURE:
<223> OTHER INFORMATION: pNOP100945

<400> SEQUENCE: 632

Asn Gly His Cys Leu Met Ser Arg Gln Gly Ala Ser Arg Val Asp Lys
1               5                   10                  15

Pro Ser Arg Met Pro Gly Pro His His Arg His Thr Leu Ser Ala Pro
            20                  25                  30

Ser Leu Ala Ala Leu Arg Asp Met Thr Val Ser Thr Ser Thr Pro Pro
        35                  40                  45

Gln Thr Ser Leu Ser Ala Leu Lys Ser Ser Gly Thr
    50                  55                  60

<210> SEQ ID NO 633
<211> LENGTH: 56
<212> TYPE: PRT
<213> ORGANISM: Artificial Sequence
<220> FEATURE:
<223> OTHER INFORMATION: pNOP114399
```

-continued

```
<400> SEQUENCE: 633

Leu Val Arg Pro Leu Gln Met Gln Ile Leu Gln Arg Ser Val Gly His
1               5                   10                  15

Cys Ser Gly Leu Thr Asp Arg Leu Tyr Gly Ala Asn Arg Ala Gly Glu
            20                  25                  30

Lys Lys Ser Ala Phe Ala Thr Tyr Lys Val Lys Ala Ala Ser Ala
        35                  40                  45

His Pro Leu Gln Met Glu Ala Tyr
    50                  55

<210> SEQ ID NO 634
<211> LENGTH: 50
<212> TYPE: PRT
<213> ORGANISM: Artificial Sequence
<220> FEATURE:
<223> OTHER INFORMATION: pNOP141050

<400> SEQUENCE: 634

Val His Val Glu Arg Lys Arg Gly His Gln Pro Asp Pro Trp Ala Glu
1               5                   10                  15

Val Ala Cys Thr Val Gln Arg Arg Ala Ser Glu Ile Leu Arg Ala Gly
            20                  25                  30

Pro Glu Gly Ala Thr Ala Ser Tyr Ala Thr Val Pro Arg Leu Val Arg
        35                  40                  45

Ala Gly
    50

<210> SEQ ID NO 635
<211> LENGTH: 47
<212> TYPE: PRT
<213> ORGANISM: Artificial Sequence
<220> FEATURE:
<223> OTHER INFORMATION: pNOP152548

<400> SEQUENCE: 635

Gly Ala Thr Val Ser Arg Leu Pro Leu His His Asp Pro Arg Pro Asp
1               5                   10                  15

Glu Pro Leu Pro Pro Gln Arg Ile Ala Leu Ala His Arg Pro Asn Pro
            20                  25                  30

Pro Phe Ser Val Arg Gln His Thr Leu Leu Cys Val Gln Asn Asp
        35                  40                  45

<210> SEQ ID NO 636
<211> LENGTH: 42
<212> TYPE: PRT
<213> ORGANISM: Artificial Sequence
<220> FEATURE:
<223> OTHER INFORMATION: pNOP182797

<400> SEQUENCE: 636

Leu Val Arg Pro Leu Gln Met Gln Ile Leu Gln Arg Ser Val Gly His
1               5                   10                  15

Cys Ser Gly Leu Thr Asp Arg Leu Tyr Gly Ala Asn Arg Ala Gly Glu
            20                  25                  30

Lys Lys Lys Val Arg Ser Leu His Thr Arg
        35                  40

<210> SEQ ID NO 637
<211> LENGTH: 42
<212> TYPE: PRT
<213> ORGANISM: Artificial Sequence
```

```
<220> FEATURE:
<223> OTHER INFORMATION: pNOP184017

<400> SEQUENCE: 637

Arg Ala Pro Thr Ser Pro Thr Asp Arg Ser Arg Pro Pro Glu Pro
1               5                   10                  15

Ser Ile Phe Ser Pro Ala Ala His Ile Thr Leu Arg Thr Lys Arg Leu
            20                  25                  30

Asn Thr Arg Leu Gln Phe Ser Ile Ser Arg
        35                  40

<210> SEQ ID NO 638
<211> LENGTH: 40
<212> TYPE: PRT
<213> ORGANISM: Artificial Sequence
<220> FEATURE:
<223> OTHER INFORMATION: pNOP194610

<400> SEQUENCE: 638

Gly Ala Thr Val Ser Arg Leu Pro Leu His His Asp Pro Arg Pro Asp
1               5                   10                  15

Glu Pro Leu Pro Pro Gln Arg Ile Ala Leu Ala His Arg Pro Asn Leu
            20                  25                  30

Ser Pro Asp Glu Met Ala Thr Ala
        35                  40

<210> SEQ ID NO 639
<211> LENGTH: 40
<212> TYPE: PRT
<213> ORGANISM: Artificial Sequence
<220> FEATURE:
<223> OTHER INFORMATION: pNOP196518

<400> SEQUENCE: 639

Leu Val Arg Pro Leu Gln Ser Leu Asn Leu Glu Tyr Tyr Asn Gly Glu
1               5                   10                  15

Lys Lys Ser Ala Phe Ala Thr Tyr Lys Val Lys Ala Ala Ala Ser Ala
            20                  25                  30

His Pro Leu Gln Met Glu Ala Tyr
        35                  40

<210> SEQ ID NO 640
<211> LENGTH: 35
<212> TYPE: PRT
<213> ORGANISM: Artificial Sequence
<220> FEATURE:
<223> OTHER INFORMATION: pNOP236046

<400> SEQUENCE: 640

Leu Ser Ala Leu Leu Pro Pro Leu Arg Leu His Cys Gln His Ser Ser
1               5                   10                  15

Leu Gln Gly His Glu Lys Glu Pro Leu Leu Thr Lys Ser Trp Gly Ala
            20                  25                  30

Leu Val Tyr
        35

<210> SEQ ID NO 641
<211> LENGTH: 35
<212> TYPE: PRT
<213> ORGANISM: Artificial Sequence
<220> FEATURE:
<223> OTHER INFORMATION: pNOP238356
```

<400> SEQUENCE: 641

Arg Gln Leu Pro Gln Pro Thr Leu Phe Arg Trp Lys Leu Thr Arg Phe
1               5                   10                  15

Ala Ser Pro Leu Pro Glu Pro Ala Arg Leu Pro Ser Pro Arg Arg Gln
            20                  25                  30

Val Thr Asp
        35

<210> SEQ ID NO 642
<211> LENGTH: 32
<212> TYPE: PRT
<213> ORGANISM: Artificial Sequence
<220> FEATURE:
<223> OTHER INFORMATION: pNOP262475

<400> SEQUENCE: 642

Gly Ala Thr Val Ser Arg Leu Pro Leu His His Asp Pro Arg Pro Asp
1               5                   10                  15

Glu Pro Leu Pro Pro Gln Arg Ile Ala Leu Ala His Arg Pro Asn Leu
            20                  25                  30

<210> SEQ ID NO 643
<211> LENGTH: 31
<212> TYPE: PRT
<213> ORGANISM: Artificial Sequence
<220> FEATURE:
<223> OTHER INFORMATION: pNOP277062

<400> SEQUENCE: 643

Pro Arg Arg Gln Arg Arg Thr Asp Phe Leu Gln Arg Arg Gly Arg Thr
1               5                   10                  15

Gly Gly Glu Glu Leu Arg Lys Leu Leu Gly Arg Glu Gly Phe Ser
            20                  25                  30

<210> SEQ ID NO 644
<211> LENGTH: 30
<212> TYPE: PRT
<213> ORGANISM: Artificial Sequence
<220> FEATURE:
<223> OTHER INFORMATION: pNOP291285

<400> SEQUENCE: 644

Thr Gln Arg Met Phe Pro Lys Ser Leu Pro Phe Thr Ser Ser Asp Tyr
1               5                   10                  15

Arg Cys Lys Tyr Ser Lys Glu Val Ser Gly Thr Val Arg Ala
            20                  25                  30

<210> SEQ ID NO 645
<211> LENGTH: 29
<212> TYPE: PRT
<213> ORGANISM: Artificial Sequence
<220> FEATURE:
<223> OTHER INFORMATION: pNOP292673

<400> SEQUENCE: 645

Ala Asp Pro Ala Ser Val Ala Val Pro Glu Ala Arg Pro Pro Gly Pro
1               5                   10                  15

Pro Val His Asp Ala Ser Ala Thr Arg Pro Pro Ala Arg
            20                  25

<210> SEQ ID NO 646
<211> LENGTH: 29
<212> TYPE: PRT

```
<213> ORGANISM: Artificial Sequence
<220> FEATURE:
<223> OTHER INFORMATION: pNOP299871

<400> SEQUENCE: 646

Pro Ser Met Leu Pro Cys Pro Gly Ser Leu Pro Ile Trp Ser His His
1               5                   10                  15

Ile Ile Arg Tyr Thr Arg Arg Ala Phe Arg Ile Arg Pro
            20                  25

<210> SEQ ID NO 647
<211> LENGTH: 26
<212> TYPE: PRT
<213> ORGANISM: Artificial Sequence
<220> FEATURE:
<223> OTHER INFORMATION: pNOP343264

<400> SEQUENCE: 647

Thr Ser Pro Gln Gly Cys Pro Val Pro Ile Thr Gly Thr His Cys Pro
1               5                   10                  15

Glu Pro Pro Pro Leu Leu His Ser Gly Thr
            20                  25

<210> SEQ ID NO 648
<211> LENGTH: 25
<212> TYPE: PRT
<213> ORGANISM: Artificial Sequence
<220> FEATURE:
<223> OTHER INFORMATION: pNOP348748

<400> SEQUENCE: 648

Gly Arg Arg Ser Gly Leu Arg Gly Leu Ser Val Pro Ala Val Gly Arg
1               5                   10                  15

Leu Ala Pro Gln Phe Glu Leu Leu Val
            20                  25

<210> SEQ ID NO 649
<211> LENGTH: 25
<212> TYPE: PRT
<213> ORGANISM: Artificial Sequence
<220> FEATURE:
<223> OTHER INFORMATION: pNOP357917

<400> SEQUENCE: 649

Thr Pro Lys Gln Glu Ser His Gly Leu Arg Thr Leu Gln Ile Tyr Pro
1               5                   10                  15

Arg Ile Thr His Tyr Arg Leu Ala Pro
            20                  25

<210> SEQ ID NO 650
<211> LENGTH: 25
<212> TYPE: PRT
<213> ORGANISM: Artificial Sequence
<220> FEATURE:
<223> OTHER INFORMATION: pNOP358118

<400> SEQUENCE: 650

Thr Ser Pro Gln Gly Cys Pro Val Pro Ile Thr Gly Thr His Cys Gln
1               5                   10                  15

Pro Pro Pro Leu Leu His Ser Gly Thr
            20                  25

<210> SEQ ID NO 651
<211> LENGTH: 23
```

```
<212> TYPE: PRT
<213> ORGANISM: Artificial Sequence
<220> FEATURE:
<223> OTHER INFORMATION: pNOP390758

<400> SEQUENCE: 651

Val Val Arg Glu Ala Gln Trp Pro Pro Gly Ser Leu Cys Ser Ser
1               5                   10                  15

Trp Ala Val Gly Thr Ser Ile
            20

<210> SEQ ID NO 652
<211> LENGTH: 22
<212> TYPE: PRT
<213> ORGANISM: Artificial Sequence
<220> FEATURE:
<223> OTHER INFORMATION: pNOP393746

<400> SEQUENCE: 652

Asp Gly Lys Val Asn Gln Cys Thr Gln Ser Arg Gln Glu Asp Ser Asp
1               5                   10                  15

Thr Pro Thr Pro Gln Leu
            20

<210> SEQ ID NO 653
<211> LENGTH: 21
<212> TYPE: PRT
<213> ORGANISM: Artificial Sequence
<220> FEATURE:
<223> OTHER INFORMATION: pNOP412605

<400> SEQUENCE: 653

Phe Lys Ala Ser Gly Leu Gln Lys Gly Arg Arg Lys Glu Glu Ala Pro
1               5                   10                  15

His Lys Glu Thr Ser
            20

<210> SEQ ID NO 654
<211> LENGTH: 21
<212> TYPE: PRT
<213> ORGANISM: Artificial Sequence
<220> FEATURE:
<223> OTHER INFORMATION: pNOP415243

<400> SEQUENCE: 654

Ile Leu Ala Phe His Phe Leu Arg Leu Gln Glu Lys Lys Val Arg
1               5                   10                  15

Ser Leu His Thr Arg
            20

<210> SEQ ID NO 655
<211> LENGTH: 91
<212> TYPE: PRT
<213> ORGANISM: Artificial Sequence
<220> FEATURE:
<223> OTHER INFORMATION: pNOP41787

<400> SEQUENCE: 655

Lys Lys Ala Arg Pro Ser Thr Arg Ser Leu Gly Gly Gly Gly Met His
1               5                   10                  15

Cys Pro Glu Lys Ser Lys Arg Asn Thr Thr Ser Trp Pro Gly Arg Ser
            20                  25                  30

Asp Ser Phe Ile Cys Asn Cys Thr Pro Ala Gly Pro Arg Gly Ile Thr
        35                  40                  45
```

```
Met Glu Arg Arg Arg Gly Lys Gly Thr Ser Ser Arg Glu Arg Pro
        50                  55                  60

Met Val Lys Lys Lys Ser Ala Phe Ala Thr Tyr Lys Val Lys Ala Ala
 65                  70                  75                  80

Ala Ser Ala His Pro Leu Gln Met Glu Ala Tyr
                 85                  90

<210> SEQ ID NO 656
<211> LENGTH: 21
<212> TYPE: PRT
<213> ORGANISM: Artificial Sequence
<220> FEATURE:
<223> OTHER INFORMATION: pNOP420332

<400> SEQUENCE: 656

Pro Thr Asp Phe Met Val Gln Thr Val Gln Glu Lys Lys Lys Val Arg
 1               5                  10                  15

Ser Leu His Thr Arg
             20

<210> SEQ ID NO 657
<211> LENGTH: 21
<212> TYPE: PRT
<213> ORGANISM: Artificial Sequence
<220> FEATURE:
<223> OTHER INFORMATION: pNOP425448

<400> SEQUENCE: 657

Thr Gln Arg Met Phe Pro Lys Ser Leu Pro Thr Ser Ser Asp Tyr
 1               5                  10                  15

Arg Pro Glu Arg Ser
             20

<210> SEQ ID NO 658
<211> LENGTH: 20
<212> TYPE: PRT
<213> ORGANISM: Artificial Sequence
<220> FEATURE:
<223> OTHER INFORMATION: pNOP428234

<400> SEQUENCE: 658

Ala Pro Leu Pro Glu Thr Pro Ser His Arg Leu Ser Arg Pro Ser Leu
 1               5                  10                  15

Cys Arg Cys Pro
             20

<210> SEQ ID NO 659
<211> LENGTH: 19
<212> TYPE: PRT
<213> ORGANISM: Artificial Sequence
<220> FEATURE:
<223> OTHER INFORMATION: pNOP458391

<400> SEQUENCE: 659

Asn Ser Phe Ser Val Val Asn Pro Ala Ala Leu Phe Met Val Leu Phe
 1               5                  10                  15

His Phe Ser

<210> SEQ ID NO 660
<211> LENGTH: 19
<212> TYPE: PRT
<213> ORGANISM: Artificial Sequence
<220> FEATURE:
```

<223> OTHER INFORMATION: pNOP460845

<400> SEQUENCE: 660

Arg Ala Pro Thr Ser Pro Thr Asp Arg Ser Arg Pro Pro Pro Glu Pro
1               5                   10                  15

Ile Ser Arg

<210> SEQ ID NO 661
<211> LENGTH: 87
<212> TYPE: PRT
<213> ORGANISM: Artificial Sequence
<220> FEATURE:
<223> OTHER INFORMATION: pNOP47070

<400> SEQUENCE: 661

Thr Leu His Ala Gly Lys Pro Thr Ser Thr Leu Thr Ser Arg Arg Arg
1               5                   10                  15

Pro Gln Asn Arg Asn Pro Thr Ala Ser Ala Pro Ser Arg Tyr Ile Pro
                20                  25                  30

Val Leu Pro Thr Ile Ala Trp His Arg Arg Thr Asn Pro Pro Ser Ala
            35                  40                  45

Arg Met Val Ser Thr Thr Ala Arg Ser Thr Ser Val Pro Asn His Asp
        50                  55                  60

Arg Arg Ile Gln Thr Pro Leu Pro His Ser Ser Asp Arg Gln Cys Phe
65                  70                  75                  80

His Val Gln Leu Ser Val Phe
                85

<210> SEQ ID NO 662
<211> LENGTH: 18
<212> TYPE: PRT
<213> ORGANISM: Artificial Sequence
<220> FEATURE:
<223> OTHER INFORMATION: pNOP478102

<400> SEQUENCE: 662

Leu Trp Lys Glu Glu Glu Glu Lys Gly Gln Ala Ala Gly Arg Asp
1               5                   10                  15

Gln Trp

<210> SEQ ID NO 663
<211> LENGTH: 17
<212> TYPE: PRT
<213> ORGANISM: Artificial Sequence
<220> FEATURE:
<223> OTHER INFORMATION: pNOP500461

<400> SEQUENCE: 663

Leu Val Arg Pro Leu Gln Glu Lys Lys Val Arg Ser Leu His Thr
1               5                   10                  15

Arg

<210> SEQ ID NO 664
<211> LENGTH: 17
<212> TYPE: PRT
<213> ORGANISM: Artificial Sequence
<220> FEATURE:
<223> OTHER INFORMATION: pNOP500497

<400> SEQUENCE: 664

Leu Trp Lys Glu Glu Glu Glu Lys Gly Gln Ala Ala Gly Arg Asp
1               5                   10                  15

Gln

<210> SEQ ID NO 665
<211> LENGTH: 83
<212> TYPE: PRT
<213> ORGANISM: Artificial Sequence
<220> FEATURE:
<223> OTHER INFORMATION: pNOP52551

<400> SEQUENCE: 665

Thr Leu His Ala Gly Lys Pro Thr Ser Thr Leu Thr Ser Arg Arg Arg
1               5                   10                  15

Pro Gln Asn Arg Asn Pro Thr Ala Ser Ala Pro Ser Arg Tyr Ile Pro
                20                  25                  30

Val Leu Pro Thr Ile Ala Trp His Arg Arg Thr Asn Pro Pro Ser Ala
            35                  40                  45

Arg Met Ala Arg Ser Thr Ser Val Pro Asn His Asp Arg Arg Ile Gln
        50                  55                  60

Thr Pro Leu Pro His Ser Ser Asp Arg Gln Cys Phe His Val Gln Leu
65                  70                  75                  80

Ser Val Phe

<210> SEQ ID NO 666
<211> LENGTH: 16
<212> TYPE: PRT
<213> ORGANISM: Artificial Sequence
<220> FEATURE:
<223> OTHER INFORMATION: pNOP533731

<400> SEQUENCE: 666

Thr Ser Pro Gln Gly Cys Pro Val Pro Ile Thr Gly Thr His Cys Leu
1               5                   10                  15

<210> SEQ ID NO 667
<211> LENGTH: 15
<212> TYPE: PRT
<213> ORGANISM: Artificial Sequence
<220> FEATURE:
<223> OTHER INFORMATION: pNOP538111

<400> SEQUENCE: 667

Cys Ile His Val Val Tyr Glu Gly Asn Glu Ser Lys Gly Arg Ser
1               5                   10                  15

<210> SEQ ID NO 668
<211> LENGTH: 185
<212> TYPE: PRT
<213> ORGANISM: Artificial Sequence
<220> FEATURE:
<223> OTHER INFORMATION: pNOP5491

<400> SEQUENCE: 668

Ala Leu Leu Arg Asn Ala Glu Arg Ala Leu Ala Leu Ile Asn Arg Ile
1               5                   10                  15

Thr Gly Ala Ala Leu Ala Asp Ala Asn Thr Pro Lys Lys Cys Arg Ala
                20                  25                  30

Leu Phe Gly Leu Asp Arg Gln Thr Leu Trp Cys Lys Pro Cys Arg Arg
            35                  40                  45

Lys Lys Lys Cys Val Arg Tyr Ile Gln Gly Glu Gly Ser Cys Leu Ser
        50                  55                  60

Pro Pro Ser Ser Asp Gly Ser Leu Leu Asp Ser Pro Pro Pro Ser Pro

```
                65                  70                  75                  80
Asn Leu Leu Gly Ser Pro Pro Arg Asp Ala Lys Ser Gln Thr Glu Gln
                    85                  90                  95

Thr Gln Pro Leu Ser Leu Ser Leu Lys Pro Asp Pro Leu Ala His Leu
                100                 105                 110

Ser Met Met Pro Pro Pro Ala Leu Leu Ala Glu Ala Thr His
                115                 120                 125

Lys Ala Ser Ala Leu Cys Pro Asn Gly Ala Leu Asp Leu Pro Pro Ala
                130                 135                 140

Ala Leu Gln Pro Ala Ala Pro Ser Ser Ile Ala Gln Pro Ser Thr
145                 150                 155                 160

Ser Ser Leu His Ser His Ser Ser Leu Ala Gly Thr Gln Pro Gln Pro
                165                 170                 175

Leu Ser Leu Val Thr Lys Ser Leu Glu
                180                 185

<210> SEQ ID NO 669
<211> LENGTH: 15
<212> TYPE: PRT
<213> ORGANISM: Artificial Sequence
<220> FEATURE:
<223> OTHER INFORMATION: pNOP559194

<400> SEQUENCE: 669

Thr Pro Asp Cys Ser Ser Val Ser Pro Asp Glu Met Ala Thr Ala
1               5                   10                  15

<210> SEQ ID NO 670
<211> LENGTH: 13
<212> TYPE: PRT
<213> ORGANISM: Artificial Sequence
<220> FEATURE:
<223> OTHER INFORMATION: pNOP592448

<400> SEQUENCE: 670

Cys Lys Tyr Ser Lys Glu Val Ser Gly Thr Val Arg Ala
1               5                   10

<210> SEQ ID NO 671
<211> LENGTH: 12
<212> TYPE: PRT
<213> ORGANISM: Artificial Sequence
<220> FEATURE:
<223> OTHER INFORMATION: pNOP627331

<400> SEQUENCE: 671

Gly His Asn Phe Ser Gly Asn Gly Arg Phe Glu Trp
1               5                   10

<210> SEQ ID NO 672
<211> LENGTH: 76
<212> TYPE: PRT
<213> ORGANISM: Artificial Sequence
<220> FEATURE:
<223> OTHER INFORMATION: pNOP62995

<400> SEQUENCE: 672

Lys Lys Ala Arg Pro Ser Thr Arg Ser Leu Gly Gly Gly Gly Met His
1               5                   10                  15

Cys Pro Glu Lys Ser Lys Arg Asn Thr Thr Ser Trp Pro Gly Arg Ser
                20                  25                  30

Asp Ser Phe Ile Cys Asn Cys Thr Pro Ala Gly Pro Arg Gly Ile Thr
```

```
                35                  40                  45
Met Glu Arg Arg Arg Gly Lys Gly Thr Ser Ser Arg Glu Arg Pro
        50                  55                  60
Met Glu Lys Lys Lys Val Arg Ser Leu His Thr Arg
65                  70                  75

<210> SEQ ID NO 673
<211> LENGTH: 11
<212> TYPE: PRT
<213> ORGANISM: Artificial Sequence
<220> FEATURE:
<223> OTHER INFORMATION: pNOP662684

<400> SEQUENCE: 673

Ile Leu Ala Phe His Phe Leu Arg Leu Gln Thr
1               5                   10

<210> SEQ ID NO 674
<211> LENGTH: 10
<212> TYPE: PRT
<213> ORGANISM: Artificial Sequence
<220> FEATURE:
<223> OTHER INFORMATION: pNOP699373

<400> SEQUENCE: 674

Lys Lys Lys Val Arg Ser Leu His Thr Arg
1               5                   10

<210> SEQ ID NO 675
<211> LENGTH: 10
<212> TYPE: PRT
<213> ORGANISM: Artificial Sequence
<220> FEATURE:
<223> OTHER INFORMATION: pNOP704386

<400> SEQUENCE: 675

Asn Ala Ala Ala Glu Arg Arg Trp Arg Gly
1               5                   10

<210> SEQ ID NO 676
<211> LENGTH: 10
<212> TYPE: PRT
<213> ORGANISM: Artificial Sequence
<220> FEATURE:
<223> OTHER INFORMATION: pNOP711788

<400> SEQUENCE: 676

Arg Asn Leu Leu Met His Ser Cys Cys Ile
1               5                   10

<210> SEQ ID NO 677
<211> LENGTH: 71
<212> TYPE: PRT
<213> ORGANISM: Artificial Sequence
<220> FEATURE:
<223> OTHER INFORMATION: pNOP72480

<400> SEQUENCE: 677

Lys Lys Ala Arg Pro Ser Thr Arg Ser Leu Gly Gly Gly Met His
1               5                   10                  15

Cys Pro Glu Lys Ser Lys Arg Asn Thr Thr Ser Trp Pro Gly Arg Ser
            20                  25                  30

Asp Ser Phe Ile Cys Asn Cys Thr Pro Ala Gly Pro Arg Gly Ile Thr
        35                  40                  45
```

Met Glu Arg Arg Arg Arg Gly Lys Gly Thr Ser Arg Glu Arg Pro
50                  55                  60

Met Asn Thr Ala Asn Val Ser
65                  70

<210> SEQ ID NO 678
<211> LENGTH: 169
<212> TYPE: PRT
<213> ORGANISM: Artificial Sequence
<220> FEATURE:
<223> OTHER INFORMATION: pNOP7370

<400> SEQUENCE: 678

Ala Leu Leu Arg Asn Ala Glu Arg Ala Leu Ala Leu Ile Asn Arg Ile
1               5                   10                  15

Thr Gly Ala Ala Leu Ala Val Phe Glu Phe Gly Ile Leu Gln Trp Arg
                20                  25                  30

Lys Lys Lys Cys Val Arg Tyr Ile Gln Gly Glu Gly Ser Cys Leu Ser
            35                  40                  45

Pro Pro Ser Ser Asp Gly Ser Leu Leu Asp Ser Pro Pro Ser Pro
50                  55                  60

Asn Leu Leu Gly Ser Pro Pro Arg Asp Ala Lys Ser Gln Thr Glu Gln
65                  70                  75                  80

Thr Gln Pro Leu Ser Leu Ser Leu Lys Pro Asp Pro Leu Ala His Leu
                85                  90                  95

Ser Met Met Pro Pro Pro Ala Leu Leu Ala Glu Ala Thr His
            100                 105                 110

Lys Ala Ser Ala Leu Cys Pro Asn Gly Ala Leu Asp Leu Pro Pro Ala
        115                 120                 125

Ala Leu Gln Pro Ala Ala Pro Ser Ser Ile Ala Gln Pro Ser Thr
    130                 135                 140

Ser Ser Leu His Ser His Ser Ser Leu Ala Gly Thr Gln Pro Gln Pro
145                 150                 155                 160

Leu Ser Leu Val Thr Lys Ser Leu Glu
                165

<210> SEQ ID NO 679
<211> LENGTH: 66
<212> TYPE: PRT
<213> ORGANISM: Artificial Sequence
<220> FEATURE:
<223> OTHER INFORMATION: pNOP83888

<400> SEQUENCE: 679

Lys Lys Ala Arg Pro Ser Thr Arg Ser Leu Gly Gly Gly Met His
1               5                   10                  15

Cys Pro Glu Lys Ser Lys Arg Asn Thr Thr Ser Trp Pro Gly Arg Ser
                20                  25                  30

Asp Ser Phe Ile Cys Asn Cys Thr Pro Ala Gly Pro Arg Gly Ile Thr
            35                  40                  45

Met Glu Arg Arg Arg Arg Gly Lys Gly Thr Ser Ser Arg Glu Arg Pro
50                  55                  60

Met Thr
65

<210> SEQ ID NO 680
<211> LENGTH: 61
<212> TYPE: PRT
<213> ORGANISM: Artificial Sequence

```
<220> FEATURE:
<223> OTHER INFORMATION: pNOP97816

<400> SEQUENCE: 680

Asn Gly His Cys Leu Met Ser Arg Gln Gly Ala Ser Arg Val Asp Lys
1               5                   10                  15

Pro Ser Arg Met Pro Gly Pro His Arg His Thr Leu Ser Arg Ala
            20                  25                  30

Pro Ser Leu Ala Ala Leu Arg Asp Met Thr Val Ser Thr Ser Thr Pro
        35                  40                  45

Pro Gln Thr Ser Leu Ser Ala Leu Lys Ser Ser Gly Thr
        50                  55                  60

<210> SEQ ID NO 681
<211> LENGTH: 85
<212> TYPE: PRT
<213> ORGANISM: Artificial Sequence
<220> FEATURE:
<223> OTHER INFORMATION: pNOP49591

<400> SEQUENCE: 681

Ser Ser Gln Asn Ala Arg Gly Cys Ser Pro Arg Gly Pro Cys Thr Ser
1               5                   10                  15

Ser Ser Tyr Thr Gly Gly Pro Cys Thr Ser Pro Leu Leu Ala Pro Val
            20                  25                  30

Ile Phe Cys Pro Phe Pro Glu Asn Leu Pro Gly Gln Leu Arg Phe Pro
        35                  40                  45

Ser Gly Leu Leu Ala Phe Trp Asp Ser Gln Val Cys Asp Leu His Val
    50                  55                  60

Leu Pro Cys Pro Gln Gln Asp Val Leu Pro Thr Gly Gln Asp Leu Pro
65                  70                  75                  80

Cys Ala Ala Val Gly
                85

<210> SEQ ID NO 682
<211> LENGTH: 103
<212> TYPE: PRT
<213> ORGANISM: Artificial Sequence
<220> FEATURE:
<223> OTHER INFORMATION: pNOP31232

<400> SEQUENCE: 682

Thr Gly Gly Pro Ser Ser Pro Ser Ser His Trp Lys Thr Pro Val Val
1               5                   10                  15

Ile Tyr Trp Asp Gly Thr Ala Leu Arg Cys Val Phe Val Pro Val Leu
            20                  25                  30

Gly Glu Thr Gly Ala Gln Arg Lys Arg Ile Ser Ala Arg Lys Gly Ser
        35                  40                  45

Leu Thr Thr Ser Cys Pro Gln Gly Ala Leu Ser Glu His Cys Pro Thr
    50                  55                  60

Thr Pro Ala Pro Leu Pro Ser Gln Arg Arg Asn His Trp Met Glu Asn
65                  70                  75                  80

Ile Ser Pro Phe Arg Thr Arg Pro Ala Phe Lys Lys Lys Ile Val Lys
                85                  90                  95

Glu Ser Met Lys Met Val Leu
            100

<210> SEQ ID NO 683
<211> LENGTH: 46
```

```
<212> TYPE: PRT
<213> ORGANISM: Artificial Sequence
<220> FEATURE:
<223> OTHER INFORMATION: pNOP158914

<400> SEQUENCE: 683

Leu Ala Arg Thr Pro Leu Pro Ser Thr Arg Cys Phe Ala Asn Trp Pro
1               5                   10                  15

Arg Pro Ala Leu Cys Ser Cys Gly Leu Ile Pro His Pro Arg Pro Ala
            20                  25                  30

Pro Ala Ser Ala Pro Trp Pro Ser Thr Ser Ser His Ser Thr
        35                  40                  45

<210> SEQ ID NO 684
<211> LENGTH: 78
<212> TYPE: PRT
<213> ORGANISM: Artificial Sequence
<220> FEATURE:
<223> OTHER INFORMATION: pNOP59073

<400> SEQUENCE: 684

Cys Cys Pro Arg Thr Ile Leu Asn Asn Gly Ser Leu Lys Thr Gln Val
1               5                   10                  15

Gln Met Lys Leu Pro Glu Cys Gln Arg Leu Leu Pro Pro Trp Pro Leu
            20                  25                  30

His Gln Gln Leu Leu His Arg Arg Pro Leu His Gln Pro Pro Gly
        35                  40                  45

Pro Cys His Leu Leu Ser Leu Pro Arg Lys Pro Thr Arg Ala Ala Thr
    50                  55                  60

Val Ser Val Trp Ala Ser Cys Ile Leu Gly Gln Pro Ser Leu
65                  70                  75

<210> SEQ ID NO 685
<211> LENGTH: 36
<212> TYPE: PRT
<213> ORGANISM: Artificial Sequence
<220> FEATURE:
<223> OTHER INFORMATION: pNOP224126

<400> SEQUENCE: 685

Cys Phe Ala Asn Trp Pro Arg Pro Ala Leu Cys Ser Cys Gly Leu Ile
1               5                   10                  15

Pro His Pro Arg Pro Ala Pro Ala Ser Ala Pro Trp Pro Ser Thr Ser
            20                  25                  30

Ser His Ser Thr
        35

<210> SEQ ID NO 686
<211> LENGTH: 72
<212> TYPE: PRT
<213> ORGANISM: Artificial Sequence
<220> FEATURE:
<223> OTHER INFORMATION: pNOP70126

<400> SEQUENCE: 686

Gly Ala Ala Pro Thr Met Ser Ala Ala Gln Ile Ala Met Val Trp Pro
1               5                   10                  15

Leu Leu Ser Ile Leu Ser Glu Trp Lys Glu Ile Cys Val Trp Ser Ile
            20                  25                  30

Trp Met Thr Glu Thr Leu Phe Asp Ile Val Trp Trp Cys Pro Met Ser
        35                  40                  45
```

```
Arg Leu Arg Leu Ala Leu Thr Val Pro Pro Ser Thr Thr Thr Cys
         50                  55                  60
Val Thr Val Pro Ala Trp Ala Ala
 65                  70
```

<210> SEQ ID NO 687
<211> LENGTH: 31
<212> TYPE: PRT
<213> ORGANISM: Artificial Sequence
<220> FEATURE:
<223> OTHER INFORMATION: pNOP272502

<400> SEQUENCE: 687

```
Phe His Thr Pro Ala Arg His Pro Arg Pro Arg His Gly His Leu Gln
 1               5                  10                  15
Ala Val Thr Ala His Asp Gly Gly Cys Glu Ala Leu Pro Pro Pro
             20                  25                  30
```

<210> SEQ ID NO 688
<211> LENGTH: 51
<212> TYPE: PRT
<213> ORGANISM: Artificial Sequence
<220> FEATURE:
<223> OTHER INFORMATION: pNOP136003

<400> SEQUENCE: 688

```
Ser Pro Lys Arg Val Ser Leu Pro Pro Ala Ile Lys Asn Ser Cys Ser
 1               5                  10                  15
Arg Gln Lys Gly Leu Thr Gln Thr Asp Ile Leu His Phe Leu Phe Pro
             20                  25                  30
Thr Asp Ser Leu Pro Pro Pro Ser Leu Pro Pro Leu Pro Phe Trp Val
         35                  40                  45
Leu Gly Leu
     50
```

<210> SEQ ID NO 689
<211> LENGTH: 22
<212> TYPE: PRT
<213> ORGANISM: Artificial Sequence
<220> FEATURE:
<223> OTHER INFORMATION: pNOP405064

<400> SEQUENCE: 689

```
Arg Trp Ser Gly Pro Ser Ser Ala Ser Tyr Pro Ser Gly Arg Lys Phe
 1               5                  10                  15
Ala Cys Gly Val Phe Gly
             20
```

<210> SEQ ID NO 690
<211> LENGTH: 40
<212> TYPE: PRT
<213> ORGANISM: Artificial Sequence
<220> FEATURE:
<223> OTHER INFORMATION: pNOP193414

<400> SEQUENCE: 690

```
Ala Ser Thr Ala Gln Gln His Gln Leu Leu Ser Pro Ala Lys Glu Glu
 1               5                  10                  15
Thr Thr Gly Trp Arg Ile Phe His Pro Ser Gly Pro Asp Gln Leu Ser
             20                  25                  30
Lys Arg Lys Leu Leu Lys Arg Ala
         35                  40
```

```
<210> SEQ ID NO 691
<211> LENGTH: 28
<212> TYPE: PRT
<213> ORGANISM: Artificial Sequence
<220> FEATURE:
<223> OTHER INFORMATION: pNOP316190

<400> SEQUENCE: 691

Val Arg Lys His Phe Gln Thr Tyr Gly Asn Tyr Phe Leu Lys Thr Thr
1               5                   10                  15

Phe Cys Pro Pro Cys Arg Pro Lys Gln Trp Met Ile
            20                  25

<210> SEQ ID NO 692
<211> LENGTH: 33
<212> TYPE: PRT
<213> ORGANISM: Artificial Sequence
<220> FEATURE:
<223> OTHER INFORMATION: pNOP252394

<400> SEQUENCE: 692

Gly Ala Cys Leu Cys Leu Ser Trp Glu Arg Pro Ala His Arg Gly Arg
1               5                   10                  15

Glu Ser Pro Gln Glu Arg Gly Ala Ser Pro Arg Ala Ala Pro Arg Glu
            20                  25                  30

His

<210> SEQ ID NO 693
<211> LENGTH: 97
<212> TYPE: PRT
<213> ORGANISM: Artificial Sequence
<220> FEATURE:
<223> OTHER INFORMATION: pNOP36301

<400> SEQUENCE: 693

Thr Gly Gly Pro Ser Ser Pro Ser Ser His Trp Lys Thr Pro Val Val
1               5                   10                  15

Ile Tyr Trp Asp Gly Thr Ala Leu Arg Cys Val Phe Val Pro Val Leu
            20                  25                  30

Gly Glu Thr Gly Ala Gln Arg Lys Arg Ile Ser Ala Arg Lys Gly Ser
        35                  40                  45

Leu Thr Thr Ser Cys Pro Gln Gly Ala Leu Ser Glu His Cys Pro Thr
    50                  55                  60

Thr Pro Ala Pro Leu Pro Ser Gln Arg Arg Asn His Trp Met Glu Asn
65                  70                  75                  80

Ile Ser Pro Phe Arg Ser Val Gly Val Ser Ala Ser Arg Cys Ser Glu
                85                  90                  95

Ser

<210> SEQ ID NO 694
<211> LENGTH: 23
<212> TYPE: PRT
<213> ORGANISM: Artificial Sequence
<220> FEATURE:
<223> OTHER INFORMATION: pNOP385655

<400> SEQUENCE: 694

Gln Phe Leu His Gly Arg His Glu Pro Glu Ala His Pro His His His
1               5                   10                  15

His Thr Gly Arg Leu Gln Trp
            20
```

-continued

```
<210> SEQ ID NO 695
<211> LENGTH: 20
<212> TYPE: PRT
<213> ORGANISM: Artificial Sequence
<220> FEATURE:
<223> OTHER INFORMATION: pNOP433152

<400> SEQUENCE: 695

His Gly His Leu Gln Ala Val Thr Ala His Asp Gly Gly Cys Glu Ala
1               5                   10                  15

Leu Pro Pro Pro
            20

<210> SEQ ID NO 696
<211> LENGTH: 13
<212> TYPE: PRT
<213> ORGANISM: Artificial Sequence
<220> FEATURE:
<223> OTHER INFORMATION: pNOP602122

<400> SEQUENCE: 696

Lys Gln Arg Ser Val Pro Leu Ala Val Pro Ser Asn Gly
1               5                   10

<210> SEQ ID NO 697
<211> LENGTH: 34
<212> TYPE: PRT
<213> ORGANISM: Artificial Sequence
<220> FEATURE:
<223> OTHER INFORMATION: pNOP243169

<400> SEQUENCE: 697

Gly Leu Gly Thr Gln Gly Cys Pro Gly Trp Glu Gly Ala Arg Gly Glu
1               5                   10                  15

Gln Gly Ser Leu Gln Pro Pro Glu Val Gln Lys Gly Ser Val Tyr Leu
            20                  25                  30

Pro Pro

<210> SEQ ID NO 698
<211> LENGTH: 30
<212> TYPE: PRT
<213> ORGANISM: Artificial Sequence
<220> FEATURE:
<223> OTHER INFORMATION: pNOP281999

<400> SEQUENCE: 698

Ala Ser Thr Ala Gln Gln His Gln Leu Leu Ser Pro Ala Lys Glu Glu
1               5                   10                  15

Thr Thr Gly Trp Arg Ile Phe His Pro Ser Asp Pro Trp Ala
            20                  25                  30

<210> SEQ ID NO 699
<211> LENGTH: 29
<212> TYPE: PRT
<213> ORGANISM: Artificial Sequence
<220> FEATURE:
<223> OTHER INFORMATION: pNOP293143

<400> SEQUENCE: 699

Ala Ser Thr Ala Gln Gln His Gln Leu Leu Ser Pro Ala Lys Glu Glu
1               5                   10                  15

Thr Thr Gly Trp Arg Ile Phe His Pro Ser Asp Ala Thr
            20                  25
```

```
<210> SEQ ID NO 700
<211> LENGTH: 24
<212> TYPE: PRT
<213> ORGANISM: Artificial Sequence
<220> FEATURE:
<223> OTHER INFORMATION: pNOP367554

<400> SEQUENCE: 700

Met Arg Pro Trp Asn Ser Arg Met Pro Arg Leu Gly Arg Ser Gln Gly
1               5                   10                  15

Gly Ala Gly Leu Thr Pro Ala Thr
            20

<210> SEQ ID NO 701
<211> LENGTH: 95
<212> TYPE: PRT
<213> ORGANISM: Artificial Sequence
<220> FEATURE:
<223> OTHER INFORMATION: pNOP38141

<400> SEQUENCE: 701

Thr Gly Gly Pro Ser Ser Pro Ser Ser His Trp Lys Thr Pro Val Val
1               5                   10                  15

Ile Tyr Trp Asp Gly Thr Ala Leu Arg Cys Val Phe Val Pro Val Leu
                20                  25                  30

Gly Glu Thr Gly Ala Gln Arg Lys Arg Ile Ser Ala Arg Lys Gly Ser
            35                  40                  45

Leu Thr Thr Ser Cys Pro Gln Gly Ala Leu Ser Glu His Cys Pro Thr
        50                  55                  60

Thr Pro Ala Pro Leu Pro Ser Gln Arg Arg Asn His Trp Met Glu Asn
65                  70                  75                  80

Ile Ser Pro Phe Arg Cys Tyr Leu Thr Tyr Asp Gly Val Thr Ser
                85                  90                  95

<210> SEQ ID NO 702
<211> LENGTH: 20
<212> TYPE: PRT
<213> ORGANISM: Artificial Sequence
<220> FEATURE:
<223> OTHER INFORMATION: pNOP445026

<400> SEQUENCE: 702

Thr Arg Arg Lys Leu Lys Ile Leu Ser Val Gly Val Ser Ala Ser Arg
1               5                   10                  15

Cys Ser Glu Ser
            20

<210> SEQ ID NO 703
<211> LENGTH: 18
<212> TYPE: PRT
<213> ORGANISM: Artificial Sequence
<220> FEATURE:
<223> OTHER INFORMATION: pNOP483390

<400> SEQUENCE: 703

Arg Arg Ala Pro Ser Glu Ser Gly Asn Ile Phe Arg Pro Met Glu Thr
1               5                   10                  15

Thr Ser

<210> SEQ ID NO 704
<211> LENGTH: 15
```

```
<212> TYPE: PRT
<213> ORGANISM: Artificial Sequence
<220> FEATURE:
<223> OTHER INFORMATION: pNOP539666

<400> SEQUENCE: 704

Asp Val Leu Pro Thr Gly Gln Asp Leu Pro Cys Ala Ala Val Gly
1               5                   10                  15

<210> SEQ ID NO 705
<211> LENGTH: 78
<212> TYPE: PRT
<213> ORGANISM: Artificial Sequence
<220> FEATURE:
<223> OTHER INFORMATION: pNOP59708

<400> SEQUENCE: 705

Leu Arg Leu Thr Phe Ser Thr Ser Cys Ser Pro Leu Thr Ala Ser His
1               5                   10                  15

Pro His Leu Ser Leu Pro Cys His Phe Gly Phe Trp Val Phe Glu Pro
            20                  25                  30

Leu Leu Ala Ile Gly Val Arg Gln Lys His Pro Gly Leu Pro Phe Ala
        35                  40                  45

Leu Ser Arg Gly Ser Thr Glu Gln Val Gly Leu His Trp Cys Phe Val
    50                  55                  60

Val Gly Arg Arg Met Gly Ser Arg Thr Tyr Gln Leu Arg Phe
65                  70                  75

<210> SEQ ID NO 706
<211> LENGTH: 13
<212> TYPE: PRT
<213> ORGANISM: Artificial Sequence
<220> FEATURE:
<223> OTHER INFORMATION: pNOP604680

<400> SEQUENCE: 706

Leu Thr Met Val Leu Leu Pro Asp Lys Leu Val Val Ser
1               5                   10

<210> SEQ ID NO 707
<211> LENGTH: 13
<212> TYPE: PRT
<213> ORGANISM: Artificial Sequence
<220> FEATURE:
<223> OTHER INFORMATION: pNOP619453

<400> SEQUENCE: 707

Trp Arg Ser Arg Ser Gln Ile Leu Ala Ser Ser Pro Leu
1               5                   10

<210> SEQ ID NO 708
<211> LENGTH: 10
<212> TYPE: PRT
<213> ORGANISM: Artificial Sequence
<220> FEATURE:
<223> OTHER INFORMATION: pNOP703537

<400> SEQUENCE: 708

Leu Tyr His His Pro Leu Gln Leu His Val
1               5                   10

<210> SEQ ID NO 709
<211> LENGTH: 158
<212> TYPE: PRT
<213> ORGANISM: Artificial Sequence
```

-continued

```
<220> FEATURE:
<223> OTHER INFORMATION: pNOP9298

<400> SEQUENCE: 709

Thr Thr Cys Trp Thr Arg Arg Arg Trp Gly Arg Leu Trp Pro Pro Pro
1               5                   10                  15

Pro Ala Arg Ala Ser Arg Arg Asp Ser Asp Gly Thr Arg Pro Ala
            20                  25                  30

Thr Cys Met His Ser Pro Thr Pro Arg Pro Ala Pro Ala Ala Ala Arg
        35                  40                  45

Pro Ser Ser Arg Ala Pro Leu Thr Ala Ala Ala Ala Ala Arg Arg
50                  55                  60

Pro Ala Val Arg Pro Pro Thr Ala Pro Leu Arg Ser Arg Arg Gly Ala
65                  70                  75                  80

Ala Ala Gln Pro Cys Ser Thr Arg Thr Asn Ser Gly Thr Ala Arg
            85                  90                  95

Leu Ala Arg Thr Ala Ile Ala Ala Ser Thr Ser Cys Thr Cys Ser Ser
            100                 105                 110

Ser Arg Arg Gly Ala Ala Ala Pro Arg Ser Thr Pro Arg Ala Thr Arg
            115                 120                 125

Pro Ser Cys Ala Gly Pro Ser Arg Arg Ala Ala Arg Ala Ser Thr Ala
130                 135                 140

Lys Ser Ala Ser Ser Arg Met Ala Ser Thr Ser Cys Ala Ala
145                 150                 155

<210> SEQ ID NO 710
<211> LENGTH: 347
<212> TYPE: PRT
<213> ORGANISM: Artificial Sequence
<220> FEATURE:
<223> OTHER INFORMATION: pNOP610

<400> SEQUENCE: 710

Arg Glu Arg Arg Ser Gln Pro Ala Pro Pro Ala Pro Ala Ala Ala Ala
1               5                   10                  15

Glu Gly Gly Arg Arg Leu Pro Asp Gln Leu His Ala Leu Gln Asp Arg
            20                  25                  30

Ala Val Pro Ala Leu Arg Gly Glu Arg His Val Gln Val Arg Arg Lys
        35                  40                  45

Val Pro Val Arg Ala Trp Leu Pro Arg Ala Ala Gln Pro Asp Ser Pro
50                  55                  60

Ser Glu Val Gln Asp Arg Ala Val Pro His Leu Ser Tyr His Arg Leu
65                  70                  75                  80

Leu Pro Leu Trp Ala Ala Leu Pro Leu His Pro Gln Arg Gly Arg Ala
            85                  90                  95

Ala Ala Arg Ala Val Gly Gly Arg Leu Arg Gly Pro Ala Cys Leu Trp
            100                 105                 110

His Ala Arg Cys Val Ala Pro Gly Leu Pro Ala Gly Ala Ala Ala Gln
            115                 120                 125

Val Ala Pro Gln Pro Gln Leu Leu Gly Leu Pro Val Gly Pro Pro Ser
130                 135                 140

Ala Pro Gly Arg Pro Arg Val Ala Ala Ala Arg Gln Pro His Val
145                 150                 155                 160

Ala His Ala Ala Ala Ala Leu Leu Leu Phe Gly Leu Val Leu Leu Leu
            165                 170                 175

Leu Arg Leu Leu Leu Leu Phe Leu Gly Leu Arg Gly Leu His Ala Leu Gly
```

```
                180             185             190
Arg Pro Asp Met Leu Arg Leu Arg Gly Gly Arg Gly Cys Gly Arg Ser
            195             200             205
Ala Val Arg His Arg Gly Arg Arg Gly Pro Ala Gly Ala Gly Gly Pro
            210             215             220
Val Arg Gly Leu Leu Val Gly Leu Val Arg Gln Gln Arg Leu Arg Leu
225             230             235             240
Arg Ser Gly Ala Gln Gln Pro His His Ala Ala Arg His Pro Asp Pro
                245             250             255
Gln Leu Cys Arg Arg Gly Arg Arg Leu Leu Pro Gln Ser Ala Ala
            260             265             270
Ala Ala Ala Ala Gly Pro Gly Ala Pro Arg Ala Ala Ala Gly Ala Ala
            275             280             285
Gln Arg Asp Pro Pro Arg Gly Arg Arg Thr Ser Leu Ala Ala Leu
            290             295             300
Gln Leu Pro Ala Ala Pro Pro Val Arg Leu Ala Arg Val Arg Arg
305             310             315             320
Ala Pro Gln Pro Pro Gly Leu Ala Val Gly Pro Arg Gln Leu Pro Lys
                325             330             335
Arg Leu Pro Glu Leu Arg Gln Pro Gln Arg Leu
            340             345

<210> SEQ ID NO 711
<211> LENGTH: 22
<212> TYPE: PRT
<213> ORGANISM: Artificial Sequence
<220> FEATURE:
<223> OTHER INFORMATION: pNOP395419

<400> SEQUENCE: 711

Gly Ala Val Gly Gly Arg Arg His Ser Pro Ala Gln Gln Gly Glu Gln
1               5                   10                  15

Ile Pro Gly Pro Leu Val
            20

<210> SEQ ID NO 712
<211> LENGTH: 82
<212> TYPE: PRT
<213> ORGANISM: Artificial Sequence
<220> FEATURE:
<223> OTHER INFORMATION: pNOP53232

<400> SEQUENCE: 712

His Val Asp His Thr Ser Val Arg Leu Leu Arg Cys Arg Leu Leu Val
1               5                   10                  15

Gln Asp Arg Glu Ile Pro Gly Gln Pro Gln Pro Glu Gln His Ala Gly
            20                  25                  30

Gln Glu Gly Gly Gly Asp Ala Cys Gly Arg Arg Pro Gln Leu Gly Leu
        35                  40                  45

Arg Ala Gly Ile Pro Pro Thr Ala Leu Gly Gln Gln Pro Ala Cys Thr
    50                  55                  60

Arg Pro Pro Arg Ala Gln Pro Arg Gln Leu Leu Ala Gln Val Pro Gly
65                  70                  75                  80

Arg Arg

<210> SEQ ID NO 713
<211> LENGTH: 273
<212> TYPE: PRT
```

```
<213> ORGANISM: Artificial Sequence
<220> FEATURE:
<223> OTHER INFORMATION: pNOP1471

<400> SEQUENCE: 713

Leu Ala Ile Arg Ser Thr Arg Pro Ser Cys Ala Ala Pro Phe Ile Pro
1               5                   10                  15

Ser Ala Ser Ala Pro Met Gly Arg Ala Ala Thr Ser Ser Thr Thr Arg
                20                  25                  30

Thr Ser Gly Gly Pro Arg Arg Gly Ala Pro Gly Thr Cys Val
        35                  40                  45

Pro Leu Ala Arg Ala Met Arg Cys Thr Trp Ala Ser Arg Gly Ser Arg
    50                  55                  60

Gly Pro Ser Cys Thr Thr Ala Ser Ala Ser Arg Ala Ser Arg Arg Ala
65                  70                  75                  80

Thr Ile Ser Pro Arg Ala Ala Ser Ser Arg Arg Cys Cys Ser Thr Ala
                85                  90                  95

Pro Arg Arg Ala Arg Arg Arg Arg Pro Pro Ala Leu Arg Pro Arg Pro
                100                 105                 110

Ala Pro Pro Pro Pro Pro Val Pro Arg Pro Arg Pro Pro Arg
    115                 120                 125

Pro Arg Ala Pro Arg His Ala Ala Pro Pro Arg Arg Pro Arg Leu Arg
    130                 135                 140

Pro Leu Cys Cys Thr Ala Pro Gly Ala Pro Arg Thr Cys Trp Arg Arg
145                 150                 155                 160

Gly Pro Arg Ala Arg Pro Ala Arg Arg Pro Arg Ala Pro Thr Thr Pro
                165                 170                 175

Ser Pro Ser Val Arg Ser Ser Ala Ala Ser Ser Arg Arg Ser Pro Ser
                180                 185                 190

Arg Pro Thr Thr Leu Pro Pro Trp Pro Pro Pro Thr Thr Ala Val
                195                 200                 205

Ser Ser Ser Ser Ser Ser Arg Ala Trp Arg Pro Arg Ser Arg Arg
    210                 215                 220

Arg Arg Pro Ala Arg Pro Ser Pro Pro Gly Pro Pro His Leu Pro Arg
225                 230                 235                 240

Arg Pro Ser Ala Ser Ser Cys Arg Ala Ala Cys Pro Thr Arg Pro Cys
                245                 250                 255

Ser Thr Arg Pro Pro Ala Pro Arg Thr Arg Cys Arg Thr Ala Thr Ala
                260                 265                 270

Thr

<210> SEQ ID NO 714
<211> LENGTH: 36
<212> TYPE: PRT
<213> ORGANISM: Artificial Sequence
<220> FEATURE:
<223> OTHER INFORMATION: pNOP223799

<400> SEQUENCE: 714

Ala Pro Ala Ala Ser Ala Ala Leu Ser Leu Pro Ala Ser Thr Leu Ala
1               5                   10                  15

Ala Ala Cys Gln Ser Ser Ala Ala Ser Pro Ser Pro Thr Thr Glu Ala
                20                  25                  30

Arg Gly Arg Gln
        35
```

```
<210> SEQ ID NO 715
<211> LENGTH: 56
<212> TYPE: PRT
<213> ORGANISM: Artificial Sequence
<220> FEATURE:
<223> OTHER INFORMATION: pNOP116065

<400> SEQUENCE: 715

Val Ser Gln Pro Arg Pro Trp Pro Pro Ala Asn Leu Gln Pro Pro
1               5                   10                  15

Leu His Leu Arg Arg Leu Arg Gln Glu Gly Ala Ser Glu Glu Gly
            20                  25                  30

Lys Ala Val Gln Arg Cys Trp Arg Thr Pro Leu Ala Ile Ser Pro Leu
        35                  40                  45

Leu Gly Ala Arg Glu Trp Gly Gly
    50                  55

<210> SEQ ID NO 716
<211> LENGTH: 26
<212> TYPE: PRT
<213> ORGANISM: Artificial Sequence
<220> FEATURE:
<223> OTHER INFORMATION: pNOP332322

<400> SEQUENCE: 716

Cys Arg Pro His Phe Cys Pro Pro Ser Thr Met Ser Thr Ser Cys Ala
1               5                   10                  15

Arg Gln Arg Asn Pro Trp Pro Thr Ser Thr
            20                  25

<210> SEQ ID NO 717
<211> LENGTH: 18
<212> TYPE: PRT
<213> ORGANISM: Artificial Sequence
<220> FEATURE:
<223> OTHER INFORMATION: pNOP483342

<400> SEQUENCE: 717

Arg Gln Gln Leu Arg Gln Arg Gly Gly Arg Arg Ser Asp Leu Leu Arg
1               5                   10                  15

His Pro

<210> SEQ ID NO 718
<211> LENGTH: 23
<212> TYPE: DNA
<213> ORGANISM: Artificial Sequence
<220> FEATURE:
<223> OTHER INFORMATION: sequence comprising a linker amino acid
      encoding sequence
<220> FEATURE:
<221> NAME/KEY: CDS
<222> LOCATION: (1)..(21)

<400> SEQUENCE: 718 cta tac agg cga atg aga tta tg                                    23
Leu Tyr Arg Arg Met Arg Leu
1               5

<210> SEQ ID NO 719
<211> LENGTH: 7
<212> TYPE: PRT
<213> ORGANISM: Artificial Sequence
<220> FEATURE:
<223> OTHER INFORMATION: Synthetic Construct

<400> SEQUENCE: 719
```

```
Leu Tyr Arg Arg Met Arg Leu
1               5

<210> SEQ ID NO 720
<211> LENGTH: 23
<212> TYPE: DNA
<213> ORGANISM: Artificial Sequence
<220> FEATURE:
<223> OTHER INFORMATION: sequence comprising a linker amino acid
      encoding sequence
<220> FEATURE:
<221> NAME/KEY: CDS
<222> LOCATION: (2)..(22)

<400> SEQUENCE: 720 c tat aca ggc gaa tga gat tat g                                    23
  Tyr Thr Gly Glu     Asp Tyr
  1               5

<210> SEQ ID NO 721
<211> LENGTH: 4
<212> TYPE: PRT
<213> ORGANISM: Artificial Sequence
<220> FEATURE:
<223> OTHER INFORMATION: Synthetic Construct

<400> SEQUENCE: 721

Tyr Thr Gly Glu
1

<210> SEQ ID NO 722
<211> LENGTH: 66
<212> TYPE: DNA
<213> ORGANISM: Artificial Sequence
<220> FEATURE:
<223> OTHER INFORMATION: p21.3 seq
<220> FEATURE:
<221> NAME/KEY: CDS
<222> LOCATION: (1)..(66)

<400> SEQUENCE: 722 gca gtt ggg ctc cgc gcc gtg gag cag cag cag ctc cgc cac tcg ggc    48
Ala Val Gly Leu Arg Ala Val Glu Gln Gln Gln Leu Arg His Ser Gly
1               5                   10                  15 gct gcc cat cat cat gac                                            66
Ala Ala His His His Asp
            20

<210> SEQ ID NO 723
<211> LENGTH: 22
<212> TYPE: PRT
<213> ORGANISM: Artificial Sequence
<220> FEATURE:
<223> OTHER INFORMATION: Synthetic Construct

<400> SEQUENCE: 723

Ala Val Gly Leu Arg Ala Val Glu Gln Gln Gln Leu Arg His Ser Gly
1               5                   10                  15

Ala Ala His His His Asp
            20

<210> SEQ ID NO 724
<211> LENGTH: 63
<212> TYPE: DNA
<213> ORGANISM: Artificial Sequence
<220> FEATURE:
<223> OTHER INFORMATION: frameshift
```

```
<220> FEATURE:
<221> NAME/KEY: CDS
<222> LOCATION: (1)..(63)

<400> SEQUENCE: 724 cag ttg ggc tcc gcg ccg tgg agc agc agc agc tcc gcc act cgg gcg      48
Gln Leu Gly Ser Ala Pro Trp Ser Ser Ser Ser Ser Ala Thr Arg Ala
1               5                   10                  15 ctg ccc atc atc atg                                                  63
Leu Pro Ile Ile Met
            20

<210> SEQ ID NO 725
<211> LENGTH: 21
<212> TYPE: PRT
<213> ORGANISM: Artificial Sequence
<220> FEATURE:
<223> OTHER INFORMATION: Synthetic Construct

<400> SEQUENCE: 725

Gln Leu Gly Ser Ala Pro Trp Ser Ser Ser Ser Ser Ala Thr Arg Ala
1               5                   10                  15

Leu Pro Ile Ile Met
            20
```